(12) United States Patent
McDonagh et al.

(10) Patent No.: US 9,073,993 B2
(45) Date of Patent: Jul. 7, 2015

(54) CD19 BINDING AGENTS AND USES THEREOF

(75) Inventors: Charlotte McDonagh, Waltham, MA (US); Charles G. Cerveny, Seattle, WA (US); Dennis Benjamin, Redmond, WA (US); Paul Carter, Mercer Island, WA (US)

(73) Assignee: Seattle Genetics, Inc., Bothell, WA (US)

( * ) Notice: Subject to any disclaimer, the term of this patent is extended or adjusted under 35 U.S.C. 154(b) by 0 days.

(21) Appl. No.: 13/530,074

(22) Filed: Jun. 21, 2012

(65) Prior Publication Data

US 2012/0294853 A1    Nov. 22, 2012

Related U.S. Application Data

(62) Division of application No. 13/109,957, filed on May 17, 2011, now Pat. No. 8,242,252, which is a division of application No. 12/253,895, filed on Oct. 17, 2008, now Pat. No. 7,968,687.

(60) Provisional application No. 60/981,206, filed on Oct. 19, 2007, provisional application No. 61/019,214, filed on Jan. 4, 2008, provisional application No. 61/080,169, filed on Jul. 11, 2008.

(51) Int. Cl.
C07K 16/28 (2006.01)
A61K 47/48 (2006.01)
A61K 39/00 (2006.01)

(52) U.S. Cl.
CPC ....... *C07K 16/2803* (2013.01); *A61K 47/48415* (2013.01); *A61K 47/48561* (2013.01); *A61K 2039/505* (2013.01); *C07K 2317/24* (2013.01); *C07K 2317/56* (2013.01); *C07K 2317/732* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 5,635,483 A | 6/1997 | Pettit et al. | |
| 5,686,072 A | 11/1997 | Uhr et al. | |
| 5,767,237 A | 6/1998 | Sakakibara et al. | |
| 5,780,588 A | 7/1998 | Pettit et al. | |
| 6,214,345 B1 | 4/2001 | Firestone et al. | |
| 6,306,393 B1 | 10/2001 | Goldenberg | |
| 6,884,869 B2 | 4/2005 | Senter et al. | |
| 7,109,304 B2 | 9/2006 | Hansen et al. | |
| 7,462,352 B2 | 12/2008 | Hansen et al. | |
| 7,659,241 B2 | 2/2010 | Senter et al. | |
| 7,745,394 B2 | 6/2010 | Doronina et al. | |
| 7,837,995 B2 | 11/2010 | Goldenberg | |
| 7,902,338 B2 | 3/2011 | Hansen et al. | |
| 7,964,566 B2 | 6/2011 | Doronina et al. | |
| 7,964,567 B2 | 6/2011 | Doronina et al. | |
| 7,968,687 B2 | 6/2011 | McDonagh et al. | |
| 8,242,252 B2 | 8/2012 | McDonagh et al. | |
| 2004/0126363 A1 | 7/2004 | Jensen et al. | |
| 2004/0136908 A1 | 7/2004 | Olson et al. | |
| 2005/0048617 A1* | 3/2005 | Wu et al. ................ | 435/69.1 |
| 2005/0238649 A1 | 10/2005 | Doronina et al. | |
| 2006/0024317 A1 | 2/2006 | Boyd et al. | |
| 2006/0074008 A1 | 4/2006 | Senter et al. | |
| 2006/0233791 A1* | 10/2006 | Tedder et al. ........... | 424/141.1 |
| 2006/0233794 A1 | 10/2006 | Law et al. | |
| 2006/0240008 A1 | 10/2006 | Benyunes | |
| 2006/0263357 A1 | 11/2006 | Tedder et al. | |
| 2006/0280738 A1 | 12/2006 | Tedder | |
| 2007/0154473 A1 | 7/2007 | Super et al. | |
| 2008/0138336 A1 | 6/2008 | Damschroder et al. | |
| 2008/0241128 A1 | 10/2008 | Jeffrey | |
| 2008/0260731 A1 | 10/2008 | Bernett et al. | |
| 2008/0300192 A1 | 12/2008 | Doronina et al. | |
| 2009/0047296 A1 | 2/2009 | Doronina et al. | |
| 2009/0142349 A1 | 6/2009 | Rao-Naik et al. | |
| 2009/0246195 A1 | 10/2009 | Tedder | |
| 2009/0285808 A1 | 11/2009 | Tedder et al. | |
| 2009/0317869 A1 | 12/2009 | Alley et al. | |
| 2010/0104509 A1 | 4/2010 | King et al. | |
| 2010/0158901 A1 | 6/2010 | Tedder et al. | |
| 2010/0260786 A1 | 10/2010 | Doronina et al. | |
| 2011/0020343 A1 | 1/2011 | Senter et al. | |
| 2011/0052489 A1 | 3/2011 | Hansen et al. | |
| 2011/0064753 A1 | 3/2011 | Senter et al. | |

FOREIGN PATENT DOCUMENTS

| | | | |
|---|---|---|---|
| JP | 2007-528209 A | | 10/2007 |
| WO | WO 2004/010957 A2 | | 2/2004 |
| WO | WO 2005-012493 A2 | | 2/2005 |
| WO | WO 2006034488 A2 | * | 3/2006 |
| WO | WO 2006/113665 A2 | | 10/2006 |
| WO | WO 2006/138737 A2 | | 12/2006 |
| WO | WO 2007/002223 A2 | | 1/2007 |
| WO | WO 2007-011968 A2 | | 1/2007 |
| WO | WO 2007/011968 A2 | | 1/2007 |
| WO | WO 2007/084693 A2 | | 7/2007 |
| WO | WO 2007/085470 A2 | | 8/2007 |
| WO | WO 2007/103288 A2 | | 9/2007 |
| WO | WO 2008/022152 A2 | | 2/2008 |
| WO | WO 2008/070593 A2 | | 6/2008 |
| WO | WO 2009/052431 A2 | | 4/2009 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Holm et al. (Mol. Immunol. Feb. 2007; 44 (6): 1075-1084).*
MacCallum et al. (J. Mol. Biol. Oct. 11, 1996; 262 (5): 732-745).*
van Zelm et al (NEJM, 354(1 8):1901-1912), 2006.*
Portell et al (Curr. Hem. Malig. Reg., 7:153-159, 2002).*
Al-Lazikani et al., "Standard Conformations for the Canonical Structures of immunoglobulins," *J. Mol. Biol.*, 273:927-948, (1997).

(Continued)

*Primary Examiner* — Brad Duffy
(74) *Attorney, Agent, or Firm* — Alston & Bird LLP

(57) ABSTRACT

This invention, inter alia, relates to CD19 binding agents and methods of using such CD19 binding agents for treating disease.

15 Claims, 26 Drawing Sheets

(56) References Cited

OTHER PUBLICATIONS

Almagro et al., "Structural differences between the repertoires of mouse and human germline genes and their evolutionary implications," *Immunogenetics*, 47:355-363, (1998).
Benjamin et al., "Humanized Anti-CD19 Auristatin Antibody-Drug Conjugates Display Potent Antitumor Activity in Preclinical Models of B-Cell Malignancies," *Proceedings of the AACR-NCI-EORTC*, San Francisco, CA, Abstract B60, (2007).
Chari et al., "Enhancement of the Selectivity and Antitumor Efficacy of a CC-1065 Analogue through Immunoconjugate Formation," *Cancer Research*, 55:4079-4084, (1995).
Chothia et al., "Canonical Structures for the Hypervariable Regions of Immunoglobulins," *J. Mol. Biol.*, 196:901-917, (1987).
Chothia et al., "Conformations of immunoglobulin hypervariable regions," *Nature*, 342:877-883, (1989).
Chothia et al., "Domain Association in Immunoglobulin Molecules the Packing of Variable Domains," *J. Mol. Biol.*, 186:651-663, (1985).
Du et al., "Differential Cellular Internalization of Anti-CD19 and -CD22 Immunotoxins Results in Different Cytotoxic Activity," *Cancer Res.*, 68(15):6300-6305, (2008).
Flavell et al., "Preclinical studies with the anti-CD19-saporin immunotoxin BU12- SAPORIN for the treatment of human-B-cell tumours," *British Journal of Cancer*, 72:1373-1379, (1995).
Flavell et al., "Therapy of Human B-Cell Lymphoma Bearing Scid Mice is more effective with Anti-CD19- and Anti-CD38-Saporin Immunotoxins used in combination than with either Immunotoxin used alone," *Int. J. Cancer*, 62:337-344, (1995).
Gerber et al., "Potent antitumor activity of the anti-CD19 auristatin antibody-drug conjugate hBU12-vcMMAE in rituximab sensitive and resistant lymphomas," *European Journal of Cancer*, Supplement, Poster 507, 6(12):161, (2008).
Gerber et al., "Potent antitumor activity of the anti-CD19 auristatin antibody-drug conjugate SGN-19A in rituximab sensitive and resistant lymphomas," *Proceedings of the AACR-NCI-EORTC*, Geneva, Switzerland, Abstract 507, (2008).
Gerber et al., "Potent antitumor activity of the anti-CD19 auristatin antibody drug conjugate hBU12-vcMMAE against rituximab-sensitive and -resistant lymphomas," *Blood*, 113(18):4352-4361, (2009).
Ghetie et al., "Anti-CD19 Inhibits the Growth of Human B-Cell Tumor Lines In Vitro and of Daudi Cells in SCID Mice by Inducing Cell Cycle Arrest," *Blood*, 83(05): 1329-1336, (1994).
Ginaldi et al., "Levels of expression of CD19 and CD20 in chronic B cell leukaemias," *J Chn Pathol*, 51:364-369, (1998).
Goulet et al., "Conjugation of Blocked Ricin to an Anti-CD19 Monoclonal Antibody Increases Antibody-Induced Cell Calcium Mobilization and CD19 Internalization," *Blood* 90(6):2364-2375, (1997).
Hekman et al., "Initial experience with treatment of human B cell lymphoma with anti-CD19 monoclonal antibody," *Cancer Immunology Immunotherapy*, 32:364-372, (1991).
Hooijberg et al., "Enhanced Antitumor Effects of CD20 over CD19 Monoclonal Antibodies in a Nude Mouse Xenograft Model," *Cancer Research*, 55, 840-846, (1995).
Ingle et al., "High CD21 expression inhibits internalization of anti-CD19 antibodies and cytotoxicity of an anti-CD19-drug conjugate," *British Journal of Haematology*, 140, 46-58, (2007).
Iwahashi et al., "CDR substitutions of a humanized monoclonal antibody (CC49): contributions of individual CDRs to antigen binding and immunogenicity," *Molecular Immunology*, 36:1079-1091, (1999).
Kansas et al., "Transmembrane signals generated through MHC class II, CD19, CD20, CD39, and CD40 antigens induce LFA-1-dependent and independent adhesion in human B cells through a tyrosine kinase-dependent pathway," *J. Immunol.*, (147):4094-4102, (1991).

Lang et al., "Chimeric CD19 antibody mediates cytotoxic activity against leukemic blasts with effector cells from pediatric patients who received T-cell-depleted allografts," *Blood*, 103:3982-3985, (2004).
Lee et al., "Complement Component C3d-Antigen Complexes Can Either Augment or Inhibit B Lymphocyte Activation and Humoral Immunity in Mice Depending on the Degree of CD21/CD19 Complex Engagement," *The Journal of Immunology*, 175, 8011-8023, (2005).
Liu et al., "Cure of Multidrug-Resistant Human B-Cell Lymphoma Xenografts by Combinations of Anti-B4-Blocked Ricin and Chemotherapeutic Drugs," *Blood*, 87(9):3892-3898, (1996).
McDonagh et al., "Engineered Antibody-drug Conjugates with Defined Sites and Stoichiometries of Drug Attachment," *Protein Engineering*, Design and Selection, 19(7):299-307 (2006).
Messmann et al., "A Phase I Study of Combination Therapy with Immunotoxins IgG-HD37-Deglycosylated Ricin A Chain (dgA) and IgG-RFB4-dgA (Combotox) in Patients with Refractory CD19(+), CD22(+) B Cell Lymphoma," *Clinical Cancer Research*, 6:1302-1313, (2000).
Mitchell et al., "Targeting Primary Human Ph+ B-Cell Precursor Leukemia-Engrafted SCID Mice Using Radiolabeled Anti-CD19 Monoclonal Antibodies," *J. Nucl. Med.*, 44:1105-1112, (2003).
Miyazaki et al., "Synthesis and Antitumor Activity of Novel Dolastatin 10 Analogs," *Chem. Pharm. Bull.*, 43(10):1706-1718, (1995).
Padlan et al., "Identification of specificity-determining residues in antibodies," *FASEB*. 9:133-139, (1995).
PCT International Preliminary Report on Patentability (Chapter I) of Apr. 20, 2010 for application PCT/US2008/080373.
PCT Search Report of Mar. 24, 2009 for application PCT/US2008/080373.
Pesando et al., "CD19 is Functionally and Physically Associated with Surface Immunoglobulin," *J. Exp. Med.*, 170:2159-2164, (1989).
Pietersz et al., "In vitro and in vivo antitumour activity of a chimeric anti-CD19 antibody," *Cancer Immunol Immunother*, 41:53-60, (1995).
Shah et al., "Anti-B4-blocked Ricin Immunotoxin Shows Therapeutic Efficacy in Four Different SCID Mouse Tumor Models," *Cancer Research*, 53:1360-1367, (1993).
Stone et al., "A Phase I Study of Bolus Versus Continuous Infusion of the Anti-CD19 Immunotoxin, IgG-HD37-dgA, in Patients With B-Cell Lymphoma," *Blood*, 88(4):1188-1197, (1996).
Supplementary European Search Report and European Search Opinion for application EP08040713.5 mailed Sep. 21, 2011.
Tamura et al., "Structural Correlates of an Anticarcinoma Antibody: Identification of Specificity-Determining Residues (SDRs) and Development of a Minimally Immunogenic Antibody Variant by Retention of SDRs Only," *The Journal of Immunology*, 164:1432-1441, (2000).
Tedder et al., "Fcγ receptor-dependent effector mechanisms regulate CD19 and CD20 antibody immunotherapies for B lymphocyte malignancies and autoimmunity," *Springer Semin Immun*, 28:351-364, (2006).
Tomlinson et al., "The structural repertoire of the human VIc domain," *The EMBO Journal*, 14(18):4628-4638, (1995).
Tsimberidou et al., "Anti-B4 Blocked Ricin Post Chemotherapy in Patients with Chronic Lymphocytic Leukemia—Long-term Follow-up of a Monoclonal Antibody-based Approach to Residual Disease," *Leukemia & Lymphoma*, 44(10):1719-1725, (2003).
U.S. Appl. No. 12/253,895, Notice of Allowance and Examiner's Interview Summary Record mailed Feb. 11, 2011.
U.S. Appl. No. 12/253,895, Requirement for Restriction/Election mailed Oct. 20, 2010.
U.S. Appl. No. 13/109,957, Notice of Allowance and Examiner's Interview Summary Record mailed Mar. 22, 2012.
U.S. Appl. No. 13/109,957, Requirement for Restriction/Election mailed Nov. 8, 2011.

(56) References Cited

OTHER PUBLICATIONS

Uckun et al., "Detailed studies on expression and function of CD19 surface determinant by using B43 monoclonal antibody and the clinical potential of anti-CD19 immunotoxins," *Blood*, 71(01):13-29, (1988).

Vallera et al., "Radiotherapy of CD19 Expressing Daudi Tumors in Nude Mice with Yttrium-90-Labeled Anti-CD19 Antibody," *Cancer Biotherapy & Radiopharmaceuticals*, 19(1):11-23, (2004).

Vaughan et al., "Human antibodies by design," *Cambridge Antibody Technology*, 5 pages, (1998).

Veillette et al, "Negative Regulation of Immunoreceptor Signaling," *Annu. Rev. Immunol.*, 20:669-707, (2002).

Wu, "Simultaneous Humanization and Affinity Optimization of Monoclonal Antibodies," *Methods in Molecular Biology*, Humana Press Inc., pp. 197-212, (2003).

Yazawa et al., "Immunotherapy using unconjugated CD19 monoclonal antibodies in animal models for B lymphocyte malignancies and autoimmune disease," *PNAS*, 102(42):15178-15183, (2005).

Zhou, "Tissue-Specific Expression of the Human CD19 Gene in Transgenic Mice Inhibits Antigen-Independent B-Lymphocyte Development," *Molecular and Cellular Biology*, p. 3884-3894 (1994).

\* cited by examiner

Figure 14

| Indication | Cell Line | CD21/Cell | CD19/Cell | IC$_{50}$ [nM] cytotox | |
|---|---|---|---|---|---|
| | | | | hBU12-mcF(4) | hBU12-vcE(4) |
| ALL | Nalm-6 | 0 | 53773 | 38 | 4 |
| | RS4;11 | 0 | 38227 | 0.08 | 0.05 |
| Follicular Lymphoma | DOHH2 | 0 | 40056 | 5 | 5 |
| | WSU-NHL | 0 | 36242 | 0.06 | 0.4 |
| DLBCL | HT* | 952 | 36834 | 0.26 | 0.20 |
| | RL | 0 | 32542 | 208 | >300 |
| | WSU-DLCL2 | 0 | 19924 | 209 | 51 |
| Burkitt's | CA46* | 2167 | 57240 | 0.5 | 2 |
| | Namalwa* | 374 | 28629 | 6 | 54 |
| | Ramos | 2369 | 41016 | 0.06 | 0.6 |
| | Daudi* | 25531 | 54074 | >300 | 30 |
| | Raji | 56660 | 78798 | >300 | 33.3 |
| CLL | MEC-2 | 33246 | 67562 | >300 | >300 |
| | JVM3 | 17850 | 26321 | 67 | 42 |
| T-cell leukemia | Jurkat: CD19- | | 0 | >300 | >300 |

* MHCII-mcMMAF(4) IC50 = 0.5 nM;

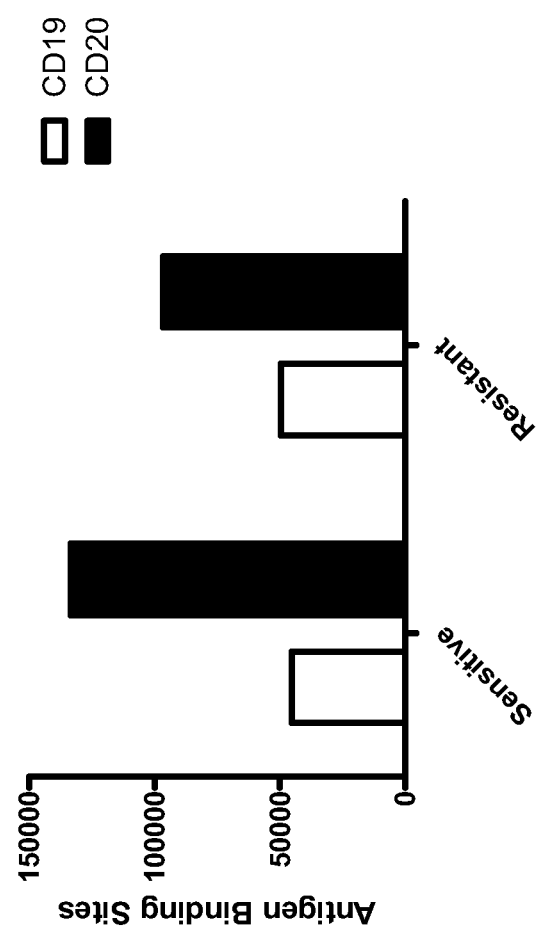

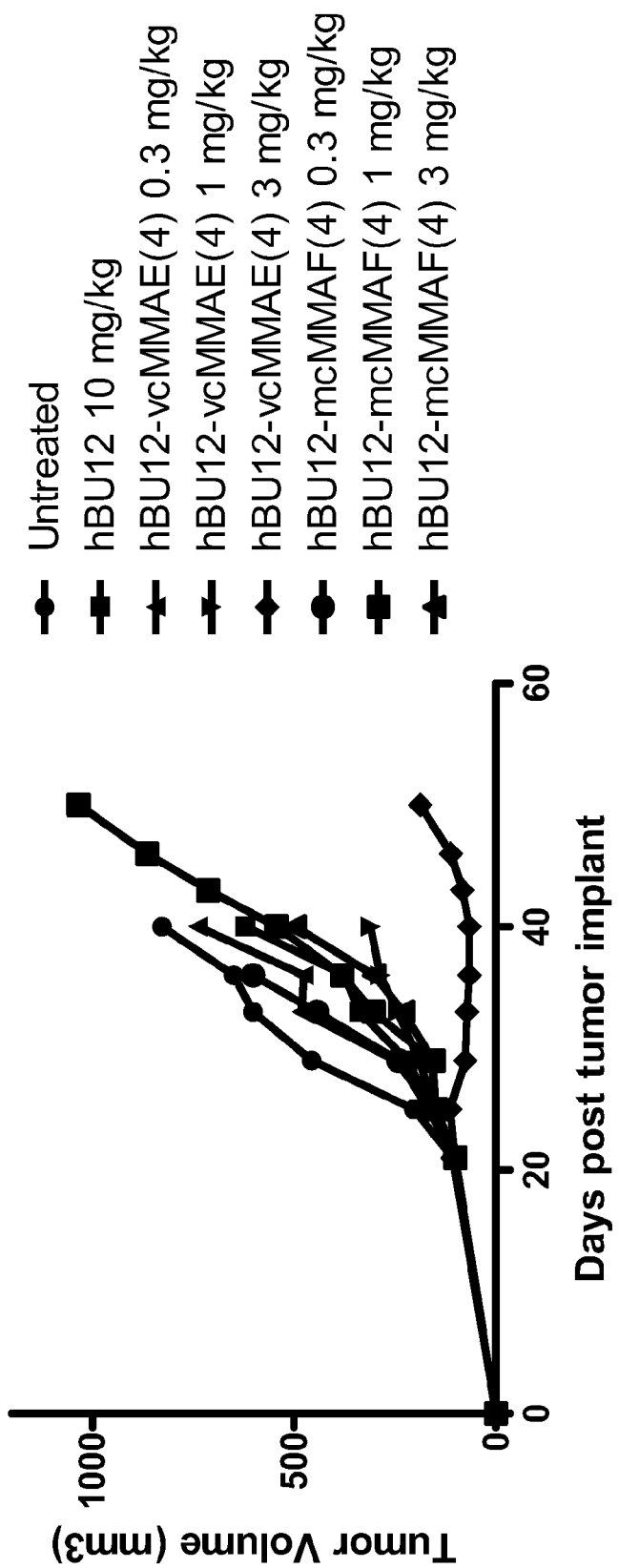

SEQUENCE LISTING

<160> NUMBER OF SEQ ID NOS: 61

<210> SEQ ID NO 1
<211> LENGTH: 19
<212> TYPE: PRT
<213> ORGANISM: Artificial

```
<220> FEATURE:
<223> OTHER INFORMATION: Synthetic hBU12 leader sequence - heavy chain
      region

<400> SEQUENCE: 1

Met Gly Arg Leu Thr Ser Ser Phe Leu Leu Leu Ile Val Pro Ala Tyr
1               5                   10                  15

Val Leu Ser

<210> SEQ ID NO 2
<211> LENGTH: 120
<212> TYPE: PRT
<213> ORGANISM: Artificial
<220> FEATURE:
<223> OTHER INFORMATION: Synthetic hBU12 Heavy Chain Variable Region
      (VH2-70/JH4 germline)- Variant HA

<400> SEQUENCE: 2

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Arg Tyr Asn Pro Ala
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
        115                 120

<210> SEQ ID NO 3
<211> LENGTH: 330
<212> TYPE: PRT
<213> ORGANISM: Artificial
<220> FEATURE:
<223> OTHER INFORMATION: Synthetic hBU12 Heavy Chain Constant domain
      (IgG1)

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 120
<212> TYPE: PRT
<213> ORGANISM: Artificial
<220> FEATURE:
<223> OTHER INFORMATION: Synthetic hBU12 Heavy Chain Variable Region
      (VH2-70/JH4 germline)- Variant  HB

<400> SEQUENCE: 4

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Ser Asn Gln Val
65                  70                  75                  80

Val Leu Thr Met Thr Asn Met Asp Pro Val Asp Thr Ala Thr Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
        115                 120

```
<210> SEQ ID NO 5
<211> LENGTH: 120
<212> TYPE: PRT
<213> ORGANISM: Artificial
<220> FEATURE:
<223> OTHER INFORMATION: Synthetic hBU12 Heavy Chain Variable Region
      (VH2-70/JH4 germline)- Variant  HC

<400> SEQUENCE: 5

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Phe Leu Thr Met Thr Asn Met Asp Pro Val Asp Ala Thr Tyr Tyr
                85                  90                  95

Cys Ala Arg Met Glu Leu Trp Ser Tyr Tyr Phe Asp Tyr Trp Gly Gln
                100                 105                 110

Gly Thr Leu Val Thr Val Ser Ser
        115                 120

<210> SEQ ID NO 6
<211> LENGTH: 120
<212> TYPE: PRT
<213> ORGANISM: Artificial
<220> FEATURE:
<223> OTHER INFORMATION: Synthetic hBU12 Heavy Chain Variable Region
      (VH2-70/JH4 germline)- Variant  HD

<400> SEQUENCE: 6

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Lys Ile Ala Ser Val Asp Pro Val Asp Ala Thr Tyr Tyr
                85                  90                  95

Cys Ala Arg Met Glu Leu Trp Ser Tyr Tyr Phe Asp Tyr Trp Gly Gln
                100                 105                 110

Gly Thr Leu Val Thr Val Ser Ser
        115                 120

<210> SEQ ID NO 7
<211> LENGTH: 120
<212> TYPE: PRT
<213> ORGANISM: Artificial
<220> FEATURE:
<223> OTHER INFORMATION: Synthetic hBU12 Heavy Chain Variable Region
      (VH2-70/JH4 germline)- Variant  HE
```

```
<400> SEQUENCE: 7

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Ala Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
        115                 120

<210> SEQ ID NO 8
<211> LENGTH: 120
<212> TYPE: PRT
<213> ORGANISM: Artificial
<220> FEATURE:
<223> OTHER INFORMATION: Synthetic hBU12 Heavy Chain Variable Region
      (Murine)

<400> SEQUENCE: 8

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Arg Tyr Asn Pro Ala
    50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Ala Tyr Tyr
                85                  90                  95

Cys Ala Arg Met Glu Leu Trp Ser Tyr Tyr Phe Asp Tyr Trp Gly Gln
            100                 105                 110

Gly Thr Thr Leu Thr Val Ser Ser
        115                 120

<210> SEQ ID NO 9
<211> LENGTH: 120
<212> TYPE: PRT
<213> ORGANISM: Artificial
<220> FEATURE:
<223> OTHER INFORMATION: Synthetic hBU12 Heavy Chain Variable Region
      (VH4-31/JH4 germline)- Variant  HF

<400> SEQUENCE: 9

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30
```

Gly Met Gly Val Gly Trp Ile Arg Gln His Pro Gly Lys Gly Leu Glu
            35                  40                  45

Trp Ile Gly His Ile Trp Trp Asp Asp Lys Arg Tyr Asn Pro Ala
 50                  55                  60

Leu Lys Ser Arg Val Thr Ile Ser Val Asp Thr Ser Lys Asn Gln Phe
65                   70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
                100                 105                 110

Gly Thr Leu Val Thr Val Ser Ser
        115                 120

<210> SEQ ID NO 10
<211> LENGTH: 120
<212> TYPE: PRT
<213> ORGANISM: Artificial
<220> FEATURE:
<223> OTHER INFORMATION: Synthetic hBU12 Heavy Chain Variable Region
      (VH4-31/JH4 germline)- Variant  HG

<400> SEQUENCE: 10

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
                20                  25                  30

Gly Met Gly Val Gly Trp Ile Arg Gln His Pro Gly Lys Gly Leu Glu
            35                  40                  45

Trp Ile Gly His Ile Trp Trp Asp Asp Lys Arg Tyr Asn Pro Ala
 50                  55                  60

Leu Lys Ser Arg Val Thr Ile Ser Lys Asp Thr Ser Lys Asn Gln Phe
65                   70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
                100                 105                 110

Gly Thr Leu Val Thr Val Ser Ser
        115                 120

<210> SEQ ID NO 11
<211> LENGTH: 120
<212> TYPE: PRT
<213> ORGANISM: Artificial
<220> FEATURE:
<223> OTHER INFORMATION: Synthetic hBU12 Heavy Chain Variable Region
      (VH4-31/JH4 germline)- Variant  HH

<400> SEQUENCE: 11

Gln Val Gln Leu Gln Glu Ser Gly Pro Gly Leu Val Lys Pro Ser Gln
1               5                   10                  15

Thr Leu Ser Leu Thr Cys Thr Phe Ser Gly Phe Ser Leu Ser Thr Ser
                20                  25                  30

Gly Met Gly Val Gly Trp Ile Arg Gln His Pro Gly Lys Gly Leu Glu
            35                  40                  45

Trp Ile Gly His Ile Trp Trp Asp Asp Lys Arg Tyr Asn Pro Ala
 50                  55                  60

Leu Lys Ser Arg Val Thr Ile Ser Val Asp Thr Ser Lys Asn Gln Phe
65                   70                  75                  80

```
Ser Leu Lys Leu Ser Ser Val Thr Ala Ala Asp Thr Ala Val Tyr Tyr
            85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
            115             120

<210> SEQ ID NO 12
<211> LENGTH: 120
<212> TYPE: PRT
<213> ORGANISM: Artificial
<220> FEATURE:
<223> OTHER INFORMATION: Synthetic hBU12 Heavy Chain Variable Region
      (VH4-31/JH4 germline)- Variant  HI

<400> SEQUENCE: 12

Gln Val Gln Leu Gln Glu Ser Gly Pro Gly Leu Val Lys Pro Ser Gln
1               5                   10                  15

Thr Leu Ser Leu Thr Cys Thr Phe Ser Gly Phe Ser Leu Ser Thr Ser
            20                  25                  30

Gly Met Gly Val Gly Trp Ile Arg Gln His Pro Gly Lys Gly Leu Glu
            35                  40                  45

Trp Ile Gly His Ile Trp Trp Asp Asp Asp Lys Arg Tyr Asn Pro Ala
    50                  55                  60

Leu Lys Ser Arg Val Thr Ile Ser Lys Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
            115             120

<210> SEQ ID NO 13
<211> LENGTH: 120
<212> TYPE: PRT
<213> ORGANISM: Artificial
<220> FEATURE:
<223> OTHER INFORMATION: Synthetic hBU12 Heavy Chain Variable Region
      (VH4-31/JH4 germline)- Variant  HJ

<400> SEQUENCE: 13

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
            35                  40                  45

Trp Ile Gly His Ile Trp Trp Asp Asp Asp Lys Arg Tyr Asn Pro Ala
    50                  55                  60

Leu Lys Ser Arg Val Thr Ile Ser Val Asp Thr Ser Ser Asn Gln Phe
65                  70                  75                  80

Ser Leu Lys Leu Ser Ser Val Thr Ala Ala Asp Thr Ala Val Tyr Tyr
            85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
            115             120
```

<210> SEQ ID NO 14
<211> LENGTH: 120
<212> TYPE: PRT
<213> ORGANISM: Artificial
<220> FEATURE:
<223> OTHER INFORMATION: Synthetic hBU12 Heavy Chain Variable Region
      (VH4-31/JH4 germline)- Variant  HK

<400> SEQUENCE: 14

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Val
65                  70                  75                  80

Phe Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
        115                 120

<210> SEQ ID NO 15
<211> LENGTH: 120
<212> TYPE: PRT
<213> ORGANISM: Artificial
<220> FEATURE:
<223> OTHER INFORMATION: Synthetic hBU12 Heavy Chain Variable Region
      (VH4-31/JH4 germline)- Variant  HL

<400> SEQUENCE: 15

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Ala Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
        115                 120

<210> SEQ ID NO 16
<211> LENGTH: 22
<212> TYPE: PRT
<213> ORGANISM: Artificial
<220> FEATURE:
<223> OTHER INFORMATION: Synthetic hBU12 Light Chain Region -
      Leader Sequence -continued

<400> SEQUENCE: 16

Met Asp Phe Gln Val Gln Ile Phe Ser Phe Leu Leu Ile Ser Ala Ser
1               5                   10                  15

Val Ile Met Ser Arg Gly
            20

<210> SEQ ID NO 17
<211> LENGTH: 107
<212> TYPE: PRT
<213> ORGANISM: Artificial
<220> FEATURE:
<223> OTHER INFORMATION: Synthetic hBU12 Light Chain Variable Region
      (VL-L6/Jk2 germline)- Variant LA

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95

Phe Gly Gln Gly Thr Lys Leu Glu Ile Lys Arg
            100                 105

<210> SEQ ID NO 18
<211> LENGTH: 106
<212> TYPE: PRT
<213> ORGANISM: Artificial
<220> FEATURE:
<223> OTHER INFORMATION: Synthetic hBU12 Light Chain Constant domain
      (Kappa domain)

<400> SEQUENCE: 18

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 19
<211> LENGTH: 107
<212> TYPE: PRT
<213> ORGANISM: Artificial

```
<220> FEATURE:
<223> OTHER INFORMATION: Synthetic hBU12 Light Chain Variable Region
      (VL-L6/Jk2 germline)- Variant LB

<400> SEQUENCE: 19

Glu Asn Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95

Phe Gly Gln Gly Thr Lys Leu Glu Ile Lys Arg
            100                 105

<210> SEQ ID NO 20
<211> LENGTH: 107
<212> TYPE: PRT
<213> ORGANISM: Artificial
<220> FEATURE:
<223> OTHER INFORMATION: Synthetic hBU12 Light Chain Variable Region
      (VL-L6/Jk2 germline)- Variant LC

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp His Thr Leu Thr Ile Ser Ser Leu Glu Pro Glu
65                  70                  75                  80

Asp Phe Ala Val Tyr Tyr Cys Phe Gln Gly Ser Val Tyr Pro Phe Thr
                85                  90                  95

Phe Gly Gln Gly Thr Lys Leu Glu Ile Lys Arg
            100                 105

<210> SEQ ID NO 21
<211> LENGTH: 107
<212> TYPE: PRT
<213> ORGANISM: Artificial
<220> FEATURE:
<223> OTHER INFORMATION: Synthetic hBU12 Light Chain Variable Region
      (VL-L6/Jk2 germline)- Variant LD

<400> SEQUENCE: 21

Glu Asn Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45
```

```
Asp Thr Ser Lys Leu Ala Ser Gly Ile Pro Ala Arg Phe Ser Gly Ser
        50                  55                  60

Gly Ser Gly Thr Asp His Thr Leu Thr Ile Ser Ser Leu Glu Pro Glu
 65                  70                  75                  80

Asp Phe Ala Val Tyr Tyr Cys Phe Gln Gly Ser Val Tyr Pro Phe Thr
                 85                  90                  95

Phe Gly Gln Gly Thr Lys Leu Glu Ile Lys Arg
            100                 105

<210> SEQ ID NO 22
<211> LENGTH: 107
<212> TYPE: PRT
<213> ORGANISM: Artificial
<220> FEATURE:
<223> OTHER INFORMATION: Synthetic hBU12 Light Chain Variable Region
      (VL-L6/Jk2 germline)- Variant LE

<400> SEQUENCE: 22

Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Val Ser Tyr Met
            20                  25                  30

His Trp Tyr Gln Gln Lys Ser Thr Ala Pro Arg Leu Leu Ile Tyr
        35                  40                  45

Asp Thr Ser Lys Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Phe Gln Gly Ser Val Tyr Pro Phe Thr
                 85                  90                  95

Phe Gly Gln Gly Thr Lys Leu Glu Ile Lys Arg
            100                 105

<210> SEQ ID NO 23
<211> LENGTH: 107
<212> TYPE: PRT
<213> ORGANISM: Artificial
<220> FEATURE:
<223> OTHER INFORMATION: Synthetic hBU12 Light Chain Variable Region
      (VL-L6/Jk2 germline)- Variant LF

<400> SEQUENCE: 23

Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
        50                  55                  60

Gly Ser Gly Asn Ser His Phe Leu Thr Ile Ser Ser Leu Glu Pro Glu
 65                  70                  75                  80

Asp Phe Ala Val Tyr Tyr Cys Phe Gln Gly Ser Val Tyr Pro Phe Thr
                 85                  90                  95

Phe Gly Gln Gly Thr Lys Leu Glu Ile Lys Arg
            100                 105
```

```
<210> SEQ ID NO 24
<211> LENGTH: 107
<212> TYPE: PRT
<213> ORGANISM: Artificial
<220> FEATURE:
<223> OTHER INFORMATION: Synthetic hBU12 Light Chain Variable Region
      (VL-L6/Jk2 germline)- Variant LG

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Val Ala Val Tyr Tyr Cys Phe Gln Gly Ser Val Tyr Pro Phe Thr
                85                  90                  95

Phe Gly Gln Gly Thr Lys Leu Glu Ile Lys Arg
            100                 105

<210> SEQ ID NO 25
<211> LENGTH: 107
<212> TYPE: PRT
<213> ORGANISM: Artificial
<220> FEATURE:
<223> OTHER INFORMATION: Synthetic hBU12 Light Chain Variable Region
      (Murine)

<400> SEQUENCE: 25

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser His Phe Leu Thr Ile Ser Ser Met Glu Ala Glu
65                  70                  75                  80

Asp Val Ala Thr Tyr Tyr Cys Phe Gln Gly Ser Val Tyr Pro Phe Thr
                85                  90                  95

Phe Gly Ser Gly Thr Lys Leu Glu Ile Lys Arg
            100                 105

<210> SEQ ID NO 26
<211> LENGTH: 107
<212> TYPE: PRT
<213> ORGANISM: Artificial
<220> FEATURE:
<223> OTHER INFORMATION: Synthetic hBU12 Light Chain Variable Region
      (VL-A10/Jk2 germline)- Variant LH

<400> SEQUENCE: 26

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Val Ser Tyr Met
            20                  25                  30
```

```
His Trp Tyr Gln Gln Lys Pro Asp Gln Ser Pro Lys Leu Leu Ile Lys
         35                  40                  45

Asp Thr Ser Lys Leu Ala Ser Gly Val Pro Ser Arg Phe Ser Gly Ser
 50                  55                  60

Gly Ser Gly Thr Asp Phe Thr Leu Thr Ile Asn Ser Leu Glu Ala Glu
 65                  70                  75                  80

Asp Ala Ala Thr Tyr Tyr Cys Phe Gln Gly Ser Val Tyr Pro Phe Thr
                 85                  90                  95

Phe Gly Gln Gly Thr Lys Leu Glu Ile Lys Arg
                100                 105

<210> SEQ ID NO 27
<211> LENGTH: 107
<212> TYPE: PRT
<213> ORGANISM: Artificial
<220> FEATURE:
<223> OTHER INFORMATION: Synthetic hBU12 Light Chain Variable Region
      (VL-A10/Jk2 germline)- Variant LI

<400> SEQUENCE: 27

Glu Asn Val Leu Thr Gln Ser Pro Asp Phe Gln Ser Val Thr Pro Lys
 1               5                  10                  15

Glu Lys Val Thr Ile Thr Cys Ser Ala Ser Ser Ser Val Ser Tyr Met
                 20                  25                  30

His Trp Tyr Gln Gln Lys Pro Asp Gln Ser Pro Lys Leu Leu Ile Lys
         35                  40                  45

Asp Thr Ser Lys Leu Ala Ser Gly Val Pro Ser Arg Phe Ser Gly Ser
 50                  55                  60

Gly Ser Gly Thr Asp His Thr Leu Thr Ile Asn Ser Leu Glu Ala Glu
 65                  70                  75                  80

Asp Ala Ala Thr Tyr Tyr Cys Phe Gln Gly Ser Val Tyr Pro Phe Thr
                 85                  90                  95

Phe Gly Gln Gly Thr Lys Leu Glu Ile Lys Arg
                100                 105

<210> SEQ ID NO 28
<211> LENGTH: 120
<212> TYPE: PRT
<213> ORGANISM: Artificial
<220> FEATURE:
<223> OTHER INFORMATION: Synthetic hBU12 Consensus sequence for Heavy
      Chain Variable Region (VH2-70/JH4 germline)
<220> FEATURE:
<221> NAME/KEY: MOD_RES
<222> LOCATION: (77)..(77)
<223> OTHER INFORMATION: Xaa is Ser or Lys
<220> FEATURE:
<221> NAME/KEY: MOD_RES
<222> LOCATION: (81)..(81)
<223> OTHER INFORMATION: Xaa is Phe or Val
<220> FEATURE:
<221> NAME/KEY: MOD_RES
<222> LOCATION: (83)..(83)
<223> OTHER INFORMATION: Xaa is Lys or Thr
<220> FEATURE:
<221> NAME/KEY: MOD_RES
<222> LOCATION: (84)..(84)
<223> OTHER INFORMATION: Xaa is Ile or Met
<220> FEATURE:
<221> NAME/KEY: MOD_RES
<222> LOCATION: (85)..(85)
<223> OTHER INFORMATION: Xaa is Ala or Thr
<220> FEATURE:
<221> NAME/KEY: MOD_RES
<222> LOCATION: (86)..(86)
<223> OTHER INFORMATION: Xaa is Ser or Asn
```

<220> FEATURE:
<221> NAME/KEY: MOD_RES
<222> LOCATION: (87)..(87)
<223> OTHER INFORMATION: Xaa is Val or Met
<220> FEATURE:
<221> NAME/KEY: MOD_RES
<222> LOCATION: (94)..(94)
<223> OTHER INFORMATION: Xaa is Ala or Thr

<400> SEQUENCE: 28

```
Gln Val Thr Leu Arg Glu Ser Gly Pro Ala Leu Val Lys Pro Thr Gln
1               5                   10                  15
Thr Leu Thr Leu Thr Cys Thr Phe Ser Gly Phe Ser Leu Ser Thr Ser
            20                  25                  30
Gly Met Gly Val Gly Trp Ile Arg Gln Pro Pro Gly Lys Ala Leu Glu
        35                  40                  45
Trp Leu Ala His Ile Trp Trp Asp Asp Lys Arg Tyr Asn Pro Ala
    50                  55                  60
Leu Lys Ser Arg Leu Thr Ile Ser Lys Asp Thr Ser Xaa Asn Gln Val
65                  70                  75                  80
Xaa Leu Xaa Xaa Xaa Xaa Xaa Asp Pro Val Asp Thr Ala Xaa Tyr Tyr
                85                  90                  95
Cys Ala Arg Met Glu Leu Trp Ser Tyr Tyr Phe Asp Tyr Trp Gly Gln
            100                 105                 110
Gly Thr Leu Val Thr Val Ser Ser
        115                 120
```

<210> SEQ ID NO 29
<211> LENGTH: 120
<212> TYPE: PRT
<213> ORGANISM: Artificial
<220> FEATURE:
<223> OTHER INFORMATION: Synthetic hBU12 Consensus sequence for Heavy
      Chain Variable Region (VH4-31/JH4 germline)
<220> FEATURE:
<221> NAME/KEY: MOD_RES
<222> LOCATION: (24)..(24)
<223> OTHER INFORMATION: Xaa is Phe or Val
<220> FEATURE:
<221> NAME/KEY: MOD_RES
<222> LOCATION: (27)..(27)
<223> OTHER INFORMATION: Xaa is Phe or Gly
<220> FEATURE:
<221> NAME/KEY: MOD_RES
<222> LOCATION: (29)..(29)
<223> OTHER INFORMATION: Xaa is Leu or Ile
<220> FEATURE:
<221> NAME/KEY: MOD_RES
<222> LOCATION: (73)..(73)
<223> OTHER INFORMATION: Xaa is Lys or Val
<220> FEATURE:
<221> NAME/KEY: MOD_RES
<222> LOCATION: (77)..(77)
<223> OTHER INFORMATION: Xaa is Ser or Lys
<220> FEATURE:
<221> NAME/KEY: MOD_RES
<222> LOCATION: (80)..(80)
<223> OTHER INFORMATION: Xaa is Val or Phe
<220> FEATURE:
<221> NAME/KEY: MOD_RES
<222> LOCATION: (81)..(81)
<223> OTHER INFORMATION: Xaa is Phe or Ser
<220> FEATURE:
<221> NAME/KEY: MOD_RES
<222> LOCATION: (94)..(94)
<223> OTHER INFORMATION: Xaa is Ala or Val -continued

<400> SEQUENCE: 29

```
Gln Val Gln Leu Gln Glu Ser Gly Pro Gly Leu Val Lys Pro Ser Gln
1               5                   10                  15

Thr Leu Ser Leu Thr Cys Thr Xaa Ser Gly Xaa Ser Xaa Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Xaa Asp Thr Ser Xaa Asn Gln Xaa
65                  70                  75                  80

Xaa Leu Lys Leu Ser Ser Val Thr Ala Ala Asp Thr Ala Xaa Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
        115                 120
```

<210> SEQ ID NO 30
<211> LENGTH: 107
<212> TYPE: PRT
<213> ORGANISM: Artificial
<220> FEATURE:
<223> OTHER INFORMATION: Synthetic hBU12 Consensus sequence for Light
      Chain Variable Region (VL-L6/Jk2 germline)
<220> FEATURE:
<221> NAME/KEY: MOD_RES
<222> LOCATION: (2)..(2)
<223> OTHER INFORMATION: Xaa is Asn or Ile
<220> FEATURE:
<221> NAME/KEY: MOD_RES
<222> LOCATION: (39)..(39)
<223> OTHER INFORMATION: Xaa is Ser or Pro
<220> FEATURE:
<221> NAME/KEY: MOD_RES
<222> LOCATION: (40)..(40)
<223> OTHER INFORMATION: Xaa is Ser or Gly
<220> FEATURE:
<221> NAME/KEY: MOD_RES
<222> LOCATION: (41)..(41)
<223> OTHER INFORMATION: Xaa is Thr or Gln
<220> FEATURE:
<221> NAME/KEY: MOD_RES
<222> LOCATION: (68)..(68)
<223> OTHER INFORMATION: Xaa is Asn or Thr
<220> FEATURE:
<221> NAME/KEY: MOD_RES
<222> LOCATION: (69)..(69)
<223> OTHER INFORMATION: Xaa is Ser or Asp
<220> FEATURE:
<221> NAME/KEY: MOD_RES
<222> LOCATION: (70)..(70)
<223> OTHER INFORMATION: Xaa is His or Phe
<220> FEATURE:
<221> NAME/KEY: MOD_RES
<222> LOCATION: (71)..(71)
<223> OTHER INFORMATION: Xaa is Phe or Thr
<220> FEATURE:
<221> NAME/KEY: MOD_RES
<222> LOCATION: (82)..(82)
<223> OTHER INFORMATION: Xaa is Val or Phe

<400> SEQUENCE: 30

```
Glu Xaa Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30
```

His Trp Tyr Gln Gln Lys Xaa Xaa Xaa Ala Pro Arg Leu Leu Ile Tyr
            35                  40                  45

Asp Thr Ser Lys Leu Ala Ser Gly Ile Pro Ala Arg Phe Ser Gly Ser
 50                  55                  60

Gly Ser Gly Xaa Xaa Xaa Xaa Leu Thr Ile Ser Ser Leu Glu Pro Glu
 65                  70                  75                  80

Asp Xaa Ala Val Tyr Tyr Cys Phe Gln Gly Ser Val Tyr Pro Phe Thr
                 85                  90                  95

Phe Gly Gln Gly Thr Lys Leu Glu Ile Lys Arg
            100                 105

<210> SEQ ID NO 31
<211> LENGTH: 107
<212> TYPE: PRT
<213> ORGANISM: Artificial
<220> FEATURE:
<223> OTHER INFORMATION: Synthetic hBU12 Consensus sequence for Light
      Chain Variable Region (VL-A10/Jk2 germline)
<220> FEATURE:
<221> NAME/KEY: MOD_RES
<222> LOCATION: (2)..(2)
<223> OTHER INFORMATION: Xaa is Asn or Ile
<220> FEATURE:
<221> NAME/KEY: MOD_RES
<222> LOCATION: (70)..(70)
<223> OTHER INFORMATION: Xaa is His or Phe

<400> SEQUENCE: 31

Glu Xaa Val Leu Thr Gln Ser Pro Asp Phe Gln Ser Val Thr Pro Lys
 1               5                  10                  15

Glu Lys Val Thr Ile Thr Cys Ser Ala Ser Ser Ser Val Ser Tyr Met
            20                  25                  30

His Trp Tyr Gln Gln Lys Pro Asp Gln Ser Pro Lys Leu Leu Ile Lys
            35                  40                  45

Asp Thr Ser Lys Leu Ala Ser Gly Val Pro Ser Arg Phe Ser Gly Ser
 50                  55                  60

Gly Ser Gly Thr Asp Xaa Thr Leu Thr Ile Asn Ser Leu Glu Ala Glu
 65                  70                  75                  80

Asp Ala Ala Thr Tyr Tyr Cys Phe Gln Gly Ser Val Tyr Pro Phe Thr
                 85                  90                  95

Phe Gly Gln Gly Thr Lys Leu Glu Ile Lys Arg
            100                 105

<210> SEQ ID NO 32
<211> LENGTH: 120
<212> TYPE: PRT
<213> ORGANISM: Artificial
<220> FEATURE:
<223> OTHER INFORMATION: Synthetic hBU12 Consensus sequence for Heavy
      Chain Variable Region (VH2-70/JH1-6 germline)
<220> FEATURE:
<221> NAME/KEY: MOD_RES
<222> LOCATION: (77)..(77)
<223> OTHER INFORMATION: Xaa is Ser or Lys
<220> FEATURE:
<221> NAME/KEY: MOD_RES
<222> LOCATION: (81)..(81)
<223> OTHER INFORMATION: Xaa is Phe or Val
<220> FEATURE:
<221> NAME/KEY: MOD_RES
<222> LOCATION: (83)..(83)
<223> OTHER INFORMATION: Xaa is Lys or Thr
<220> FEATURE:
<221> NAME/KEY: MOD_RES
<222> LOCATION: (84)..(84)
<223> OTHER INFORMATION: Xaa is Ile or Met

```
<220> FEATURE:
<221> NAME/KEY: MOD_RES
<222> LOCATION: (85)..(85)
<223> OTHER INFORMATION: Xaa is Ala or Thr
<220> FEATURE:
<221> NAME/KEY: MOD_RES
<222> LOCATION: (86)..(86)
<223> OTHER INFORMATION: Xaa is Ser or Asn
<220> FEATURE:
<221> NAME/KEY: MOD_RES
<222> LOCATION: (87)..(87)
<223> OTHER INFORMATION: Xaa is Val or Met
<220> FEATURE:
<221> NAME/KEY: MOD_RES
<222> LOCATION: (94)..(94)
<223> OTHER INFORMATION: Xaa is Ala or Thr
<220> FEATURE:
<221> NAME/KEY: MOD_RES
<222> LOCATION: (112)..(112)
<223> OTHER INFORMATION: Xaa is Gln or Arg
<220> FEATURE:
<221> NAME/KEY: MOD_RES
<222> LOCATION: (115)..(115)
<223> OTHER INFORMATION: Xaa is  Leu, Thr, or Met

<400> SEQUENCE: 32

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Arg Tyr Asn Pro Ala
50                  55                  60

Leu Lys Ser Arg Leu Thr Ile Ser Lys Asp Thr Ser Xaa Asn Gln Val
65                  70                  75                  80

Xaa Leu Xaa Xaa Xaa Xaa Xaa Asp Pro Val Asp Thr Ala Xaa Tyr Tyr
                85                  90                  95

Cys Ala Arg Met Glu Leu Trp Ser Tyr Tyr Phe Asp Tyr Trp Gly Xaa
            100                 105                 110

Gly Thr Xaa Val Thr Val Ser Ser
        115                 120

<210> SEQ ID NO 33
<211> LENGTH: 120
<212> TYPE: PRT
<213> ORGANISM: Artificial
<220> FEATURE:
<223> OTHER INFORMATION: Synthetic hBU12 Consensus sequence for Heavy
      Chain Variable Region (VH4-31/JH1-6 germline)
<220> FEATURE:
<221> NAME/KEY: MOD_RES
<222> LOCATION: (24)..(24)
<223> OTHER INFORMATION: Xaa is Phe or Val
<220> FEATURE:
<221> NAME/KEY: MOD_RES
<222> LOCATION: (27)..(27)
<223> OTHER INFORMATION: Xaa is Phe or Gly
<220> FEATURE:
<221> NAME/KEY: MOD_RES
<222> LOCATION: (29)..(29)
<223> OTHER INFORMATION: Xaa is Leu or Ile
<220> FEATURE:
<221> NAME/KEY: MOD_RES
<222> LOCATION: (73)..(73)
<223> OTHER INFORMATION: Xaa is Lys or Val
<220> FEATURE:
<221> NAME/KEY: MOD_RES
<222> LOCATION: (77)..(77)
<223> OTHER INFORMATION: Xaa is Ser or Lys
```

```
<220> FEATURE:
<221> NAME/KEY: MOD_RES
<222> LOCATION: (80)..(80)
<223> OTHER INFORMATION: Xaa is Val or Phe
<220> FEATURE:
<221> NAME/KEY: MOD_RES
<222> LOCATION: (81)..(81)
<223> OTHER INFORMATION: Xaa is Phe or Ser
<220> FEATURE:
<221> NAME/KEY: MOD_RES
<222> LOCATION: (94)..(94)
<223> OTHER INFORMATION: Xaa is Ala or Val
<220> FEATURE:
<221> NAME/KEY: MOD_RES
<222> LOCATION: (112)..(112)
<223> OTHER INFORMATION: Xaa is Gln or Arg
<220> FEATURE:
<221> NAME/KEY: MOD_RES
<222> LOCATION: (115)..(115)
<223> OTHER INFORMATION: Xaa is Leu, Thr, or Met

<400> SEQUENCE: 33

Gln Val Gln Leu Gln Glu Ser Gly Pro Gly Leu Val Lys Pro Ser Gln
1               5                   10                  15

Thr Leu Ser Leu Thr Cys Thr Xaa Ser Gly Xaa Ser Xaa Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Asp Lys Arg Tyr Asn Pro Ala
50                  55                  60

Leu Lys Ser Arg Val Thr Ile Ser Xaa Asp Thr Ser Xaa Asn Gln Xaa
65                  70                  75                  80

Xaa Leu Lys Leu Ser Ser Val Thr Ala Ala Asp Thr Ala Xaa Tyr Tyr
                85                  90                  95

Cys Ala Arg Met Glu Leu Trp Ser Tyr Tyr Phe Asp Tyr Trp Gly Xaa
            100                 105                 110

Gly Thr Xaa Val Thr Val Ser Ser
        115                 120

<210> SEQ ID NO 34
<211> LENGTH: 107
<212> TYPE: PRT
<213> ORGANISM: Artificial
<220> FEATURE:
<223> OTHER INFORMATION: Synthetic hBU12 Consensus sequence for Light
      Chain Variable Region (VL-L6/Jk1-5 germline)
<220> FEATURE:
<221> NAME/KEY: MOD_RES
<222> LOCATION: (2)..(2)
<223> OTHER INFORMATION: Xaa is Asn or Ile
<220> FEATURE:
<221> NAME/KEY: MOD_RES
<222> LOCATION: (39)..(39)
<223> OTHER INFORMATION: Xaa is Ser or Pro
<220> FEATURE:
<221> NAME/KEY: MOD_RES
<222> LOCATION: (40)..(40)
<223> OTHER INFORMATION: Xaa is Ser or Gly
<220> FEATURE:
<221> NAME/KEY: MOD_RES
<222> LOCATION: (41)..(41)
<223> OTHER INFORMATION: Xaa is Thr or Gln
<220> FEATURE:
<221> NAME/KEY: MOD_RES
<222> LOCATION: (68)..(68)
<223> OTHER INFORMATION: Xaa is Asn or Thr
<220> FEATURE:
<221> NAME/KEY: MOD_RES
<222> LOCATION: (69)..(69)
<223> OTHER INFORMATION: Xaa is Ser or Asp
```

```
<220> FEATURE:
<221> NAME/KEY: MOD_RES
<222> LOCATION: (70)..(70)
<223> OTHER INFORMATION: Xaa is His or Phe
<220> FEATURE:
<221> NAME/KEY: MOD_RES
<222> LOCATION: (71)..(71)
<223> OTHER INFORMATION: Xaa is Phe or Thr
<220> FEATURE:
<221> NAME/KEY: MOD_RES
<222> LOCATION: (82)..(82)
<223> OTHER INFORMATION: Xaa is Val or Phe
<220> FEATURE:
<221> NAME/KEY: MOD_RES
<222> LOCATION: (99)..(99)
<223> OTHER INFORMATION: Xaa is Gln, Pro or Gly
<220> FEATURE:
<221> NAME/KEY: MOD_RES
<222> LOCATION: (102)..(102)
<223> OTHER INFORMATION: Xaa is Lys or Arg
<220> FEATURE:
<221> NAME/KEY: MOD_RES
<222> LOCATION: (103)..(103)
<223> OTHER INFORMATION: Xaa is  Leu or Val
<220> FEATURE:
<221> NAME/KEY: MOD_RES
<222> LOCATION: (104)..(104)
<223> OTHER INFORMATION: Xaa is Glu or Asp

<400> SEQUENCE: 34

Glu Xaa Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Met
            20                  25                  30

His Trp Tyr Gln Gln Lys Xaa Xaa Xaa Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Xaa Xaa Xaa Leu Thr Ile Ser Ser Leu Glu Pro Glu
65                  70                  75                  80

Asp Xaa Ala Val Tyr Tyr Cys Phe Gln Gly Ser Val Tyr Pro Phe Thr
        85                  90                  95

Phe Gly Xaa Gly Thr Xaa Xaa Xaa Ile Lys Arg
            100                 105

<210> SEQ ID NO 35
<211> LENGTH: 107
<212> TYPE: PRT
<213> ORGANISM: Artificial
<220> FEATURE:
<223> OTHER INFORMATION: Synthetic hBU12 Consensus sequence for Light
      Chain Variable Region (VL-A10/Jk1-5 germline)
<220> FEATURE:
<221> NAME/KEY: MOD_RES
<222> LOCATION: (2)..(2)
<223> OTHER INFORMATION: Xaa is Asn or Ile
<220> FEATURE:
<221> NAME/KEY: MOD_RES
<222> LOCATION: (70)..(70)
<223> OTHER INFORMATION: Xaa is His or Phe
<220> FEATURE:
<221> NAME/KEY: MOD_RES
<222> LOCATION: (99)..(99)
<223> OTHER INFORMATION: Xaa is Gln, Pro or Gly
<220> FEATURE:
<221> NAME/KEY: MOD_RES
<222> LOCATION: (102)..(102)
<223> OTHER INFORMATION: Xaa is Lys or Arg
```

```
<220> FEATURE:
<221> NAME/KEY: MOD_RES
<222> LOCATION: (103)..(103)
<223> OTHER INFORMATION: Xaa is Leu or Val
<220> FEATURE:
<221> NAME/KEY: MOD_RES
<222> LOCATION: (104)..(104)
<223> OTHER INFORMATION: Xaa is Glu or Asp

<400> SEQUENCE: 35

Glu Xaa Val Leu Thr Gln Ser Pro Asp Phe Gln Ser Val Thr Pro Lys
1               5                   10                  15

Glu Lys Val Thr Ile Thr Cys Ser Ala Ser Ser Ser Val Ser Tyr Met
            20                  25                  30

His Trp Tyr Gln Gln Lys Pro Asp Gln Ser Pro Lys Leu Leu Ile Lys
        35                  40                  45

Asp Thr Ser Lys Leu Ala Ser Gly Val Pro Ser Arg Phe Ser Gly Ser
    50                  55                  60

Gly Ser Gly Thr Asp Xaa Thr Leu Thr Ile Asn Ser Leu Glu Ala Glu
65                  70                  75                  80

Asp Ala Ala Thr Tyr Tyr Cys Phe Gln Gly Ser Val Tyr Pro Phe Thr
                85                  90                  95

Phe Gly Xaa Gly Thr Xaa Xaa Xaa Ile Lys Arg
            100                 105

<210> SEQ ID NO 36
<211> LENGTH: 326
<212> TYPE: PRT
<213> ORGANISM: Artificial
<220> FEATURE:
<223> OTHER INFORMATION: Synthetic hBU12 Heavy Chain Constant Domain
      (IgG2)

<400> SEQUENCE: 36

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190
```

```
Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 37
<211> LENGTH: 290
<212> TYPE: PRT
<213> ORGANISM: Artificial
<220> FEATURE:
<223> OTHER INFORMATION: Synthetic hBU12 Heavy Chain Constant Domain
      (IgG3)

<400> SEQUENCE: 37

Gln Met Gln Gly Val Asn Cys Thr Val Ser Ser Glu Leu Lys Thr Pro
1               5                   10                  15

Leu Gly Asp Thr Thr His Thr Cys Pro Arg Cys Pro Glu Pro Lys Ser
            20                  25                  30

Cys Asp Thr Pro Pro Pro Cys Pro Arg Cys Pro Glu Pro Lys Ser Cys
        35                  40                  45

Asp Thr Pro Pro Pro Cys Pro Arg Cys Pro Glu Pro Lys Ser Cys Asp
    50                  55                  60

Thr Pro Pro Pro Cys Pro Arg Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Gln Phe Lys Trp Tyr Val Asp Gly Val Gln Val His
        115                 120                 125

Asn Ala Lys Thr Lys Pro Arg Glu Gln Gln Phe Asn Ser Thr Phe Arg
    130                 135                 140

Val Val Ser Val Leu Thr Val Leu His Gln Asn Trp Leu Asp Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Thr Lys Gly Gln Pro Arg Glu Pro Gln Val Tyr
            180                 185                 190

Thr Leu Pro Pro Ser Arg Glu Glu Met Thr Lys Asn Gln Val Ser Leu
        195                 200                 205

Thr Cys Leu Val Lys Gly Phe Tyr Pro Ser Asp Ile Ala Val Glu Trp
    210                 215                 220
```

```
Glu Ser Ser Gly Gln Pro Glu Asn Asn Tyr Asn Thr Thr Pro Pro Met
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Ile Phe Ser Cys Ser Val Met His
            260                 265                 270

Glu Ala Leu His Asn Arg Phe Thr Gln Lys Ser Leu Ser Leu Ser Pro
        275                 280                 285

Gly Lys
    290

<210> SEQ ID NO 38
<211> LENGTH: 327
<212> TYPE: PRT
<213> ORGANISM: Artificial
<220> FEATURE:
<223> OTHER INFORMATION: Synthetic hBU12 Heavy Chain Constant Domain
      (IgG4)

<400> SEQUENCE: 38

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 39
<211> LENGTH: 330
<212> TYPE: PRT
<213> ORGANISM: Artificial
<220> FEATURE:
<223> OTHER INFORMATION: Synthetic hBU12 Heavy Chain Constant Domain
      Variant (IgG1V1)

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 40
<211> LENGTH: 57
<212> TYPE: DNA
<213> ORGANISM: Artificial
<220> FEATURE:
<223> OTHER INFORMATION: Synthetic hBU12 Heavy Chain Region - Leader
      Sequence

<400> SEQUENCE: 40

```
atgggcaggc ttacttcttc attcttgttg ctgattgtcc ctgcatatgt cctgtcc         57
```

<210> SEQ ID NO 41
<211> LENGTH: 360
<212> TYPE: DNA
<213> ORGANISM: Artificial
<220> FEATURE:
<223> OTHER INFORMATION: Synthetic hBU12 Heavy Chain Variable Region
      (VH4-31/JH4 germline)- Variant HF

<400> SEQUENCE: 41

```
caggttcagc tgcaagagtc tggccctggg ttggttaagc cctcccagac cctcagtctg      60
acttgtactg tgtctggggg ttcaatcagc acttctggta tgggtgtagg ctggattagg     120
cagcacccag ggaagggtct ggagtggatt ggacacattt ggtgggatga tgacaagaga     180
tataacccag ccctgaagag cagagtgaca atctctgtgg atacctccaa gaaccagttt     240
agcctcaagc tgtccagtgt gacagctgca gatactgctg tctactactg tctagaatg      300
gaactttggt cctactattt tgactactgg ggccaaggca cccttgtcac agtctcctca     360
```

<210> SEQ ID NO 42
<211> LENGTH: 993
<212> TYPE: DNA
<213> ORGANISM: Artificial
<220> FEATURE:
<223> OTHER INFORMATION: Synthetic hBU12 Heavy Chain Constant domain
      (IgG1)

<400> SEQUENCE: 42

```
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
```

```
gccgtggagt gggagagcaa tgggcagccg agaacaact acaagaccac gcctcccgtg    840
ctggactccg acggctcctt cttcctctac agcaagctca ccgtggacaa gagcaggtgg    900 cagcaggga acgtcttctc atgctccgtg atgcatgagg ctctgcacaa ccactacacg    960
cagaagagcc tctccctgtc tccgggtaaa tga                                 993
```

```
<210> SEQ ID NO 43
<211> LENGTH: 66
<212> TYPE: DNA
<213> ORGANISM: Artificial
<220> FEATURE:
<223> OTHER INFORMATION: Synthetic hBU12 Light Chain Region - Leader
      Sequence

<400> SEQUENCE: 43
atggattttc aagtgcagat tttcagcttc ctgctaatca gtgcctcagt cataatgtcc    60
agagga                                                               66
```

```
<210> SEQ ID NO 44
<211> LENGTH: 321
<212> TYPE: DNA
<213> ORGANISM: Artificial
<220> FEATURE:
<223> OTHER INFORMATION: Synthetic hBU12 Light Chain Variable Region
      (VL-L6/Jk2 germline)- Variant LG

<400> SEQUENCE: 44
gaaattgttc tcacccagtc tccagcaacc ctgtctctct ctccagggga aagggctacc    60
ctgagctgca gtgccagctc aagtgtaagt tacatgcact ggtaccagca gaagccaggg   120
caggctccca gactcctgat ttatgacaca tccaaactgg cttctggtat tccagcaagg   180
ttcagtggca gtgggtctgg aacagatttt acactcacaa tcagcagcct ggagccagag   240
gatgttgctg tctattactg ttttcagggg agtgtatacc cattcacttt tggccaaggg   300
acaaagttgg aaatcaaaag a                                             321
```

```
<210> SEQ ID NO 45
<211> LENGTH: 321
<212> TYPE: DNA
<213> ORGANISM: Artificial
<220> FEATURE:
<223> OTHER INFORMATION: Synthetic hBU12 Light Chain Constant domain
      (Kappa domain)

<400> SEQUENCE: 45
actgtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321
```

```
<210> SEQ ID NO 46
<211> LENGTH: 7
<212> TYPE: PRT
<213> ORGANISM: Artificial
<220> FEATURE:
<223> OTHER INFORMATION: Synthetic hBU12 Heavy Chain CDR1
```

```
<400> SEQUENCE: 46

Thr Ser Gly Met Gly Val Gly
1               5

<210> SEQ ID NO 47
<211> LENGTH: 16
<212> TYPE: PRT
<213> ORGANISM: Artificial
<220> FEATURE:
<223> OTHER INFORMATION: Synthetic hBU12 Heavy Chain CDR2

<400> SEQUENCE: 47

His Ile Trp Trp Asp Asp Lys Arg Tyr Asn Pro Ala Leu Lys Ser
1               5                   10                  15

<210> SEQ ID NO 48
<211> LENGTH: 10
<212> TYPE: PRT
<213> ORGANISM: Artificial
<220> FEATURE:
<223> OTHER INFORMATION: Synthetic hBU12 Heavy Chain CDR3

<400> SEQUENCE: 48

Met Glu Leu Trp Ser Tyr Tyr Phe Asp Tyr
1               5                   10

<210> SEQ ID NO 49
<211> LENGTH: 10
<212> TYPE: PRT
<213> ORGANISM: Artificial
<220> FEATURE:
<223> OTHER INFORMATION: Synthetic hBU12 Light Chain CDR1

<400> SEQUENCE: 49

Ser Ala Ser Ser Ser Val Ser Tyr Met His
1               5                   10

<210> SEQ ID NO 50
<211> LENGTH: 7
<212> TYPE: PRT
<213> ORGANISM: Artificial
<220> FEATURE:
<223> OTHER INFORMATION: Synthetic hBU12 Light Chain CDR2

<400> SEQUENCE: 50

Asp Thr Ser Lys Leu Ala Ser
1               5

<210> SEQ ID NO 51
<211> LENGTH: 9
<212> TYPE: PRT
<213> ORGANISM: Artificial
<220> FEATURE:
<223> OTHER INFORMATION: Synthetic hBU12 Light Chain CDR3

<400> SEQUENCE: 51

Phe Gln Gly Ser Val Tyr Pro Phe Thr
1               5

<210> SEQ ID NO 52
<211> LENGTH: 4
<212> TYPE: PRT
<213> ORGANISM: Artificial
<220> FEATURE:
<223> OTHER INFORMATION: Synthetic linker
```

<400> SEQUENCE: 52

Gly Phe Leu Gly
1

<210> SEQ ID NO 53
<211> LENGTH: 1410
<212> TYPE: DNA
<213> ORGANISM: Artificial
<220> FEATURE:
<223> OTHER INFORMATION: Synthetic alternative sequence for hBU12 Heavy
      Chain

<400> SEQUENCE: 53

```
atgggatgga gctggatctt tcttttcctc ctgtcaggaa ctgcaggtgt ccattgtcag      60
gttcagctgc aagagtctgg ccctggggttg gttaagccct cccagaccct cagtctgact     120
tgtactgtgt ctgggggttc aatcagcact tctggtatgg gtgtaggctg gattaggcag     180
cacccaggga agggtctgga gtggattgga cacatttggt gggatgatga caagagatat     240
aacccagccc tgaagagcag agtgacaatc tctgtggata cctccaagaa ccagtttagc     300
ctcaagctgt ccagtgtgac agctgcagat actgctgtct actactgtgc tagaatggaa     360 cttttggtcct actattttga ctactgggggc caaggcaccc ttgtcacagt ctcctcagct     420
agcaccaagg gcccatctgt cttccccctg gcaccctcct ccaagagcac ctctgggggc     480
acagctgccc tgggctgcct ggtcaaggac tacttccctg aacctgtgac agtgtcctgg     540
aactcaggcg ccctgaccag cggcgtgcac accttccggg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggatgagctg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacacag    1380
aagagcctct ccctgtctcc gggtaaatga                                     1410
```

<210> SEQ ID NO 54
<211> LENGTH: 57
<212> TYPE: DNA
<213> ORGANISM: Artificial
<220> FEATURE:
<223> OTHER INFORMATION: Synthetic alternative leader sequence for hBU12
      Heavy Chain

<400> SEQUENCE: 54

```
atgggatgga gctggatctt tcttttcctc ctgtcaggaa ctgcaggtgt ccattgt           57
```

```
<210> SEQ ID NO 55
<211> LENGTH: 993
<212> TYPE: DNA
<213> ORGANISM: Artificial
<220> FEATURE:
<223> OTHER INFORMATION: Synthetic alternative sequence for hBU12 Heavy
      Chain - Constant domain

<400> SEQUENCE: 55
gctagcacca agggcccatc tgtcttcccc ctggcaccct cctccaagag cacctctggg    60
ggcacagctg ccctgggctg cctggtcaag gactacttcc ctgaacctgt gacagtgtcc   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgcccag cacctgaact cctggggggga   360 ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacaca   960
cagaagagcc tctccctgtc tccgggtaaa tga                                993

<210> SEQ ID NO 56
<211> LENGTH: 469
<212> TYPE: PRT
<213> ORGANISM: Artificial
<220> FEATURE:
<223> OTHER INFORMATION: Synthetic alternative sequence for hBU12 Heavy
      Chain

<400> SEQUENCE: 56

Met Gly Trp Ser Trp Ile Phe Leu Phe Leu Leu Ser Gly Thr Ala Gly
1               5                   10                  15

Val His Cys Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Ser Thr Ser Gly Met Gly Val Gly Trp Ile Arg Gln His Pro Gly Lys
    50                  55                  60

Gly Leu Glu Trp Ile Gly His Ile Trp Trp Asp Asp Asp Lys Arg Tyr
65                  70                  75                  80

Asn Pro Ala Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Met Glu Leu Trp Ser Tyr Tyr Phe Asp Tyr
        115                 120                 125
```

```
Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 57
<211> LENGTH: 19
<212> TYPE: PRT
<213> ORGANISM: Artificial
<220> FEATURE:
<223> OTHER INFORMATION: Synthetic alternative leader sequence for hBU12
      Heavy Chain
```

-continued

<400> SEQUENCE: 57

Met Gly Trp Ser Trp Ile Phe Leu Phe Leu Leu Ser Gly Thr Ala Gly
1               5                   10                  15

Val His Cys

<210> SEQ ID NO 58
<211> LENGTH: 699
<212> TYPE: DNA
<213> ORGANISM: Artificial
<220> FEATURE:
<223> OTHER INFORMATION: Synthetic alternative sequence for hBU12 Light
      Chain

<400> SEQUENCE: 58
atgaagttgc ctgttaggct gttggtgctg atgttctgga ttcctgcttc cagcagtgaa    60
attgttctca cccagtctcc agcaaccctg tctctctctc aggggaaaag ggctaccctg   120
agctgcagtg ccagctcaag tgtaagttac atgcactggt accagcagaa gccagggcag   180
gctcccagac tcctgattta tgacacatcc aaactggctt ctggtattcc agcaaggttc   240
agtggcagtg ggtctggaac agattttaca ctcacaatca gcagcctgga gccagaggat   300
gttgctgtct attactgttt tcaggggagt gtatacccat tcacttttgg ccaagggaca   360
aagttggaaa tcaaaagaac tgtggctgca ccatctgtct tcatcttccc gccatctgat   420
gagcagttga aatctggaac tgcctctgtt gtgtgcctgc tgaataactt ctatcccaga   480
gaggccaaag tacagtggaa ggtggataac gccctccaat cgggtaactc ccaggagagt   540
gtcacagagc aggacagcaa ggacagcacc tacagcctca gcagcaccct gacgctgagc   600
aaagcagact acgagaaaca caaagtctac gcctgcgaag tcacccatca gggcctgagc   660
tcgcccgtca caaagagctt caacagggga gagtgttag                           699

<210> SEQ ID NO 59
<211> LENGTH: 57
<212> TYPE: DNA
<213> ORGANISM: Artificial
<220> FEATURE:
<223> OTHER INFORMATION: Synthetic alternative leader sequence for hBU12
      Light Chain

<400> SEQUENCE: 59
atgaagttgc ctgttaggct gttggtgctg atgttctgga ttcctgcttc cagcagt        57

<210> SEQ ID NO 60
<211> LENGTH: 232
<212> TYPE: PRT
<213> ORGANISM: Artificial
<220> FEATURE:
<223> OTHER INFORMATION: Synthetic alternative sequence for hBU12 Light
      Chain

<400> SEQUENCE: 60

Met Lys Leu Pro Val Arg Leu Leu Val Leu Met Phe Trp Ile Pro Ala
1               5                   10                  15

Ser Ser Ser Glu Ile Val Leu Thr Gln Ser Pro Ala Thr Leu Ser Leu
            20                  25                  30

Ser Pro Gly Glu Arg Ala Thr Leu Ser Cys Ser Ala Ser Ser Ser Val
        35                  40                  45

Ser Tyr Met His Trp Tyr Gln Gln Lys Pro Gly Gln Ala Pro Arg Leu
    50                  55                  60

```
Leu Ile Tyr Asp Thr Ser Lys Leu Ala Ser Gly Ile Pro Ala Arg Phe
 65              70                  75                  80

Ser Gly Ser Gly Ser Gly Thr Asp Phe Thr Leu Thr Ile Ser Ser Leu
             85                  90                  95

Glu Pro Glu Asp Val Ala Val Tyr Tyr Cys Phe Gln Gly Ser Val Tyr
            100                 105                 110

Pro Phe Thr Phe Gly Gln Gly Thr Lys Leu Glu Ile Lys Arg Thr Val
        115                 120                 125

Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
                180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 61
<211> LENGTH: 19
<212> TYPE: PRT
<213> ORGANISM: Artificial
<220> FEATURE:
<223> OTHER INFORMATION: Synthetic alternative leader sequence for
      hBU12 Light Chain

<400> SEQUENCE: 61

Met Lys Leu Pro Val Arg Leu Leu Val Leu Met Phe Trp Ile Pro Ala
1               5                   10                  15

Ser Ser Ser
```

CD19 BINDING AGENTS AND USES THEREOF

This application is a divisional of Ser. No. 13/109,957 filed May 17, 2001, which is a divisional of Ser. No. 12/253,895 filed Oct. 17, 2008, now U.S. Pat. No. 7,968,697, which claims the benefit of U.S. Provisional App. No. 60/981,206 filed Oct. 19, 2007; U.S. Provisional App. No. 60/019,214 filed Jan. 4, 2008; and U.S. Provisional App. No. 61/080,169 filed Jul. 11, 2008, each of which is incorporated by reference in its entirety for all purposes.

REFERENCE TO A SEQUENCE LISTING

This application includes a sequence listing submitted herewith as a text file named "Seqlist018891004030PC.txt" created on Oct. 15, 2008, and containing 73,602 bytes. The material contained in this text file is incorporated by reference in its entirety for all purposes.

FIELD

This invention, relates to CD19 binding agents and methods of using such CD19 binding agents for treating disease.

BACKGROUND

In humans, B cells can produce an enormous number of antibody molecules. Such antibody production typically ceases (or substantially decreases) when a foreign antigen has been neutralized. Occasionally, however, proliferation of a particular B cell will continue unabated and can result in a cancer known as a B cell lymphoma. B-cell lymphomas, such as the B-cell subtype of non-Hodgkin lymphoma, are significant contributors to cancer mortality. The response of B-cell malignancies to various forms of treatment is mixed. Despite the medical importance, research in B-cell mediated diseases such as non-Hodgkin lymphoma has produced only a small number of clinically usable data and conventional approaches to treat such diseases remain tedious and unpleasant and/or have a high risk of relapse. For example, although high dose chemotherapy as a primary treatment for high grade non-Hodgkin lymphoma can improve overall survival, about 50% of the patients still die of this disease. Devesa et al., *J. Nat'l Cancer Inst.* 79: 701 (1987). Moreover, low-grade non-Hodgkin lymphoma-like chronic lymphocytic leukemia and mantle cell lymphoma are still incurable. This has stimulated the search for alternative strategies like immunotherapy. Antibodies directed against cell surface molecules defined by CD antigens represent a unique opportunity for the development of therapeutic reagents.

The majority of chronic lymphocytic leukemias are of the B-cell lineage. Freedman, *Hematol. Oncol. Clin. North Am.* 4: 405, 1990. This type of B-cell malignancy is the most common leukemia in the Western world. Goodman et al., *Leukemia and Lymphoma* 22: 1, 1996. The natural history of chronic lymphocytic leukemia falls into several phases. In the early phase, chronic lymphocytic leukemia is an indolent disease, characterized by the accumulation of small mature functionally-incompetent malignant B-cells having a lengthened life span. Eventually, the doubling time of the malignant B-cells decreases and patients become increasingly symptomatic. While treatment can provide symptomatic relief, the overall survival of the patients is only minimally affected. The late stages of chronic lymphocytic leukemia are characterized by significant anemia and/or thrombocytopenia. At this point, the median survival is less than two years. Foon et al., *Annals Int. Medicine* 113: 525 (1990).

B cells express cell surface proteins which can be utilized as markers for differentiation and identification. CD19 is a pan-B cell membrane glycoprotein that is expressed from early stages of pre-B cell development through terminal differentiation, regulating B lymphocyte development and function. Expression of CD19 was identified on most cancers of lymphoid origin, on the vast majority of Non-Hodgkin lymphoma (NHL) and on leukemias, including Chronic Lymphocytic Leukemia (CLL), Acute Lymphoblastic Leukemia (ALL) and Waldenstrom's Macroglobulinemia (WM). Despite major improvements in the treatment of NHL and CLL patients, the majority will continue to relapse and salvage regimens with non-cross resistant compounds are required to improve patient survival. A need exists in the art for improved methods of treatment. The present invention addresses this and other needs.

SUMMARY

The invention provides, inter alia, CD19 binding agents and methods of using them. In some aspects, the binding agents comprise the amino acid sequence(s) of a humanized heavy chain variable region and/or a humanized light chain variable region and specifically bind to human CD19. In some embodiments, the CD19 binding agent is an antigen-binding antibody fragment that specifically binds to human CD19. The antibody fragment can be, for example, a Fab, Fab', F(ab')$_2$, Fv fragment, a diabody, a linear antibody, an scFv, or an scFv-Fc.

In some aspects, the CD19 binding agent has a cytotoxic, cytostatic and/or immunomodulatory effect on CD19-expressing cells. Such an effect can be mediated, for example, by the depletion or inhibition of the proliferation or differentiation of CD19-expressing cells. In some embodiments, the CD19 binding agent can mediate effector function. In some embodiments, the CD19 binding agent is conjugated to a therapeutic agent (e.g., a ligand-drug conjugate compound). In other embodiments, the CD19 binding agent is unconjugated, i.e., not conjugated to a therapeutic agent (for example, an anti-CD19 naked antibody).

The present invention provides, inter alia, ligand-drug conjugate compounds wherein the ligand unit is a CD19 binding agent of the present invention. The ligand-drug conjugates can be used, for example, to treat an immune disorder or cancer.

Cancers to be treated by the methods of the present invention include CD19-expressing cancers, including, for example, B-cell lineage malignancies such as, for example, B cell lymphomas or B cell leukemias, including, but not limited to, non-Hodgkin lymphoma, chronic lymphocytic leukemia, and acute lymphoblastic leukemia.

Also provided are methods for killing tumor cells expressing CD19 and methods for inhibiting the proliferation or differentiation of tumor cells expressing CD19. Such methods can include administering to the cells a CD19 binding agent that specifically binds to and can, for example, kill or inhibit the proliferation or differentiation of cells expressing human CD19. In some embodiments, an anti-CD19 full length antibody or antigen-binding fragment thereof or derivative thereof that is not conjugated to a cytotoxic, cytostatic and/or therapeutic agent will be administered. In some other embodiments, a ligand-drug conjugate (e.g., a CD19 binding agent (e.g., a full length antibody or antigen-binding fragment thereof or derivative thereof) conjugated to a cytotoxic, cytostatic and/or therapeutic agent) will be administered. In some embodiments, the methods of the present invention will be effective for depleting B cells, e.g., periphery; spleen, mesenteric and mandibular lymph nodes.

The present invention encompasses methods for inducing the depletion of B cells, e.g., peripheral B cells, which are associated with an immune disorder. Such methods can include administering to the cells a CD19 binding agent. In some embodiments, an anti-CD19 full length antibody or antigen-binding fragment thereof or derivative thereof that is not conjugated to a cytotoxic, cytostatic and/or therapeutic agent will be administered. In some other embodiments, a ligand-drug conjugate (e.g., a CD19 binding agent (e.g., a full length antibody or antigen-binding fragment thereof or derivative thereof) conjugated to a cytotoxic, cytostatic and/or therapeutic agent) will be administered. In some embodiments, the immune disorder is rheumatoid arthritis, systemic lupus erythematosus, multiple sclerosis or inflammatory bowel disease.

Also provided by the present invention is the use of a CD19 binding agent in the manufacture of a medicament for the treatment of disease. In some embodiments, an anti-CD19 full length antibody or antigen-binding fragment thereof or derivative thereof that is not conjugated to a cytotoxic, cytostatic and/or therapeutic agent will be used. In some other embodiments, a ligand-drug conjugate (e.g., a CD19 binding agent (e.g., a full length antibody or antigen-binding fragment thereof or derivative thereof) conjugated to a cytotoxic, cytostatic and/or therapeutic agent) will be used.

Also provided by the present invention is the use of a CD19 binding agent in the manufacture of a medicament for the depletion of B cells. In some embodiments, an anti-CD19 full length antibody or antigen-binding fragment thereof or derivative thereof that is not conjugated to a cytotoxic, cytostatic and/or therapeutic agent will be used. In some other embodiments, a ligand-drug conjugate (e.g., a CD19 binding agent (e.g., a full length antibody or antigen-binding fragment thereof or derivative thereof) conjugated to a cytotoxic, cytostatic and/or therapeutic agent) will be used.

Also provided by the present invention is the use of a CD19 binding agent in the manufacture of a medicament for the killing or inhibition of the proliferation or differentiation of CD19-expressing cells. In some embodiments, an anti-CD19 full length antibody or antigen-binding fragment thereof or derivative thereof that is not conjugated to a cytotoxic, cytostatic and/or therapeutic agent will be used. In some other embodiments, a ligand-drug conjugate (e.g., a CD19 binding agent (e.g., a full length antibody or antigen-binding fragment thereof or derivative thereof) conjugated to a cytotoxic, cytostatic and/or therapeutic agent) will be used.

In another aspect, pharmaceutical compositions are provided in which the composition comprises a CD19 binding agent and a pharmaceutically acceptable excipient. In some embodiments, the pharmaceutical composition will comprise an anti-CD19 full length antibody or antigen-binding fragment thereof or derivative thereof that is not conjugated to a cytotoxic, cytostatic and/or therapeutic agent. In some other embodiments, the pharmaceutical composition will comprise a ligand-drug conjugate (e.g., a CD19 binding agent (e.g., a full length antibody or antigen-binding fragment thereof or derivative thereof) conjugated to a cytotoxic, cytostatic and/or therapeutic agent).

In another aspect, methods of manufacturing ligand-drug conjugate compounds are provided. In one aspect, a CD19 binding agent is conjugated to a cytotoxic, cytostatic and/or therapeutic agent either directly or through a linker, as described more fully below.

The present invention may be more fully understood by reference to the following detailed description, non-limiting examples of specific embodiments, and the appended figures and sequence listing.

BRIEF DESCRIPTION OF THE DRAWINGS

FIG. 14: CD19 and CD21 expression levels and cytotoxicity of hBU12-vcMMAE4 and hBU12-mcMMAF4 against ALL, CLL, and NHL tumor cell lines grown in culture.

FIGS. 17A-17D: Efficacy of hBU12-vcE in rituximab resistant lymphomas. 17A.) SCID mice were implanted with 5×10$^6$ of the parental Ramos-P cell lines used to generate rituximab resistant tumors. Comparable levels of tumor growth inhibition were achieved by rituximab (12 mg/kg, q4dx4) and hBU12-vcE (3 mg/kg, q4dx4) 17B.) Tumor growth curve of rituximab resistant Ramos tumors (R-Ramos) treated with hBU12-vcE (1 and 3 mg/kg, IP, q4dx4) or rituximab (12 mg/kg, q4dx4, IP). There was a statistically significant difference in tumor growth delay induced by these compounds 17C.) FACS analysis of CD19 and CD20 expression on cells isolated from Ramos-P (sensitive) and R-Ramos (resistant) tumors. Comparable expression levels for both antigens were identified in both tumors. 17D.) Anti-lymphoma effects of hBU12-vcE against subcutaneously implanted, rituximab resistant Raji2R tumors (NHL, Burkitt's lymphoma) treated with 1 and 3 mg/kg, q4dx4 of hBU12-vcE or control conjugate. 9 out of 10 durable regressions were observed in hBU12-vcE treated mice, while rituximab (12 mg/kg, q4dx4) did not significantly impact tumor growth. There were 5-10 mice per group. A durable response (DR) is defined as complete absence of palpable tumor during the entire experiment.

FIG. 19: Limited anti-tumor effects of hBU12 in a subcutaneous model of NHL (SUDHL4). There were 8-10 mice per treatment group. The dose schedule was Q4dx4, IP.

DETAILED DESCRIPTION

Figure 1:
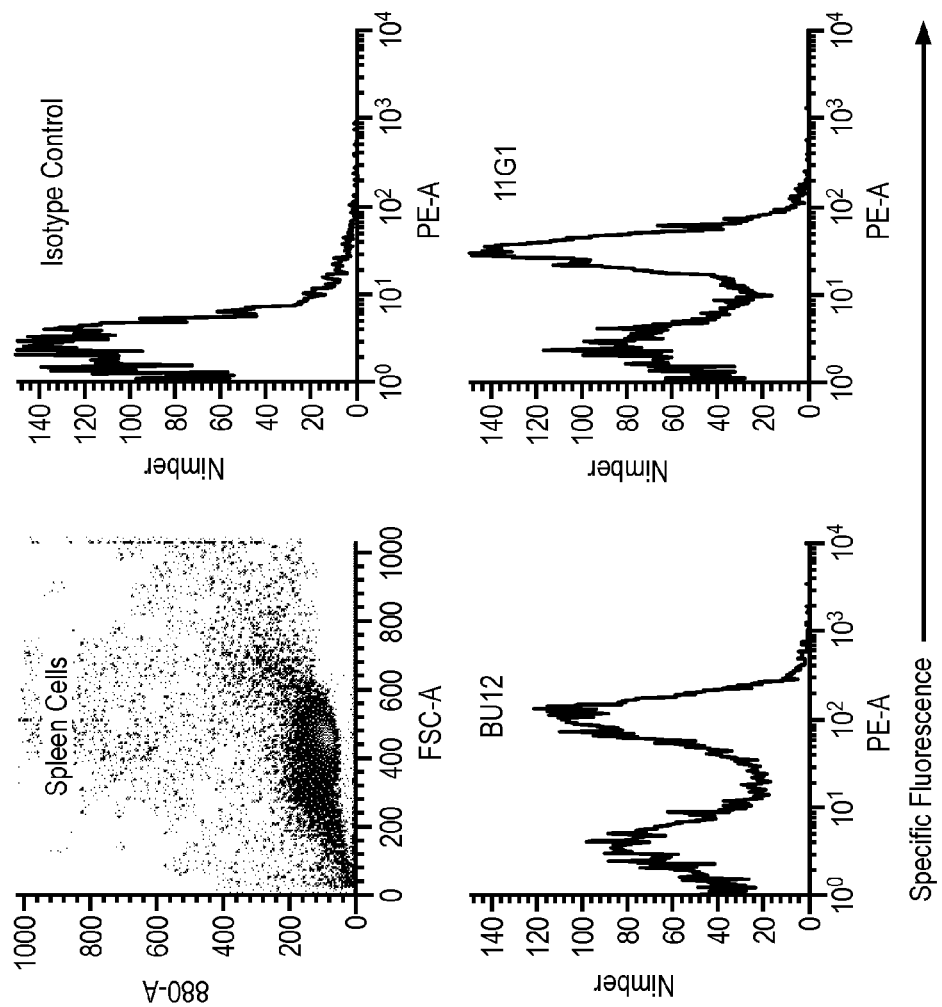
FIG. 1: FACS Results for Binding of CD19 antibodies to non-human primate spleen cells.

The present invention provides, inter alia, CD19 binding agents that specifically bind to human CD19. Specifically, the present inventors have designed humanized BU12 antibodies and ligand-drug conjugate compounds comprising humanized BU12 antibodies.

In certain aspects, the CD19 binding agents of the present invention comprise at least one of the CDR regions of the antibody mBU12. In certain aspects, the CD19 binding agents comprise all six of the CDR regions of the mBU12 antibody. In some embodiments, the CDR regions have at least one, at least two, or at least three conservative amino acid substitutions of a CDR of antibody mBU12.

In certain aspects, the CD19 binding agents of the present invention comprise an antibody heavy chain variable region and/or an antibody light chain variable region, including derivatives thereof.

In some aspects, the compositions and methods relate to antibodies, including antibody derivatives, that bind to CD19. In certain aspects, the anti-CD19 antibodies and derivatives comprise the amino acid sequence of a humanized heavy chain variable region and/or a humanized light chain variable region of antibody BU12, including derivatives thereof. In certain aspects, the anti-CD19 antibodies and derivatives comprise at least one, at least two, at least three, at least four, at least five, or all six of the CDR regions of antibody mBU12. In some embodiments, the anti-CD19 antibodies include at least one immunoglobulin constant region domain, or an entire constant region of an antibody, such as a human constant region or, optionally, a functionally active portion thereof. In some embodiments, the antibody constant region or domain(s) is of the IgG class. In some embodiments, the antibody constant domain is IgG1, IgG2, or IgG1V1.

In certain aspects, the compositions and methods relate to antibodies, including antibody derivatives, that bind to CD19 and are conjugated to cytotoxic, cytostatic and/or therapeutic agents. In certain embodiments, the antibodies have altered glycosylation patterns.

For clarity of disclosure, and not by way of limitation, the detailed description of the invention is divided into the subsections which follow.

Definitions and Abbreviations

When a trade name is used herein, reference to the trade name also refers to the product formulation, the generic drug, and the active pharmaceutical ingredient(s) of the trade name product, unless otherwise indicated by context.

The terms "CD19 binding agent" and "anti-CD19 binding agent" as used herein refers to a molecule, e.g., protein, that specifically binds to CD19. Examples can include a full length anti-CD19 antibody, a fragment of a full length anti-CD19 antibody, or other agent that includes an antibody heavy and/or light chain variable region, and derivatives thereof.

The terms "specific binding" and "specifically binds" mean that the CD19 binding agent will react, in a highly selective manner, with its corresponding target, CD19 and not with the multitude of other antigens. Typically, the C19 binding agent binds with an affinity of at least about $1\times10^{-7}$ M, and preferably $10^{-8}$ M to $10^{-9}$ M, $10^{-10}$ M, $10^{-11}$ M, or $10^{-12}$ M and binds to the predetermined antigen with an affinity that is at least two-fold greater than its affinity for binding to a non-specific antigen (e.g., BSA, casein) other than the predetermined antigen or a closely-related antigen.

As used herein, the term "functional," in the context of a CD19 binding agent, indicates that the binding agent is capable of specifically binding to CD19.

The terms "inhibit" or "inhibition of" as used herein means to reduce by a measurable amount, or to prevent entirely.

The term "deplete," in the context of the effect of a CD19 binding agent on CD19-expressing cells, refers to a reduction in the number of or elimination of the CD19-expressing cells.

"Native antibodies" and "native immunoglobulins" are defined herein as heterotetrameric glycoproteins, typically of about 150,000 daltons, composed of two light (L) chain and two heavy (H) chains. Each light chain is covalently linked to a heavy chain by a disulfide bond to form a heterodimer. The heterotetramer is formed by covalent disulfide linkage between the two heavy chains of such heterodimers. Although the light and heavy chains are linked together by a disulfide bond, the number of disulfide linkages between the two heavy chains varies by immunoglobulin (Ig) isotype. Each heavy and light chain also has regularly spaced intrachain disulfide bridges. Each heavy chain has at the amino-terminus a variable domain ($V_H$), followed by three or four constant domains ($C_H1$, $C_H2$, $C_H3$, and/or $C_H4$, as appropriate for the antibody type), as well as a hinge (J) region between $C_H1$ and $C_H2$. Each light chain has two domains, an amino-terminal variable domain ($V_L$) and a carboxy-terminal constant domain ($C_L$). The $V_L$ domain associates non-covalently with the $V_H$ domain, whereas the $C_L$ domain is commonly covalently linked to the $C_H1$ domain via a disulfide bond. Particular amino acid residues are believed to form an interface between the light and heavy chain variable domains (see, e.g., Chothia et al., 1985, *J. Mol. Biol.* 186:651-663).

The term "hypervariable" refers to certain sequences within the variable domains of an immunoglobulin that differ extensively in sequence among antibodies and contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). The locations of the CDRs are defined by sequence comparison in Kabat et al., 1991, In: *Sequences of Proteins of Immunological Interest*, 5$^{th}$ Ed. Public Health Service, National Institutes of Health, Bethesda, Md., whereas HVLs are structurally defined according to the three-dimensional structure of the variable domain, as described by Chothia and Lesk, 1987, *J. Mol. Biol.* 196:901-917. As defined by Kabat, CDR-L1 is positioned at about residues 24-34, CDR-L2 at about residues 50-56, and CDR-L3 at about residues 89-97 in the light chain variable domain. CDR-H1 is positioned at about residues 31-35, CDR-H2 at about residues 50-65, and CDR-H3 at about 95-102 in the heavy chain variable domain.

The three CDRs within each of the heavy and light chains are separated by framework regions (FR). From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains to close proximity to each other as well as to the CDRs from the other chain. The resulting conformation contributes to the antigen binding site (see, e.g., Kabat et al., 1991, NIH Publ. No. 91-3242, Vol. I, pages 647-669), although not all CDR residues are necessarily directly involved in antigen binding.

FR residues and Ig constant domains are typically not directly involved in antigen binding, but may contribute to antigen binding or mediate antibody effector function. Some FR residues can have a significant effect on antigen binding in at least three ways: by noncovalently binding directly to an epitope, by interacting with one or more CDR residues, and by affecting the interface between the heavy and light chains. In some embodiments, the constant domains mediate various Ig effector functions, such as participation of the antibody in antibody dependent cellular cytotoxicity (ADCC), complement dependent cytotoxicity (CDC) and/or antibody dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, and $IgG_4$; and $IgA_1$, and $IgA_2$, respectively. The heavy chain constant domains that correspond to the different classes of immunoglobulins are called α, δ, ε, γ, and μ, respectively. The subunit structures and three-dimensional configurations of the classes of native immunoglobulins are well known.

The terms "antibody", "anti-CD19 antibody", "humanized anti-CD19 antibody", and "variant humanized anti-CD19 antibody" are used herein in the broadest sense and specifically encompass full-length and native antibodies, monoclonal antibodies (including full-length monoclonal antibodies), polyclonal antibodies, multispecific antibodies (e.g., bispecific antibodies), and antibody fragments thereof, such as variable domains and other portions of antibodies that exhibit a desired biological activity (e.g., CD19 binding). The terms "anti-CD19 antibody fragment", "humanized anti-CD19 antibody fragment", and "variant humanized anti-CD19 antibody fragment" refer to a portion of a full-length anti-CD19 antibody in which a variable region or a functional capability is retained, for example, specific CD19 epitope binding. Examples of antibody fragments include, but are not limited to, a Fab, Fab', F(ab')$_2$, Fd, Fv, scFv and scFv-Fc fragment, a diabody, a linear antibody, a minibody and a multispecific antibody formed from antigen-binding antibody fragments. Antibody fragments are specifically included within the definition of "antibody".

The terms "monoclonal antibody" or "mAb" refer to an antibody obtained from a population of substantially homogeneous antibodies; that is, the individual antibodies comprising the population are identical except for naturally occurring mutations that may be present in minor amounts. Monoclonal antibodies are highly specific, being directed against a single antigenic determinant, also referred to as an epitope. The modifier "monoclonal" is indicative of a substantially homogeneous population of antibodies directed to the identical epitope and is not to be construed as requiring production of the antibody by any particular method. Monoclonal antibodies can be made by any technique or methodology known in the art; for example, the hybridoma method first described by Kohler et al., 1975, *Nature* 256:495, or recombinant DNA methods known in the art (see, e.g., U.S. Pat. No. 4,816,567). In another example, monoclonal antibodies also can be isolated from phage antibody libraries, using techniques described in Clackson et al., 1991, *Nature* 352: 624-628, and Marks et al., 1991, *J. Mol. Biol.* 222: 581-97.

The term "chimeric" antibody, as used herein, refers to a type of monoclonal antibody in which a portion of or the complete amino acid sequence in one or more regions or domains of the heavy and/or light chain is identical with, homologous to, or a variant of, the corresponding sequence in a monoclonal antibody from another species or belonging to another immunoglobulin class or isotype, or from a consensus sequence. An example of a chimeric antibody is one which has a variable region derived from a non-human monoclonal antibody and a human IgG immunoglobulin constant region. Chimeric antibodies include fragments of such antibodies, provided that the antibody fragment exhibits the desired biological activity of its parent antibody, for example binding to the same epitope (see, e.g., U.S. Pat. No. 4,816,567; and Morrison et al., 1984, *Proc. Natl. Acad. Sci. USA* 81:6851-6855). Methods for producing chimeric antibodies are known in the art. (See, e.g., Morrison, 1985, *Science* 229:1202; Oi et al., 1986, *BioTechniques* 4:214; Gillies et al., 1989, *J. Immunol. Methods* 125:191-202; U.S. Pat. Nos. 5,807,715; 4,816,567; and 4,816,397.)

A "single-chain Fv" or "scFv" antibody fragment is a single chain Fv variant comprising the $V_H$ and $V_L$ domains of an antibody in which the domains are present in a single polypeptide chain and which is capable of recognizing and binding antigen. The scFv polypeptide optionally contains a polypeptide linker positioned between the $V_H$ and $V_L$ domains that enables the scFv to form a desired three-dimensional structure for antigen binding, (see, e.g., Plückthun, 1994, In *The Pharmacology of Monoclonal Antibodies*, Vol. 113, Rosenburg and Moore eds., Springer-Verlag, New York, pp. 269-315).

The term "diabody" refers to a small antibody fragment having two antigen-binding sites. Each fragment contains a heavy chain variable domain ($V_H$) concatenated to a light chain variable domain ($V_L$) to form a $V_H$-$V_L$ or $V_L$-$V_H$ polypeptide. By using a linker that is too short to allow pairing between the two domains on the same chain, the linked $V_H$-$V_L$ domains are forced to pair with complementary domains of another chain, creating two antigen-binding sites. Diabodies are described more fully, for example, in EP 0 404 097; WO 93/11161; and Hollinger et al., 1993, *Proc. Natl. Acad. Sci. USA* 90:6444-6448.

The term "linear antibody" refers to an antibody that has a pair of tandem Fd segments ($V_H$-$C_H$1-$V_H$-$C_H$1) that form a pair of antigen binding regions. Linear antibodies can be bispecific or monospecific, as described in Zapata et al., 1995, *Protein Eng.* 8(10):1057-1062.

A "humanized" antibody for the purposes herein is an immunoglobulin amino acid sequence variant or fragment thereof which is capable of binding to a predetermined antigen and which comprises a framework region having substantially the amino acid sequence of a human immunoglobulin and a CDR having substantially the amino acid sequence of a non-human immunoglobulin.

Generally, a humanized antibody has one or more amino acid residues introduced into it from a source which is non-human. These non-human amino acid residues are referred to herein as "import" residues, which are typically taken from an "import" antibody domain, particularly a variable domain. An import residue, sequence, or antibody has a desired affinity and/or specificity, or other desirable antibody biological activity as discussed herein.

In general, the humanized antibody will comprise substantially all of at least one, and sometimes two, variable domains in which all or substantially all of the CDR regions correspond to those of a non-human immunoglobulin and all or substantially all of the FR regions are those of a human immunoglobulin sequence from, e.g., a consensus or germline sequence. The humanized antibody optionally also will comprise at least a portion of an immunoglobulin Fc region, typically that of a human immunoglobulin. In certain aspects, the antibody will contain both the light chain variable region as well as the heavy chain variable region. The antibody also may include the $C_H1$, hinge (J), $C_H2$, $C_H3$, and/or $C_H4$ regions of the heavy chain, and the $C_L$ region of the light chain, as appropriate.

The humanized antibody will be selected from any class of immunoglobulins, including IgM, IgG, IgD, IgA and IgE, and any isotype, including $IgG_1$, $IgG_2$, $IgG_3$ and $IgG_4$, and $IgA_1$, and $IgA_2$. The choice of which immunoglobulin class or isotype will depend, in part, on the desired effector function. For example, the ability of human immunoglobulins to mediate CDC and ADCC/ADCP is generally in the order of $IgM \approx IgG_1 \approx IgG_3 > IgG_2 > IgG_4$ and $IgG_1 \approx G_3 > IgG_2/IgM/IgG_4$, respectively. The humanized antibody may comprise sequences from more than one class or isotype, and selecting particular constant domains to optimize desired effector functions is within the ordinary skill in the art. The humanized antibody may or may not have effector function.

The FRs and CDRs of the humanized antibody need not correspond precisely to the parental sequences, e.g., the import CDR or the consensus FR may be altered by substitution, insertion or deletion of at least one residue so that the CDR or FR residue at that site does not correspond to either the consensus or the import antibody. Typically, such changes will not be extensive. Usually, at least 75% of the humanized antibody residues will correspond to those of the parental FR and CDR sequences, more often 90%, 91%, 92%, 93%, 94%, 95%, 96%, 97%, 98%, or at least 99%.

A "therapeutic agent" is an agent that exerts a cytotoxic, cytostatic, and/or immunomodulatory effect on cancer cells or activated immune cells. Examples of therapeutic agents include cytotoxic agents, chemotherapeutic agents, cytostatic agents, and immunomodulatory agents.

A "chemotherapeutic agent" is a chemical compound useful in the treatment of cancer.

A "cytotoxic effect" refers to the depletion, elimination and/or the killing of a target cell(s). A "cytotoxic agent" refers to an agent that has a cytotoxic and/or cytostatic effect on a cell. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant, or animal origin, and fragments thereof.

A "cytostatic effect" refers to the inhibition of cell proliferation. A "cytostatic agent" refers to an agent that has a cytostatic effect on a cell, thereby inhibiting the growth and/or expansion of a specific subset of cells.

The term "label" refers to a detectable compound or composition that is conjugated directly or indirectly to a binding agent (e.g., an antibody). The label may itself be detectable (e.g., a radioisotope label or a fluorescent label) or, in the case of an enzymatic label, may catalyze a chemical alteration of a substrate compound or composition that is detectable. Labeled CD19 binding agents can be prepared and used in various applications including in vitro and in vivo diagnostics. Useful labels include diagnostic agents such as contrast agents (such as for magnetic resonance imaging, computed tomography or ultrasound, e.g., manganese, iron or gadolinium).

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the nucleic acid where, for example, the nucleic acid molecule is in a chromosomal location different from that of natural cells.

The term "control sequence" refers to a polynucleotide sequence necessary for expression of an operably linked coding sequence in a particular host organism. The control sequences suitable for use in prokaryotic cells include, for example, a promoter, operator and ribosome binding site sequences. Eukaryotic control sequences include, but are not limited to, promoters, polyadenylation signals, and enhancers. These control sequences can be utilized for expression and production of CD19 binding agents in prokaryotic and eukaryotic host cells.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the nucleic acid sequences being linked are contiguous, and, in the case of a secretory leader, contiguous and in reading frame. However, enhancers are optionally contiguous. Linking can be accomplished, for example, by ligation at convenient restriction sites. If such sites do not exist, synthetic oligonucleotide adaptors, linkers or other methods known in the art can be used.

The term "polypeptide" refers to a polymer of amino acids and its equivalent and does not refer to a specific length of a product; thus, "peptides" and "proteins" are included within the definition of a polypeptide. Also included within the definition of polypeptides are "antibodies" as defined herein. A "polypeptide region" refers to a segment of a polypeptide, which segment may contain, for example, one or more domains or motifs (e.g., a polypeptide region of an antibody can contain, for example, one or more complementarity determining regions (CDRs)). The term "fragment" refers to a portion of a polypeptide preferably having at least 20 contiguous or at least 50 contiguous amino acids of the polypeptide.

Unless otherwise indicated by context, a "derivative" is a polypeptide or fragment thereof having one or more non-conservative or conservative amino acid substitutions relative to a second polypeptide (also referred to as a "variant"); or a polypeptide or fragment thereof that is modified by covalent attachment of a second molecule such as, e.g., by attachment of a heterologous polypeptide, or by glycosylation, acetylation, phosphorylation, and the like. Further included within the definition of "derivative" are, for example, polypeptides containing one or more analogs of an amino acid (e.g., unnatural amino acids and the like), polypeptides with unsubstituted linkages, as well as other modifications known in the art, both naturally and non-naturally occurring.

An "isolated" polypeptide is one which has been identified and separated and/or recovered from a component of its natural environment. Contaminant components of its natural environment are materials which would interfere with diagnostic or therapeutic uses for the polypeptide, and may include enzymes, hormones, and other proteinaceous or nonproteinaceous solutes. An isolated polypeptide includes an isolated antibody, or a fragment or derivative thereof.

In certain embodiments, the polypeptide will be purified (1) to greater than 95% by weight of polypeptide as determined by the Lowry method, and in other aspects to more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. "Isolated antibody" includes the antibody in situ within recombinant cells since at least one component of the antibody's natural environment will not be present.

The term "heterologous," in the context of a polypeptide, means from a different source (e.g., a cell, tissue, organism, or species) as compared with another polypeptide, so that the two polypeptides are different. Typically, a heterologous polypeptide is from a different species.

In the context of immunoglobulin polypeptides, or fragments thereof, as defined above, "conservative substitution" means one or more amino acid substitutions that do not substantially reduce specific binding (e.g., as measured by the $K_D$) of the immunoglobulin polypeptide or fragment thereof to an antigen (e.g., substitutions that increase binding, that do not significantly alter binding, or that reduce binding by no more than about 40%, typically no more than about 30%, more typically no more than about 20%, even more typically no more than about 10%, or most typically no more than about 5%, as determined by standard binding assays such as, e.g., ELISA).

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences are the same length.

The term "substantially identical," in the context of two nucleic acids or polypeptides, refers to two or more sequences or subsequences that have at least 90%, at least 91%, at least 92%, at least 93%, at least 94%, at least 95%, at least 96%, at least 97%, at least 98% identity, or at least 99% identity (e.g., as determined using one of the methods set forth infra).

In the context of CD19 binding agents of the present invention, a protein that has one or more polypeptide regions substantially identical to one or more antigen-binding regions (e.g., a heavy or light chain variable region, or a heavy or light chain CDR) of an anti-CD19 antibody retains specific binding to an epitope of CD19 recognized by the anti-CD19 antibody, as determined using any of various standard immunoassays known in the art or as referred to herein.

The determination of percent identity between two sequences can be accomplished using a mathematical algorithm. A non-limiting example of a mathematical algorithm utilized for the comparison of two sequences is the algorithm of Karlin and Altschul, 1990, *Proc. Natl. Acad. Sci. USA* 87:2264-2268, modified as in Karlin and Altschul, 1993, *Proc. Natl. Acad. Sci. USA* 90:5873-5877. Such an algorithm is incorporated into the NBLAST and XBLAST programs of Altschul et al., 1990, *J. Mol. Biol.* 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to a protein of interest. To obtain gapped alignments for comparison purposes, Gapped BLAST can be utilized as described in Altschul et al., 1997, *Nucleic Acids Res.* 25:3389-3402. Alternatively, PSI-Blast can be used to perform an iterated search which detects distant relationships between molecules (id.). When utilizing BLAST, Gapped BLAST, and PSI-BLAST programs, the default parameters of the respective programs (e.g., XBLAST and NBLAST) can be used. Another non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, *Comput. Appl. Biosci.* 10:3-5; and FASTA described in Pearson and Lipman, 1988, *Proc. Natl. Acad. Sci. USA* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, *Methods Enzymol.* 266:383-402.

Optionally, any two antibody sequences can be aligned, for example to determine percent identity, by using the Kabat numbering system so that each amino acid in one antibody sequence is aligned with the amino acid in the other sequence that has the same Kabat number. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

"Effector cell" as used herein refers to a cell that expresses a surface receptor for the Fc region of an immunoglobulin (FcR). For example, cells that express surface FcR for IgGs including FcγRIII (CD16), FcγRII (CD32) and FcγRI (CD64) can act as effector cells. Such effector cells include monocytes, macrophages, natural killer (NK) cells, neutrophils and eosinophils.

The term "antibody effector function(s)" as used herein refers to a function contributed by an Fc region(s) of an Ig. Such function can be effected by, for example, binding of an Fc effector region(s) to an Fc receptor on an immune cell with phagocytic or lytic activity or by binding of an Fc effector region(s) to components of the complement system. The CD19 binding agents of the present invention may or may not have effector function.

A "disorder", as used herein, and the terms "CD19-associated disorder" and "CD19-associated disease" refer to any condition that would benefit from treatment with a CD19 binding agent described herein. This includes chronic and acute disorders or diseases including those pathological conditions that predispose the mammal to the disorder in question. Non-limiting examples or disorders to be treated herein include CD19 expressing cancers, including hematological malignancies, benign and malignant tumors, leukemias and lymphoid malignancies, as well as inflammatory, angiogenic and immunologic disorders. Specific examples of disorders are disclosed infra.

B cell malignancies also referred to as B-cell lineage malignancies are treatable by the methods of the present invention. The term B cell malignancies include any malignancy that is derived from a cell of the B cell lineage.

The terms "treatment" and "therapy", and the like, as used herein, are meant to include therapeutic or suppressive measures for a disease or disorder leading to any clinically desirable or beneficial effect, including, but not limited to, alleviation or relief of one or more symptoms, regression, slowing or cessation of progression of the disease or disorder. For example, treatment can include a decrease or elimination of a clinical or diagnostic symptom of a CD19-expressing disorder after the onset of the clinical or diagnostic symptom by administration of an anti-CD19 antibody or other CD19 binding agent to a subject. Treatment can be evidenced as a decrease in the severity of a symptom, the number of symptoms, or frequency of relapse.

Except when noted, the terms "subject" or "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the CD19 binding agents of the invention can be administered. Subjects of the present invention include those that have been diagnosed with a CD19 expressing cancer, including, for example, B cell lymphoma or B cell leukemia, including, but not limited to, non-Hodgkin lymphoma, chronic lymphocytic leukemia, and acute lymphoblastic leukemia. In certain embodiments, the subject will have a refractory or relapsed CD19 expressing cancer. Subjects of the present invention include those that have been diagnosed with an autoimmune disorder.

A subject with a refractory CD19 expressing cancer is a subject who does not respond to therapy, i.e., the subject continues to experience disease progression despite therapy.

A subject with a relapsed CD19 expressing cancer is a subject who has responded to the therapy at one point, but has had a reoccurrence or further progression of disease following the response.

The term "effective amount" refers to the amount of a CD19 binding agent or ligand-drug conjugate that is sufficient to inhibit the occurrence or ameliorate one or more clinical or diagnostic symptoms of a CD19-associated disorder in a subject. An effective amount of an agent is administered according to the methods described herein in an "effective regimen." The term "effective regimen" refers to a combination of amount of the agent and dosage frequency adequate to accomplish treatment or prevention of a CD19-associated disorder.

The term "leukemia" refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "pharmaceutically acceptable" as used herein refers to those compounds, materials, compositions, and/or dosage forms that are, within the scope of sound medical judgment, suitable for contact with the tissues of human beings and animals without excessive toxicity, irritation, allergic response, or other problems or complications commensurate with a reasonable benefit/risk ratio. The term "pharmaceutically compatible ingredient" refers to a pharmaceutically acceptable diluent, adjuvant, excipient, or vehicle with which a CD19 binding agent or a ligand-drug conjugate is administered.

The term "pharmaceutically compatible ingredient" refers to a pharmaceutically acceptable diluent, adjuvant, excipient, or vehicle with which a CD19 binding agent is administered.

The term "compound" refers to and encompasses the chemical compound itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and/or solvates, however, this reference is for emphasis only, and is not to be construed as excluding other of the above forms as identified above.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine Unless otherwise noted, the term "alkyl" refers to a saturated straight or branched hydrocarbon having from about 1 to about 20 carbon atoms (and all combinations and subcombinations of ranges and specific numbers of carbon atoms therein), with from about 1 to about 8 carbon atoms being preferred. Examples of alkyl groups are methyl, ethyl, n-propyl, iso-propyl, n-butyl, iso-butyl, sec-butyl, tert-butyl, n-pentyl, 2-pentyl, 3-pentyl, 2-methyl-2-butyl, n-hexyl, n-heptyl, n-octyl, n-nonyl, n-decyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

Alkyl groups, whether alone or as part of another group, can be optionally substituted with one or more groups, preferably 1 to 3 groups (and any additional substituents selected from halogen), including, but not limited to, halogen, optionally substituted —O—($C_1$-$C_8$ alkyl), optionally substituted —O—($C_2$-$C_8$ alkenyl), optionally substituted —O—($C_2$-$C_8$ alkynyl), optionally substituted aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, =O, —$N_3$, —$NH_2$, —NH(R'), —N(R')$_2$ and —CN, where each R' is independently selected from H, optionally substituted —$C_1$-$C_8$ alkyl, optionally substituted —$C_2$-$C_8$ alkenyl, optionally substituted —$C_2$-$C_8$ alkynyl, or optionally substituted aryl, and wherein said optionally substituted O—($C_1$-

$C_8$ alkyl), optionally substituted —O—($C_2$-$C_8$ alkenyl), optionally substituted —O—($C_2$-$C_8$ alkynyl), optionally substituted aryl, optionally substituted $C_1$-$C_8$ alkyl, optionally substituted —$C_2$-$C_8$ alkenyl, and optionally substituted —$C_2$-$C_8$ alkynyl groups can be optionally further substituted with one or more groups including, but not limited to, —$C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$—NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from H, —$C_1$-$C_8$ alkyl, —$C_2$-$C_8$ alkenyl, —$C_2$-$C_8$ alkynyl, or aryl.

Unless otherwise noted, the terms "alkenyl" and "alkynyl" refer to straight and branched carbon chains having from about 2 to about 20 carbon atoms (and all combinations and subcombinations of ranges and specific numbers of carbon atoms therein), with from about 2 to about 8 carbon atoms being preferred. An alkenyl chain has at least one double bond in the chain and an alkynyl chain has at least one triple bond in the chain. Examples of alkenyl groups include, but are not limited to, ethylene or vinyl, allyl, -1-butenyl, -2-butenyl, -isobutylenyl, -1-pentenyl, -2-pentenyl, -3-methyl-1-butenyl, -2-methyl-2-butenyl, and -2,3-dimethyl-2-butenyl. Examples of alkynyl groups include, but are not limited to, acetylenic, propargyl, acetylenyl, propynyl, -1-butynyl, -2-butynyl, -1-pentynyl, -2-pentynyl, and -3-methyl-1 butynyl.

Alkenyl and alkynyl groups, whether alone or as part of another group, can be optionally substituted with one or more groups, preferably 1 to 3 groups (and any additional substituents selected from halogen), including but not limited halogen, optionally substituted —O—($C_1$-$C_8$ alkyl), optionally substituted —O—($C_2$-$C_8$ alkenyl), optionally substituted —O—($C_2$-$C_8$ alkynyl), optionally substituted aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from H, optionally substituted —$C_1$-$C_8$ alkyl, optionally substituted —$C_2$-$C_8$ alkyenl, optionally substituted —$C_2$-$C_8$ alkynyl, or optionally substituted aryl and wherein said optionally substituted —O—($C_1$-$C_8$ alkyl), optionally substituted —O—($C_2$-$C_8$ alkenyl), optionally substituted —O—($C_2$-$C_8$ alkynyl), optionally substituted aryl, optionally substituted $C_1$-$C_8$ alkyl, optionally substituted —$C_2$-$C_8$ alkenyl, and optionally substituted —$C_2$-$C_8$ alkynyl groups can be optionally further substituted with one or more substituents including, but not limited to, —$C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$$C_8$ alkynyl), -aryl, —C(O)R", —OC(O)R", —C(O)OR", —C(O)NH$_2$, —C(O)NHR", —C(O)N(R")$_2$—NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from H, —$C_1$-$C_8$ alkyl, —$C_2$-$C_8$ alkenyl, —$C_2$-$C_8$ alkynyl, or aryl.

Unless otherwise noted, the term "alkylene" refers to a saturated branched or straight chain hydrocarbon radical having from about 1 to about 20 carbon atoms (and all combinations and subcombinations of ranges and specific numbers of carbon atoms therein), with from about 1 to about 8 carbon atoms being preferred and having two monovalent radical centers derived by the removal of two hydrogen atoms from the same or two different carbon atoms of a parent alkane. Typical alkylenes include, but are not limited to, methylene, ethylene, propylene, butylene, pentylene, hexylene, heptylene, ocytylene, nonylene, decalene, 1,4-cyclohexylene, and the like. Alkylene groups, whether alone or as part of another group, can be optionally substituted with one or more groups, preferably 1 to 3 groups (and any additional substituents selected from halogen), including, but not limited to, halogen, optionally substituted —O—($C_1$-$C_8$ alkyl), optionally substituted —O—($C_2$-$C_8$ alkenyl), optionally substituted —O—($C_2$-$C_8$ alkynyl), optionally substituted aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from H, optionally substituted —$C_1$-$C_8$ alkyl, optionally substituted —$C_2$-$C_8$ alkenyl, optionally substituted —$C_2$-$C_8$ alkynyl, or optionally substituted aryl and wherein said optionally substituted —O—($C_1$-$C_8$ alkyl), optionally substituted —O—($C_2$-$C_8$ alkenyl), optionally substituted —O—($C_2$-$C_8$ alkynyl), optionally substituted aryl, optionally substituted $C_1$-$C_8$ alkyl, optionally substituted —$C_2$-$C_8$ alkenyl, and optionally substituted —$C_2$-$C_8$ alkynyl groups can be further optionally substituted with one or more substituents including, but not limited to, $C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$—NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from H, —$C_1$-$C_8$ alkyl, —$C_2$-$C_8$ alkenyl, —$C_2$-$C_8$ alkynyl, or aryl.

Unless otherwise noted, the term "alkenylene" refers to an optionally substituted alkylene group containing at least one carbon-carbon double bond. Exemplary alkenylene groups include, for example, ethenylene (—CH=CH—) and propenylene (—CH=CHCH$_2$—).

Unless otherwise noted, the term "alkynylene" refers to an optionally substituted alkylene group containing at least one carbon-carbon triple bond. Exemplary alkynylene groups include, for example, acetylene (—C≡C—), propargyl (—CH$_2$C≡C—), and 4-pentynyl (—CH$_2$CH$_2$CH$_2$C≡CH—).

Unless otherwise noted, the term "aryl" refers to a monovalent aromatic hydrocarbon radical of 6-20 carbon atoms (and all combinations and subcombinations of ranges and specific numbers of carbon atoms therein) derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, phenyl, naphthalene, anthracene, biphenyl, and the like.

An aryl group, whether alone or as part of another group, can be optionally substituted with one or more, preferably 1 to 5, or even 1 to 2 groups including, but not limited to, halogen, optionally substituted —$C_1$-$C_8$ alkyl, optionally substituted —$C_2$-$C_8$ alkenyl, optionally substituted —$C_2$-$C_8$ alkynyl, optionally substituted —O—($C_1$-$C_8$ alkyl), optionally substituted —O—($C_2$-$C_8$ alkenyl), optionally substituted —O—($C_2$-$C_8$ alkynyl), optionally substituted aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —NO$_2$, —N$_3$, —NH$_2$, —NH(R'), —N(R')$_2$ and —CN, where each R' is independently selected from H, optionally substituted —$C_1$-$C_8$ alkyl, optionally substituted —$C_2$-$C_8$ alkenyl, optionally substituted —$C_2$-$C_8$ alkynyl, or optionally substituted aryl and wherein said optionally substituted $C_1$-$C_8$ alkyl, optionally substituted —$C_2$-$C_8$ alkenyl, optionally substituted —$C_2$-$C_8$ alkynyl, optionally substituted —O—($C_1$-$C_8$ alkyl), optionally substituted —O—($C_2$-

C$_8$ alkenyl), optionally substituted —O—(C$_2$-C$_8$ alkynyl), and optionally substituted aryl groups can be further optionally substituted with one or more substituents including, but not limited to, C$_1$-C$_8$ alkyl, —C$_2$-C$_8$ alkenyl, —C$_2$-C$_8$ alkynyl, halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from H, —C$_1$-C$_8$ alkyl, —C$_2$-C$_8$ alkenyl, —C$_2$-C$_8$ alkynyl, or aryl.

Unless otherwise noted, the term "arylene" refers to an optionally substituted aryl group which is divalent (i.e., derived by the removal of two hydrogen atoms from the same or two different carbon atoms of a parent aromatic ring system) and can be in the ortho, meta, or para configurations as shown in the following structures with phenyl as the exemplary aryl group:

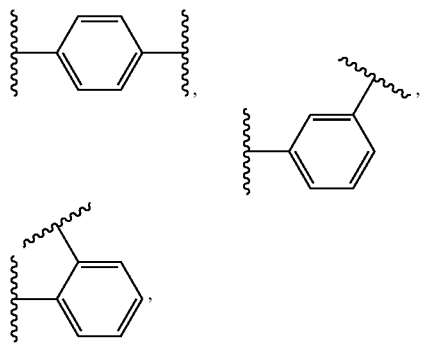

Typical "—(C$_1$-C$_8$ alkylene)aryl," "—(C$_2$-C$_8$ alkenylene) aryl," "and —(C$_2$-C$_8$ alkynylene)aryl" groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

Unless otherwise noted, the term "heterocycle," refers to a monocyclic, bicyclic, or polycyclic ring system having from 3 to 14 ring atoms (also referred to as ring members) wherein at least one ring atom in at least one ring is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocylic heterocycle preferably has 3 to 7 ring members (e.g., 2 to 6 carbon atoms and 1 to 3 heteroatoms independently selected from N, O, P, or S), and a bicyclic heterocycle preferably has 5 to 10 ring members (e.g., 4 to 9 carbon atoms and 1 to 3 heteroatoms independently selected from N, O, P, or S). The ring that includes the heteroatom can be aromatic or non-aromatic. Unless otherwise noted, the heterocycle is attached to its pendant group at any heteroatom or carbon atom that results in a stable structure.

Heterocycles are described in Paquette, "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 82:5566 (1960).

Unless otherwise noted, the term "heterocyclo" refers to an optionally substituted heterocycle group as defined herein that is divalent (i.e., derived by the removal of two hydrogen atoms from the same or two different carbon atoms of a parent heterocyclic ring system).

Examples of "heterocycle" groups include by way of example and not limitation pyridyl, dihydropyridyl, tetrahydropyridyl (piperidyl), thiazolyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl. Preferred "heterocycle" groups include, but are not limited to, benzofuranyl, benzothiophenyl, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl.

A heterocycle group, whether alone or as part of another group, can be optionally substituted with one or more groups, preferably 1 to 2 groups, including but not limited to, optionally substituted —C$_1$-C$_8$ alkyl, optionally substituted —C$_2$-C$_8$ alkenyl, optionally substituted —C$_2$-C$_8$ alkynyl, halogen, optionally substituted —O—(C$_1$-C$_8$ alkyl), optionally substituted —O—(C$_2$-C$_8$ alkenyl), optionally substituted —O—(C$_2$-C$_8$ alkynyl), optionally substituted -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —N$_3$, —NH$_2$, —NH(R'), —N(R')$_2$ and —CN, where each R' is independently selected from H, optionally substituted —C$_1$-C$_8$ alkyl, optionally substituted —C$_2$-C$_8$ alkenyl, optionally substituted —C$_2$-C$_8$ alkynyl, or optionally substituted aryl and wherein said optionally substituted O—(C$_1$-C$_8$ alkyl), optionally substituted —O—(C$_2$-C$_8$ alkenyl), optionally substituted —O—(C$_2$-C$_8$ alkynyl), optionally substituted —C$_1$-C$_8$ alkyl, optionally substituted —C$_2$-C$_8$ alkenyl, optionally substituted —C$_2$-C$_8$ alkynyl, and optionally substituted aryl groups can be further optionally substituted with one or more substituents including, but not limited to, —C$_1$-C$_8$ alkyl, —C$_2$-C$_8$ alkenyl, —C$_2$-C$_8$ alkynyl, halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from H, —C$_1$-C$_8$ alkyl, —C$_2$-C$_8$ alkenyl, —C$_2$-C$_8$ alkynyl, or aryl.

By way of example and not limitation, carbon-bonded heterocycles can be bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; position 2, 3, or 4 of an azetidine; position 2, 3, 4, 5, 6, 7, or 8 of a quinoline; or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole; position 2 of a isoindole, or isoindoline; position 4 of a morpholine; and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Unless otherwise noted, the term "carbocycle," refers to a saturated or unsaturated non-aromatic monocyclic, bicyclic, or polycyclic ring system having from 3 to 14 ring atoms (and all combinations and subcombinations of ranges and specific numbers of carbon atoms therein) wherein all of the ring atoms are carbon atoms. Monocyclic carbocycles preferably have 3 to 6 ring atoms, still more preferably 5 or 6 ring atoms. Bicyclic carbocycles preferably have 7 to 12 ring atoms, e.g., arranged as a bicyclo [4,5], [5,5], [5,6] or [6,6] system, or 9 or 10 ring atoms arranged as a bicyclo [5,6] or [6,6] system. The term "carbocycle" includes, for example, a monocyclic carbocycle ring fused to an aryl ring (e.g., a monocyclic carbocycle ring fused to a benzene ring). Carbocyles preferably have 3 to 8 carbon ring atoms.

Carbocycle groups, whether alone or as part of another group, can be optionally substituted with, for example, one or more groups, preferably 1 or 2 groups (and any additional substituents selected from halogen), including, but not limited to, halogen, optionally substituted $C_1$-$C_8$ alkyl, optionally substituted —$C_2$-$C_8$ alkenyl, optionally substituted —$C_2$-$C_8$ alkynyl, optionally substituted —O—($C_1$-$C_8$ alkyl), optionally substituted —O—($C_2$-$C_8$ alkenyl), optionally substituted —O—($C_2$-$C_8$ alkynyl), optionally substituted aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R',—OH, =O, —N$_3$, —NH$_2$, —NH(R'), —N(R')$_2$ and —CN, where each R' is independently selected from H, optionally substituted —$C_1$-$C_8$ alkyl, optionally substituted —$C_2$-$C_8$ alkenyl, optionally substituted —$C_2$-$C_8$ alkynyl, or optionally substituted aryl and wherein said optionally substituted —$C_1$-$C_8$ alkyl, optionally substituted —$C_2$-$C_8$ alkenyl, optionally substituted —$C_2$-$C_8$ alkynyl, optionally substituted —O—($C_1$-$C_8$ alkyl), optionally substituted —O—($C_2$-$C_8$ alkenyl), optionally substituted —O—($C_2$-$C_8$ alkynyl), and optionally substituted aryl groups can be further optionally substituted with one or more substituents including, but not limited to, $C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from H, —$C_1$-$C_8$ alkyl, —$C_2$-$C_8$ alkenyl, —$C_2$-$C_8$ alkynyl, or aryl.

Examples of monocyclic carbocylic substituents include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl. -1,3-cyclohexadienyl, -1,4-cyclohexadienyl, -1,3-cycloheptadienyl, -1,3,5-cycloheptatrienyl, and -cyclooctadienyl.

A "carbocyclo," whether used alone or as part of another group, refers to an optionally substituted carbocycle group as defined above that is divalent (i.e., derived by the removal of two hydrogen atoms from the same or two different carbon atoms of a parent carbocyclic ring system).

When any variable occurs more than one time in any constituent or in any formula, its definition in each occurrence is independent of its definition at every other. Combinations of substituents and/or variables are permissible only if such combinations result in stable compounds.

Unless otherwise indicated by context, a hyphen (-) designates the point of attachment to the pendant molecule. Accordingly, the term "—($C_1$-$C_8$ alkylene)aryl" or "—$C_1$-$C_8$ alkylene(aryl)" refers to a $C_1$-$C_8$ alkylene radical as defined herein wherein the alkylene radical is attached to the pendant molecule at any of the carbon atoms of the alkylene radical and one of the hydrogen atom bonded to a carbon atom of the alkylene radical is replaced with an aryl radical as defined herein.

When a particular group is "substituted", that group may have one or more substituents, preferably from one to five substituents, more preferably from one to three substituents, most preferably from one to two substituents, independently selected from the list of substituents. The group can, however, generally have any number of substituents selected from halogen. Groups that are substituted are so indicated.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Protective groups as used herein refer to groups which selectively block, either temporarily or permanently, one reactive site in a multifunctional compound. Suitable hydroxy-protecting groups for use in the present invention can be administered to a subject in the context of the present invention and may or may not need to be cleaved from the parent compound after administration to a subject in order for the compound to be active. Cleavage is through normal metabolic processes within the body. Hydroxy protecting groups are well known in the art, see, Protective Groups in Organic Synthesis by T. W. Greene and P. G. M. Wuts (John Wiley & sons, $3^{rd}$ Edition) incorporated herein by reference in its entirety and for all purposes and include, for example, ether (e.g., alkyl ethers and silyl ethers including, for example, dialkylsilylether, trialkylsilylether, dialkylalkoxysilylether), ester, carbonate, carbamates, sulfonate, and phosphate protecting groups. Examples of hydroxy protecting groups include, but are not limited to, methyl ether; methoxymethyl ether, methylthiomethyl ether, (phenyldimethylsilyl)methoxymethyl ether, benzyloxymethyl ether, p-methoxybenzyloxymethyl ether, p-nitrobenzyloxymethyl ether, o-nitrobenzyloxymethyl ether, (4-methoxyphenoxy)methyl ether, guaiacolmethyl ether, t-butoxymethyl ether, 4-pentenyloxymethyl ether, siloxymethyl ether, 2-methoxyethoxymethyl ether, 2,2,2-trichloroethoxymethyl ether, bis(2-chloroethoxy)methyl ether, 2-(trimethylsilyl)ethoxymethyl ether, menthoxymethyl ether, tetrahydropyranyl ether, 1-methoxycylcohexyl ether, 4-methoxytetrahydrothiopyranyl ether, 4-methoxytetrahydrothiopyranyl ether S,S-Dioxide, 1-[(2-choro-4-methyl)phenyl]-4-methoxypiperidin-4-yl ether, 1-(2-fluorophenyl)-4-methoxypiperidin-4-yl ether, 1,4-dioxan-2-yl ether, tetrahydrofuranyl ether, tetrahydrothiofuranyl ether; substituted ethyl ethers such as 1-ethoxyethyl ether, 1-(2-chloroethoxy)ethyl ether, 1-[2-(trimethylsilyl)ethoxy]ethyl ether, 1-methyl-1-methoxyethyl ether, 1-methyl-1-benzyloxyethyl ether, 1-methyl-1-benzyloxy-2-fluoroethyl ether, 1-methyl-lphenoxyethyl ether, 2-trimethylsilyl ether, t-butyl ether, allyl ether, propargyl ethers, p-chlorophenyl ether, p-methoxyphenyl ether, benzyl ether, p-methoxybenzyl ether 3,4-dimethoxybenzyl ether, trimethylsilyl ether, triethylsilyl ether, tripropylsilylether, dimethylisopropylsilyl ether, diethylisopropylsilyl ether, dimethylhexylsilyl ether, t-butyldimethylsilyl ether, diphenylmethylsilyl ether, benzoylformate ester, acetate ester, chloroacetate ester, dichloroacetate ester, trichloroacetate ester, trifluoroacetate ester, methoxyacetate ester, triphenylmethoxyacetate ester, phenylacetate ester, benzoate ester, alkyl methyl carbonate, alkyl 9-fluorenylmethyl carbonate, alkyl ethyl carbonate, alkyl 2,2,2,-trichloroethyl carbonate, 1,1,-dimethyl-2,2,2-trichloroethyl carbonate, alkylsulfonate, methanesulfonate, benzylsulfonate, tosylate, methylene acetal, ethylidene acetal, and t-butylmethylidene ketal. Preferred protecting groups are represented by the formulas —$R^a$, —$Si(R^a)(R^a)(R^a)$, —$C(O)R^a$, —$C(O)OR^a$, —$C(O)NH(R^a)$, —$S(O)_2R^a$, —$S(O)_2OH$, $P(O)(OH)_2$, and —$P(O)(OH)OR^a$, wherein $R^a$ is $C_1$-$C_{20}$ alkyl, $C_2$-$C_{20}$ alkenyl, $C_2$-$C_{20}$ alkynyl, —$C_1$-$C_{20}$ alkylene(carbocycle), —$C_2$-$C_{20}$ alkenylene(carbocycle), —$C_2$-$C_{20}$ alkynylene(carbocycle), $C_6$-$C_{10}$ aryl, —$C_1$-$C_{20}$ alkylene(aryl), —$C_2$-$C_{20}$ alkenylene(aryl), —$C_2$-$C_{20}$ alkynylene(aryl), —$C_1$-$C_{20}$ alkylene(heterocycle), —$C_2$-$C_{20}$ alkenylene(heterocycle), or —$C_2$-$C_{20}$ alkynylene(heterocycle) wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4. A1, A2, A3, and A4 are as defined herein.

The abbreviation "AFP" refers to dimethylvaline-valine-dolaisoleuine-dolaproine-phenylalanine-p-phenylenediamine (see Formula XVI infra).

The abbreviation "MMAE" refers to monomethyl auristatin E (see Formula XI infra).

The abbreviation "AEB" refers to an ester produced by reacting auristatin E with paraacetyl benzoic acid (see Formula XX infra)

The abbreviation "AEVB" refers to an ester produced by reacting auristatin E with benzoylvaleric acid (see Formula XXI infra).

The abbreviation "MMAF" refers to dovaline-valine-dolaisoleuine-dolaproine-phenylalanine (see Formula XVIV infra).

A. CD19 Binding Agents

The methods described herein encompass the use of CD19 binding agents and ligand-drug conjugate compounds wherein the ligand unit is an anti-CD19 binding agent that specifically binds to CD19. The CD19 binding agent can be, for example, an anti-CD19 antibody, an anti-CD19 antigen-binding fragment, or other CD19 binding agent comprising the amino acid sequence of a humanized antibody heavy and/or light chain variable region, or derivative thereof.

In certain aspects, the CD19 binding agents of the present invention include a heavy and/or light chain variable domain, the heavy and light chain variable domains each have (a) a set of three CDRs identical or substantially identical to the corresponding CDRs of mAb mBU12, and (b) a set of four variable region framework regions identical or substantially identical to framework regions from a human immunoglobulin.

The present invention encompasses embodiments wherein the framework regions chosen for the heavy chain variable region of the CD19 binding agents of the present invention are the human germline $V_H$ exons $V_H2$-70 or $V_H4$-31 and the human germline $J_H4$ exon for the humanized FR4 sequence. In some embodiments, the human germline $J_H1$, $J_H2$, $J_H3$, $J_H5$, or $J_H6$ exon is used in place of the human germline $J_H4$ exon for the humanized FR4 sequence.

The present invention encompasses embodiments wherein the framework regions chosen for the light chain variable region of the CD19 binding agents of the present invention are the human germline $V_L$ exons $V_L$-L6 or $V_L$A10 and the human germline $J_k2$ exon for the humanized FR4 sequence. In some embodiments, the human germline $J_k1$, $J_k3$, $J_k4$, or $J_k5$ exon is used in place of the human germline $J_k2$ exon for the humanized FR4 sequence.

The present invention encompasses embodiments wherein mouse donor residues are reintroduced into the sequence of the framework region of the CD19 binding agents. Such residues can include, for example, reintroduction of the mouse donor residue at one or more of positions 75, 79, 81, 82, 82A, 82B, 82C and 89, according to the Kabat numbering system, of the $V_H2$-70/$J_H4$ germline, positions 24, 27, 29, 71, 75, 78, 79, and 89, according to the Kabat numbering system, of the $V_H4$-31/$J_H4$ germline, positions 2, 40, 41, 42, 69, 70, 71, 72, and 83, according to the Kabat numbering system, of the $V_L$-L6/$J_k2$ germline, and positions 2 and 71, according to the Kabat numbering system, of the $V_L$A10/$J_k2$ germline. Additional mouse donor residues at alternate positions can be reintroduced into the sequences.

The present invention emcompasses embodiments wherein the CD19 binding agents described herein have amino acid sequence modification(s) in the acceptor human germline exon in addition to the reintroduction of mouse donor residues as well as amino acid sequence modification(s) in the hypervariable regions. For example, it may be desirable to improve the binding affinity and/or other biological properties of an antibody Amino acid sequence variants of CD19 binding agents can be prepared by introducing appropriate nucleotide changes into an antibody nucleic acid, or by peptide synthesis. Such modifications include, for example, deletions from, and/or insertions into and/or substitutions of, residues within the amino acid sequences of an antibody. Any combination of deletion, insertion, and substitution can be made to arrive at the final construct, provided that the final construct possesses the desired characteristics. Substitutions may be conservative or non-conservative substitutions. The amino acid changes also may alter post-translational processes of an antibody, such as changing the number or position of glycosylation sites.

A useful method for identification of certain residues or regions of the CD19 binding agent that are favored locations for mutagenesis is called "alanine scanning mutagenesis" as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed variants are screened for the desired activity.

Amino acid sequence insertions include amino- and/or carboxyl-terminal fusions as well as intrasequence insertions of single or multiple amino acid residues. Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated.

Substantial modifications in the biological properties of the CD19 binding agent are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally-occurring residues are divided into groups based on common side-chain properties:

(1) hydrophobic: met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Conservative substitutions will entail exchanging members of the same class.

One type of substitutional variant involves substituting one or more hypervariable region residues. In some embodiments, the resulting variant(s) selected for further development will have improved biological properties relative to the parent binding agent from which they are generated. A convenient way for generating such substitutional variants involves affinity maturation using phage display. Briefly, several hypervariable region sites (e.g., 6-7 sites) are mutated to generate all possible amino substitutions at each site. The variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the binding agent and the antigen. Such contact residues and neighboring residues are candidates for substitution according to the techniques elaborated herein. Once such variants are generated, the panel of variants is subjected to screening as described herein and binding agents with superior properties in one or more relevant assays may be selected for further development.

In some embodiments, CD19 binding agents of the present invention (e.g., anti-CD19 antibodies or derivatives thereof) have modifications (e.g., substitutions, deletions or additions) in amino acid residues that interact with Fcγ receptors. In some aspects, CD19 binding agents of the present invention include binding agents (e.g., anti-CD19 antibodies or derivatives thereof) that have modifications in amino acid residues that are involved in the binding interaction between the Fc domain and one or more Fcγ receptors. In some embodiments, CD19 binding agents of the present invention include binding agents (e.g., anti-CD19 antibodies or derivatives thereof) that have modifications in amino acid residues that are involved in the interaction between the anti-Fc domain and the FcRn receptor (see, e.g., International Publication No. WO 97/34631, which is incorporated herein by reference in its entirety).

In some embodiments, the binding of a target binding agent to one or more Fcγ receptors can be impaired using one or more antibody engineering approaches known in the art. In some embodiments, the binding of a target binding agent to one or more Fcγ receptors can be impaired by reducing the target binding agent's effector functions using one or more antibody engineering approaches known in the art. Illustrative, non-limiting examples for such approaches are provided below.

Fcγ receptor binding is mediated through the interaction of a region of an antibody with an Fc gamma (Fcγ) receptor (FcγR). The Fc region or domain refers to the region(s) of an antibody constant region (e.g., IgG1, IgG2, IgG3, or IgG4) that is involved in the binding interaction of the Fc region to one or more Fcγ receptors (e.g., FcγRI (CD64), FcγRIIb (CD32b) or FcγRIIIa (CD16). Both the glycosylation status and primary amino acid sequence of the IgG Fc region have functional effects on the Fc region-FcγR interaction.

Substitution of particular amino acid positions in the Fc region of IgG isotype constant regions are known to have functional effects on the ability of an antibody to bind to one or more Fcγ receptors. See, e.g., Shields et al., 2001, *J. Biol. Chem.* 276:6591-6604, and Canfield and Morrison, 1991, *J. Exp. Med.* 173:1483-1491. The Fc region includes, for example and not for limitation, amino acid residues in the hinge region and the $C_H2$ domain. Substitution of one or more amino acid residues in the Fc region or portion of an IgG constant region with non-conservative amino acids can be expected to alter, i.e., reduce or increase the affinity of the Fc region-FcγR interaction. Methods for introducing non-conservative amino acid substitutions are well known in the art.

Alternatively or additionally, cysteine residue(s) may be introduced in or in proximity to the Fc region or portion of an IgG constant region, thereby allowing interchain disulfide bond formation in this region. Such interchain disulfide bond formation can be expected to cause steric hindrance, thereby reducing the affinity of the Fc region-FcγR binding interaction. The cysteine residue(s) introduced in or in proximity to the Fc region of an IgG constant region may also serve as sites for conjugation to therapeutic agents (i.e., coupling cytotoxic drugs using thiol specific reagents such as maleimide derivatives of drugs). The presence of a therapeutic agent can be expected to cause steric hindrance, thereby reducing the affinity of the Fc region-FcγR binding interaction. Methods for introducing cysteine residues in antibodies or derivatives thereof are well known in the art.

Alternatively or additionally, one or more N-linked glycosylation sites may be introduced in or in proximity to the Fc region of an IgG constant region, thereby allowing post-translational glycosylation in this region. Such N-linked glycosylation can be expected to cause steric hindrance, thereby reducing the affinity of the Fc region-FcγR binding interaction. Methods for introducing N-linked glycosylation sites in an antibodies or derivatives thereof are well known in the art.

A systemic substitution of solvent-exposed amino acids of human IgG1 Fc region has generated IgG derivatives with altered FcγR binding affinities (Shields et al., 2001, *J. Biol. Chem.* 276:6591-604). For example, when compared to parental IgG1, a subset of these derivatives involving substitutions at Thr256/Ser298, Ser298/Glu333, Ser298/Lys334, or Ser298/Glu333/Lys334 to Ala demonstrate increases in both binding affinity toward FcγR and ADCC activity (Shields et al., 2001, *J. Biol. Chem.* 276:6591-604; Okazaki et al., 2004, *J. Mol. Biol.* 336:1239-49). In contrast, when compared to parental IgG1, a subset of these derivatives involving substitutions at Glu233 to Pro/Leu234 to Val/Leu235 to Ala and Gly 236 deletion, Pro238 to Ala, Asp265 to Ala, Asn297 to Ala, Ala 327 to Gln, or Pro329 to Ala demonstrate decreases in binding affinities to all FcγR; the Asp265 to Ala substitution also resulted in decreased ADCC activity (Shields et al., 2001, *J. Biol. Chem.* 276:6591-604) Amino acids in the hinge region and the $C_H2$ domain have been shown to contribute to high affinity of human IgG for FcγR (Canfield and Morrison, 1991, *J. Exp. Med.* 173:1483-1491). These amino acid positions, or amino acids in proximity thereto, involved in mediating the Fc region-FcγR binding interaction are potential targets for replacement by non-conservative amino acids and/or introduction of one or more cysteines, and/or introduction of one or more N-linked glycosylation sites.

The in vivo half-life of an antibody can also impact on its effector functions. In some embodiments, it is desirable to increase the half-life of an antibody to modify its therapeutic activities. In some embodiments, it is desirable to decrease the half-life of an antibody to modify its therapeutic activities. FcRn is a receptor that is structurally similar to MHC Class I antigen that non-covalently associates with β2-microglobulin. FcRn regulates the catabolism of IgGs and their transcytosis across tissues (Ghetie and Ward, 2000, *Annu. Rev. Immunol.* 18:739-766; Ghetie and Ward, 2002, *Immunol. Res.* 25:97-113). The IgG-FcRn interaction takes place at pH 6.0 (pH of intracellular vesicles) but not at pH 7.4 (pH of blood); this interaction enables IgGs to be recycled back to the circulation (Ghetie and Ward, 2000, *Ann. Rev. Immunol.* 18:739-766; Ghetie and Ward, 2002, *Immunol. Res.* 25:97-113). The region on human $IgG_1$ involved in FcRn binding has been mapped (Shields et al., 2001, *J. Biol. Chem.* 276:6591-604). Alanine substitutions at positions Pro238, Thr256, Thr307, Gln311, Asp312, Glu380, Glu382, or Asn434 of human $IgG_1$ enhance FcRn binding (Shields et al., 2001, *J. Biol. Chem.* 276:6591-604). $IgG_1$ molecules harboring these substitutions are expected to have longer serum half-lives. Consequently, these modified $IgG_1$ molecules may be able to carry out their effector functions, and hence exert their therapeutic efficacies, over a longer period of time compared to unmodified $IgG_1$.

In some embodiments, the binding agents of the present invention having impaired binding to one or more FcγR retain, at least to some extent, the ability to bind FcRn. In some embodiments, the binding agents, which have impaired binding to one or more FcγR, retain the ability to bind FcRn. The ability of an antibody or derivative thereof or other binding agent to bind to FcRn can be measured by techniques known in the art (e.g., Shields et al., 2001, *J. Biol. Chem.* 276:6591-604).

A CD19 binding agent modified with respect to effector function may, in some embodiments, have improved internalization capability and/or increased complement-mediated cell killing and antibody-dependent cellular cytotoxicity (ADCC). See Caron et al. J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

In certain embodiments, cysteine residue(s) may be introduced in the Fc region in order to affect the binding interaction of the Fc region with the FcγRIIIa receptor. In some embodiments, an amino acid substitution of the native amino acid to a cysteine residue is introduced at amino acid position 239, 265, 269 or 327, according to the Kabat numbering system. In some embodiments, an amino acid substitution of the native amino acid to a cysteine residue is introduced at amino acid position 239 or 269, according to the Kabat numbering system. In some embodiments, an amino acid substitution of the native amino acid to a cysteine residue is introduced at amino acid position 239, according to the Kabat numbering system. In some embodiments, an amino acid substitution of the native amino acid to a cysteine residue is introduced at amino acid position 265, according to the Kabat numbering system. In some embodiments, an amino acid substitution of the native amino acid to a cysteine residue is introduced at amino acid position 269, according to the Kabat numbering system. In some embodiments, an amino acid substitution of the native amino acid to a cysteine residue is introduced at amino acid position 327, according to the Kabat numbering system.

In other embodiments, an amino acid substitution of the native amino acid to a cysteine residue is introduced at amino acid position 236 or 238, according to the Kabat numbering system. In some embodiments, an amino acid substitution of the native amino acid to a cysteine residue is introduced at amino acid position 236, according to the Kabat numbering system. In some embodiments, an amino acid substitution of the native amino acid to a cysteine residue is introduced at amino acid position 238, according to the Kabat numbering system.

In other embodiments, an amino acid substitution of the native amino acid to a cysteine residue is introduced at amino acid position 234, 235, 237, 267, 298, 299, 326, 330, or 332, according to the Kabat numbering system. In other embodiments, an amino acid substitution of the native amino acid to a cysteine residue is introduced at amino acid position 237, 298, 299, 326, 330, or 332, according to the Kabat numbering system. In other embodiments, an amino acid substitution of the native amino acid to a cysteine residue is introduced at amino acid position 298, 299, 326 or 330, according to the Kabat numbering system. In some embodiments, an amino acid substitution of the native amino acid to a cysteine residue is introduced at amino acid position 234, according to the Kabat numbering system. In some embodiments, an amino acid substitution of the native amino acid to a cysteine residue is introduced at amino acid position 235, according to the Kabat numbering system. In some embodiments, an amino acid substitution of the native amino acid to a cysteine residue is introduced at amino acid position 237, according to the Kabat numbering system. In some embodiments, an amino acid substitution of the native amino acid to a cysteine residue is introduced at amino acid position 267, according to the Kabat numbering system. In some embodiments, an amino acid substitution of the native amino acid to a cysteine residue is introduced at amino acid position 298, according to the Kabat numbering system. In some embodiments, an amino acid substitution of the native amino acid to a cysteine residue is introduced at amino acid position 299, according to the Kabat numbering system. In some embodiments, an amino acid substitution of the native amino acid to a cysteine residue is introduced at amino acid position 326, according to the Kabat numbering system. In some embodiments, an amino acid substitution of the native amino acid to a cysteine residue is introduced at amino acid position 330, according to the Kabat numbering system. In some embodiments, an amino acid substitution of the native amino acid to a cysteine residue is introduced at amino acid position 332, according to the Kabat numbering system.

In some embodiments, to further increase the serum half life of a CD19 binding agent of the present invention, a salvage receptor binding epitope of the binding agent may be modified as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. Alternatively, the serum half-life of a CD19 binding agent may be increased by modifying the Fc region of an antibody (e.g., IgG constant domain) with respect to binding to Fc gamma (Fcγ) receptors, as described infra.

Antibodies may be glycosylated at conserved positions in their constant regions (see, e.g., Jefferis and Lund, 1997, Chem. Immunol. 65:111-128; Wright and Morrison, 1997, TibTECH 15:26-32). The oligosaccharide side chains of the immunoglobulins can affect the protein's function (see, e.g., Boyd et al., 1996, Mol. Immunol. 32:1311-1318; Wittwe and Howard, 1990, Biochem. 29:4175-4180), and the intramolecular interaction between portions of the glycoprotein which can affect the conformation and presented three-dimensional surface of the glycoprotein (see, e.g., Jefferis and Lund, supra; Wyss and Wagner, 1996, Current Opin. Biotech. 7:409-416). Oligosaccharides may also serve to target a given glycoprotein to certain molecules based upon specific recognition structures. For example, it has been reported that in agalactosylated IgG, the oligosaccharide moiety 'flips' out of the inter-$C_H2$ space and terminal N-acetylglucosamine residues become available to bind mannose binding protein (see, e.g., Malhotra et al., 1995, Nature Med. 1:237-243). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., 1996, Mol. Immunol. 32:1311-1318), while selective removal of sialic acid residues using neuraminidase resulted in no loss of DMCL. Glycosylation of antibodies has also been reported to affect ADCC. In particular, CHO cells with tetracycline-regulated expression of β(1, 4)-N-acetylglucosaminyltransferase III (GnTIII), a glycosyltransferase catalyzing formation of bisecting GlcNAc, was reported to have improved ADCC activity (see, e.g., Umana et al., 1999, Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Glycosylation derivatives of antibodies are derivatives in which the glycosylation pattern of an antibody is altered. Certain antibodies of the present invention have altered glycosylation patterns. By altering is meant deleting one or more carbohydrate moieties found in the antibody, adding one or more carbohydrate moieties to the antibody, changing the composition of glycosylation (i.e., glycosylation pattern), the extent of glycosylation, or the like. In certain embodiments, the antibodies of the present invention have reduced core fucosylation.

Addition of glycosylation sites to the antibody can be conveniently accomplished, for example, by altering the amino acid sequence such that it contains one or more of the above-described tripeptide sequences (for N-linked glycosylation sites). The alteration may also be made, for example, by the addition of, or substitution by, one or more serine or threonine residues to the sequence of the original antibody (for O-linked glycosylation sites). Similarly, removal of glycosylation sites can be accomplished by amino acid alteration within the native glycosylation sites of the antibody.

The amino acid sequence is usually altered by altering the underlying nucleic acid sequence. These methods include, but are not limited to, isolation from a natural source (in the case of naturally-occurring amino acid sequence derivatives) or preparation by oligonucleotide-mediated (or site-directed) mutagenesis, PCR mutagenesis, or cassette mutagenesis of an earlier prepared derivative or a non-derivative version of the antibody.

The glycosylation (including glycosylation pattern) of antibodies may also be altered without altering the amino acid sequence or the underlying nucleotide sequence. Glycosylation largely depends on the host cell used to express the antibody. Since the cell type used for expression of recombinant glycoproteins, e.g., antibodies, as potential therapeutics is rarely the native cell, significant variations in the glycosylation pattern of the antibodies can be expected. See, e.g., Hse et al., 1997, J. Biol. Chem. 272:9062-9070. In addition to the choice of host cells, factors which affect glycosylation during recombinant production of antibodies include growth mode, media formulation, culture density, oxygenation, pH, purification schemes, and the like. Various methods have been proposed to alter the glycosylation pattern achieved in a particular host organism, including introducing or overexpressing certain enzymes involved in oligosaccharide production (see, e.g., U.S. Pat. Nos. 5,047,335; 5,510,261; and 5,278,299). Glycosylation, or certain types of glycosylation, can be enzymatically removed from the glycoprotein, for example using endoglycosidase H (Endo H). In addition, the recombinant host cell can be genetically engineered, e.g., made defective in processing certain types of polysaccharides. These and similar techniques are well known in the art.

The glycosylation structure of antibodies can be readily analyzed by conventional techniques of carbohydrate analysis, including lectin chromatography, NMR, mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

The following table provides a summary of the regions of chimeric and humanized BU12 to which each sequence identifier (SEQ ID NO.) corresponds.

| MOLECULE | Nucleotide or Amino Acid | SEQ ID NO |
|---|---|---|
| Leader Sequence (Heavy Chain Region) | Amino Acid | 1 |
| Heavy Chain Variable Region (VH2-70/$J_H$4 germline)/Also referred to as Variant HA | Amino Acid | 2 |
| Heavy Chain Constant domain (IgG$_1$) | Amino Acid | 3 |
| Variant HB Heavy Chain Variable Region (VH2-70/$J_H$4 germline) | Amino Acid | 4 |
| Variant HC Heavy Chain Variable Region (VH2-70/$J_H$4 germline) | Amino Acid | 5 |
| Variant HD Heavy Chain Variable Region (VH2-70/$J_H$4 germline) | Amino Acid | 6 |
| Variant HE Heavy Chain Variable Region (VH2-70/$J_H$4 germline) | Amino Acid | 7 |
| Heavy Chain Variable Region (Murine) | Amino Acid | 8 |
| Heavy Chain Variable Region (VH4-31/$J_H$4 germline)/also referred to as Variant HF | Amino Acid | 9 |
| Variant HG Heavy Chain Variable Region (VH4-31/$J_H$4 germline) | Amino Acid | 10 |
| Variant HH Heavy Chain Variable Region (VH4-31/$J_H$4 germline) | Amino Acid | 11 |
| Variant HI Heavy Chain Variable Region (VH4-31/$J_H$4 germline) | Amino Acid | 12 |
| Variant HJ Heavy Chain Variable Region (VH4-31/$J_H$4 germline) | Amino Acid | 13 |
| Variant HK Heavy Chain Variable Region (VH4-31/$J_H$4 germline) | Amino Acid | 14 |
| Variant HL Heavy Chain Variable Region (VH4-31/$J_H$4 germline) | Amino Acid | 15 |
| Leader Sequence (Light Chain Region) | Amino Acid | 16 |
| Light Chain Variable Region (VL-L6/$J_k$2 germline)/Also referred to as Variant LA | Amino Acid | 17 |
| Light Chain Constant domain (Kappa domain) | Amino Acid | 18 |
| Variant LB Light Chain Variable Region (VL-L6/$J_k$2 germline) | Amino Acid | 19 |
| Variant LC Light Chain Variable Region (VL-L6/$J_k$2 germline) | Amino Acid | 20 |
| Variant LD Light Chain Variable Region (VL-L6/$J_k$2 germline) | Amino Acid | 21 |
| Variant LE Light Chain Variable Region (VL-L6/$J_k$2 germline) | Amino Acid | 22 |
| Variant LF Light Chain Variable Region (VL-L6/$J_k$2 germline) | Amino Acid | 23 |
| Variant LG Light Chain Variable Region (VL-L6/$J_k$2 germline) | Amino Acid | 24 |
| Light Chain Variable Region (Murine) | Amino Acid | 25 |
| Light Chain Variable Region (VL-A10/$J_k$2 germline)/Also referred to as Variant LH domain | Amino Acid | 26 |
| Variant LI Light Chain Variable Region (VL-A10/$J_k$2 germline) | Amino Acid | 27 |
| Consensus sequence for Heavy Chain Variable Region (VH2-70/$J_H$4 germline) | Amino Acid | 28 |
| Consensus sequence for Heavy Chain Variable Region (VH4-31/$J_H$4 germline) | Amino Acid | 29 |
| Consensus sequence for Light Chain Variable Region (VL-L6/$J_k$2 germline) | Amino Acid | 30 |
| Consensus sequence for Light Chain Variable Region (VL-A10/$J_k$2 germline) | Amino Acid | 31 |
| Consensus sequence for Heavy Chain Variable Region (VH2-70/$J_H$1-6 germline) | Amino Acid | 32 |
| Consensus sequence for Heavy Chain Variable Region (VH4-31/$J_H$1-6 germline) | Amino Acid | 33 |
| Consensus sequence for Light Chain Variable Region (VL-L6/$J_k$1-5 germline) | Amino Acid | 34 |
| Consensus sequence for Light Chain Variable Region (VL-A10/$J_k$1-5 germline) | Amino Acid | 35 |
| Heavy Chain Constant Domain (IgG$_2$) | Amino Acid | 36 |
| Heavy Chain Constant Domain (IgG$_3$) | Amino Acid | 37 |
| Heavy Chain Constant Domain (IgG$_4$) | Amino Acid | 38 |
| Heavy Chain Constant Domain Variant (IgG$_1$V$_1$) | Amino Acid | 39 |
| Leader Sequence (Heavy Chain Region) | Nucleotide | 40 |
| Heavy Chain Variable Region (VH4-31/$J_H$4 germline)/also referred to as Variant HF | Nucleotide | 41 |
| Heavy Chain Constant domain (IgG$_1$) | Nucleotide | 42 |
| Leader Sequence (Light Chain Region) | Nucleotide | 43 |
| Variant LG Light Chain Variable Region (VL-L6/$J_k$2 germline) | Nucleotide | 44 |
| Light Chain Constant domain (Kappa domain) | Nucleotide | 45 |
| Heavy Chain CDR1 | Amino Acid | 46 |
| Heavy Chain CDR2 | Amino Acid | 47 |
| Heavy Chain CDR3 | Amino Acid | 48 |
| Light Chain CDR1 | Amino Acid | 49 |
| Light Chain CDR2 | Amino Acid | 50 |
| Light Chain CDR3 | Amino Acid | 51 |
| Alternative Heavy Chain Sequence (including leader, variable region (Variant HF), and constant domain) | Nucleotide | 53 |
| Alternative Leader Sequence (Heavy Chain Region) | Nucleotide | 54 |
| Alternative Heavy Chain Constant Domain (IgG1) | Nucleotide | 55 |
| Alternative Heavy Chain Sequence (including leader, variable region (Variant HF), and constant domain) | Amino Acid | 56 |
| Alternative Leader Sequence (Heavy Chain Region) | Amino Acid | 57 |
| Alternative Light Chain Sequence (including leader, variable region (Variant LG), and constant domain) | Nucleotide | 58 |
| Alternative Leader Sequence (Light Chain Region) | Nucleotide | 59 |
| Alternative Light Chain Sequence (including leader, variable region (Variant LG), and constant domain) | Amino Acid | 60 |
| Alternative Leader Sequence (Light Chain Region) | Amino Acid | 61 |

The present invention encompasses embodiments wherein the CD19 binding agent comprises a heavy chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:2. The amino acid sequence can be, for example, the amino acid sequence of SEQ ID NO:2 having any number of substitutions provided that the CD19 binding agent retains functional activity (i.e., CD19 binding activity) and that the sequence retains substantial or complete identity to the amino acid sequence set forth in SEQ ID NO:2. Exemplary heavy chain variable regions comprise an amino acid sequence that is identical to the amino acid sequence set forth in SEQ ID NO:2 optionally having at least one amino acid substitution, preferably 0, 1 or 2 amino acid substitutions, at positions 75, 79, 81, 82, 82A, 82B, 82C or 89 of the amino acid sequence set forth in SEQ ID NO:2, according to the Kabat numbering systems. Exemplary sequences include, for example, the amino acid sequences set forth in SEQ ID NOs:2, 4, 5, 6, and 7. In one aspect, the CD19 binding agent that comprises a heavy chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:2 comprises the CDR regions of the antibody mBU12, i.e., SEQ ID NO:46, 47, and 48.

The present invention encompasses embodiments wherein the CD19 binding agent comprises a heavy chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:9. The amino acid sequence can be, for example, the amino acid sequence of SEQ ID NO:9 having any number of substitutions provided that the CD19 binding agent retains functional activity and that the sequence retains substantial or complete identity to the amino acid sequence set forth in SEQ ID NO:9. Exemplary heavy chain variable regions comprise an amino acid sequence that is identical to the amino acid sequence set forth in SEQ ID NO:9 optionally having at least one amino acid substitution, preferably 0, 1 or 2 amino acid substitutions, at positions 24, 27, 29, 71, 75, 78, 79, or 89 of the amino acid sequence set forth in SEQ ID NO:9, according to the Kabat numbering systems. Exemplary sequences include, for example, the amino acid sequences set forth in SEQ ID NOs: 9, 10, 11, 12, 13, 14, and 15. In one aspect, the CD19 binding agent that comprises a heavy chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:9 comprises the CDR regions of antibody mBU12, i.e., SEQ ID NO:46, 47, and 48.

The present invention encompasses embodiments wherein the CD19 binding agent comprises a light chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:17. The amino acid sequence can be, for example, the amino acid sequence of SEQ ID NO:17 having any number of substitutions provided that the CD19 binding agent retains functional activity and that the sequence retains substantial or complete identity to the amino acid sequence set forth in SEQ ID NO:17. Exemplary light chain variable regions comprise an amino acid sequence that is identical to the amino acid sequence set forth in SEQ ID NO:17 optionally having at least one amino acid substitution, preferably 0, 1 or 2 amino acid substitutions, at positions 2, 40, 41, 42, 69, 70, 71, 72 and 83 of the amino acid sequence set forth in SEQ ID NO:17, according to the Kabat numbering systems. Exemplary sequences include, for example, the amino acid sequences set forth in SEQ ID NOs:17, 19, 20, 21, 22, 23, and 24. In one aspect, the CD19 binding agent that comprises a light chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:17 comprises the CDR regions of the antibody mBU12, i.e., SEQ ID NO:49 50, and 51.

The present invention encompasses embodiments wherein the CD19 binding agent comprises a light chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:26. The amino acid sequence can be, for example, the amino acid sequence of SEQ ID NO:26 having any number of substitutions provided that the CD19 binding agent retains functional activity and that the sequence retains substantial or complete identity to the amino acid sequence set forth in SEQ ID NO:26. Exemplary light chain variable regions comprise an amino acid sequence that is identical to the amino acid sequence set forth in SEQ ID NO:26 optionally having at least one amino acid substitution at positions 2 and 71 of the amino acid sequence set forth in SEQ ID NO:26, according to the Kabat numbering systems. Exemplary sequences include, for example, the amino acid sequences set forth in SEQ ID NOs: 26 and 27. In one aspect, the CD19 binding agent that comprises a light chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:26 comprises the CDR regions of the antibody mBU12, i.e., SEQ ID NO:49, 50, and 51.

The present invention encompasses embodiments wherein the CD19 binding agent comprises a heavy chain variable region comprising an amino acid sequence that is identical or substantially identical (i.e., having at least 90%, 91%, 92%, 93%, 94%, 95%, 96%, 97%, 98%, 99%, or 100% identity) to SEQ ID NO:2 as provided above, and further comprises a light chain variable region comprising an amino acid sequence that is identical or substantially identical (i.e., having at least 90%, 91%, 92%, 93%, 94%, 95%, 96%, 97%, 98%, 99%, or 100% identity) to SEQ ID NO:17, as provided above. In any of these embodiments, the heavy chain variable region can be joined to a constant region and the light chain variable region can be joined to a constant region. In some embodiments, the heavy chain constant region will comprise the amino acid sequence set forth in SEQ ID NOs:3, or 36-39. In some embodiments, the light chain constant region will comprise the amino acid sequence set forth in SEQ ID NO:18. In certain embodiments, the heavy chain variable region will further comprise the amino acid sequence set forth in SEQ ID NO:1 or SEQ ID NO:57 and the light chain variable region will further comprise the amino acid sequence set forth in SEQ ID NO:16 or SEQ ID NO:61.

Accordingly, in certain embodiments, the CD19 binding agent will comprise a heavy chain comprising the amino acid sequence set forth in SEQ ID NO:2 and a light chain comprising the amino acid sequence set forth in SEQ ID NO: 17, 19, 20, 21, 22, 23 or 24; a heavy chain comprising the amino acid sequence set forth in SEQ ID NO:4 and a light chain comprising the amino acid sequence set forth in SEQ ID NO: 17, 19, 20, 21, 22, 23 or 24; a heavy chain comprising the amino acid sequence set forth in SEQ ID NO:5 and a light chain comprising the amino acid sequence set forth in SEQ ID NO: 17, 19, 20, 21, 22, 23 or 24; a heavy chain comprising the amino acid sequence set forth in SEQ ID NO:6 and a light chain comprising the amino acid sequence set forth in SEQ ID NO: 17, 19, 20, 21, 22, 23 or 24; or a heavy chain comprising the amino acid sequence set forth in SEQ ID NO:7 and a light chain comprising the amino acid sequence set forth in SEQ ID NO: 17, 19, 20, 21, 22, 23 or 24. In any of these embodiments, the heavy chain variable region can be joined to a constant region and the light chain variable region can be joined to a constant region. In some embodiments, the heavy chain constant region will comprise the amino acid sequence set forth in SEQ ID NOs:3, or 36-39. In some embodiments, the light chain constant region will comprise the amino acid sequence set forth in SEQ ID NO:18. In certain embodiments, the heavy chain variable region will further comprise the amino acid sequence set forth in SEQ ID NO:1 or SEQ ID NO:57 and the light chain variable region will further comprise the amino acid sequence set forth in SEQ ID NO:16 or SEQ ID NO:61.

The present invention encompasses embodiments wherein the CD19 binding agent comprises a heavy chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:2 as provided above, and further comprises a light chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:26, as provided above. In any of these embodiments, the heavy chain variable region can be joined to a constant region and the light chain variable region can be joined to a constant region. In some embodiments, the heavy chain constant region will comprise the amino acid sequence set forth in SEQ ID NOs:3, or 36-39. In some embodiments, the light chain constant region will comprise the amino acid sequence set forth in SEQ ID NO:18. In certain embodiments, the heavy chain variable region will further comprise the amino acid sequence set forth in SEQ ID NO:1 or SEQ ID NO:57 and the light chain variable region will further comprise the amino acid sequence set forth in SEQ ID NO:16 or SEQ ID NO:61.

Accordingly, in certain embodiments, the CD19 binding agent will comprise a heavy chain comprising the amino acid sequence set forth in SEQ ID NO:2 and a light chain comprising the amino acid sequence set forth in SEQ ID NO: 26 or 27; a heavy chain comprising the amino acid sequence set forth in SEQ ID NO:4 and a light chain comprising the amino acid sequence set forth in SEQ ID NO: 26 or 27; a heavy chain comprising the amino acid sequence set forth in SEQ ID NO:5 and a light chain comprising the amino acid sequence set forth in SEQ ID NO: 26 or 27; a heavy chain comprising the amino acid sequence set forth in SEQ ID NO:6 and a light chain comprising the amino acid sequence set forth in SEQ ID NO: 26 or 27; or a heavy chain comprising the amino acid sequence set forth in SEQ ID NO:7 and a light chain comprising the amino acid sequence set forth in SEQ ID NO: 26 or 27. In any of these embodiments, the heavy chain variable region can be joined to a constant region and the light chain variable region can be joined to a constant region. In some embodiments, the heavy chain constant region will comprise the amino acid sequence set forth in SEQ ID NOs:3, or 36-39. In some embodiments, the light chain constant region will comprise the amino acid sequence set forth in SEQ ID NO:18. In certain embodiments, the heavy chain variable region will further comprise the amino acid sequence set forth in SEQ ID NO:1 or SEQ ID NO:57 and the light chain variable region will further comprise the amino acid sequence set forth in SEQ ID NO:16 or SEQ ID NO:61.

The present invention encompasses embodiments wherein the CD19 binding agent comprises a heavy chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:9 as provided above, and further comprises a light chain variable region comprising an amino acid sequence that is identical or substantially identical (i.e., having at least 90%, 91%, 92%, 93%, 94%, 95%, 96%, 97%, 98%, 99%, or 100% identity) to SEQ ID NO:17, as provided above. In any of these embodiments, the heavy chain variable region can be joined to a constant region and the light chain variable region can be joined to a constant region. In some embodiments, the heavy chain constant region will comprise the amino acid sequence set forth in SEQ ID NOs:3, or 36-39. In some embodiments, the light chain constant region will comprise the amino acid sequence set forth in SEQ ID NO:18. In certain embodiments, the heavy chain variable region will further comprise the amino acid sequence set forth in SEQ ID NO:1 or SEQ ID NO:57 and the light chain variable region will further comprise the amino acid sequence set forth in SEQ ID NO:16 or SEQ ID NO:61.

Accordingly, in certain embodiments, the CD19 binding agent will comprise a heavy chain comprising the amino acid sequence set forth in SEQ ID NO:9 and a light chain comprising the amino acid sequence set forth in SEQ ID NO: 17, 19, 20, 21, 22, 23 or 24; a heavy chain comprising the amino acid sequence set forth in SEQ ID NO:10 and a light chain comprising the amino acid sequence set forth in SEQ ID NO: 17, 19, 20, 21, 22, 23 or 24; a heavy chain comprising the amino acid sequence set forth in SEQ ID NO:11 and a light chain comprising the amino acid sequence set forth in SEQ ID NO: 17, 19, 20, 21, 22, 23 or 24; a heavy chain comprising the amino acid sequence set forth in SEQ ID NO:12 and a light chain comprising the amino acid sequence set forth in SEQ ID NO: 17, 19, 20, 21, 22, 23 or 24; a heavy chain comprising the amino acid sequence set forth in SEQ ID NO:13 and a light chain comprising the amino acid sequence set forth in SEQ ID NO: 17, 19, 20, 21, 22, 23 or 24 a heavy chain comprising the amino acid sequence set forth in SEQ ID NO:14 and a light chain comprising the amino acid sequence set forth in SEQ ID NO: 17, 19, 20, 21, 22, 23 or 24 or a heavy chain comprising the amino acid sequence set forth in SEQ ID NO:15 and a light chain comprising the amino acid sequence set forth in SEQ ID NO: 17, 19, 20, 21, 22, 23 or 24. In any of these embodiments, the heavy chain variable region can be joined to a constant region and the light chain variable region can be joined to a constant region. In some embodiments, the heavy chain constant region will comprise the amino acid sequence set forth in SEQ ID NOs:3, or 36-39. In some embodiments, the light chain constant region will comprise the amino acid sequence set forth in SEQ ID NO:18. In certain embodiments, the heavy chain variable region will further comprise the amino acid sequence set forth in SEQ ID NO:1 or SEQ ID NO:57 and the light chain variable region will further comprise the amino acid sequence set forth in SEQ ID NO:16 or SEQ ID NO:61.

The present invention encompasses embodiments wherein the CD19 binding agent comprises a heavy chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:9 as provided above, and further comprises a light chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:26, as provided above. In any of these embodiments, the heavy chain variable region can be joined to a constant region and the light chain variable region can be joined to a constant region. In some embodiments, the heavy chain constant region will comprise the amino acid sequence set forth in SEQ ID NOs:3, or 36-39. In some embodiments, the light chain constant region will comprise the amino acid sequence set forth in SEQ ID NO:18. In certain embodiments, the heavy chain variable region will further comprise the amino acid sequence set forth in SEQ ID NO:1 or SEQ ID NO:57 and the light chain variable region will further comprise the amino acid sequence set forth in SEQ ID NO:16 or SEQ ID NO:61.

Accordingly, in certain embodiments, the CD19 binding agent will comprise a heavy chain comprising the amino acid sequence set forth in SEQ ID NO:9 and a light chain comprising the amino acid sequence set forth in SEQ ID NO: 26 or 27; a heavy chain comprising the amino acid sequence set forth in SEQ ID NO:10 and a light chain comprising the amino acid sequence set forth in SEQ ID NO: 26 or 27; a heavy chain comprising the amino acid sequence set forth in SEQ ID NO:11 and a light chain comprising the amino acid sequence set forth in SEQ ID NO: 26 or 27; a heavy chain comprising the amino acid sequence set forth in SEQ ID NO:12 and a light chain comprising the amino acid sequence set forth in SEQ ID NO: 26 or 27; a heavy chain comprising the amino acid sequence set forth in SEQ ID NO:13 and a light chain comprising the amino acid sequence set forth in SEQ ID NO: 26 or 27; heavy chain comprising the amino acid sequence set forth in SEQ ID NO:14 and a light chain comprising the amino acid sequence set forth in SEQ ID NO: 26 or 27; or a heavy chain comprising the amino acid sequence set forth in SEQ ID NO:15 and a light chain comprising the amino acid sequence set forth in SEQ ID NO: 26 or 27. In any of these embodiments, the heavy chain variable region can be joined to a constant region and the light chain variable region can be joined to a constant region. In some embodiments, the heavy chain constant region will comprise the amino acid sequence set forth in SEQ ID NOs:3, or 36-39. In some embodiments, the light chain constant region will comprise the amino acid sequence set forth in SEQ ID NO:18. In certain embodiments, the heavy chain variable region will further comprise the amino acid sequence set forth in SEQ ID NO:1 or SEQ ID NO:57 and the light chain variable region will further comprise the amino acid sequence set forth in SEQ ID NO:16 or SEQ ID NO:61.

The present invention encompasses embodiments wherein the CD19 binding agent comprises a heavy chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:28 or SEQ ID NO:32. The amino acid sequence can be, for example, the amino acid consensus sequence of SEQ ID NO:28 or SEQ ID NO:32 having any number of substitutions provided that the CD19 binding agent retains functional activity (i.e., CD19 binding activity) and that the sequence retains substantial or complete identity to the amino acid consensus sequence set forth in SEQ ID NO:28 or SEQ ID NO:32, respectively.

The present invention encompasses embodiments wherein the CD19 binding agent comprises a heavy chain variable region comprising an amino acid sequence that is identical or substantially identical (i.e., having at least 90%, 91%, 92%, 93%, 94%, 95%, 96%, 97%, 98%, 99%, or 100% identity) to the amino acid consensus sequence set forth in SEQ ID NO:29 or SEQ ID NO:33. The amino acid sequence can be, for example, the amino acid sequence of SEQ ID NO:29 or SEQ ID NO:33 having any number of substitutions provided that the CD19 binding agent retains functional activity and that the sequence retains substantial or complete identity to the amino acid consensus sequence set forth in SEQ ID NO: 29 or SEQ ID NO:33, respectively.

The present invention encompasses embodiments wherein the CD19 binding agent comprises a light chain variable region comprising an amino acid sequence that is identical or substantially identical (i.e., having at least 90%, 91%, 92%, 93%, 94%, 95%, 96%, 97%, 98%, 99%, or 100% identity) to the amino acid consensus sequence set forth in SEQ ID NO:30 or SEQ ID NO:34. The amino acid sequence can be, for example, the amino acid sequence of SEQ ID NO: 30 or SEQ ID NO:34 having any number of substitutions provided that the CD19 binding agent retains functional activity and that the sequence retains substantial or complete identity to the amino acid consensus sequence set forth in SEQ ID NO: 30 or SEQ ID NO:34, respectively.

The present invention encompasses embodiments wherein the CD19 binding agent comprises a light chain variable region comprising an amino acid sequence that is identical or substantially identical (i.e., having at least 90%, 91%, 92%, 93%, 94%, 95%, 96%, 97%, 98%, 99%, or 100% identity) to the amino acid consensus sequence set forth in SEQ ID NO:31 or SEQ ID NO:35. The amino acid sequence can be, for example, the amino acid sequence of SEQ ID NO:31 or SEQ ID NO:35 having any number of substitutions provided that the CD19 binding agent retains functional activity and that the sequence retains substantial or complete identity to the amino acid consensus sequence set forth in SEQ ID NO: 31 or SEQ ID NO:35, respectively.

The present invention encompasses embodiments wherein the CD19 binding agent comprises a heavy chain variable region comprising an amino acid sequence that is identical or substantially identical (i.e., having at least 90%, 91%, 92%, 93%, 94%, 95%, 96%, 97%, 98%, 99%, or 100% identity) to SEQ ID NO:28 or SEQ ID NO:32 as provided above, and further comprises a light chain variable region comprising an amino acid sequence that is identical or substantially identical (i.e., having at least 90%, 91%, 92%, 93%, 94%, 95%, 96%, 97%, 98%, 99%, or 100% identity) to SEQ ID NO:30 or SEQ ID NO:34, as provided above.

The present invention encompasses embodiments wherein the CD19 binding agent comprises a heavy chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:28 or SEQ ID NO:32 as provided above, and further comprises a light chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:31 or SEQ ID NO:35, as provided above.

The present invention encompasses embodiments wherein the CD19 binding agent comprises a heavy chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:29 or SEQ ID NO:33 as provided above, and further comprises a light chain variable region comprising an amino acid sequence that is identical or substantially identical (i.e., having at least 90%, 91%, 92%, 93%, 94%, 95%, 96%, 97%, 98%, 99%, or 100% identity) to SEQ ID NO:30 or SEQ ID NO:34 as provided above.

The present invention encompasses embodiments wherein the CD19 binding agent comprises a heavy chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:29 or SEQ ID NO:33 as provided above, and further comprises a light chain variable region comprising an amino acid sequence that is identical or substantially identical (i.e., having at least 90%, 91%, 92%, 93%, 94%, 95%, 96%, 97%, 98%, 99%, or 100% identity) to the amino acid sequence set forth in SEQ ID NO:31 or SEQ ID NO:35, as provided above.

In some embodiments, a CD19 binding agent of the present comprises a humanized antibody. A humanized antibody comprising a heavy chain variable region of SEQ ID NO:9 and a light chain variable region of SEQ ID NO:17 has all six intact CDRs from the mouse BU12 antibody and entirely human variable region framework amino acids. In contrast to many other humanized antibodies, such an antibody has useful binding affinity to its antigen even without any further substitutions. However, such an antibody also provides a starting point for making variants. Some such variants comprise a heavy chain variable region having at least 90% sequence identity (spanning its entire length) to SEQ ID NO:9 and a light chain variable region having at least 90% sequence identity to SEQ ID NO:17. Some variants have no more than 5, 4, 3, 2 or 1 amino acids that differ from SEQ ID NO:9 in the heavy chain variable region and no more than 5, 4, 3, 2, or 1 amino acids that differ from SEQ ID NO:17 in the light chain variable region.

Figure 2:
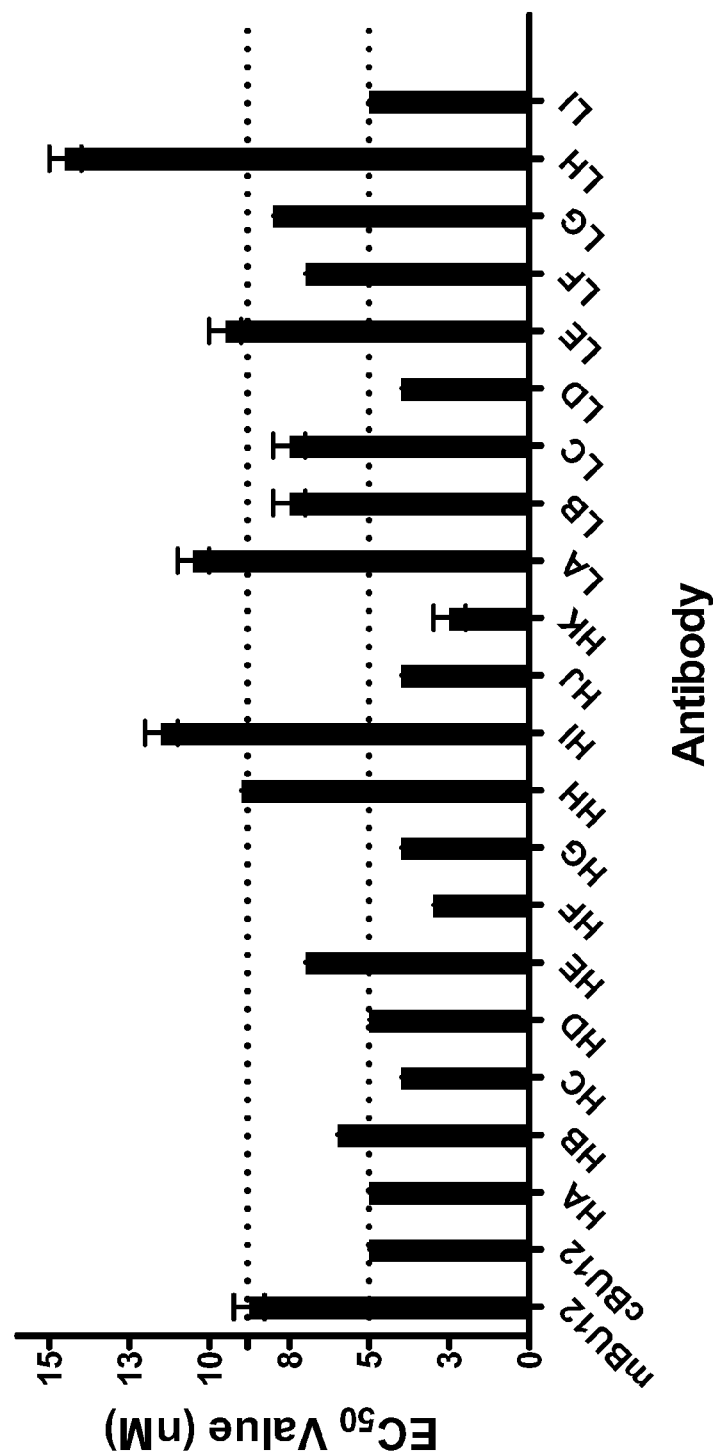
FIG. 2: Binding Analysis of heavy and light chain variable regions to CD19.
Figure 3:
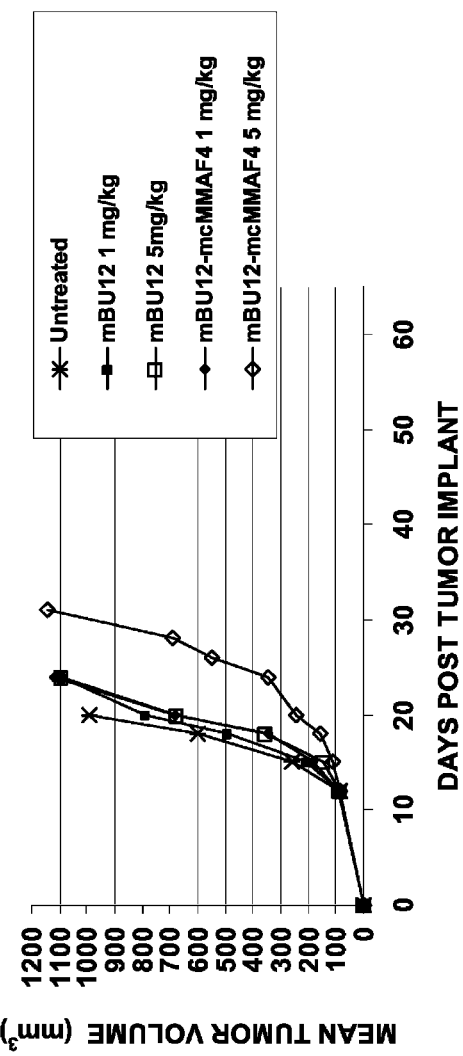
FIG. 3: Antitumor activity of naked mBU12 antibody and mBU12-mcMMAF on Ramos xenograft SCID model. Groups of mice (5/group) were untreated or received mBU12 naked antibody (1 mg/kg), mBU12 naked antibody (5 mg/kg), mBU12-mcMMAF4 (1 mg/kg) and mBU12-mcMMAF4 (5 mg/kg) when tumor sizes averaged approximately 100 mm$^3$. The dose schedule was q4dx3.
Figure 4:
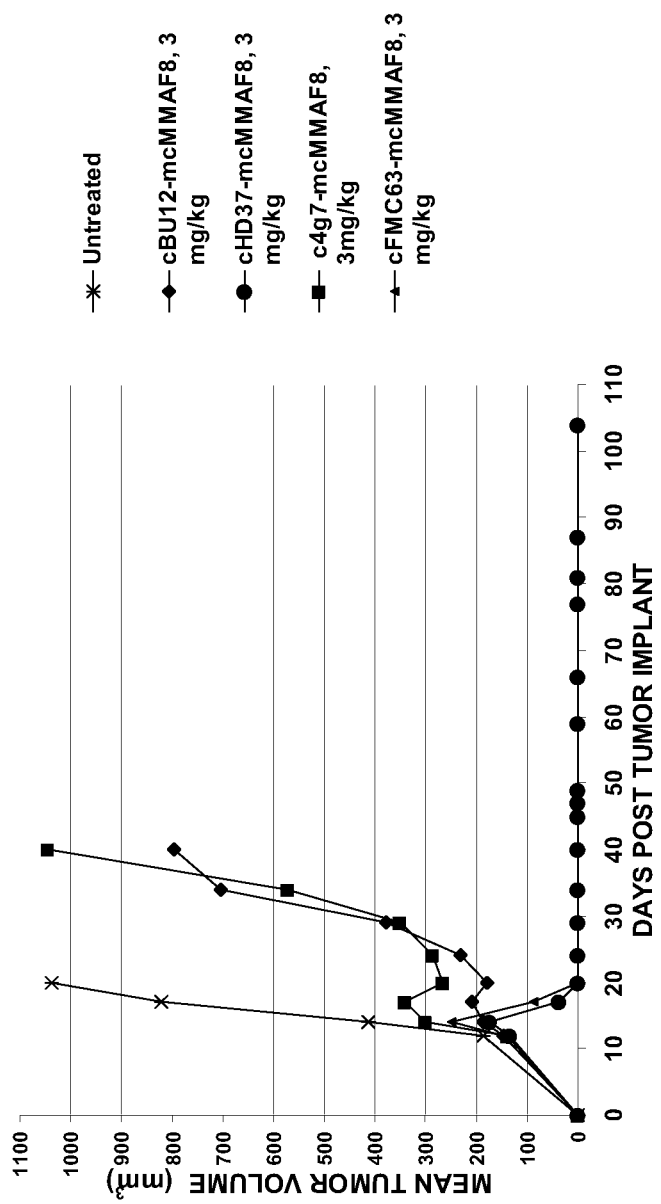
FIG. 4: Antitumor activity of anti-CD19 antibody-drug conjugates on Ramos tumor model in SCID mice. Groups of mice (5/group) were untreated or treated with cBU12-mcMMAF8 (3 mg/kg; complete response 1/5 mice), cHD37-mcMMAF8 (3 mg/kg; complete response 5/5 mice), c4g7-mcMMAF8 (3 mg/kg; complete response 0/5 mice), or cFMC63-mcMMAF8 (3 mg/kg; complete response 5/5 mice) when tumor size averaged approximately 100 mm$^3$. The dose schedule was q4dx3 iv. In a CR response, the tumor volume is less than 13.5 mm$^3$ for three consecutive measurements during the course of the study.
Figure 5:
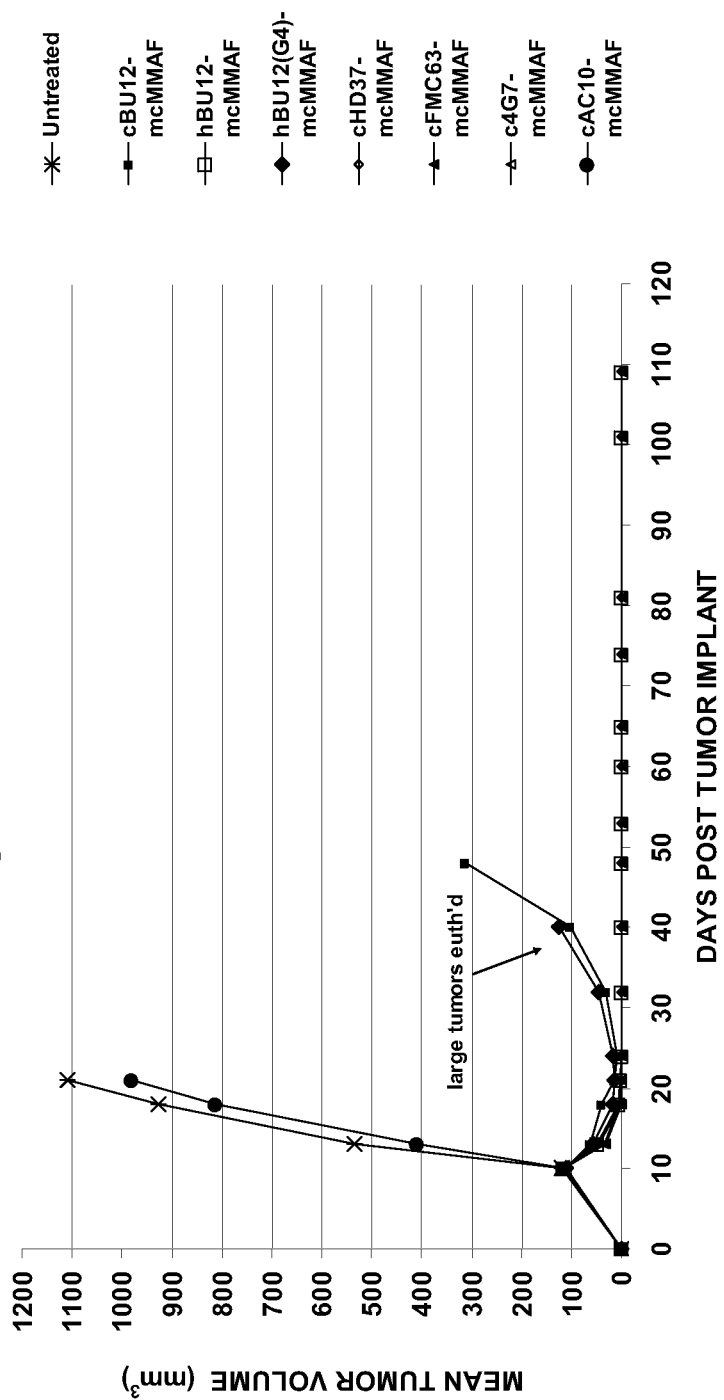
FIG. 5: Antitumor activity of anti-CD19 antibody-drug conjugates on Ramos tumor model in SCID mice. Groups of mice (10/group) were untreated or treated with cBU12-mcMMAF8 (3 mg/kg; complete response 6/10 mice), hBU12-mcMMAF8 (3 mg/kg; complete response 10/10 mice; IgG$_1$ constant region),), hBU12-mcMMAF8 (3 mg/kg; complete response 6/10 mice; IgG$_4$ constant region),), cHD37-mcMMAF8 (3 mg/kg; complete response 10/10 mice), cFMC63-mcMMAF8 (3 mg/kg; complete response 10/10 mice), c4G7-mcMMAF8 (3 mg/kg; complete response 10/10 mice), or cAC10-mcMMAF8 (3 mg/kg; complete response 0/10 mice) when tumor size averaged approximately 100 mm$^3$. The dose schedule was q4dx4 iv.
Figure 6:
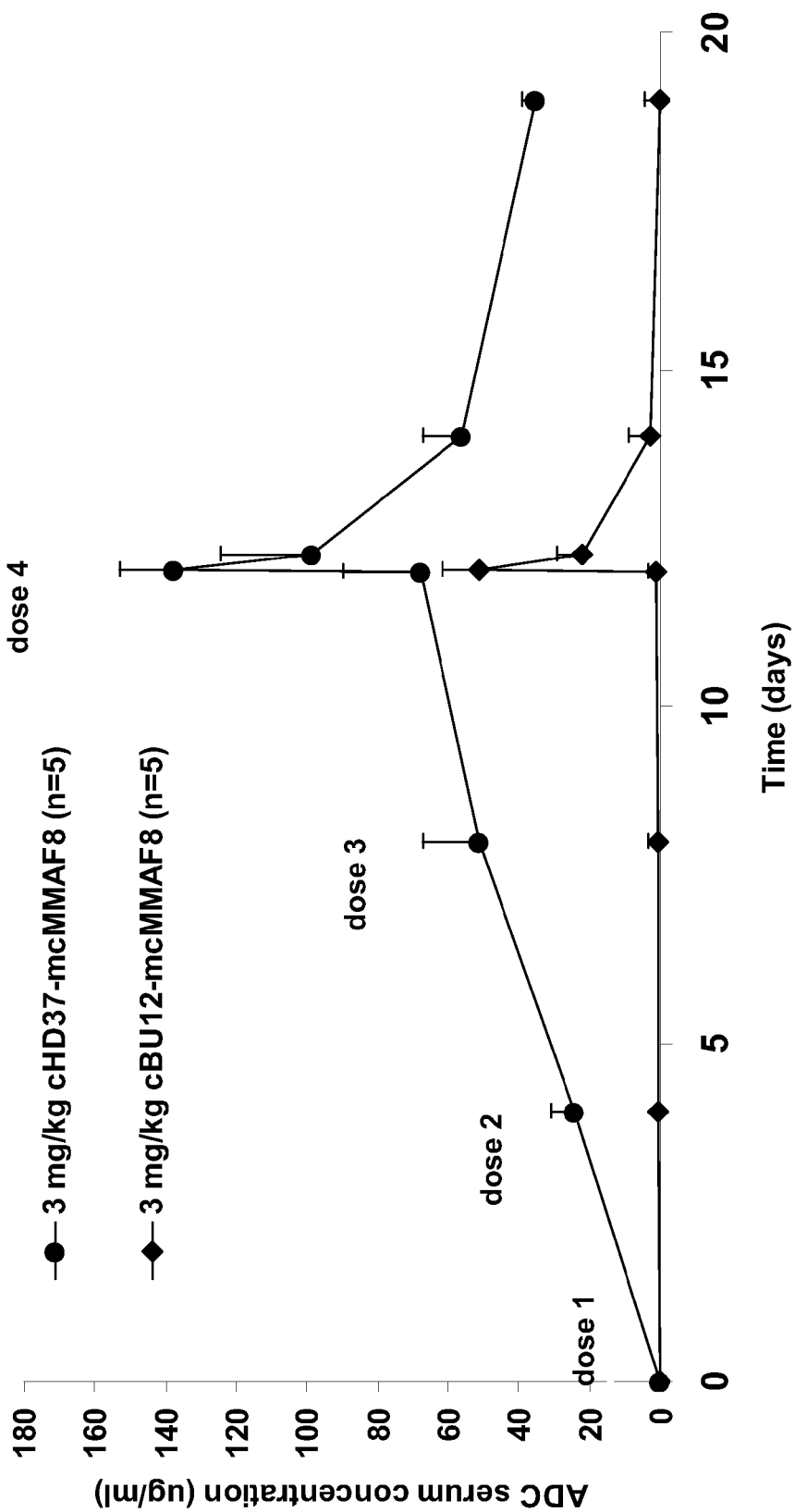
FIG. 6: Trough levels of cBU12-mcMMAF8 vs cHD37-mcMMAF8.
Figure 7:
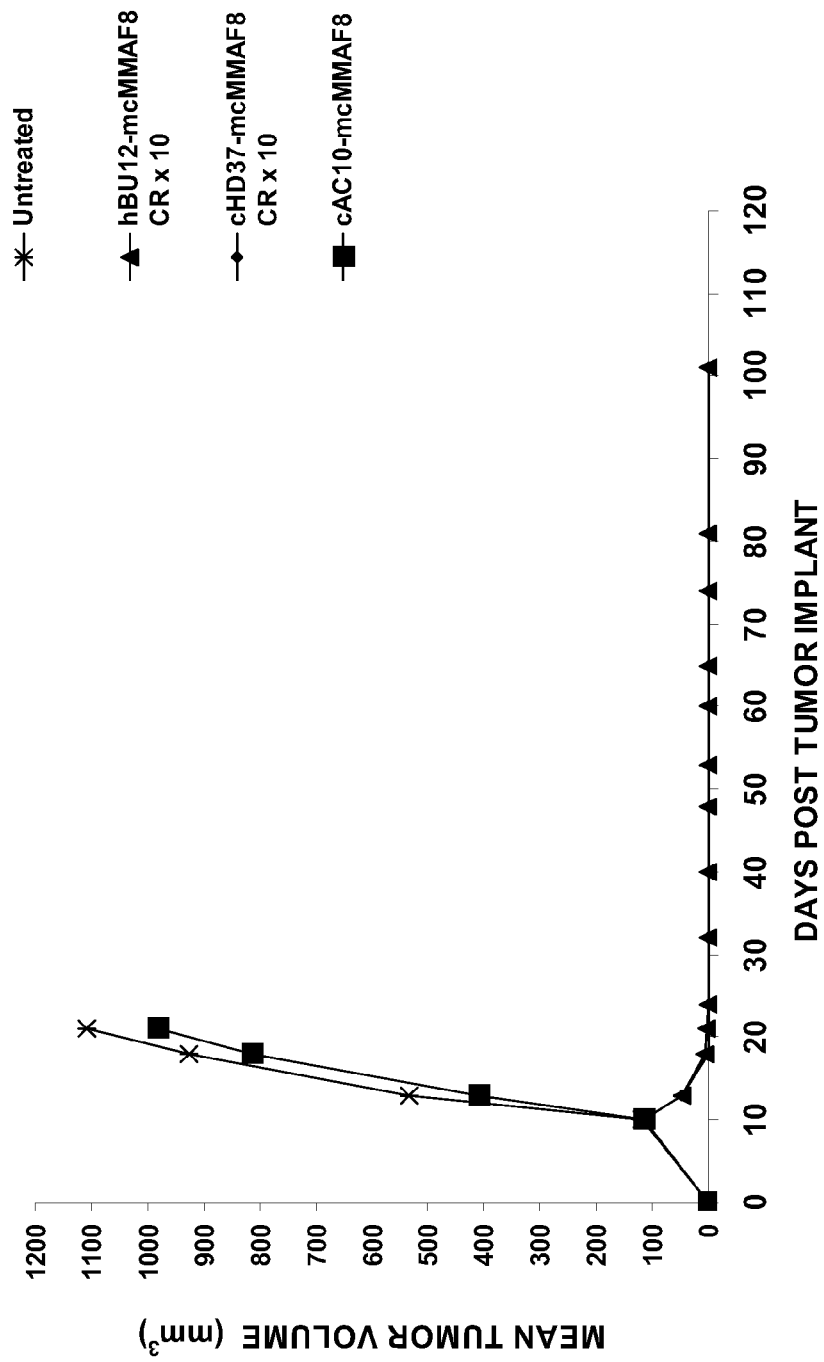
FIG. 7: Antitumor activity of anti-CD19 antibody-drug conjugates in a Ramos tumor model in SCID mice. Groups of mice (10/group) were untreated or treated with hBU12-mcMMAF8 (3 mg/kg; complete response 10/10 mice), cHD37-mcMMAF8 (3 mg/kg; complete response 10/10 mice), or cAC10-mcMMAF8 (3 mg/kg; complete response 0/10 mice) when tumor size averaged approximately 100 mm$^3$. The dose schedule was q4dx4 iv.
Figure 8:
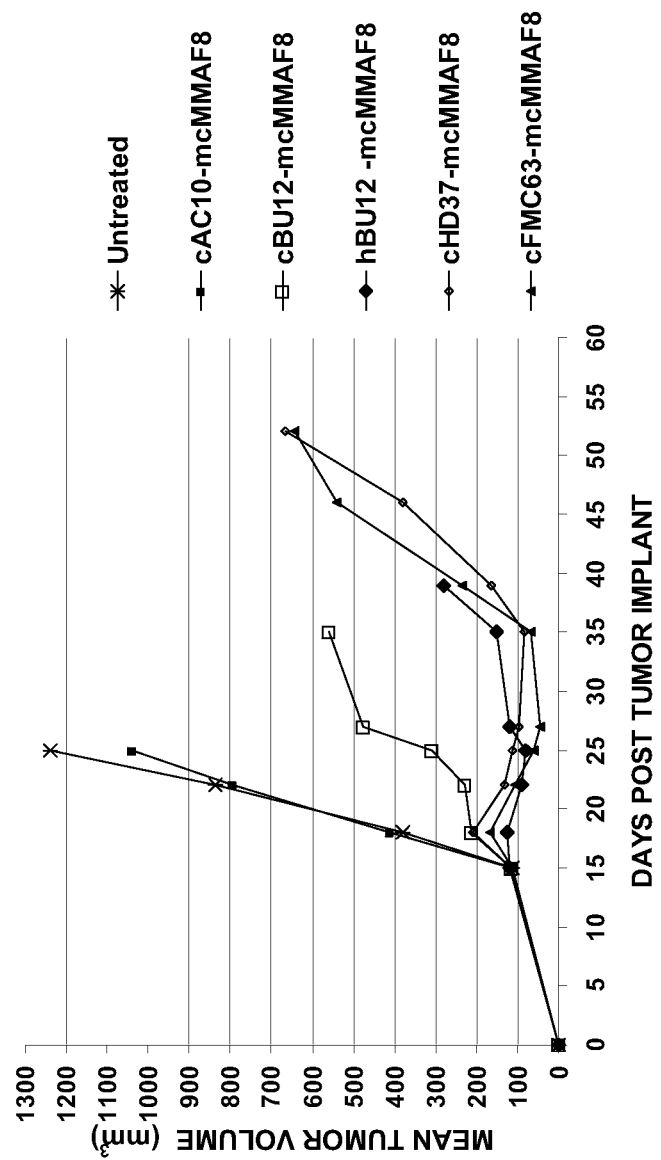
FIG. 8: Antitumor activity of anti-CD19 antibody-drug conjugates in DoHH2 tumor model in SCID mice. Groups of mice (5/group) were untreated or treated with cAC10-mcMMAF8 (3 mg/kg), cBU12-mcMMAF8 (3 mg/kg), hBU12-mcMMAF8 (3 mg/kg); cHD37-mcMMAF8 (3 mg/kg) or cFMC63-mcMMAF8 (3 mg/kg) when tumor size averaged approximately 100 mm$^3$. The dose schedule was q4dx4, ip.
Figure 9:
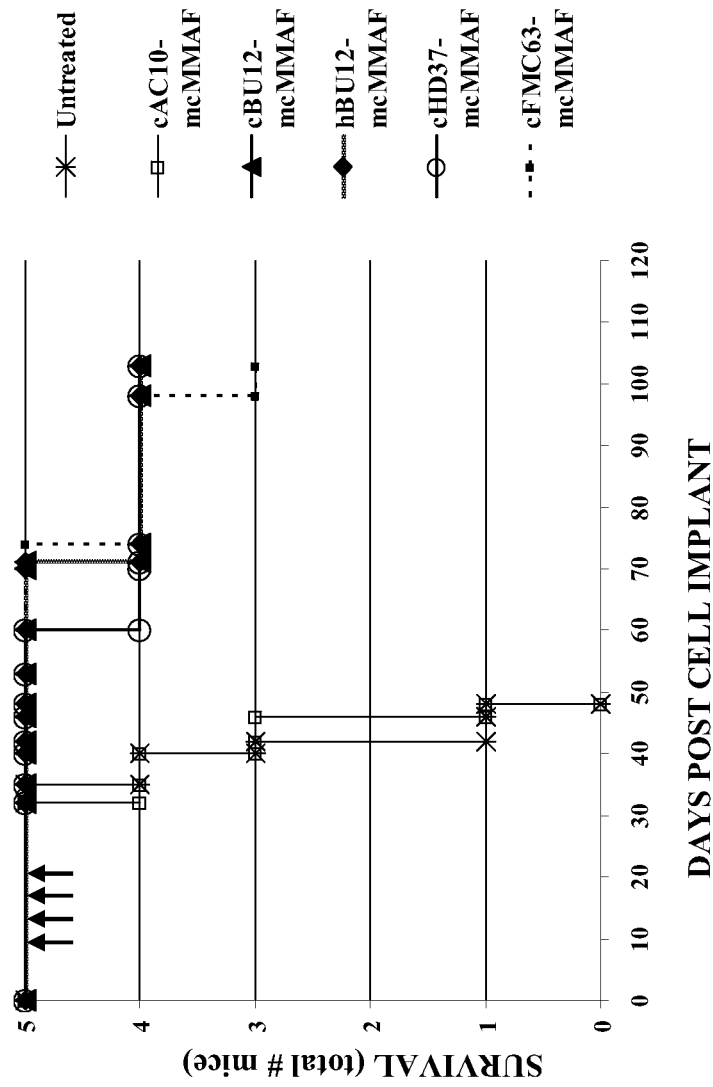
FIG. 9: Survival assay for SCID mice treated with anti-CD19 antibody-drug conjugates in Nalm-6 tumor model. Groups of mice (5/group) were untreated or treated with cAC10-mcMMAF8 (3 mg/kg), cBU12-mcMMAF8 (3 mg/kg), hBU12-mcMMAF8 (3 mg/kg); cHD37-mcMMAF8 (3 mg/kg) or cFMC63-mcMMAF8 (3 mg/kg). The dose schedule was q4dx4, iv.
Figure 10:
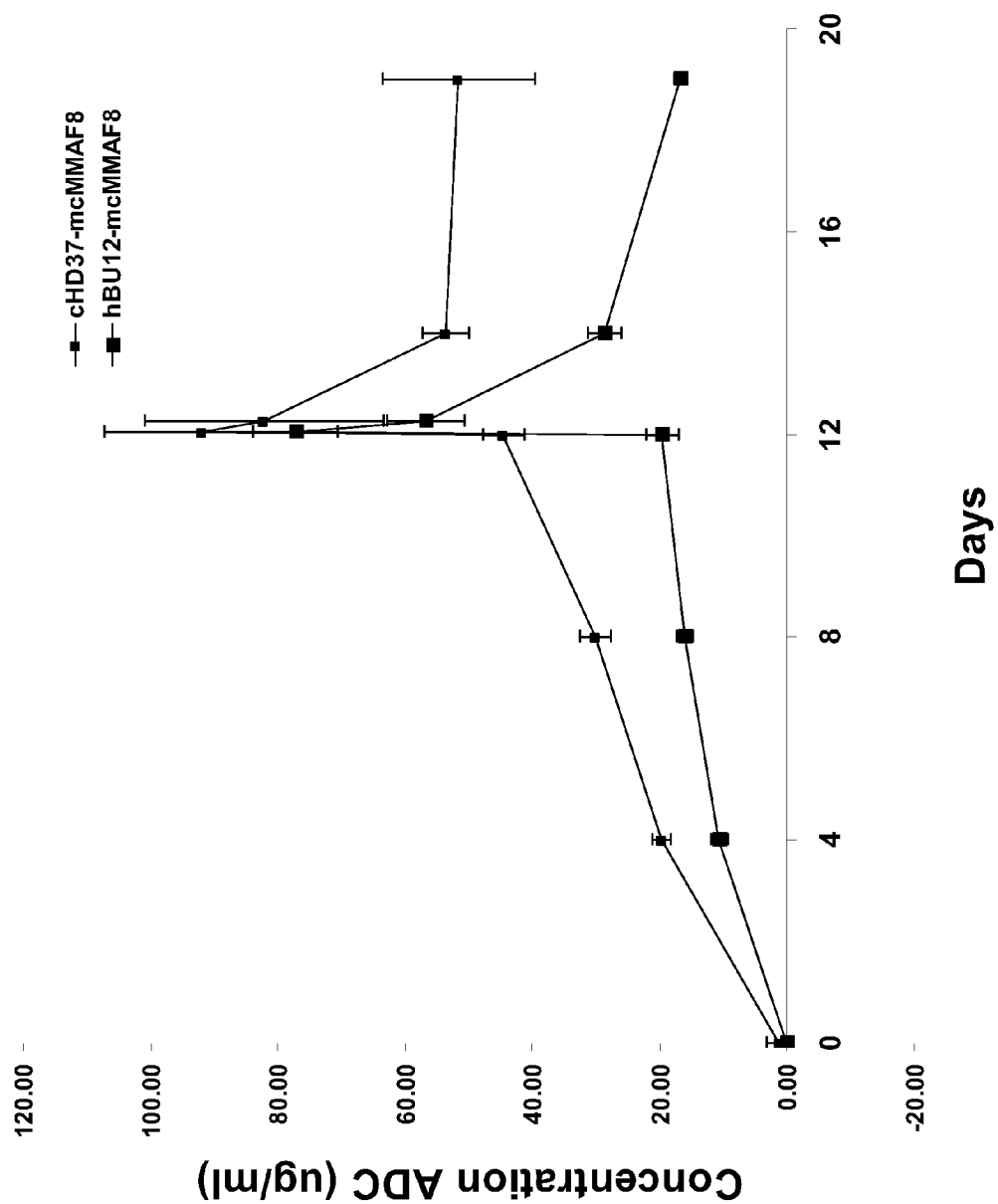
FIG. 10: Trough levels of hBU12-mcMMAF8 (3 mg/kg) vs cHD37-mcMMAF8 (3 mg/kg). 5 mice were treated in each group.
Figure 11:
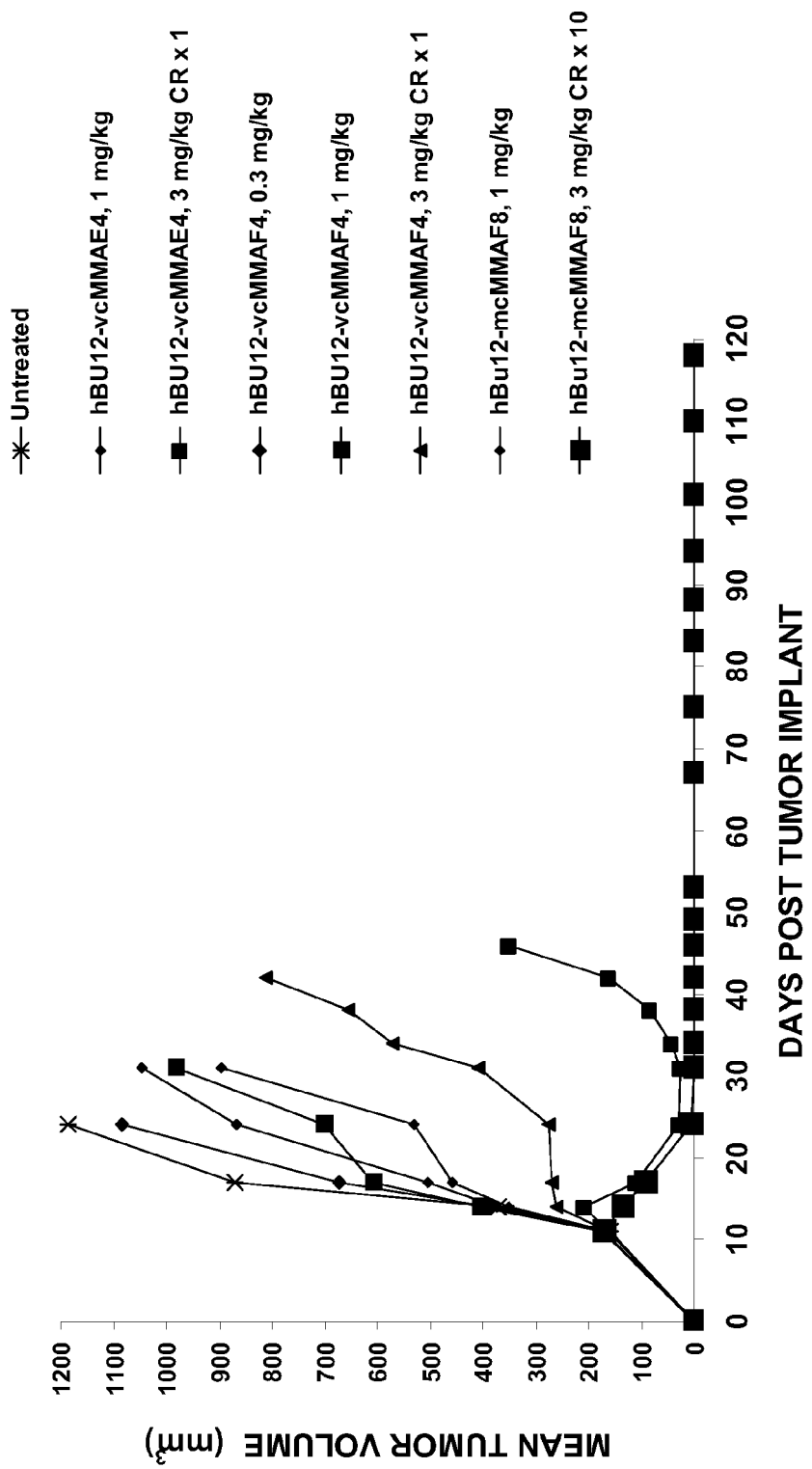
FIG. 11: Antitumor activity of hBU12 antibody-drug conjugates in Ramos tumor model in SCID mice. Groups of mice (10/group) were untreated or treated with hBU12-vcMMAE4 (1 mg/kg; complete response 0/10), hBU12-vcMMAE4 (3 mg/kg; complete response 7/10), hBU12-vcMMAF4 (0.3 mg/kg; complete response 0/10) hBU12-vcMMAF4 (1 mg/kg; complete response 0/10), hBU12-vcMMAF4 (3 mg/kg; complete response 1/10), hBU12-mcMMAF8 (1 mg/kg; complete response 0/10), or hBU12-mcMMAF8 (3 mg/kg; complete response 10/10). The dose schedule was q4dx4, iv.
Figure 12:
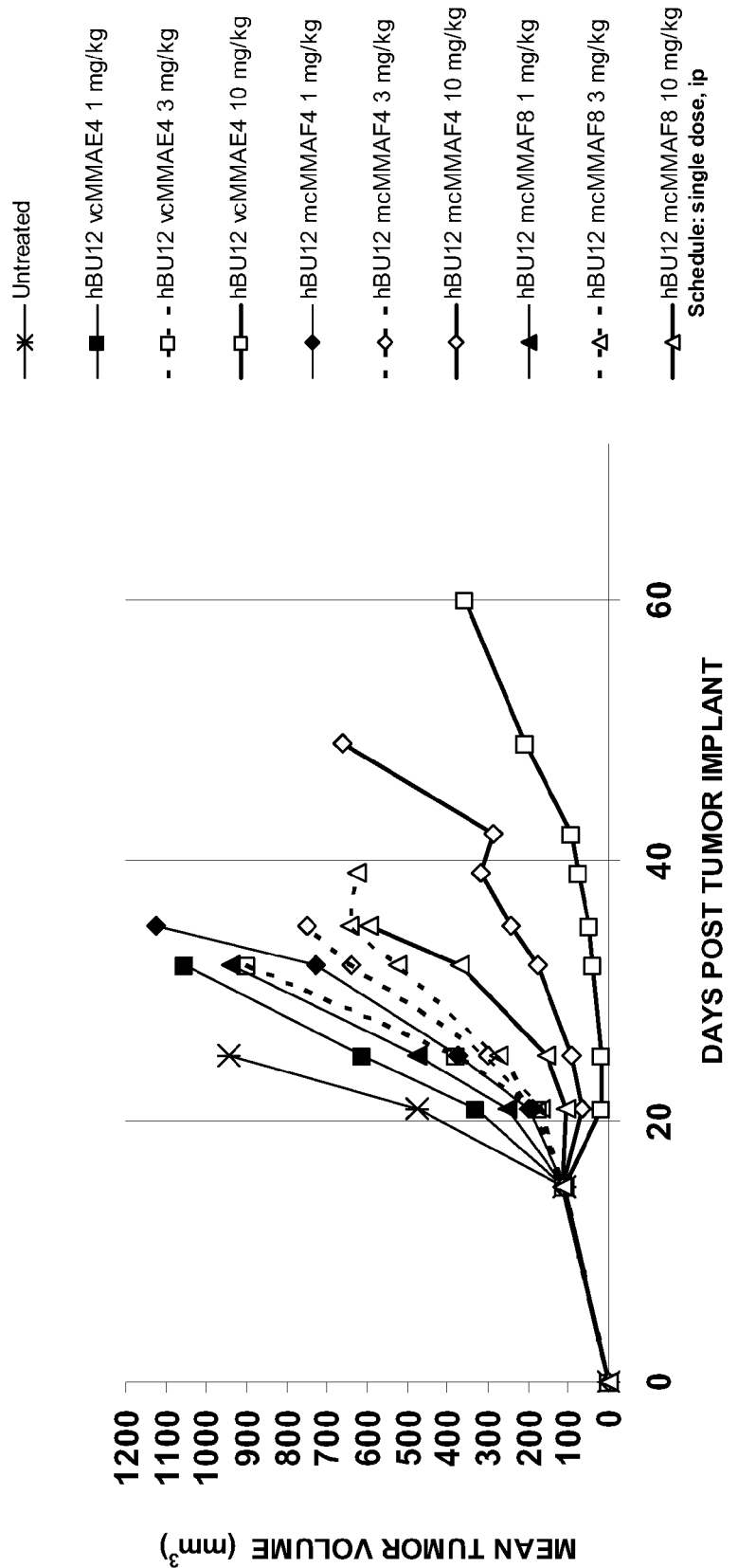
FIG. 12: Antitumor activity of anti-CD19 antibody-drug conjugates in DoHH2 tumor model in SCID mice. Groups of mice (1/group) were treated with varying 1 mg/kg, 3 mg/kg, or 10 mg/kg of hBU12-vcMMAE4, -mcMMAF4, and -mcMMAF8. The dose schedule was a single dose, ip.

Some variants differ from the above antibody by substitution of one or more amino acids in the variable region framework relative to SEQ ID NO:9 or SEQ ID NO:17. The substitution can be with an amino acid occupying the corresponding position (unless otherwise indicated positions are by Kabat numbering) in the heavy or light chain variable region respectively of the BU12 antibody (sometimes referred to as a donor antibody). Substitutions with donor amino acids often increase the affinity of the resulting humanized antibody for its antigen by conferring a framework conformation in the humanized antibody more closely resembling that in the donor mouse antibody. A donor substitution at position L83 is particularly advantageous in increasing affinity as shown in FIG. 2 (compare light chain G with the substitution and A without the substitution). Other positions differing between SEQ ID NO:9 and the BU12 heavy chain in which donor substitutions can be performed include, for example, H24, H27, H29, H71, H75, H789, H79, and H89 in which, after donor substitution, the positions are occupied by F, F, L, K, S, V, F, and A respectively. Light chain variable region framework positions differing between SEQ ID NO:17 and the BU12 light chain include positions L2, L40, L41, L42, L69, L70, L71, L72 and L83 occupied by N, S, S, T, N, S, H, F, and V respectively in the mouse BU12 light chain. The effect of many of these substitutions on antibody affinity is also shown in FIG. 2. It can be seen that some of these substitutions or combinations of substitutions increase affinity. Some preferred heavy chain substitution include one or more of H71, H75, H78 and H79 occupied by K, S, V, and F respectively after donor substitution. Some preferred light chain substitutions include one or more of positions L2, L69, L71, L72 and L83 occupied by N, N, H, F, and V respectively after donor substitution. None of the tested substitutions or combinations of substitutions caused an unacceptable loss of affinity.

How many donor substitutions to include reflects a balance of competing considerations. In general, substitutions which significantly increase affinity are desirable. However, minimizing the total number of variable region framework substitutions is also advantageous in reducing potential immunogenicity. A humanized antibody having no substitutions in the heavy chain variable region framework and a L83 donor substitution of the light chain variable region framework represents a preferred balance between maximizing affinity and minimizing immunogenicity. Many other permutations are possible.

As well as or instead of donor substitutions, a variable region framework amino acid can be substituted with the amino acid occupying the corresponding position in another human antibody sequence or a consensus of human antibody sequences (see, e.g., Queen, U.S. Pat. No. 7,022,500). The rationale for such a substitution is often to substitute a relatively rare amino acid in human immunoglobulin sequences with a more common amino acid for that position with a view to reducing immunogenicity. In humanized antibodies in which the variable region frameworks are provided by germline sequences, such substitutions are possible but generally not necessary because germline sequences lack rare amino acids that may be introduced by somatic mutation.

Variable region framework amino acids can also be substituted with amino acids that are neither donor amino acids or consensus amino acids. Such substitutions are preferably conservative amino acid substitutions. Although many substitutions have little effect on affinity, they may increase immunogenicity and thus in general are not preferred.

Substitution of one or more CDR residues or omission of one or more CDRs is also possible. Numerous antibodies have been described in the scientific literature in which one or two CDRs can be dispensed with for binding. Padlan et al., FASEB Journal 9: 133-139 (1995) analyzed the contact regions between antibodies and their antigens, based on published crystal structures, and concluded that only about one fifth to one third of CDR residues actually contact the antigen. Padlan et al. termed these residues SDR (for specificity determining residues). Padlan also found many antibodies in which one or two CDRs had no amino acids in contact with an antigen. Likewise, Vajdos et al (Journal of Molecular Biology, vol. 320, pp. 415-428 (2002) reported that CDR1 of the light chain of an antibody against ErbB2 was not involved in binding. Such teaching has been applied to antibody humanization by, for example, Iwahashi et al., Mol. Immunol. 36:1079-1091, (1999), who showed that they could graft only L1 and L3, or L2 and L3, of the CR49 murine antibody onto a human framework and retain high affinity interaction with the antigen. Similarly, Tamura et al, Journal of Immunology, 2000, 164:1432-1441 (2000) reported that light chain CDRs 1 and 2 could be dispensed with entirely in a humanized anti-carcinoma antibody, as could several residues in the remaining CDRs. The substitution of certain regions within CDRs is based on the same principle as omitting dispensable CDRs, namely that only a small subset of CDR residues, the SDR's, actually contact antigen.

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in human acceptor sequence supplying the variable region framework sequences (in this example, VH4-31/JH4 for the heavy chain and VL-L6 JK2 for the light chain). The number of such substitutions to include reflects a balance of competing considerations Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically. Empirical substitutions can be conservative or non-conservative substitutions. However, in general empirical substitutions do not have the advantage of mouse to human substitutions in reducing immunogenicity. Empirical substitutions can increase or decrease affinity of the resulting humanized antibody.

In general humanized antibodies with satisfactory binding affinity to CD19 and lack of substantial immunogenicity can be obtained by individual screening of variants made according to the above principles and/or in accordance with the present examples. However, very large numbers of variants can be simultaneously screened using a display selection method such as phage display (see (Dower et al., WO91/17271; McCafferty et al., WO92/001047; and Winter, WO92/20791). The same considerations apply mutatis mutandis in designing variants of other humanized antibodies or antibody chains disclosed herein. For example, SEQ ID NO:2 provides an alternative starting point to SEQ ID NO:9 for design of heavy chain variants. SEQ ID NO:2 comprises the three heavy chain CDRs of the BU12 antibody with a fully human variable region framework sequence of the VH2-70 and JH4 genes. SEQ ID NO:26 provides an alternative starting point to SEQ ID NO:17 for design of light chain variants. SEQ ID NO:26 comprises the three light chain CDRs of the BU12 antibody in a fully human framework sequence of the A10 and JK2 genes. Specific heavy chain variable region framework positions for potential substitution and the amino acids to substitute into such positions are indicated in the table "non-homologous FR residues BU12 v.s VH431" in Example 1. Specific light chain variable region framework positions for potential substitution in SEQ ID NO:26 are indicated in the table "Nono-homologous FR residues BU12 VL vs. L6 and A10" in Example 2.

The present invention encompasses embodiments wherein the heavy chain variable region further comprises a leader sequence. Exemplary heavy chain leader sequences are set forth in SEQ ID NO:1 and SEQ ID NO:57.

The present invention encompasses embodiments wherein the light chain variable region further comprises a leader sequence. Exemplary light chain leader sequences are set forth in SEQ ID NO:16 and SEQ ID NO:61.

The CD19 binding agent can optionally include an antibody effector region. The effector domain(s) can be, for example, an Fc region such as a hinge-$C_H2$-$C_H3$ region of an immunoglobulin, or a portion or fragment of an effector region preferably having effector function. Antigen-binding antibody fragments, including single-chain antibodies, can comprise, for example, the variable region(s) in combination with the entirety or a portion of an effector region (e.g., a $C_H2$ and/or $C_H3$ domain alone or in combination with a $C_H1$, hinge and/or $C_L$ domain). Also, antigen-binding fragments can comprise any combination of effector regions. In some embodiments, the anti-CD19 antibody can be a single chain antibody comprising a CD19-binding variable region joined to hinge-$C_H2$-$C_H3$ domains.

The effector region of the anti-CD19 antibody can be from any suitable immunoglobulin isotype. A CD19 binding agent can be expressed as a recombinant fusion protein comprising of the appropriate constant domains to yield the desired effector function(s).

The present invention encompasses embodiments wherein the heavy chain variable region of a CD19 binding agent is joined to a constant region, such an IgG, i.e., IgG1 constant region or IgG2 constant region, or altered constant region, e.g., IgG1V1. Exemplary constant region domains are provided as SEQ ID NO:3 and 36-39.

The present invention also encompasses embodiments wherein the light chain variable region of a CD19 binding agent is joined to a constant region, such as a kappa constant region. An exemplary constant region domain is provided as SEQ ID NO:18.

The present invention encompasses embodiments wherein the light chain variable region of a CD19 binding agent is joined to a constant region, such as a kappa constant region. An exemplary constant region domain is provided as SEQ ID NO:18 and the heavy chain variable region of a CD19 binding agent is joined to a constant region, such an IgG, e.g., IgG1 constant region or IgG2 constant region, or altered constant region, e.g., IgG1V1. Exemplary constant region domains are provided as SEQ ID NO: 3 and 36-39.

In some embodiments, a CD19 binding agent can be a CD19 binding agent, comprising a human or non-human Fc region or portion thereof. For example, the antibody can include an Fc region or portion thereof of non-human origin, e.g., rodent (e.g., mouse or rat), donkey, sheep, rabbit, goat, guinea pig, camelid, horse, chicken or monkey (e.g., macaque, rhesus, cynomolgous or the like) linked to humanized heavy and/or light chain variable regions.

A CD19 binding agent, such as an antibody, can be monospecific, bispecific, trispecific, or of greater multispecificity. Multispecific antibodies may be specific for different epitopes of CD19 and/or may be specific for both CD19 as well as for a heterologous protein. (See, e.g., PCT Publications WO 93/17715, WO 92/08802, WO 91/00360, and WO 92/05793; Tutt et al., 1991, J. Immunol. 147:60-69; U.S. Pat. Nos. 4,474,893; 4,714,681; 4,925,648; 5,573,920; and 5,601,819; Kostelny et al., 1992, J. Immunol. 148:1547-1553.) Multispecific antibodies, including bispecific and trispecific antibodies, useful for practicing the methods described herein are antibodies that immunospecifically bind to both CD19 and a second cell surface receptor or receptor complex, i.e., one that mediates ADCC, ADCP, and/or CDC.

CD19 binding agents may also be described or specified in terms of their binding affinity to CD19. Typical binding affinities include those with a dissociation constant or Kd less than $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The present invention encompasses nucleic acids encoding a CD19 binding agent. The CD19 binding agent can be, for example, a fully humanized antibody or a humanized antigen-binding fragment. In some embodiments, a nucleic acid of the present invention will encode a polypeptide chain having the amino acid sequence or having substantial identity to the amino acid sequences set forth in SEQ ID NOs: 2, 4, 5, 6, 7, 9, 10, 11, 12, 13, 14, 15, 17, 19, 20, 21, 22, 23, 24, 26 or 27. In some embodiments, a nucleic acid of the present invention will encode a polypeptide chain having the amino acid sequence or having substantial identity to the amino acid sequence set forth in SEQ ID NOs: 1, 3, 16, 18, 56, 57, 60 or 61. In certain embodiments, a nucleic acid of the present invention will comprise the nucleotide sequence set forth in SEQ ID NOS. 40, 41, 42, 43, 44, 45, 53, 54, 55, 58, or 59. In certain embodiments, the nucleic acid will encode a heavy chain variable region of an antibody and will comprise SEQ ID NO. 41, and optionally one or more of the sequences set forth in SEQ ID NOS. 40, and 42. In certain embodiments, the nucleic acid will encode a heavy chain variable region of an antibody and will comprise SEQ ID NO. 41, and optionally one or more of the sequences set forth in SEQ ID NOS. 54, and 55. In certain embodiments, the nucleic acid will encode a heavy chain variable region of an antibody and will comprise SEQ ID NO. 53. In certain embodiments, the nucleic acid will encode a light chain variable region of an antibody and will comprise SEQ ID NO. 44, and optionally one or more of the sequences set forth in SEQ ID NOS. 43, and 45. In certain embodiments, the nucleic acid will encode a light chain variable region of an antibody and will comprise SEQ ID NO. 44, and optionally one or more of the sequences set forth in SEQ ID NOS. 59, and 45. In certain embodiments, the nucleic acid will encode a light chain variable region of an antibody and will comprise SEQ ID NO. 58.

Also included in some embodiments are nucleic acids encoding a CD19 binding agent that hybridize under low, moderate, and high stringency conditions, as defined herein, to all or a portion of a nucleotide sequence encoding a CD19 binding agent disclosed herein, or by its complement. High stringency, moderate stringency and low stringency conditions for nucleic acid hybridization are known in the art. Ausubel, F. M. et al., "Current Protocols in Molecular Biology" (John Wiley & Sons 1998), pages 2.10.1-2.10.16; 6.3.1-6.3.6. The exact conditions which determine the stringency of hybridization depend not only on ionic strength (e.g., 0.2× SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. For example, a low stringency wash can comprise washing in a solution containing 0.2×SSC/0.1% SDS for 10 min at room temperature; a moderate stringency wash can comprise washing in a prewarmed solution (42° C.) solution containing 0.2×SSC/0.1% SDS for 15 min at 42° C.; and a high stringency wash can comprise washing in prewarmed (68° C.) solution containing 0.1×SSC/0.1% SDS for 15 min at 68° C. Furthermore, washes can be performed repeatedly or sequentially to obtain a desired result as known in the art.

The present invention encompasses embodiments wherein the CD19 binding agent is, for example, a humanized full length antibody, humanized antibody fragment, or a derivative thereof.

CD19 binding agents can be generated by methods known in the art. For example, monoclonal antibodies can be prepared using a wide variety of techniques including, e.g., the use of hybridoma, recombinant, and phage display technologies, or a combination thereof. Hybridoma techniques are generally discussed in, for example, Harlow et al., *Antibodies: A Laboratory Manual* (Cold Spring Harbor Laboratory Press, 2nd ed., 1988; Harlow and Lane, *Using Antibodies, A Laboratory Manual*, Cold Spring Harbor Laboratory, New York (1999); and Hammerling et al., In *Monoclonal Antibodies and T-Cell Hybridomas*, pp. 563-681 (Elsevier, N.Y., 1981). Examples of phage display methods that can be used to make anti-CD19 antibodies include, e.g., those disclosed in Hoogenboom and Winter, 1991, *J. Mol. Biol.* 227:381; Marks et al., 1991, *J. Mol. Biol.* 222:581; Quan and Carter, 2002, *The rise of monoclonal antibodies as therapeutics in Anti-IgE and Allergic Disease*, Jardieu and Fick Jr., eds., Marcel Dekker, New York, N.Y., Chapter 20, pp. 427-469; Brinkman et al., 1995, *J. Immunol. Methods* 182:41-50; Ames et al., 1995, *J. Immunol. Methods* 184:177-186; Kettleborough et al., 1994, *Eur. J. Immunol.* 24:952-958; *Persic et al.,* 1997, Gene 187: 9-18; Burton et al., 1994, *Advances in Immunology* 57:191-280; PCT Application No. PCT/GB91/01134; PCT Publications WO 90/02809, WO 91/10737, WO 92/01047, WO 92/18619, WO 93/11236, WO 95/15982, WO 95/20401, and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108 (the disclosures of which are incorporated by reference herein).

As discussed herein, the CD19 binding agents can include the amino acid sequence of a humanized heavy and/or light chain variable region. Antibodies can be humanized using a variety of techniques known in the art including, for example, CDR-grafting (see, e.g., EP 0 239 400; PCT publication WO 91/09967; U.S. Pat. Nos. 5,225,539; 5,530,101; and 5,585, 089), veneering or resurfacing (see, e.g., EP 0 592 106; EP 0 519 596; Padlan, *Molecular Immunology,* 1991, 28(4/5):489-498; Studnicka et al., 1994, *Protein Engineering* 7(6):805-814; Roguska et al., 1994, *Proc. Natl. Acad. Sci. USA* 91:969-973), and chain shuffling (see, e.g., U.S. Pat. No. 5,565,332) (all of these references are incorporated by reference herein). Humanized antibodies and fragments thereof can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 0 012 023; Berter et al., 1988, *Science* 240:1041-43; *Liu et al.,* 1987, Proc. Natl. Acad. Sci. USA 84:3439-43; Liu et al., 1987, *J. Immunol.* 139:3521-26; Sun et al., 1987, *Proc. Natl. Acad. Sci. USA* 84:214-18; Nishimura et al., 1987, *Cancer. Res.* 47:999-1005; Wood et al., 1985, *Nature* 314:446-449; Shaw et al., 1988, *J. Natl. Cancer Inst.* 80:1553-59; Morrison, 1985, *Science* 229:1202-07; Oi et al., 1986, *BioTechniques* 4:214; U.S. Pat. No. 5,225,539; Jones et al., 1986, Nature 321:552-25; Verhoeyan et al., 1988, *Science* 239:1534; and Beidler et al., 1988, *J. Immunol.* 141:4053-60; each of which is incorporated herein by reference in its entirety.

Examples of techniques that can be used to produce single-chain antibodies include those described in U.S. Pat. Nos. 4,946,778 and 5,258,498; Huston et al., 1991, *Methods in Enzymology* 203:46-88; Shu et al., 1993, *Proc. Natl. Acad. Sci. USA* 90:7995-7999; and Skerra et al., 1988, *Science* 240:1038-1040.

Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, *Nature* 305:537-39). Because of the random assortment of immunoglobulin heavy and light chains, these hybridomas (quadromas) produce a potential mixture of different antibody molecules, of which one has the correct bispecific structure. Similar procedures are disclosed in International Publication No. WO 93/08829, and in Traunecker et al., 1991, *EMBO J.* 10:3655-59.

According to a different approach, antibody variable domains with the desired binding specificities (antibody-antigen combining sites) are fused to immunoglobulin constant domain sequences. The fusion typically is with an immunoglobulin heavy chain constant domain, comprising at least part of the hinge, $C_H2$, and $C_H3$ regions. In some embodiments, the fusion includes a first heavy-chain constant region ($C_H1$) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In an example of this approach, the bispecific antibodies have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (see, e.g., International Publication No. WO 94/04690, which is incorporated herein by reference in its entirety).

For further discussion of bispecific antibodies see, for example, Suresh et al., 1986, *Methods in Enzymology* 121: 210; Rodrigues et al., 1993, *J. Immunology* 151:6954-61; Carter et al., 1992, *Bio/Technology* 10:163-67; Carter et al., 1995, *J. Hematotherapy* 4:463-70; Merchant et al., 1998, *Nature Biotechnology* 16:677-81. Using such techniques, bispecific antibodies can be prepared for use in the treatment or prevention of disease as defined herein.

Bifunctional antibodies are also described in European Patent Publication No. 0 105 360. As disclosed in this reference, hybrid or bifunctional antibodies can be derived biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example in International Publication WO 83/03679 and European Patent Publication No. 0 217 577, both of which are incorporated herein by reference.

A CD19 binding agent can be a derivative of an anti-CD19 antibody. In certain embodiments, an anti-CD19 antibody derivative comprises an anti-CD19 antibody (e.g., an intact antibody, an antigen-binding fragment or conservatively substituted polypeptide) and at least one polypeptide region or other moiety heterologous to the anti-CD19 antibody. For example, an anti-CD19 antibody can be modified, e.g., by the covalent attachment of any type of molecule, such that the covalent attachment does not prevent the antibody derivative from specifically binding to CD19 via the antigen-binding region or region derived therefrom, or, if desired, the effector region or portion thereof from specifically binding Fc receptor. Typical modifications include, e.g., glycosylation, deglycosylation, acetylation, pegylation, phosphorylation, amidation, derivatization by known protecting/blocking groups, proteolytic cleavage, linkage to a cellular ligand or other protein, and the like. Any of numerous chemical modifications may be carried out by known techniques, including, but not limited to specific chemical cleavage, acetylation, formylation, metabolic synthesis of tunicamycin, etc.

In some embodiments, the antibody derivative is a multimer, such as, for example, a dimer, comprising one or more monomers, where each monomer includes (i) an antigen-binding region of an anti-CD19 antibody, or a polypeptide region derived therefrom (such as, for example, by conservative substitution of one or more amino acids), and (ii) a multimerizing (e.g., dimerizing) polypeptide region, such that the antibody derivative forms multimers (e.g., homodimers) that specifically bind to CD19. In typical embodiments, an antigen binding region of an anti-CD19 antibody, or a polypeptide region derived therefrom, is recombinantly or chemically fused with a heterologous protein, wherein the heterologous protein comprises a dimerization or multimerization domain. Prior to administration of the antibody derivative to a subject for the purpose of treating or preventing CD19-expressing cancers, the derivative is subjected to conditions that allow formation of a homodimer or heterodimer. A heterodimer, as used herein, may comprise identical dimerization domains but different CD19 antigen-binding regions, identical CD19 antigen-binding regions but different dimerization domains, or different CD19 antigen-binding regions and dimerization domains.

Typical dimerization domains are those that originate from transcription factors. In one embodiment, the dimerization domain is that of a basic region leucine zipper ("bZIP") (see, e.g., Vinson et al., 1989, *Science* 246:911-916). Useful leucine zipper domains include, for example, those of the yeast transcription factor GCN4, the mammalian transcription factor CCAAT/enhancer-binding protein C/EBP, and the nuclear transform in oncogene products, Fos and Jun. (See, e.g., Landschultz et al., 1988, *Science* 240:1759-64; Baxevanis and Vinson, 1993, *Curr. Op. Gen. Devel.* 3:278-285; O'Shea et al., 1989, *Science* 243:538-542.) In another embodiment, the dimerization domain is that of a basic region helix-loop-helix ("bHLH") protein. (See Murre et al., 1989, *Cell* 56:777-783. See also Davis et al., 1990, *Cell* 60:733-746; Voronova and Baltimore, 1990, *Proc. Natl. Acad. Sci. USA* 87:4722-26.) Particularly useful hHLH proteins are myc, max, and mac.

In yet other embodiments, the dimerization domain is an immunoglobulin constant region such as, for example, a heavy chain constant region or a domain thereof (e.g., a $C_H1$ domain, a $C_H2$ domain, and/or a $C_H3$ domain). (See, e.g., U.S. Pat. Nos. 5,155,027; 5,336,603; 5,359,046; and 5,349,053; EP 0 367 166; and WO 96/04388.)

Heterodimers are known to form between Fos and Jun (Bohmann et al., 1987, *Science* 238:1386-1392), among members of the ATF/CREB family (Hai et al., 1989, *Genes Dev.* 3:2083-2090), among members of the C/EBP family (Cao et al., 1991, *Genes Dev.* 5:1538-52; Williams et al., 1991, *Genes Dev.* 5:1553-67; Roman et al., 1990, *Genes Dev.* 4:1404-15), and between members of the ATF/CREB and Fos/Jun families (Hai and Curran, 1991, *Proc. Natl. Acad. Sci. USA* 88:3720-24). Therefore, when a CD19 binding agent is administered to a subject as a heterodimer comprising different dimerization domains, any combination of the foregoing may be used.

In other embodiments, an anti-CD19 antibody derivative is an anti-CD19 antibody conjugated to a second antibody (an "antibody heteroconjugate") (see, e.g., U.S. Pat. No. 4,676, 980). Heteroconjugates can be formed, for example, between an antibody that binds to CD19 and an antibody that binds to a surface receptor or receptor complex that mediates ADCC, phagocytosis, and/or CDC, such as CD16/FcγRIII, CD64/FcγRI, killer cell activating or inhibitory receptors, or the complement control protein CD59. In one embodiment, the binding of the portion of the multispecific antibody to the second cell surface molecule or receptor complex enhances the effector functions of an anti-CD19 antibody.

Antibodies and other binding agents can be assayed for specific binding to CD19 (e.g., human CD19) by any of various known methods Immunoassays which can be used include, for example, competitive and non-competitive assay systems. Such assays are routine and well-known in the art. (See, e.g., Ausubel et al., eds., *Short Protocols in Molecular Biology* (John Wiley and Sons, Inc., New York, 4th ed. 1999); Harlow and Lane, *Using Antibodies: A Laboratory Manual* (Cold Spring Harbor Laboratory Press, Cold Spring Harbor, N.Y., 1999.))

Further, the binding affinity of a CD19 binding agent (e.g., anti-CD19 antibody or derivative thereof) to CD19 and the off-rate of a binding agent-CD19 interaction can be determined by competitive binding assays. One example of a competitive binding assay is a radioimmunoassay comprising the incubation of labeled CD19 (e.g., $^3$H or $^{125}$I) with the antibody of interest in the presence of increasing amounts of unlabeled CD19, and the detection of the antibody bound to the labeled CD19. The affinity of the antibody for CD19 and the binding off-rates can then be determined from the data by Scatchard plot analysis. Competition with a second antibody can also be determined using radioimmunoassays. In this case, CD19 is incubated with the antibody of interest conjugated to a labeled compound (e.g., $^3$H or $^{125}$I) in the presence of increasing amounts of an unlabeled second antibody. Alternatively, the binding affinity of an antibody to CD19 and the on- and off-rates of an antibody-CD19 interaction can be determined by surface plasmon resonance. In some embodiments, the anti-CD19 antibodies or derivatives thereof can be targeted to and accumulate on the membrane of a CD19-expressing cell.

CD19 binding agents (e.g., anti-CD19 antibody or derivative thereof) can be produced by methods known in the art for the synthesis of proteins, typically, e.g., by recombinant expression techniques. Recombinant expression of an antibody or derivative thereof typically involves construction of an expression vector containing a nucleic acid that encodes the binding agent. A vector for the production of the protein molecule may be produced by recombinant DNA technology using techniques known in the art. Standard techniques such as, for example, those described in Sambrook and Russell, *Molecular Cloning: A Laboratory Manual* (Cold Spring Harbor Laboratory Press, Cold Spring Harbor, N.Y., 3rd ed., 2001); Sambrook et al., *Molecular Cloning: A Laboratory Manual* (Cold Spring Harbor Laboratory Press, Cold Spring Harbor, N.Y., 2nd ed., 1989); *Short Protocols in Molecular Biology* (Ausubel et al., John Wiley and Sons, New York, 4th ed., 1999); and Glick and Pasternak, *Molecular Biotechnology: Principles and Applications of Recombinant DNA* (ASM Press, Washington, D.C., 2nd ed., 1998) can be used for recombinant nucleic acid methods, nucleic acid synthesis, cell culture, transgene incorporation, and recombinant protein expression.

For example, for recombinant expression of an anti-CD19 antibody, an expression vector may encode a heavy or light chain thereof, or a heavy or light chain variable domain, operably linked to a promoter. An expression vector may include, for example, the nucleotide sequence encoding the constant region of the antibody molecule (see, e.g., PCT Publication WO 86/05807; PCT Publication WO 89/01036; and U.S. Pat. No. 5,122,464), and the variable domain of the antibody may be cloned into such a vector for expression of the entire heavy or light chain. The expression vector is transferred to a host cell by conventional techniques, and the transfected cells are then cultured by conventional techniques to produce the anti-CD19 antibody. In typical embodiments for the expression of double-chain antibodies, vectors encoding both the heavy and light chains can be co-expressed in the host cell for expression of the entire immunoglobulin molecule.

A variety of prokaryotic and eukaryotic host-expression vector systems can be utilized to express a CD19 binding agent (e.g., anti-CD19 antibody or derivative thereof). Typically, eukaryotic cells, particularly for whole recombinant anti-CD19 antibody molecules, are used for the expression of the recombinant protein. For example, mammalian cells such as Chinese hamster ovary cells (CHO; e.g., DG44), in conjunction with a vector such as the major intermediate early gene promoter element from human cytomegalovirus, is an effective expression system for the production of anti-CD19 antibodies and derivatives thereof (see, e.g., Foecking et al., 1986, *Gene* 45:101; Cockett et al., 1990, *Bio/Technology* 8:2). CD19 binding aagents can also be expressed using the CHEF system. (See, e.g., U.S. Pat. No. 5,888,809.)

Other host-expression systems include, for example, plasmid-based expression systems in bacterial cells (see, e.g., Ruther et al., 1983, *EMBO* 1, 2:1791; Inouye and Inouye, 1985, *Nucleic Acids Res.* 13:3101-3109; Van Heeke and Schuster, 1989, *J. Biol. Chem.* 24:5503-5509); insect systems such as, e.g., the use of *Autographa californica* nuclear polyhedrosis virus (AcNPV) expression vector in *Spodoptera frugiperda* cells; and viral-based expression systems in mammalian cells, such as, e.g., adenoviral-based systems (see, e.g., Logan and Shenk, 1984, *Proc. Natl. Acad. Sci. USA* 81:355-359; Bittner et al., 1987, *Methods in Enzymol.* 153:51-544).

In addition, a host cell strain can be chosen that modulates the expression of the inserted sequences, or modifies and processes the gene product in the specific fashion desired. Appropriate cell lines or host systems can be chosen to ensure the correct modification and processing (e.g., glycosylation, phosphorylation, and cleavage) of the protein expressed. To this end, eukaryotic host cells which possess the cellular machinery for proper processing of the primary transcript and gene product can be used. Such mammalian host cells include, for example, CHO, VERO, BHK, HeLa, COS, MDCK, 293, 3T3, and W138.

A stable expression system is typically used for long-term, high-yield production of a recombinant CD19 binding agent. For example, cell lines that stably express the anti-CD19 antibody or derivative thereof can be engineered by transformation of host cells with DNA controlled by appropriate expression control elements (e.g., promoter, enhancer, sequences, transcription terminators, polyadenylation sites) and a selectable marker, followed by growth of the transformed cells in a selective media. The selectable marker confers resistance to the selection and allows cells to stably integrate the DNA into their chromosomes and grow to form foci which in turn can be cloned and expanded into cell lines. A number of selection systems can be used, including, for example, the herpes simplex virus thymidine kinase, hypoxanthineguanine phosphoribosyltransferase, and adenine phosphoribosyltransferase genes, which can be employed in tk$^-$, hgprt$^-$ or aprt$^-$ cells, respectively. Also, antimetabolite resistance can be used as the basis of selection for the following genes: dhfr, which confers resistance to methotrexate; gpt, which confers resistance to mycophenolic acid; neo, which confers resistance to the aminoglycoside G-418; and hygro, which confers resistance to hygromycin. Methods commonly known in the art of recombinant DNA technology can be routinely applied to select the desired recombinant clone, and such methods are described, for example, in Ausubel et al., eds., in the *Current Protocols in Molecular Biology* series of laboratory technique manuals, 1987-1999 *Current Protocols,*© 1994-1999 John Wiley and Sons, Inc.);

Kriegler, *Gene Transfer and Expression, A Laboratory Manual* (Stockton Press, N.Y., 1990); *Current Protocols in Human Genetics* (Dracopoli et al. eds., John Wiley and Sons, N.Y., 1994, Chapters 12 and 13); and Colberre-Garapin et al., 1981, *J. Mol. Biol.* 150:1.

The expression levels of an antibody or derivative can be increased by vector amplification. (See generally Bebbington and Hentschel, *The Use of Vectors Based on Gene Amplification for the Expression of Cloned Genes in Mammalian Cells in DNA Cloning*, Vol. 3 (Academic Press, New York, 1987).) When a marker in the vector system expressing an anti-CD19 antibody or derivative thereof is amplifiable, an increase in the level of inhibitor present in host cell culture media will select host cells that have increased copy number of a marker gene conferring resistance to the inhibitor. The copy number of an associated antibody gene will also be increased, thereby increasing expression of the antibody or derivative thereof (see, e.g., Crouse et al., 1983, Mol. Cell. Biol. 3:257).

Where a CD19 binding agent comprises both a heavy and a light chain, the host cell may be co-transfected with two expression vectors, the first vector encoding the heavy chain protein and the second vector encoding the light chain protein. The two vectors may contain identical selectable markers which enable equal expression of heavy and light chain proteins. Alternatively, a single vector may be used which encodes, and is capable of expressing, both heavy and light chain proteins. In such situations, the light chain is typically placed before the heavy chain to avoid an excess of toxic free heavy chain (see, e.g., Proudfoot, 1986, Nature 322:52; Kohler, 1980, *Proc. Natl. Acad. Sci. USA* 77:2197). The coding sequences for the heavy and light chains may comprise cDNA or genomic DNA.

Once a CD19 binding agent has been produced (e.g., by an animal, chemical synthesis, or recombinant expression), it can be purified by any suitable method for purification of proteins, including, for example, by chromatography (e.g., ion exchange or affinity chromatography (such as, for example, Protein A chromatography for purification of antibodies having an intact Fc region)), centrifugation, differential solubility, or by any other standard technique for the purification of proteins. An anti-CD19 antibody or derivative thereof can, for example, be fused to a marker sequence, such as a peptide, to facilitate purification by affinity chromatography. Suitable marker amino acid sequences include, e.g., a hexa-histidine peptide, such as the tag provided in a pQE vector (QIAGEN, Inc., Chatsworth, Calif., 91311), and the "HA" tag, which corresponds to an epitope derived from the influenza hemagglutinin protein (Wilson et al., 1984, *Cell* 37:767), and the "flag" tag.

Typically, the CD19 binding agent is substantially purified (e.g., substantially free from substances that limit its effect or produce undesired side-effects). In some embodiments, the CD19 binding agent is at least about 40% pure, at least about 50% pure, or at least about 60% pure. In some embodiments, the CD19 binding agent is at least about 60-65%, 65-70%, 70-75%, 75-80%, 80-85%, 85-90%, 90-95%, or 95-98% pure. In some embodiments, the CD19 binding agent is approximately 99% pure.

Further CD19 binding agents can include fusion proteins (i.e., proteins that are recombinantly fused or chemically conjugated, including both covalent and non-covalent conjugation) to heterologous proteins (of typically at least 10, 20, 30, 40, 50, 60, 70, 80, 90 or at least 100 amino acids). In some embodiments, such a CD19 binding agent includes the amino acid sequence of a humanized heavy and/or light chain variable region that specifically binds to CD19 and optionally an immunoglobulin effector region or a functional equivalent thereof. As used herein, a functional equivalent of an immunoglobulin effector region binds to an Fc receptor on an immune cell with phagocytic or lytic activity, or the immunoglobulin effector region binds to one or more components of the complement system. The linkage of the CD19 binding portion to the heterologous protein is not necessarily direct, but may occur through a linker sequence(s).

For example, a CD19 binding agent can be produced recombinantly by fusing a humanized variable region in frame with a sequence coding for a heterologous protein. The heterologous protein optionally can include an effector region or a functional equivalent thereof and may provide one or more of the following characteristics: promote stable expression; provide a means of facilitating high yield recombinant expression; and/or provide a multimerization domain.

A CD19 binding agent can be identified using any method suitable for screening for protein-protein interactions. Typically, proteins are initially identified by their ability to specifically bind to CD19. Among the traditional methods which can be employed are "interaction cloning" techniques which entail probing expression libraries with labeled CD19 in a manner similar to the technique of antibody probing of λgt11 libraries. By way of example and not limitation, this can be achieved as follows: a cDNA clone encoding CD19 can be modified at the C-terminus by inserting the phosphorylation site for the heart muscle kinase (HMK) (see, e.g., Blanar and Rutter, 1992, *Science* 256:1014-18). The recombinant protein is expressed in *E. coli* and purified on a GDP-affinity column to homogeneity (Edery et al., 1988, *Gene* 74:517-25) and labeled using $\gamma^{32}$P-ATP and bovine heart muscle kinase (Sigma-Aldrich Co., St. Louis, Mo.) to a specific activity of $1 \times 10^8$ cpm/µg, and used to screen a human placenta λgt11 cDNA library in a "far-Western assay" (Blanar and Rutter, 1992, *Science* 256:1014-18). Plaques that interact with the CD19 probe are isolated. The cDNA inserts of positive λ, plaques are released and subcloned into a vector suitable for sequencing, such as pBluescript KS (Stratagene, La Jolla, Calif.).

One method which detects protein interactions in vivo is the two-hybrid system. One version of this system has been described (Chien et al., 1991, *Proc. Natl. Acad. Sci. USA* 88:9578-82) and is commercially available from Clontech (Palo Alto, Calif.).

Ligand-Drug Conjugate Compounds

The present invention provides, inter alia, ligand-drug conjugate compounds for targeted delivery of drugs. The inventors have made the discovery that the ligand-drug conjugate compounds have potent cytotoxic and/or cytostatic activity against B cells expressing CD19. The ligand-drug conjugate compounds comprise a Ligand unit covalently linked to at least one Drug unit. The Drug units can be covalently linked directly or via a Linker unit (-LU-).

In some embodiments, the ligand drug conjugate compound has the following formula:

$$L\text{-}(LU\text{-}D)_p \qquad (I)$$

or a pharmaceutically acceptable salt or solvate thereof; wherein:

L is the Ligand unit, i.e., CD19 binding agent of the present invention, and (LU-D) is a Linker unit-Drug unit moiety, wherein:

LU- is a Linker unit, and

-D is a drug unit having cytostatic or cytotoxic activity against a target cell; and p is an integer from 1 to about 20.

In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 10, 2 to 9, 2 to 8, 2 to 7, 2 to 6, 2 to 5, 2 to 4 or 2 to 3. In other embodiments, p is 1, 2, 3, 4, 5 or 6. In some embodiments, p is 2 or 4.

In some embodiments, the ligand drug conjugate compound has the following formula:

$$L\text{-}(A_a\text{-}W_w\text{-}Y_y\text{-}D)_p \quad \text{(II)}$$

or a pharmaceutically acceptable salt or solvate thereof;
wherein:
L is the Ligand unit, i.e. CD19 binding agent; and
-$A_a$-$W_w$-$Y_y$- is a Linker unit (LU), wherein:
-A- is a Stretcher unit,
a is 0 or 1,
each -W- is independently an Amino Acid unit,
w is an integer ranging from 0 to 12,
-Y- is a self-immolative spacer unit,
y is 0, 1 or 2;
-D is a drug units having cytostatic or cytotoxic activity against the target cell; and
p is an integer from 1 to about 20.

In some embodiments, a is 0 or 1, w is 0 or 1, and y is 0, 1 or 2. In some embodiments, a is 0 or 1, w is 0 or 1, and y is 0 or 1. In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 8, 2 to 7, 2 to 6, 2 to 5, 2 to 4 or 2 to 3. In other embodiments, p is 1, 2, 3, 4, 5 or 6. In some embodiments, p is 2 or 4. In some embodiments, when w is not zero, y is 1 or 2. In some embodiments, when w is 1 to 12, y is 1 or 2. In some embodiments, w is 2 to 12 and y is 1 or 2. In some embodiments, a is 1 and w and y are 0.

The drug loading is represented by p, the average number of drug molecules per Ligand, e.g., antibody in a molecule. Drug loading may range from 1 to 20 drugs (D) per Ligand. The average number of drugs per ligand in preparation of conjugation reactions may be characterized by conventional means such as mass spectroscopy, ELISA assay, and HPLC. The quantitative distribution of Ligand-Drug-Conjugates in terms of p may also be determined. In some instances, separation, purification, and characterization of homogeneous Ligand-Drug-conjugates where p is a certain value from Ligand-Drug-Conjugates with other drug loadings may be achieved by means such as reverse phase HPLC or electrophoresis. In exemplary embodiments, p is from 2 to 8.

The generation of ligand-drug conjugate compounds can be accomplished by any technique known to the skilled artisan. Briefly, the ligand-drug conjugate compounds comprise a CD19 binding agent as the ligand unit, a drug, and optionally a linker that joins the drug and the binding agent. A number of different reactions are available for covalent attachment of drugs and/or linkers to binding agents. This is often accomplished by reaction of the amino acid residues of the binding agent, e.g., antibody molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention.

In certain embodiments, an intermediate, which is the precursor of the linker, is reacted with the drug under appropriate conditions. In certain embodiments, reactive groups are used on the drug and/or the intermediate. The product of the reaction between the drug and the intermediate, or the derivatized drug, is subsequently reacted with the CD19 binding agent under appropriate conditions.

Each of the particular units of the ligand-drug conjugate compounds is described in more detail herein. The synthesis and structure of exemplary linker units, stretcher units, amino acid units, self-immolative spacer unit, and drug units are also described in U.S. Patent Application Publication Nos. 2003-0083263, 2005-0238649 and 2005-0009751, each if which is incorporated herein by reference in its entirety and for all purposes.

Linker Units

Typically, the ligand-drug conjugate compounds comprise a linker region between the drug unit and the ligand unit. In some embodiments, the linker is cleavable under intracellular conditions, such that cleavage of the linker releases the drug unit from the ligand in the intracellular environment. In yet other embodiments, the linker unit is not cleavable and the drug is released, for example, by antibody degradation.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in CD19-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO: 52)). Other examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP(N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT (See, e.g., Thorpe et al., 1987, *Cancer Res.* 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.)

In yet other specific embodiments, the linker is a malonate linker (Johnson et al., 1995, *Anticancer Res.* 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10):1305-12).

In yet other embodiments, the linker unit is not cleavable and the drug is released by antibody degradation. (See U.S. Publication No. 20050238649 incorporated by reference herein in its entirety and for all purposes).

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of ligand-drug conjugate compound, are cleaved when the ligand-drug conjugate compound presents in an extracellular environment (e.g., in plasma). Whether a linker is not substantially sensitive to the extracellular environment can be determined, for example, by incubating with plasma the ligand-drug conjugate compound for a predetermined time period (e.g., 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (i.e., in the milieu of the linker-therapeutic agent moiety of the ligand-drug conjugate compound as described herein). In yet other embodiments, the linker promotes cellular internalization when conjugated to both the auristatin compound and the anti-CD19 antibody.

A variety of exemplary linkers that can be used with the present compositions and methods are described in WO 2004-010957, U.S. Publication No. 20060074008, U.S. Publication No. 20050238649, and U.S. Publication No. 20060024317 (each of which is incorporated by reference herein in its entirety and for all purposes).

A "Linker unit" (LU) is a bifunctional compound that can be used to link a Drug unit and a Ligand unit to form a ligand-drug conjugate compound. In some embodiments, the Linker unit has the formula:

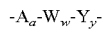

wherein: -A- is a Stretcher unit,
a is 0 or 1,
each -W- is independently an Amino Acid unit,
w is an integer ranging from 0 to 12,
-Y- is a self-immolative Spacer unit, and
y is 0, 1 or 2.

In some embodiments, a is 0 or 1, w is 0 or 1, and y is 0, 1 or 2. In some embodiments, a is 0 or 1, w is 0 or 1, and y is 0 or 1. In some embodiments, when w is 1 to 12, y is 1 or 2. In some embodiments, w is 2 to 12 and y is 1 or 2. In some embodiments, a is 1 and w and y are 0.

The Stretcher Unit

The Stretcher unit (A), when present, is capable of linking a Ligand unit to an Amino Acid unit (-W-), if present, to a Spacer unit (-Y-), if present; or to a Drug unit (-D). Useful functional groups that can be present on a CD19 binding agent, either naturally or via chemical manipulation include, but are not limited to, sulfhydryl, amino, hydroxyl, the anomeric hydroxyl group of a carbohydrate, and carboxyl. Suitable functional groups are sulfhydryl and amino. In one example, sulfhydryl groups can be generated by reduction of the intramolecular disulfide bonds of an anti-CD19 antibody. In another embodiment, sulfhydryl groups can be generated by reaction of an amino group of a lysine moiety of an anti-CD19 antibody with 2-iminothiolane (Traut's reagent) or other sulfhydryl generating reagents. In certain embodiments, the anti-CD19 antibody is a recombinant antibody and is engineered to carry one or more lysines. In certain other embodiments, the recombinant anti-CD19 antibody is engineered to carry additional sulfhydryl groups, e.g., additional cysteines.

In one embodiment, the Stretcher unit forms a bond with a sulfur atom of the Ligand unit. The sulfur atom can be derived from a sulfhydryl group of a Ligand. Representative Stretcher units of this embodiment are depicted within the square brackets of Formulas IIIa and Mb, wherein L-, -W-, -Y-, -D, w and y are as defined above, and $R_{17}$ is selected from —$C_1$-$C_{10}$ alkylene-, —$C_1$-$C_{10}$ alkenylene-, —$C_1$-$C_{10}$ alkynylene-, carbocyclo-, —O—($C_1$-$C_8$ alkylene)-, O—($C_1$-$C_8$ alkenylene)-, —O—($C_1$-$C_8$ alkynylene)-, -arylene-, —$C_1$-$C_{10}$ alkylene-arylene-, —$C_2$-$C_{10}$ alkenylene-arylene, —$C_2$-$C_{10}$ alkynylene-arylene, -arylene-$C_1$-$C_{10}$ alkylene-, -arylene-$C_2$-$C_{10}$ alkenylene-, -arylene-$C_2$-$C_{10}$ alkynylene-, —$C_1$-$C_{10}$ alkylene-(carbocyclo)-, —$C_2$-$C_{10}$ alkenylene-(carbocyclo)-, —$C_2$-$C_{10}$ alkynylene-(carbocyclo)-, -(carbocyclo)-$C_1$-$C_{10}$ alkylene-, -(carbocyclo)-$C_2$-$C_{10}$ alkenylene-, -(carbocyclo)-$C_2$-$C_{10}$ alkynylene, -heterocyclo-, —$C_1$-$C_{10}$ alkylene-(heterocyclo)-, —$C_2$-$C_{10}$ alkenylene-(heterocyclo)-, —$C_2$-$C_{10}$ alkynylene-(heterocyclo)-, -(heterocyclo)-$C_1$-$C_{10}$ alkylene-, -(heterocyclo)-$C_2$-$C_{10}$ alkenylene-, -(heterocyclo)-$C_1$-$C_{10}$ alkynylene-, —($CH_2CH_2O)_r$—, or —($CH_2CH_2O)_r$—$CH_2$—, and r is an integer ranging from 1-10, wherein said alkyl, alkenyl, alkynyl, alkylene, alkenylene, alkynyklene, aryl, carbocyle, carbocyclo, heterocyclo, and arylene radicals, whether alone or as part of another group, are optionally substituted. Alkylene, alkenylene, alkynylene radicals, whether alone or as part of another group, can be optionally substituted with, for example, one or more groups independently selected from A1; carbocyclo radicals, whether alone or as part of another group, can be optionally substituted with, for example, one or more groups independently selected from A2; arylene radicals, whether alone or as part of another group, can be optionally substituted with, for example, one or more groups independently selected from A3; heterocyclo radicals, whether alone or as part of another group, can be optionally substituted with, for example, one or more groups independently selected from A4. A1, A2, A3, and A4 are as defined herein. It is to be understood from all the exemplary embodiments that even where not denoted expressly, from 1 to 20 drug moieties can be linked to a Ligand (p=1-20).

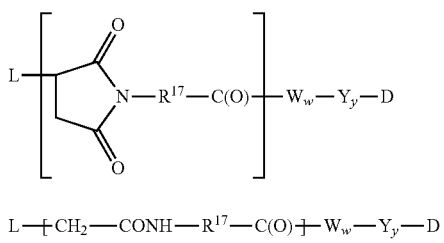
IIIa

L—[CH₂—CONH—R¹⁷—C(O)]—W_w—Y_y—D    IIIb

An illustrative Stretcher unit is that of Formula IIIa wherein $R^{17}$ is —(CH₂)₅—:

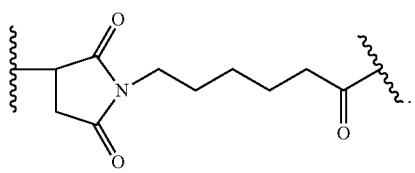 [SMILES: *C(=O)CCCCCN1C(=O)CC(*)C1=O]

Another illustrative Stretcher unit is that of Formula IIIa wherein $R^{17}$ is —(CH₂CH₂O)_r—CH₂—; and r is 2:

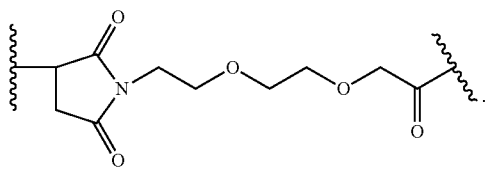 [SMILES: *C(=O)COCCOCCN1C(=O)CC(*)C1=O]

An illustrative Stretcher unit is that of Formula IIIa wherein $R^{17}$ is -arylene- or arylene-$C_1$-$C_{10}$ alkylene-. In some embodiments, the aryl group is an unsubstituted phenyl group.

Still another illustrative Stretcher unit is that of Formula IIIb wherein $R^{17}$ is —(CH₂)₅—:

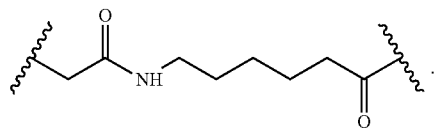 [SMILES: *CC(=O)NCCCCCC(*)=O]

In certain embodiments, the Stretcher unit is linked to the Ligand unit via a disulfide bond between a sulfur atom of the Ligand unit and a sulfur atom of the Stretcher unit. A representative Stretcher unit of this embodiment is depicted within the square brackets of Formula IV, wherein $R^{17}$, L-, -W-, -Y-, -D, w and y are as defined above.

L—S—[S—R¹⁷—C(O)]—W_w—Y_y—D    IV

It should be noted that throughout this application, the S moiety in the formula below refers to a sulfur atom of the Ligand unit, unless otherwise indicated by context.

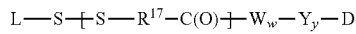

In yet other embodiments, the Stretcher contains a reactive site that can form a bond with a primary or secondary amino group of a Ligand. Examples of these reactive sites include, but are not limited to, activated esters such as succinimide esters, 4 nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va and Vb, wherein —$R^{17}$—, L-, -W-, -Y-, -D, w and y are as defined above;

L—[C(O)NH—R¹⁷—C(O)]—W_w—Y_y—D    Va $$L-\left[\overset{\overset{S}{\|}}{C}-NH-R^{17}-C(O)\right]-W_w-Y_y-D \quad Vb$$

In some embodiments, the Stretcher contains a reactive site that is reactive to a modified carbohydrate's (—CHO) group that can be present on a Ligand. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko et al., 1991, *Bioconjugate Chem.* 2:133-41. Representative Stretcher units of this embodiment are depicted within the square brackets of Formulas VIa, VIb, and VIc, wherein —$R^{17}$—, L-, -W-, -Y-, -D, w and y are as defined as above.

L=N—NH—R¹⁷—C(O)—W_w—Y_y—D    VIa

L=N—O—R¹⁷—C(O)—W_w—Y_y—D    VIb $$L=N-NH-\overset{\overset{O}{\|}}{C}-R^{17}-C(O)-W_w-Y_y-D \quad VIc$$

The Amino Acid Unit

The Amino Acid unit (-W-), when present, links the Stretcher unit to the Spacer unit if the Spacer unit is present, links the Stretcher unit to the Drug moiety if the Spacer unit is absent, and links the Ligand unit to the Drug unit if the Stretcher unit and Spacer unit are absent.

$W_w$— can be, for example, a monopeptide, dipeptide, tripeptide, tetrapeptide, pentapeptide, hexapeptide, heptapeptide, octapeptide, nonapeptide, decapeptide, undecapeptide or dodecapeptide unit. Each -W- unit independently has the formula denoted below in the square brackets, and w is an integer ranging from 0 to 12:

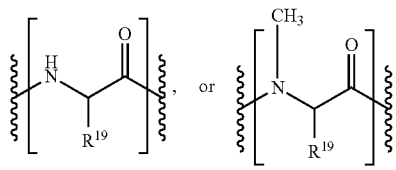 or wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl,

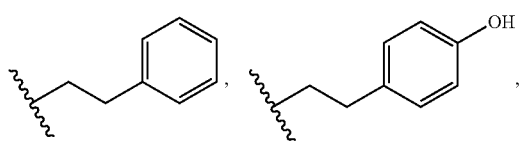

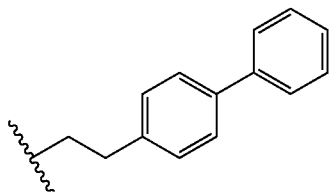

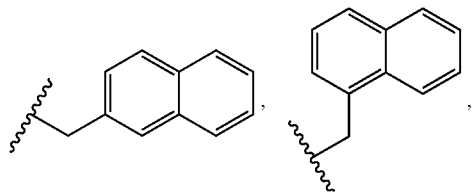

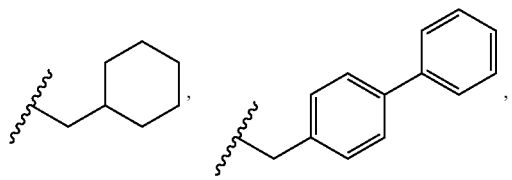

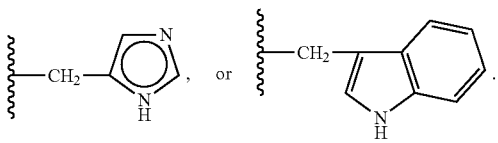

In some embodiments, the Amino Acid unit can be enzymatically cleaved by one or more enzymes, including a cancer or tumor-associated protease, to liberate the Drug unit (-D), which in one embodiment is protonated in vivo upon release to provide a Drug (D).

In certain embodiments, the Amino Acid unit can comprise natural amino acids. In other embodiments, the Amino Acid unit can comprise non-natural amino acids. Illustrative Ww units are represented by formulas (VII)-(IX):

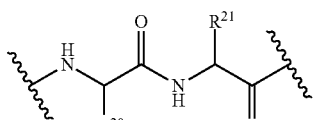

wherein $R^{20}$ and $R^{21}$ are as follows:

| $R^{20}$ | $R^{21}$ |
|---|---|
| Benzyl | $(CH_2)_4NH_2$; |
| methyl | $(CH_2)_4NH_2$; |
| isopropyl | $(CH_2)_4NH_2$; |
| isopropyl | $(CH_2)_3NHCONH_2$; |
| benzyl | $(CH_2)_3NHCONH_2$; |
| isobutyl | $(CH_2)_3NHCONH_2$; |
| sec-butyl | $(CH_2)_3NHCONH_2$; |
| 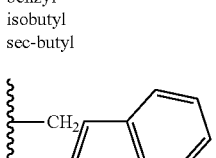 | $(CH_2)_3NHCONH_2$; |
| benzyl | methyl; |
| benzyl | $(CH_2)_3NHC(=NH)NH_2$; |

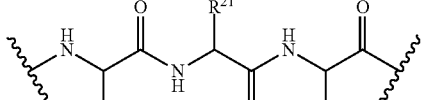

wherein $R^{20}$, $R^{21}$ and $R^{22}$ are as follows:

| $R^{20}$ | $R^{21}$ | $R^{22}$ |
|---|---|---|
| benzyl | benzyl | $(CH_2)_4NH_2$; |
| isopropyl | benzyl | $(CH_2)_4NH_2$; and |
| H | benzyl | $(CH_2)_4NH_2$; |

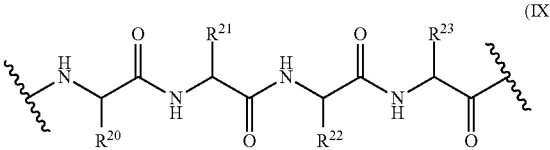

wherein $R^{20}$, $R^{21}$, $R^{22}$ and $R^{23}$ are as follows:

| $R^{20}$ | $R^{21}$ | $R^{22}$ | $R^{23}$ |
|---|---|---|---|
| H | benzyl | isobutyl | H; and |
| methyl | isobutyl | methyl | isobutyl. |

Exemplary Amino Acid units include, but are not limited to, units of formula VII where: $R^{20}$ is benzyl and $R^{21}$ is —$(CH_2)_4NH_2$; $R^{20}$ is isopropyl and $R^{21}$ is —$(CH_2)_4NH_2$; or $R^{20}$ is isopropyl and $R^{21}$ is —$(CH_2)_3NHCONH_2$. Another exemplary Amino Acid unit is a unit of formula VIII wherein $R^{20}$ is benzyl, $R^{21}$ is benzyl, and $R^{22}$ is —$(CH_2)_4NH_2$.

Useful -$W_w$— units can be designed and optimized in their selectivity for enzymatic cleavage by a particular enzyme, for example, a tumor-associated protease. In one embodiment, a -$W_w$— unit is that whose cleavage is catalyzed by cathepsin B, C and D, or a plasmin protease.

In one embodiment, -W$_w$— is a dipeptide, tripeptide, tetrapeptide or pentapeptide. When R$^{19}$, R$^{20}$, R$^{21}$, R$^{22}$ or R$^{23}$ is other than hydrogen, the carbon atom to which R$^{19}$, R$^{22}$ or R$^{23}$ is attached is chiral.

Each carbon atom to which R$^{19}$, R$^{20}$, R$^{21}$, R$^{22}$ or R$^{23}$ is attached is independently in the (S) or (R) configuration.

In one aspect of the Amino Acid unit, the Amino Acid unit is valine-citrulline (vc or val-cit). In another aspect, the Amino Acid unit is phenylalanine-lysine (i.e., fk). In yet another aspect of the Amino Acid unit, the Amino Acid unit is N-methylvaline-citrulline. In yet another aspect, the Amino Acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

The Spacer Unit

The Spacer unit (-Y-), when present, links an Amino Acid unit to the Drug unit when an Amino Acid unit is present. Alternately, the Spacer unit links the Stretcher unit to the Drug unit when the Amino Acid unit is absent. The Spacer unit also links the Drug unit to the Ligand unit when both the Amino Acid unit and Stretcher unit are absent.

Spacer units are of two general types: non self-immolative or self-immolative. A non self-immolative Spacer unit is one in which part or all of the Spacer unit remains bound to the Drug moiety after cleavage, particularly enzymatic, of an Amino Acid unit from the ligand-drug conjugate. Examples of a non self-immolative Spacer unit include, but are not limited to a (glycine-glycine) Spacer unit and a glycine Spacer unit (both depicted in Scheme 1) (infra). When a conjugate containing a glycine-glycine Spacer unit or a glycine Spacer unit undergoes enzymatic cleavage via an enzyme (e.g., a tumor-cell associated-protease, a cancer-cell-associated protease or a lymphocyte-associated protease), a glycine-glycine-Drug moiety or a glycine-Drug moiety is cleaved from L-Aa-Ww-. In one embodiment, an independent hydrolysis reaction takes place within the target cell, cleaving the glycine-Drug moiety bond and liberating the Drug.

Scheme 1

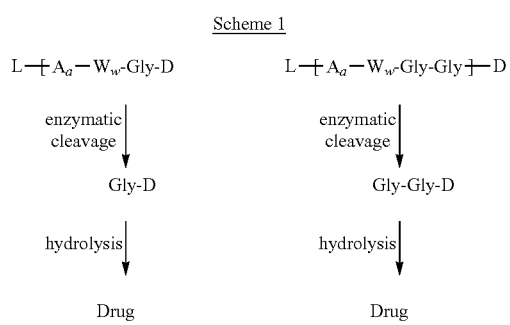

In some embodiments, a non self-immolative Spacer unit (-Y-) is -Gly-. In some embodiments, a non self-immolative Spacer unit (-Y-) is -Gly-Gly-.

In one embodiment, a Drug-Linker conjugate is provided in which the Spacer unit is absent (y=0), or a pharmaceutically acceptable salt or solvate thereof.

Alternatively, a conjugate containing a self-immolative Spacer unit can release -D. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved.

In some embodiments, -Y$_y$- is a p-aminobenzyl alcohol (PAB) unit (see Schemes 2 and 3) whose phenylene portion is substituted with Q$_m$ wherein Q is —C$_1$-C$_8$ alkyl, —C$_1$-C$_8$ alkenyl, —C$_1$-C$_8$ alkynyl, —O—(C$_1$-C$_8$ alkyl), —O—(C$_1$-C$_8$ alkenyl), —O—(C$_1$-C$_8$ alkynyl), -halogen, -nitro or -cyano; and m is an integer ranging from 0-4. The alkyl, alkenyl and alkynyl groups, whether alone or as part of another group, can be optionally substituted with A1 as defined herein.

In some embodiments, -Y- is a PAB group that is linked to -W$_w$— via the amino nitrogen atom of the PAB group, and connected directly to -D via a carbonate, carbamate or ether group. Without being bound by any particular theory or mechanism, Scheme 2 depicts a possible mechanism of Drug release of a PAB group which is attached directly to -D via a carbamate or carbonate group as described by Toki et al., 2002, *J. Org. Chem.* 67:1866-1872.

Scheme 2

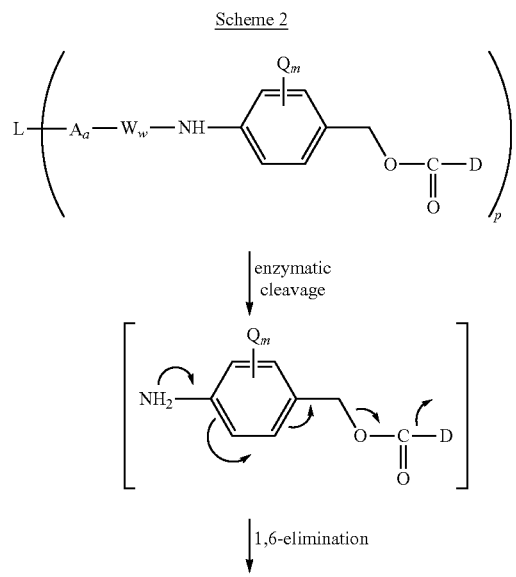

In Scheme 2, Q is —C$_1$-C$_8$ alkyl, —C$_1$-C$_8$ alkenyl, —C$_1$-C$_8$ alkynyl, —O—(C$_1$-C$_8$ alkyl), —O—(C$_1$-C$_8$ alkenyl), —O—(C$_1$-C$_8$ alkynyl), -halogen, -nitro or -cyano; m is an integer ranging from 0-4; and p ranges from 1 to about 20. The alkyl, alkenyl and alkynyl groups, whether alone or as part of another group, can be optionally substituted with A1 as defined herein.

Without being bound by any particular theory or mechanism, Scheme 3 depicts a possible mechanism of Drug release of a PAB group which is attached directly to -D via an ether or amine linkage, wherein D includes the oxygen or nitrogen group that is part of the Drug unit.

Scheme 3

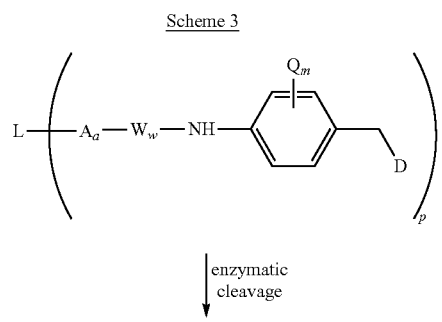

-continued

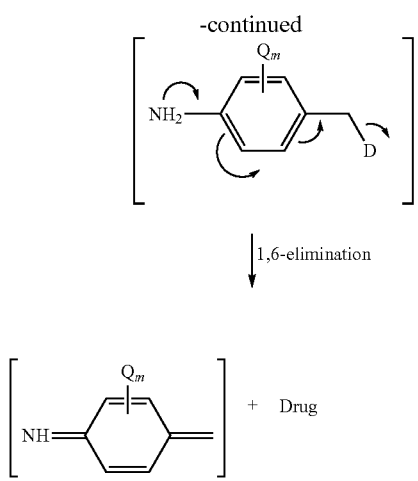

1,6-elimination

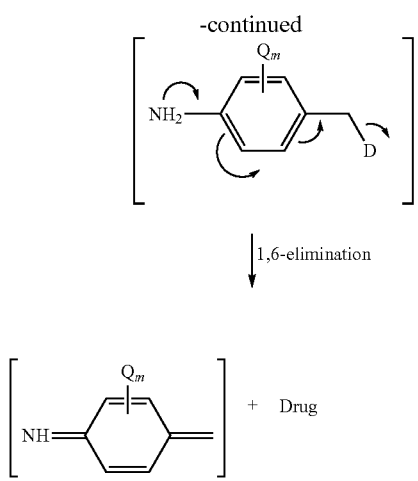 + Drug

In Scheme 3, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; and p ranges from 1 to about 20. The alkyl, alkenyl and alkynyl groups, whether alone or as part of another group, can be optionally substituted with A1 as defined herein.

Other examples of self-immolative spacers include, but are not limited to, aromatic compounds that are electronically similar to the PAB group such as 2-aminoimidazol-5-methanol derivatives (Hay et al., 1999, *Bioorg. Med. Chem. Lett.* 9:2237) and ortho or para-aminobenzylacetals. Spacers can be used that undergo cyclization upon amide bond hydrolysis, such as substituted and unsubstituted 4-aminobutyric acid amides (Rodrigues et al., 1995, *Chemistry Biology* 2:223), appropriately substituted bicyclo[2.2.1] and bicyclo[2.2.2] ring systems (Storm et al., 1972, *J. Amer. Chem. Soc.* 94:5815) and 2-aminophenylpropionic acid amides (Amsberry et al., 1990, *J. Org. Chem.* 55:5867) Elimination of amine-containing drugs that are substituted at the α-position of glycine (Kingsbury et al., 1984, *J. Med. Chem.* 27:1447) are also examples of self-immolative spacers.

In one embodiment, the Spacer unit is a branched bis (hydroxymethyl)-styrene (BHMS) unit as depicted in Scheme 4, which can be used to incorporate and release multiple drugs.

Scheme 4

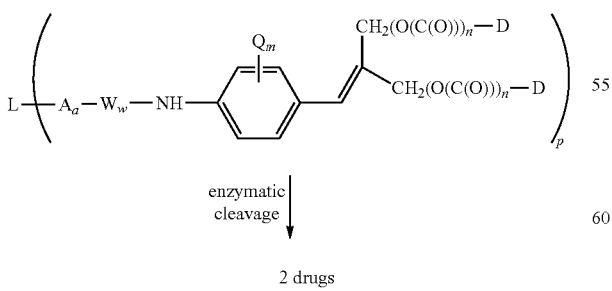

enzymatic cleavage 2 drugs

In Scheme 4, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; n is 0 or 1; and p ranges raging from 1 to about 20. The alkyl, alkenyl and alkynyl groups, whether alone or as part of another group, can be optionally substituted with A1 as defined herein.

In some embodiments, the -D moieties are the same. In yet another embodiment, the -D moieties are different.

In one aspect, Spacer units (-$Y_r$-) are represented by Formulas (X)-(XII):

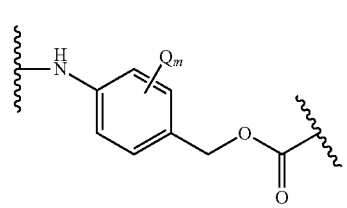

X wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4. The alkyl, alkenyl and alkynyl groups, whether alone or as part of another group, can be optionally substituted with A1 as defined herein.

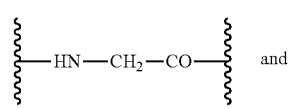

XI

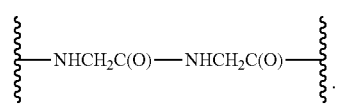

XII

Embodiments of the Formula I and II comprising Ligand-drug conjugate compounds can include:

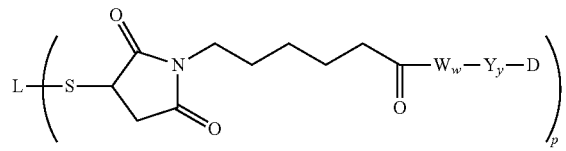

wherein w and y are each 0, 1 or 2, and,

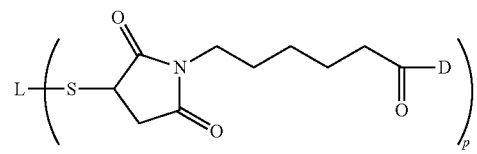

wherein w and y are each 0,

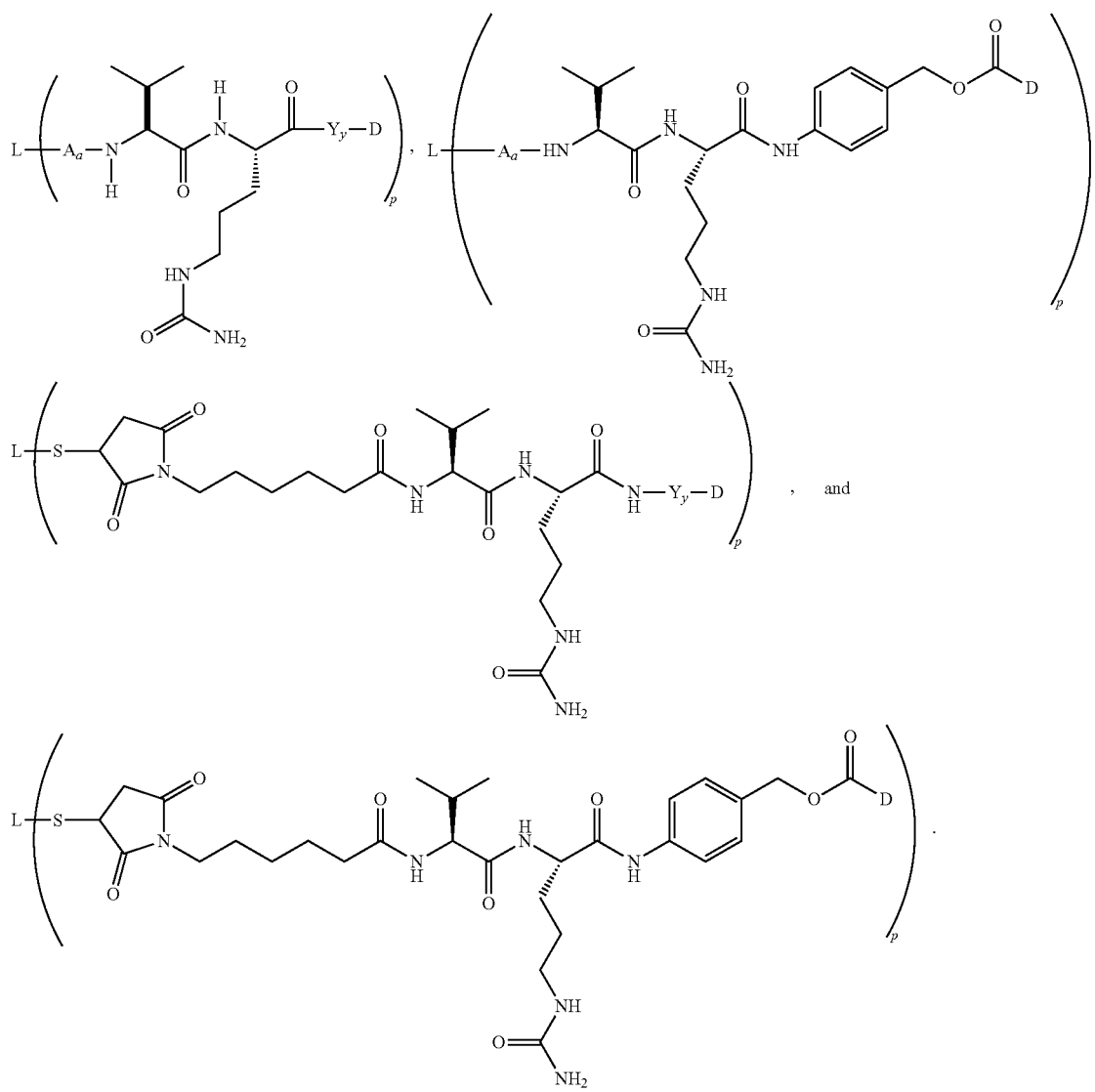

The Drug Unit

The drug moiety (D) can be any cytotoxic, cytostatic or immunomodulatory (e.g., immunosuppressive) or drug. D is a Drug unit (moiety) having an atom that can form a bond with the Spacer unit, with the Amino Acid unit, with the Stretcher unit or with the Ligand unit. In some embodiments, the Drug unit D has a nitrogen atom that can form a bond with the Spacer unit. As used herein, the terms "drug unit" and "drug moiety" are synonymous and used interchangeably.

Useful classes of cytotoxic or immunomodulatory agents include, for example, antitubulin agents, auristatins, DNA minor groove binders, DNA replication inhibitors, alkylating agents (e.g., platinum complexes such as cis-platin, mono (platinum), bis(platinum) and tri-nuclear platinum complexes and carboplatin), anthracyclines, antibiotics, antifolates, antimetabolites, chemotherapy sensitizers, duocarmycins, camptothecins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic or immunomodulatory agents include, for example, an androgen, anthramycin (AMC), asparaginase, 5-azacytidine, azathioprine, bleomycin, busulfan, buthionine sulfoximine, calicheamicin, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, etoposide, an estrogen, 5-fluordeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16 and VM-26.

In some typical embodiments, suitable cytotoxic agents include, for example, DNA minor groove binders (e.g., enediynes and lexitropsins, a CBI compound; see also U.S. Pat. No. 6,130,237), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, the Drug is an anti-tubulin agent. Examples of anti-tubulin agents include, but are not limited to, auristatins, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs (e.g., epothilone A and B), nocodazole, colchicine and colcimid, estramustine, cryptophycins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, *Cancer Res.* 52:127-131).

In some embodiments, the Drug is an auristatin, such as auristatin E (also known in the art as a derivative of dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein in its entirety and for all purposes.

Auristatins have been shown to interfere with microtubule dynamics and nuclear and cellular division and have anticancer activity. Auristatins of the present invention bind tubulin and can exert a cytotoxic or cytostatic effect on a CD19 expressing cell line. There are a number of different assays, known in the art, that can be used for determining whether an auristatin or resultant antibody-drug conjugate exerts a cytostatic or cytotoxic effect on a desired cell line, see e.g., Example 7.

Methods for determining whether a compound binds tubulin are known in the art. See, for example, Muller et al., *Anal. Chem.* 2006, 78, 4390-4397; Hamel et al., *Molecular Pharmacology,* 1995 47: 965-976; and Hamel et al., *The Journal of Biological Chemistry,* 1990 265:28, 17141-17149. For purposes of the present invention, the relative affinity of a compound to tubulin can be determined. Some preferred auristatins of the present invention bind tubulin with an affinity ranging from 10 fold lower (weaker affinity) than the binding affinity of MMAE to tubulin to 10 fold, 20 fold or even 100 fold higher (higher affinity) than the binding affinity of MMAE to tublin.

In some embodiments, -D is an auristatin of the formula $D_E$, $D_F$ or $D_Z$:

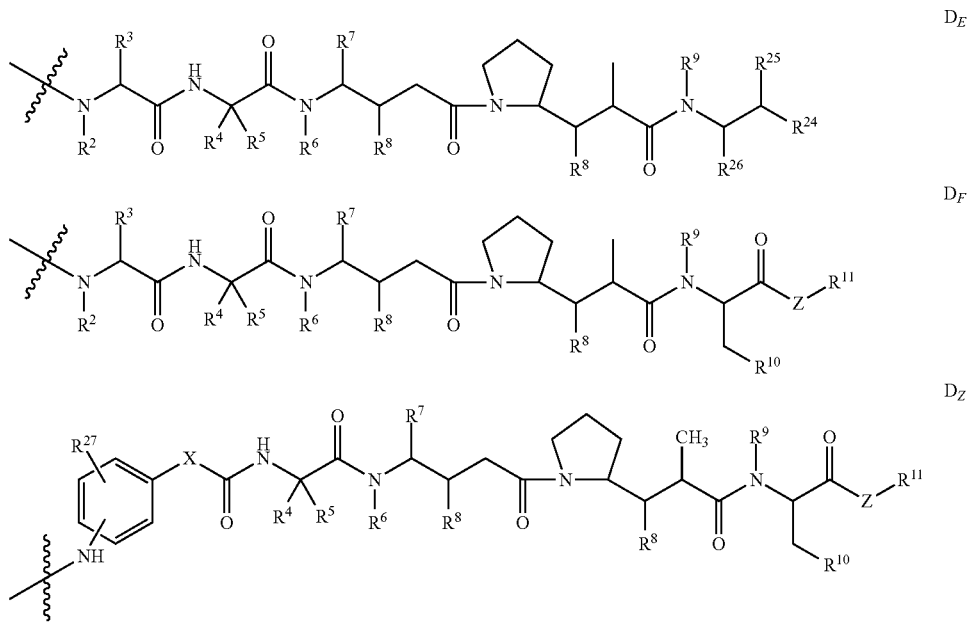

or a pharmaceutically acceptable salt or solvate form thereof;

wherein, independently at each location:

$R^2$ is $C_1$-$C_{20}$ alkyl, $C_2$-$C_{20}$ alkenyl, or $C_2$-$C_{20}$ alkynyl;

$R^3$ is H, $C_1$-$C_{20}$ alkyl, $C_2$-$C_{20}$ alkenyl, $C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), aryl, —$C_1$-$C_{20}$ alkylene(aryl), —$C_2$-$C_{20}$ alkenylene(aryl), —$C_2$-$C_{20}$ alkynylene(aryl), heterocycle, —$C_1$-$C_{20}$ alkylene(heterocycle), —$C_2$-$C_{20}$ alkenylene (heterocycle), or —$C_2$-$C_{20}$ alkynylene(heterocycle);

$R^4$ is H, $C_1$-$C_{20}$ alkyl, $C_2$-$C_{20}$ alkenyl, $C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), aryl, —$C_1$-$C_{20}$ alkylene(aryl), —$C_2$-$C_{20}$ alkenylene(aryl), —$C_2$-$C_{20}$ alkynylene(aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle);

$R^5$ is H or $C_1$-$C_8$ alkyl;

or $R^4$ and $R^5$ jointly form a carbocyclic ring and have the formula —$(CR^aR^b)_s$— wherein $R^a$ and $R^b$ are independently H, $C_1$-$C_{20}$ alkyl, $C_2$-$C_{20}$ alkenyl, $C_2$-$C_{20}$ alkynyl, or carbocycle and s is 2, 3, 4, 5 or 6, $R^6$ is H, $C_1$-$C_{20}$ alkyl, $C_2$-$C_{20}$ alkenyl, or $C_2$-$C_{20}$ alkynyl;

$R^7$ is H, $C_1$-$C_{20}$ alkyl, $C_2$-$C_{20}$ alkenyl, $C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), aryl, —$C_1$-$C_{20}$ alkylene(aryl), —$C_2$-$C_{20}$ alkenylene(aryl), —$C_2$-$C_{20}$ alkynylene(aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle);

each $R^8$ is independently H, OH, $C_1$-$C_{20}$ alkyl, $C_2$-$C_{20}$ alkenyl, $C_2$-$C_{20}$ alkynyl, —O—($C_1$-$C_{20}$ alkyl), —O—($C_2$-$C_{20}$ alkenyl), —O—($C_1$-$C_{20}$ alkynyl), or carbocycle;

$R^9$ is H, $C_1$-$C_{20}$ alkyl, $C_2$-$C_{20}$ alkenyl, or $C_2$-$C_{20}$ alkynyl;

$R^{24}$ is aryl, heterocycle, or carbocycle;

$R^{25}$ is H, $C_1$-$C_{20}$ alkyl, $C_2$-$C_{20}$ alkenyl, $C_2$-$C_{20}$ alkynyl, carbocycle, —O—($C_1$-$C_{20}$ alkyl), —O—($C_2$-$C_{20}$ alkenyl), —O-($C_2$-$C_{20}$ alkynyl), or $OR^{18}$ wherein $R^{18}$ is H, a hydroxyl protecting group, or a direct bond where $OR^{18}$ represents =O;

$R^{26}$ is H, $C_1$-$C_{20}$ alkyl, $C_2$-$C_{20}$ alkenyl, or $C_2$-$C_{20}$ alkynyl, aryl, heterocycle, or carbocycle;

$R^{10}$ is aryl or heterocycle;

Z is O, S, NH, or $NR^{12}$, wherein $R^{12}$ is $C_1$-$C_{20}$ alkyl, $C_2$-$C_{20}$ alkenyl, or $C_2$-$C_{20}$ alkynyl;

$R^{11}$ is H, $C_1$-$C_{20}$ alkyl, $C_2$-$C_{20}$ alkenyl, $C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), aryl, —$C_1$-$C_{20}$ alkylene(aryl), —$C_2$-$C_{20}$ alkenylene(aryl), —$C_2$-$C_{20}$ alkynylene(aryl), heterocycle, —$C_1$-$C_{20}$ alkylene(heterocycle), —$C_2$-$C_{20}$ alkenylene(heterocycle), —$C_2$-$C_{20}$ alkynylene(heterocycle) —$(R^{13}O)_m$—$R^{14}$, or —$(R^{13}O)_m$—$CH(R^{15})_2$;

m is an integer ranging from 1-1000;

$R^{13}$ is $C_2$-$C_{20}$ alkylene, $C_2$-$C_{20}$ alkenylene, or $C_2$-$C_{20}$ alkynylene;

$R^{14}$ is H, $C_1$-$C_{20}$ alkyl, $C_2$-$C_{20}$ alkenyl, or $C_2$-$C_{20}$ alkynyl;

each occurrence of $R^{15}$ is independently H, COOH, —$(CH_2)_n$—$N(R^{16})_2$, —$(CH_2)_n$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl;

each occurrence of $R^{16}$ is independently H, $C_1$-$C_{20}$ alkyl, $C_2$-$C_{20}$ alkenyl, $C_2$-$C_{20}$ alkynyl or —$(CH_2)_n$—COOH;

n is an integer ranging from 0 to 6;

$R^{27}$ is H, $C_1$-$C_{20}$ alkyl, $C_2$-$C_{20}$ alkenyl, $C_2$-$C_{20}$ alkynyl, O—($C_1$-$C_{20}$ alkyl), —O—($C_2$-$C_{20}$ alkenyl), —O—($C_2$-$C_{20}$ alkynyl), halogen, —$NO_2$, —COOH, or —C(O)$OR^{28}$ wherein $R^{28}$ is H, $C_1$-$C_{20}$ alkyl, $C_2$-$C_{20}$ alkenyl, $C_2$-$C_{20}$ alkynyl, aryl, heterocycle, —$(CH_2CH_2O)_r$—H, —$(CH_2CH_2O)_r$—$CH_3$, or —$(CH_2CH_2O)_r$—$CH_2CH_2C(O)OH$; wherein r is an integer ranging from 1-10; and X is —$(CR^{29}_2)_l$— wherein $R^{29}$ is H, $C_1$-$C_{20}$ alkyl, $C_2$-$C_{20}$ alkenyl, $C_2$-$C_{20}$ alkynyl and I is an integer ranging from 0 to 10;

wherein said alkyl, alkenyl, alkynyl, alkylene, alkenylene, alkynyklene, aryl, carbocyle, and heterocycle radicals, whether alone or as part of another group, are optionally substituted.

Auristatins of the formula $D_E$, $D_F$ or $D_Z$ include those wherein $R^2$ is $C_1$-$C_{20}$ alkyl, $C_2$-$C_{20}$ alkenyl, or $C_2$-$C_{20}$ alkynyl, each of which is optionally substituted with one or more groups independently selected from A1;

$R^3$ is H, $C_1$-$C_{20}$ alkyl, $C_2$-$C_{20}$ alkenyl, $C_2$-$C_{20}$ alkynyl, monocyclic $C_3$-$C_6$ carbocycle, —$C_1$-$C_{20}$ alkylene (monocyclic $C_3$-$C_6$ carbocycle), —$C_2$-$C_{20}$ alkenylene (monocyclic $C_3$-$C_6$ carbocycle), —$C_2$-$C_{20}$ alkynylene (monocyclic $C_3$-$C_6$ carbocycle), $C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

$R^4$ is H, $C_1$-$C_{20}$ alkyl, $C_2$-$C_{20}$ alkenyl, $C_2$-$C_{20}$ alkynyl, monocyclic $C_3$-$C_6$ carbocycle, —$C_1$-$C_{20}$ alkylene (monocyclic $C_3$-$C_6$ carbocycle), —$C_2$-$C_{20}$ alkenylene (monocyclic $C_3$-$C_6$ carbocycle), —$C_2$-$C_{20}$ alkynylene (monocyclic $C_3$-$C_6$ carbocycle), $C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), heterocycle, —$C_1$-$C_{20}$ alkylene(heterocycle), —$C_2$-$C_{20}$ alkenylene (heterocycle), or —$C_2$-$C_{20}$ alkynylene(heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

$R^5$ is H or $C_1$-$C_8$ alkyl;

or $R^4$ and $R^5$ jointly form a carbocyclic ring and have the formula —$(CR^aR^b)_s$— wherein $R^a$ and $R^b$ are independently H, $C_1$-$C_8$ alkyl, $C_2$-$C_8$ alkenyl, $C_2$-$C_8$ alkynyl, or carbocycle, and s is 2, 3, 4, 5 or 6;

$R^6$ is H, $C_1$-$C_{20}$ alkyl, $C_2$-$C_{20}$ alkenyl, or $C_2$-$C_{20}$ alkynyl, wherein said alkyl, alkenyl and alkynyl radicals are optionally substituted with one or more groups independently selected from A1;

$R^7$ is H, $C_1$-$C_{20}$ alkyl, $C_2$-$C_{20}$ alkenyl, $C_2$-$C_{20}$ alkynyl, monocyclic $C_3$-$C_6$ carbocycle, —$C_1$-$C_{20}$ alkylene (monocyclic $C_3$-$C_6$ carbocycle), —$C_2$-$C_{20}$ alkenylene (monocyclic $C_3$-$C_6$ carbocycle), —$C_2$-$C_{20}$ alkynylene (monocyclic $C_3$-$C_6$ carbocycle), $C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), heterocycle, —$C_1$-$C_{20}$ alkylene(heterocycle), —$C_2$-$C_{20}$ alkenylene (heterocycle), or —$C_2$-$C_{20}$ alkynylene(heterocycle);

wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

each $R^8$ is independently H, OH, $C_1$-$C_{20}$ alkyl, $C_2$-$C_{20}$ alkenyl, $C_2$-$C_{20}$ alkynyl, —O—($C_1$-$C_{20}$ alkyl), —O—($C_2$-$C_{20}$ alkenyl), —O—($C_1$-$C_{20}$ alkynyl), or carbocycle, wherein said alkyl, alkenyl, and alkynyl radicals, whether alone or as part of another group, are optionally substituted with one or more groups independently selected from A1 and said carbocycle is optionally substituted with one or more groups independently selected from A2;

$R^9$ is H, $C_1$-$C_{20}$ alkyl, $C_2$-$C_{20}$ alkenyl, or $C_2$-$C_{20}$ alkynyl; wherein said alkyl, alkenyl and alkynyl radical are optionally substituted with one or more groups independently selected from A1;

$R^{24}$ is aryl, heterocycle, or carbocycle; wherein said carbocycle radical is optionally substituted with one or more groups independently selected from A2, said aryl radical is optionally substituted with one or more groups independently selected from A3, and said heterocycle radical is optionally substituted with one or more groups independently selected from A4;

$R^{25}$ is selected from H, $C_1$-$C_{20}$ alkyl, $C_2$-$C_{20}$ alkenyl, $C_2$-$C_{20}$ alkynyl, carbocycle, OH, —O—($C_1$-$C_{20}$ alkyl), —O—($C_2$-$C_{20}$ alkenyl), —O—($C_2$-$C_{20}$ alkynyl) or $OR^{18}$; wherein said alkyl, alkenyl, and alkynyl radicals, whether alone or as part of another group, are optionally substituted with one or more groups independently selected from A1, and said carbocycle is optionally substituted with one or more groups independently selected from A2;

$R^{18}$ is H, a hydroxyl protecting group, or a direct bond where $OR^{18}$ represents =O;

$R^{26}$ is selected from H, $C_1$-$C_{20}$ alkyl, $C_2$-$C_{20}$ alkenyl, $C_2$-$C_{20}$ alkynyl, or carbocycle; wherein said alkyl, alkenyl, and alkynyl radicals are optionally substituted with one or more groups independently selected from A1, and said carbocycle radical is optionally substituted with one or more groups independently selected from A2;

$R^{10}$ is aryl optionally substituted with one or more groups independently selected from A3, or heterocycle optionally substituted with one or more groups independently selected from A4;

Z is O, S, NH, or $NR^{12}$, wherein $R^{12}$ is $C_1$-$C_{20}$ alkyl, $C_2$-$C_{20}$ alkenyl, or $C_2$-$C_{20}$ alkynyl, each of which is optionally substituted with one or more groups independently selected from A1;

$R^{11}$ is H, $C_1$-$C_{20}$ alkyl, $C_2$-$C_{20}$ alkenyl, $C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), aryl, —$C_1$-$C_{20}$ alkylene(aryl), —$C_2$-$C_{20}$ alkenylene(aryl), —$C_2$-$C_{20}$ alkynylene(aryl), heterocycle, —$C_1$-$C_{20}$ alkylene(heterocycle), —$C_2$-$C_{20}$ alkenylene (heterocycle), —$C_2$-$C_{20}$ alkynylene(heterocycle) —($R^{13}$O)$_m$—$R^{14}$, or —($R^{13}$O)$_m$—CH($R^{15}$)$_2$ wherein said alkyl, alkenyl and alkynyl radicals are optionally substituted with one or more groups independently selected from A1, said carbocycle radical is optionally substituted with one or more groups independently selected from A2, said aryl radical is optionally substituted with one or more groups independently selected from A3, and said heterocycle is optionally substituted with one or more groups independently selected from A4;

m is an integer ranging from 1-1000;

$R^{13}$ is $C_2$-$C_{20}$ alkylene, $C_2$-$C_{20}$ alkenylene, or $C_2$-$C_{20}$ alkynylene, each of which is optionally substituted with one or more groups independently selected from A1;

$R^{14}$ is H, $C_1$-$C_{20}$ alkyl, $C_2$-$C_{20}$ alkenyl, or $C_2$-$C_{20}$ alkynyl wherein said alkyl, alkenyl and alkynyl radicals are optionally substituted with one or more groups independently selected from A1;

each occurrence of $R^{15}$ is independently H, COOH, —(CH$_2$)$_n$—N($R^{16}$)$_2$, —(CH$_2$)$_n$—SO$_3$H, —(CH$_2$)$_n$—SO$_3$—$C_1$-$C_{20}$ alkyl, —(CH$_2$)$_n$—SO$_3$—$C_2$-$C_{20}$ alkenyl, or —(CH$_2$)$_n$—SO$_3$—$C_2$-$C_{20}$ alkynyl wherein said alkyl, alkenyl and alkynyl radicals are optionally substituted with one or more groups independently selected from A1;

each occurrence of $R^{16}$ is independently H, $C_1$-$C_{20}$ alkyl, $C_2$-$C_{20}$ alkenyl, $C_2$-$C_{20}$ alkynyl or —(CH$_2$)$_n$—COOH wherein said alkyl, alkenyl and alkynyl radicals are optionally substituted with one or more groups independently selected from A1;

n is an integer ranging from 0 to 6;

$R^{27}$ is H, $C_1$-$C_{20}$ alkyl, $C_2$-$C_{20}$ alkenyl, $C_2$-$C_{20}$ alkynyl, O—($C_1$-$C_{20}$ alkyl), —O—($C_2$-$C_{20}$ alkenyl), —O—($C_2$-$C_{20}$ alkynyl), halogen, —NO$_2$, —COOH, or —C(O)OR$^{28}$ wherein said alkyl, alkenyl and alkynyl radicals are optionally substituted with one or more groups independently selected from A1 and $R^{28}$ is H, $C_1$-$C_{20}$ alkyl, $C_2$-$C_{20}$ alkenyl, $C_2$-$C_{20}$ alkynyl, aryl, heterocycle, —(CH$_2$CH$_2$O)$_r$—H, —(CH$_2$CH$_2$O)$_r$—CH$_3$, or —(CH$_2$CH$_2$O), CH$_2$CH$_2$C(O)OH; wherein r is an integer ranging from 1-10 and wherein said alkyl, alkenyl and alkynyl radicals are optionally substituted with one or more groups independently selected from A1; said aryl radical is optionally substituted with one or more groups independently selected from A3; and said heterocycle radical is optionally substituted with one or more groups independently selected from A4; and X is —(CR$^{29}$$_2$)$_l$— wherein $R^{29}$ is H, $C_1$-$C_{20}$ alkyl, $C_2$-$C_{20}$ alkenyl, $C_2$-$C_{20}$ alkynyl and l is an integer ranging from 0 to 10 and wherein said alkyl, alkenyl and alkynyl radicals are optionally substituted with one or more groups independently selected from A1;

A1 is halogen, optionally substituted —O—($C_1$-$C_8$ alkyl), optionally substituted —O—($C_2$-$C_8$ alkenyl), optionally substituted —O—($C_2$-$C_8$ alkynyl), optionally substituted -aryl, —C(O)R', —OC(O)R', —C(O)OR', —C(O)NH$_2$, —C(O)NHR', —C(O)N(R')$_2$, —NHC(O) R', —SR', —SO$_3$R', —S(O)$_2$R', —S(O)R', —OH, =O, —N$_3$, —NH$_2$, —NH(R'), —N(R')$_2$ and —CN, where each R' is independently selected from H, optionally substituted —$C_1$-$C_8$ alkyl, optionally substituted —$C_2$-$C_8$ alkenyl, optionally substituted —$C_2$-$C_8$ alkynyl, or optionally substituted aryl, and wherein said optionally substituted O—($C_1$-$C_8$ alkyl), optionally substituted —O—($C_2$-$C_8$ alkenyl), optionally substituted —O—($C_2$-$C_8$ alkynyl), optionally substituted aryl, optionally substituted $C_1$-$C_8$ alkyl, optionally substituted —$C_2$-$C_8$ alkenyl, and optionally substituted —$C_2$-$C_8$ alkynyl groups can be optionally substituted with one or more groups independently selected from —$C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from H, —$C_1$-$C_8$ alkyl, —$C_2$-$C_8$ alkenyl, —$C_2$-$C_8$ alkynyl, or aryl;

A2 is halogen, optionally substituted $C_1$-$C_8$ alkyl, optionally substituted —$C_2$-$C_8$ alkenyl, optionally substituted —$C_2$-$C_8$ alkynyl, optionally substituted —O—($C_1$-$C_8$ alkyl), optionally substituted —O—($C_2$-$C_8$ alkenyl), optionally substituted —O—($C_2$-$C_8$ alkynyl), optionally substituted aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from H, optionally substituted —$C_1$-$C_8$ alkyl, optionally substituted —$C_2$-$C_8$ alkenyl, optionally substituted —$C_2$-$C_8$ alkynyl, or optionally substituted aryl and wherein said optionally substituted —$C_1$-$C_8$ alkyl, optionally substituted —$C_2$-$C_8$ alkenyl, optionally substituted —$C_2$-$C_8$ alkynyl, optionally substituted —O—($C_1$-$C_8$ alkyl), optionally substituted —O—($C_2$-$C_8$ alkenyl), optionally substituted —O—($C_2$-$C_8$ alkynyl), and optionally substituted aryl groups can be optionally substituted with one or more substituents independently selected from $C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$—NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from H, —$C_1$-$C_8$ alkyl, —$C_2$-$C_8$ alkenyl, —$C_2$-$C_8$ alkynyl, or aryl;

A3 is halogen, optionally substituted —$C_1$-$C_8$ alkyl, optionally substituted —$C_2$-$C_8$ alkenyl, optionally substituted —$C_2$-$C_8$ alkynyl, optionally substituted —O—($C_1$-$C_8$ alkyl), optionally substituted —O—($C_2$-$C_8$ alkenyl), optionally substituted —O—($C_2$-$C_8$ alkynyl), optionally substituted -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —NO$_2$, —N$_3$, —NH$_2$, —NH(R'), —N(R')$_2$ and —CN, where each R' is independently selected from H, optionally substituted —$C_1$-$C_8$ alkyl, optionally substituted —$C_2$-$C_8$ alkenyl, optionally substituted —$C_2$-$C_8$ alkynyl, or optionally substituted aryl and wherein said optionally substituted —$C_1$-$C_8$ alkyl, optionally substituted —$C_2$-$C_8$ alkenyl, optionally substituted —$C_2$-$C_8$ alkynyl, optionally substituted O—($C_1$-$C_8$ alkyl), optionally substituted —O—($C_2$-$C_8$ alkenyl), optionally substituted —O—($C_2$-$C_8$ alkynyl), and optionally substituted aryl, groups can be further optionally substituted with one or more substituents independently selected from $C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from H, —$C_1$-$C_8$ alkyl, —$C_2$-$C_8$ alkenyl, —$C_2$-$C_8$ alkynyl, or aryl;

and A4 is optionally substituted —$C_1$-$C_8$ alkyl, optionally substituted —$C_2$-$C_8$ alkenyl, optionally substituted —$C_2$-$C_8$ alkynyl, halogen, optionally substituted —O—($C_1$-$C_8$ alkyl), optionally substituted —O—($C_2$-$C_8$ alkenyl), optionally substituted —O—($C_2$-$C_8$ alkynyl), optionally substituted -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —N$_3$, —NH$_2$, —NH(R'), —N(R')$_2$ and —CN, where each R' is independently selected from H, optionally substituted —$C_1$-$C_8$ alkyl, optionally substituted —$C_2$-$C_8$ alkenyl, optionally substituted —$C_2$-$C_8$ alkynyl, or optionally substituted aryl and wherein said optionally substituted O—($C_1$-$C_8$ alkyl), optionally substituted —O—($C_2$-$C_8$ alkenyl), optionally substituted —O—($C_2$-$C_8$ alkynyl), optionally substituted —$C_1$-$C_8$ alkyl, optionally substituted —$C_2$-$C_8$ alkenyl, optionally substituted —$C_2$-$C_8$ alkynyl, and optionally substituted aryl groups can be further optionally substituted with one or more substituents independently selected from —$C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$—NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from H, —$C_1$-$C_8$ alkyl, —$C_2$-$C_8$ alkenyl, —$C_2$-$C_8$ alkynyl, or aryl; or a pharmaceutically acceptable salt or solvate form thereof.

Auristatins of the formula $D_E$ include those wherein said alkyl, alkenyl, alkynyl, alkylene, alkenylene, alkynyklene, aryl, carbocyle, and heterocycle radicals are unsubstituted.

Auristatins of the formula $D_E$ include those wherein the groups of $R^2$, $R^3$, $R^4$, $R^5$, $R^6$, $R^7$, $R^8$, and $R^9$ are unsubstituted and the groups of $R^{24}$, $R^{25}$ and $R^{26}$ are optionally substituted as described herein.

Auristatins of the formula $D_E$ include those wherein
$R^2$ is $C_1$-$C_{20}$ alkyl optionally substituted with one or more groups independently selected from A1;
$R^3$ and $R^7$ are independently selected from H, $C_1$-$C_{20}$ alkyl, $C_2$-$C_{20}$ alkenyl, $C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), $C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;
$R^4$ is H, $C_1$-$C_{20}$ alkyl, $C_2$-$C_{20}$ alkenyl, $C_2$-$C_{20}$ alkynyl, monocyclic $C_3$-$C_6$ carbocycle, —$C_1$-$C_{20}$ alkylene (monocyclic $C_3$-$C_6$ carbocycle), —$C_2$-$C_{20}$ alkenylene (monocyclic $C_3$-$C_6$ carbocycle), —$C_2$-$C_{20}$ alkynylene (monocyclic $C_3$-$C_6$ carbocycle), $C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), heterocycle, —$C_1$-$C_{20}$ alkylene(heterocycle), —$C_2$-$C_{20}$ alkenylene (heterocycle), or —$C_2$-$C_{20}$ alkynylene(heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

$R^5$ is H or $C_1$-$C_8$ alkyl;

or $R^4$ and $R^5$ jointly form a carbocyclic ring and have the formula —$(CR^aR^b)_s$— wherein $R^a$ and $R^b$ are independently selected from H, $C_1$-$C_8$ alkyl, $C_2$-$C_8$ alkenyl, $C_2$-$C_8$ alkynyl, or carbocycle, and s is selected from 2, 3, 4, 5 or 6;

$R^6$ is $C_1$-$C_{20}$ alkyl optionally substituted with one or more groups independently selected from A1;

each $R^8$ is independently selected from OH, O—($C_1$-$C_{20}$ alkyl), —O—($C_2$-$C_{20}$ alkenyl), or —O—($C_2$-$C_{20}$ alkynyl) wherein said alkyl, alkenyl, and alkynyl radicals are optionally substituted with one or more groups independently selected from A1;

$R^9$ is hydrogen or $C_1$-$C_{20}$ alkyl optionally substituted with one or more groups independently selected from A1;

$R^{24}$ is aryl, heterocycle, or carbocycle; wherein said carbocycle radical is optionally substituted with one or more groups independently selected from A2, said aryl radical is optionally substituted with one or more groups independently selected from A3, and said heterocycle radical is optionally substituted with one or more groups independently selected from A4;

$R^{25}$ is $OR^{18}$; wherein $R^{18}$ is H, a hydroxyl protecting group, or a direct bond where $OR^{18}$ represents =O;

$R^{26}$ is selected from H, $C_1$-$C_{20}$ alkyl, $C_2$-$C_{20}$ alkenyl, $C_2$-$C_{20}$ alkynyl, or carbocycle; wherein said alkyl, alkenyl, and alkynyl radicals are optionally substituted with one or more groups independently selected from A1, and said carbocycle radical is optionally substituted with one or more groups independently selected from A2; and A1, A2, A3, and A4 are as defined herein; or a pharmaceutically acceptable salt or solvate form thereof.

Auristatins of the formula $D_E$ include those wherein $R^2$ is $C_1$-$C_8$ alkyl;

$R^3$, $R^4$ and $R^7$ are independently selected from H, $C_1$-$C_{20}$ alkyl, $C_2$-$C_{20}$ alkenyl, $C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), $C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

$R^5$ is hydrogen;

$R^6$ is $C_1$-$C_8$ alkyl;

each $R^8$ is independently selected from OH, O—($C_1$-$C_{20}$ alkyl), —O—($C_2$-$C_{20}$ alkenyl), or —O—($C_2$-$C_{20}$ alkynyl) wherein said alkyl, alkenyl, and alkynyl radicals are optionally substituted with one or more groups independently selected from A1;

$R^9$ is hydrogen or $C_1$-$C_8$ alkyl;

$R^{24}$ is phenyl optionally substituted with one or more groups independently selected from A3;

$R^{25}$ is $OR^{18}$; wherein $R^{18}$ is H, a hydroxyl protecting group, or a direct bond where $OR^{18}$ represents =O;

$R^{26}$ is selected from H, $C_1$-$C_{20}$ alkyl, $C_2$-$C_{20}$ alkenyl, $C_2$-$C_{20}$ alkynyl, or carbocycle; wherein said alkyl, alkenyl, and alkynyl radicals are optionally substituted with one or more groups independently selected from A1, and said carbocycle radical is optionally substituted with one or more groups independently selected from A2; and A1, A2, A3, and A4 are as defined herein; or a pharmaceutically acceptable salt or solvate form thereof.

Auristatins of the formula $D_E$ include those wherein $R^2$ is methyl;

$R^3$ is H, $C_1$-$C_8$ alkyl, $C_2$-$C_8$ alkenyl, or $C_2$-$C_8$ alkynyl, wherein said alkyl, alkenyl and alkynyl radicals are optionally substituted with one or more groups independently selected from A1;

$R^4$ is H, $C_1$-$C_8$ alkyl, $C_2$-$C_8$ alkenyl, $C_2$-$C_8$ alkynyl, monocyclic $C_3$-$C_6$ carbocycle, $C_6$-$C_{10}$ aryl, —$C_1$-$C_8$ alkylene($C_6$-$C_{10}$ aryl), $C_2$-$C_8$ alkenylene($C_6$-$C_{10}$ aryl), —$C_2$-$C_8$ alkynylene($C_6$-$C_{10}$ aryl), —$C_1$-$C_8$ alkylene (monocyclic $C_3$-$C_6$ carbocycle), —$C_2$-$C_8$ alkenylene (monocyclic $C_3$-$C_6$ carbocycle), —$C_2$-$C_8$ alkynylene(monocyclic $C_3$-$C_6$ carbocycle); wherein said alkyl, alkenyl, alkynyl, alkylene, alkenylene, and alkynylene radicals whether alone or as part of another group are optionally substituted with one or more groups independently selected from A1; said carbocyle radicals whether alone or as part of another group are optionally substituted with one or more groups independently selected from A2; and said aryl radicals whether alone or as part of another group are optionally substituted with one or more groups independently selected from A3;

$R^5$ is H; $R^6$ is methyl;

$R^7$ is $C_1$-$C_8$ alkyl, $C_2$-$C_8$ alkenyl or $C_2$-$C_8$ alkynyl;

each $R^8$ is methoxy;

$R^9$ is hydrogen or $C_1$-$C_8$ alkyl;

$R^{24}$ is phenyl;

$R^{25}$ is $OR^{18}$; wherein $R^{18}$ is H, a hydroxyl protecting group, or a direct bond where $OR^{18}$ represents =O;

$R^{26}$ is methyl; and A1, A2, and A3 are as defined herein; or a pharmaceutically acceptable salt or solvate form thereof.

Auristatins of the formula $D_E$ include those wherein $R^2$ is methyl; $R^3$ is H or $C_1$-$C_3$ alkyl; $R^4$ is $C_1$-$C_5$ alkyl; $R^5$ is H; $R^6$ is methyl; $R^7$ is isopropyl or sec-butyl; $R^8$ is methoxy; $R^9$ is hydrogen or $C_1$-$C_8$ alkyl; $R^{24}$ is phenyl; $R^{25}$ is $OR^{18}$; wherein $R^{18}$ is H, a hydroxyl protecting group, or a direct bond where $OR^{18}$ represents =O; and $R^{26}$ is methyl; or a pharmaceutically acceptable salt or solvate form thereof.

Auristatins of the formula $D_F$ or $D_Z$ include those wherein
$R^2$ is $C_1$-$C_{20}$ alkyl, $C_2$-$C_{20}$ alkenyl, or $C_2$-$C_{20}$ alkynyl, each of which is optionally substituted with one or more groups independently selected from A1;

$R^3$, $R^4$, and $R^7$ are independently selected from H, $C_1$-$C_{20}$ alkyl, $C_2$-$C_{20}$ alkenyl, $C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), $C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

$R^5$ is H;

$R^6$ is H, $C_1$-$C_{20}$ alkyl, $C_2$-$C_{20}$ alkenyl, or $C_2$-$C_{20}$ alkynyl, wherein said alkyl, alkenyl and alkynyl radicals are optionally substituted with one or more groups independently selected from A1;

each $R^8$ is independently selected from H, OH, $C_1$-$C_{20}$ alkyl, $C_2$-$C_{20}$ alkenyl, $C_2$-$C_{20}$ alkynyl, —O—($C_1$-$C_{20}$ alkyl), —O—($C_2$-$C_{20}$ alkenyl), —O—($C_1$-$C_{20}$ alkynyl), or carbocycle, wherein said alkyl, alkenyl, and alkynyl radicals, whether alone or as part of another group, are optionally substituted with one or more groups independently selected from A1 and said carbocycle is optionally substituted with one or more groups independently selected from A2;

$R^9$ is H, $C_1$-$C_{20}$ alkyl, $C_2$-$C_{20}$ alkenyl, or $C_2$-$C_{20}$ alkynyl; wherein said alkyl, alkenyl and alkynyl radical are optionally substituted with one or more groups independently selected from A1;

$R^{10}$ is phenyl optionally substituted with one or more groups independently selected from A3;

Z is O, S, NH, or $NR^{12}$, wherein $R^{12}$ is $C_1$-$C_{20}$ alkyl, $C_2$-$C_{20}$ alkenyl, or $C_2$-$C_{20}$ alkynyl, each of which is optionally substituted with one or more groups independently selected from A1;

$R^{11}$ is H, $C_1$-$C_{20}$ alkyl, $C_2$-$C_{20}$ alkenyl, $C_2$-$C_{20}$ alkynyl, aryl, heterocycle, —$(R^{13}O)_m$—$R^{14}$, or —$(R^{13}O)_m$—CH$(R^{15})_2$ wherein said alkyl, alkenyl and alkynyl radicals are optionally substituted with one or more groups independently selected from A1, said aryl radical is optionally substituted with one or more groups independently selected from A3, and said heterocycle is optionally substituted with one or more groups independently selected from A4;

m is an integer ranging from 1-1000;

$R^{13}$ is $C_2$-$C_{20}$ alkylene, $C_2$-$C_{20}$ alkenylene, or $C_2$-$C_{20}$ alkynylene, each of which is optionally substituted with one or more groups independently selected from A1;

$R^{14}$ is H, $C_1$-$C_{20}$ alkyl, $C_2$-$C_{20}$ alkenyl, or $C_2$-$C_{20}$ alkynyl wherein said alkyl, alkenyl and alkynyl radicals are optionally substituted with one or more groups independently selected from A1;

each occurrence of $R^{15}$ is independently H, COOH, —$(CH_2)_n$—$N(R^{16})_2$, —$(CH_2)_n$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl wherein said alkyl, alkenyl and alkynyl radicals are optionally substituted with one or more groups independently selected from A1;

each occurrence of $R^{16}$ is independently H, $C_1$-$C_{20}$ alkyl, $C_2$-$C_{20}$ alkenyl, $C_2$-$C_{20}$ alkynyl or —$(CH_2)_n$—COOH wherein said alkyl, alkenyl and alkynyl radicals are optionally substituted with one or more groups independently selected from A1;

n is an integer ranging from 0 to 6;

$R^{27}$ is H; and

X is —$(CR^{29}_2)_I$— wherein I is 0; and A1, A2, A3, and A4 are as defined herein; or a pharmaceutically acceptable salt or solvate form thereof.

Auristatins of the formula $D_F$ or $D_Z$ include those wherein
$R^2$ is methyl;

$R^3$, $R^4$, and $R^7$ are independently selected from H, $C_1$-$C_{20}$ alkyl, $C_2$-$C_{20}$ alkenyl, $C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), $C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene($C_6$-$C_{10}$ aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle); wherein said alkyl, alkenyl, alkynyl, alkylene, alkenylene, and alkynylene radicals whether alone or as part of another group are optionally substituted with one or more groups independently selected from A1, said carbocycle radicals whether alone or as part of another group are optionally substituted with one or more groups independently selected from A2, said aryl radicals whether alone or as part of another group are optionally substituted with one or more groups independently selected from A3, and said heterocycle radicals whether alone or as part of another group are optionally substituted with one or more groups independently selected from A4;

$R^5$ is H;

$R^6$ is methyl;

each $R^8$ is methoxy;

$R^9$ is H, $C_1$-$C_{20}$ alkyl, $C_2$-$C_{20}$ alkenyl, or $C_2$-$C_{20}$ alkynyl; wherein said alkyl, alkenyl and alkynyl radical are optionally substituted with one or more groups independently selected from A1;

$R^{10}$ is aryl optionally substituted with one or more groups independently selected from A3, or heterocycle optionally substituted with one or more groups independently selected from A4;

Z is O, S, NH, or $NR^{12}$, wherein $R^{12}$ is $C_1$-$C_{20}$ alkyl, $C_2$-$C_{20}$ alkenyl, or $C_2$-$C_{20}$ alkynyl, each of which is optionally substituted with one or more groups independently selected from A1;

$R^{11}$ is H, $C_1$-$C_{20}$ alkyl, $C_2$-$C_{20}$ alkenyl, $C_2$-$C_{20}$ alkynyl, aryl, heterocycle, —$(R^{13}O)_m$—$R^{14}$, or —$(R^{13}O)_m$—CH$(R^{15})_2$ wherein said alkyl, alkenyl and alkynyl radicals are optionally substituted with one or more groups independently selected from A1, said aryl radical is optionally substituted with one or more groups independently selected from A3, and said heterocycle is optionally substituted with one or more groups independently selected from A4;

m is an integer ranging from 1-1000;

$R^{13}$ is $C_2$-$C_{20}$ alkylene, $C_2$-$C_{20}$ alkenylene, or $C_2$-$C_{20}$ alkynylene, each of which is optionally substituted with one or more groups independently selected from A1;

$R^{14}$ is H, $C_1$-$C_{20}$ alkyl, $C_2$-$C_{20}$ alkenyl, or $C_2$-$C_{20}$ alkynyl wherein said alkyl, alkenyl and alkynyl radicals are optionally substituted with one or more groups independently selected from A1;

each occurrence of $R^{15}$ is independently H, COOH, $-(CH_2)_n-N(R^{16})_2$, $-(CH_2)_n-SO_3H$, $-(CH_2)_n-SO_3-C_1-C_{20}$ alkyl, $-(CH_2)_n-SO_3-C_2-C_{20}$ alkenyl, or $-(CH_2)_n-SO_3-C_2-C_{20}$ alkynyl wherein said alkyl, alkenyl and alkynyl radicals are optionally substituted with one or more groups independently selected from A1;

each occurrence of $R^{16}$ is independently H, $C_1$-$C_{20}$ alkyl, $C_2$-$C_{20}$ alkenyl, $C_2$-$C_{20}$ alkynyl or $-(CH_2)_n-COOH$ wherein said alkyl, alkenyl and alkynyl radicals are optionally substituted with one or more groups independently selected from A1;

n is an integer ranging from 0 to 6;

$R^{27}$ is H; and

X is $-(CR^{29}_2)_l-$ wherein I is 0; and A1, A2, A3, and A4 are as defined herein; or a pharmaceutically acceptable salt or solvate form thereof.

Auristatins of the formula $D_Z$ include those wherein $R^1$ is hydrogen; $R^2$ is methyl; $R^3$ is H or $C_1$-$C_3$ alkyl; $R^4$ is $C_1$-$C_5$ alkyl; $R^5$ is H; $R^6$ is methyl; $R^7$ is isopropyl or sec-butyl; $R^8$ is methoxy; $R^9$ is hydrogen or $C_1$-$C_8$ alkyl; $R^{10}$ is phenyl optionally substituted with one or more groups independently selected from A3; Z is O, S, or NH; $R^{11}$ is as defined herein; $R^{27}$ is H; and X is $-(CR^{29}_2)_l-$ wherein I is 0; or a pharmaceutically acceptable salt or solvate form thereof.

Auristatins of the formula $D_Z$ include those wherein $R^1$ is hydrogen; $R^2$ is methyl; $R^3$ is H or $C_1$-$C_3$ alkyl; $R^4$ is $C_1$-$C_5$ alkyl; $R^5$ is H; $R^6$ is methyl; $R^7$ is isopropyl or sec-butyl; $R^8$ is methoxy; $R^9$ is hydrogen or $C_1$-$C_8$ alkyl; $R^{10}$ is phenyl; $R^{11}$ is as defined herein; $R^{27}$ is H; X is $-(CR^{29}_2)_l-$ wherein I is 0; and Z is O or NH; or a pharmaceutically acceptable salt or solvate form thereof.

Auristatins of the formula $D_Z$ include those wherein $R^{11}$ is $-(CH_2CH_2O)_r-H$, $-(CH_2CH_2O)_r-CH_3$, or $-(CH_2CH_2O)_r-CH_2CH_2C(O)OH$; wherein r is an integer ranging from 1-10; or a pharmaceutically acceptable salt or solvate form thereof.

Auristatins of the formula $D_Z$ include those wherein the phenyl group at the amino terminus is para substituted as shown below:

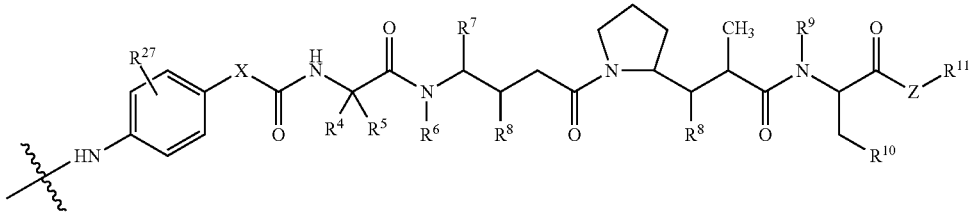

In certain of these embodiments, $R^{10}$ is phenyl optionally substituted with one or more groups independently selected from A3.

Auristatins of the formula $D_F$ include those wherein the groups of $R^2$, $R^3$, $R^4$, $R^5$, $R^6$, $R^7$, $R^8$, and $R^9$ are unsubstituted and the groups of $R^{10}$ and $R^{11}$ are as described herein.

Auristatins of the formula $D_F$ include those wherein said alkyl, alkenyl, alkynyl, alkylene, alkenylene, alkynyklene, aryl, carbocyle, and heterocycle radicals are unsubstituted Auristatins of the formula $D_F$ include those wherein $R^2$ is methyl; $R^3$ is H or $C_1$-$C_3$ alkyl; $R^4$ is $C_1$-$C_5$ alkyl; $R^5$ is H; $R^6$ is methyl; $R^7$ is isopropyl or sec-butyl; $R^8$ is methoxy; $R^9$ is hydrogen or $C_1$-$C_8$ alkyl; $R^{10}$ is phenyl optionally substituted with one or more groups independently selected from A3; Z is O, S, or NH; $R^{11}$ is as defined herein; or a pharmaceutically acceptable salt or solvate form thereof.

Auristatins of the formula $D_F$ include those wherein $R^1$ is hydrogen; $R^2$ is methyl; $R^3$ is H or $C_1$-$C_3$ alkyl; $R^4$ is $C_1$-$C_5$ alkyl; $R^5$ is H; $R^6$ is methyl; $R^7$ is isopropyl or sec-butyl; $R^8$ is methoxy; $R^9$ is hydrogen or $C_1$-$C_8$ alkyl; $R^{10}$ is phenyl; Z is O or NH; $R^{11}$ is as defined herein; or a pharmaceutically acceptable salt or solvate form thereof.

Auristatins of the formula $D_Z$ include those wherein the groups of $R^2$, $R^3$, $R^4$, $R^5$, $R^6$, $R^7$, $R^8$, $R^9$, $R^{27}$, $R^{28}$, and $R^{29}$ are unsubstituted and the groups of $R^{10}$ and $R^{11}$ are as described herein.

Auristatins of the formula $D_Z$ include those wherein said alkyl, alkenyl, alkynyl, alkylene, alkenylene, alkynyklene, aryl, carbocyle, and heterocycle radicals are unsubstituted Auristatins of the formula $D_E$, $D_F$ or $D_Z$ include those wherein $R^3$, $R^4$ and $R^7$ are independently isopropyl or sec-butyl and $R^5$ is $-H$. In an exemplary embodiment, $R^3$ and $R^4$ are each isopropyl, $R^5$ is H, and $R^7$ is sec-butyl. The remainder of the substituents are as defined herein.

Auristatins of the formula $D_E$, $D_F$ or $D_Z$ include those wherein $R^2$ and $R^6$ are each methyl, and $R^9$ is H. The remainder of the substituents are as defined herein.

Auristatins of the formula $D_E$, $D_F$ or $D_Z$ include those wherein each occurrence of $R^8$ is $-OCH_3$. The remainder of the substituents are as defined herein.

Auristatins of the formula $D_E$, $D_F$ or $D_Z$ include those wherein $R^3$ and $R^4$ are each isopropyl, $R^2$ and $R^6$ are each methyl, $R^5$ is H, $R^7$ is sec-butyl, each occurrence of $R^8$ is $-OCH_3$, and $R^9$ is H. The remainder of the substituents are as defined herein.

Auristatins of the formula $D_F$ or $D_Z$ include those wherein Z is $-O-$ or $-NH-$. The remainder of the substituents are as defined herein.

Auristatins of the formula $D_F$ or $D_Z$ include those wherein $R^{10}$ is aryl. The remainder of the substituents are as defined herein.

Auristatins of the formula $D_F$ or $D_Z$ include those wherein, $R^{10}$ is -phenyl. The remainder of the substituents are as defined herein.

Auristatins of the formula $D_F$ or $D_Z$ include those wherein Z is $-O-$, and $R^{11}$ is H, methyl or t-butyl. The remainder of the substituents are as defined herein.

Auristatins of the formula $D_F$ or $D_Z$ include those wherein, when Z is $-NH$, $R^{11}$ is $-(R^{13}O)_m-CH(R^{15})_2$, wherein $R^{15}$ is —$(CH_2)_n$—$N(R^{16})_2$, and $R^{16}$ is —$C_1$-$C_8$ alkyl or —$(CH_2)_n$—COOH. The remainder of the substituents are as defined herein.

Auristatins of the formula $D_F$ or $D_Z$ include those wherein when Z is —NH, $R^{11}$ is —$(R^{13}O)_m$—$CH(R^{15})_2$, wherein $R^{15}$ is —$(CH_2)_n$—$SO_3H$. The remainder of the substituents are as defined herein.

In preferred embodiments, when D is an auristatin of formula $D_E$, w is an integer ranging from 1 to 12, preferably 2 to 12, y is 1 or 2, and a is preferably 1.

In some embodiments, wherein D is an auristatin of formula $D_F$, a is 1 and w and y are 0.

Illustrative Drug units (-D) include the drug units having the following structures:

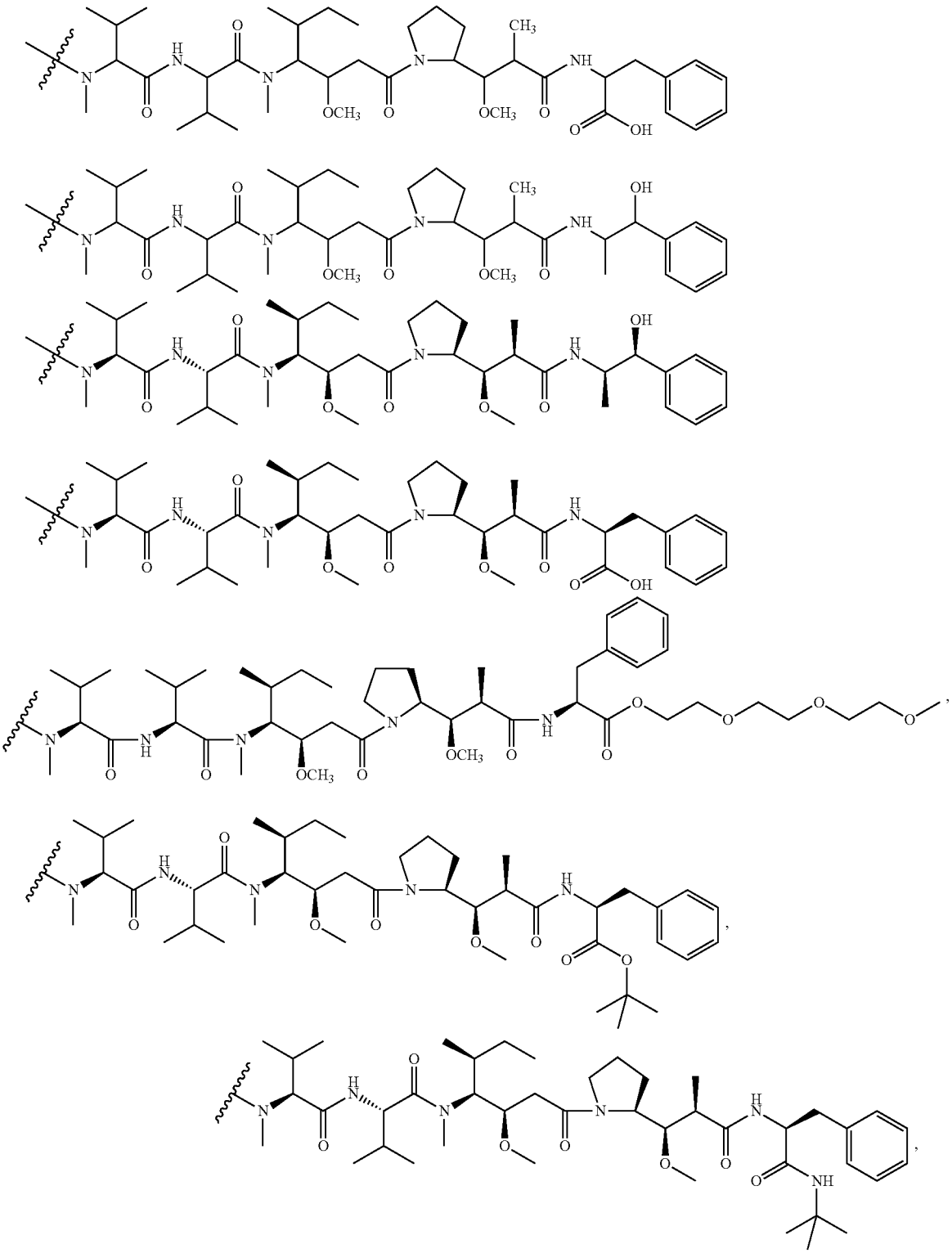

-continued
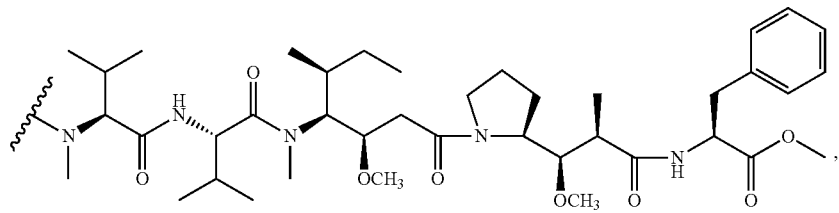
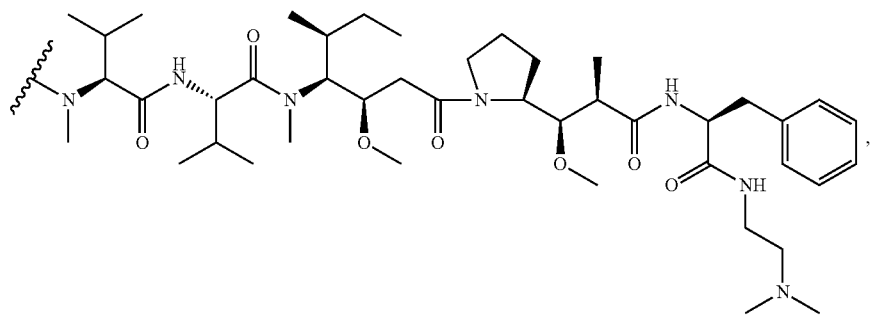
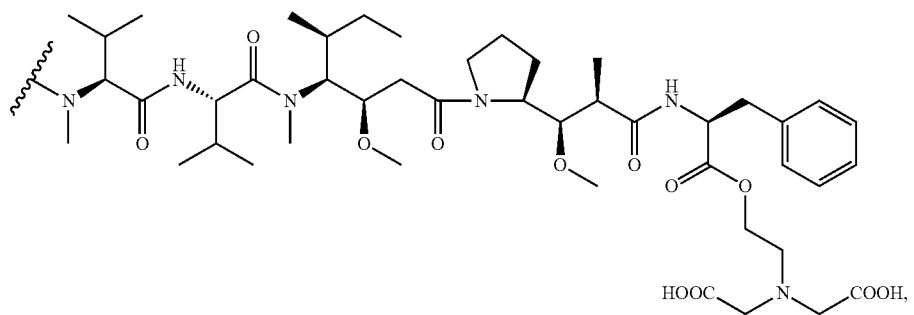
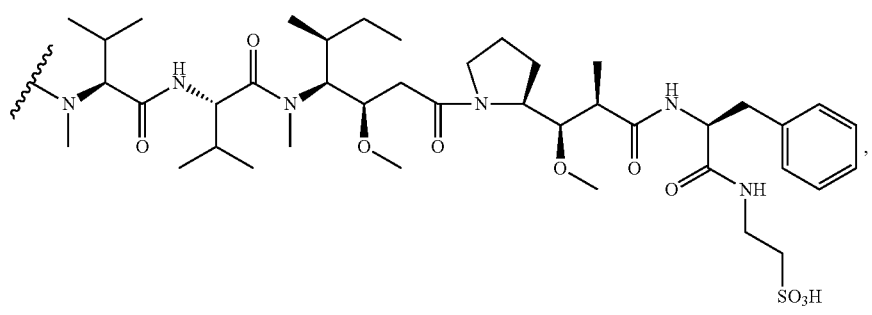
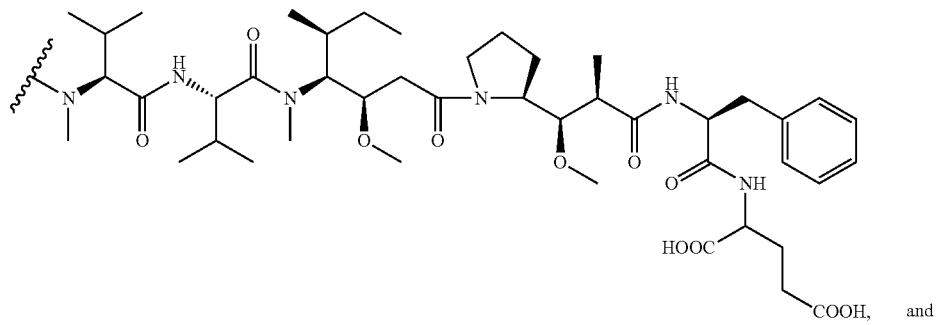
and

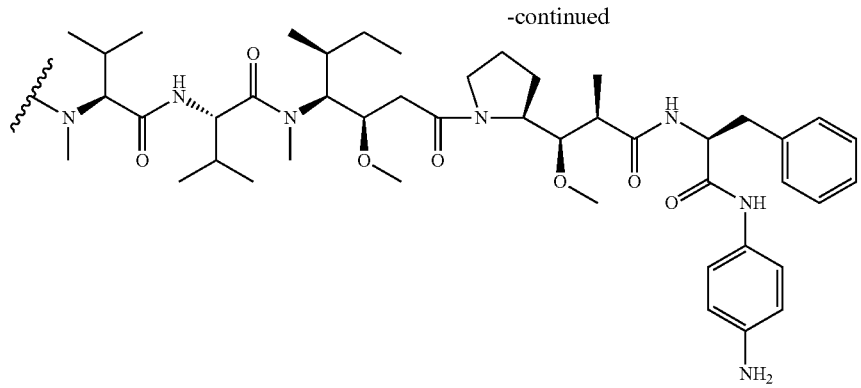

or pharmaceutically acceptable salts or solvates thereof.

In one aspect, hydrophilic groups, such as but not limited to triethylene glycol esters (TEG) can be attached to the Drug Unit at $R^{11}$. Without being bound by theory, the hydrophilic groups assist in the internalization and non-agglomeration of the Drug Unit.

In some embodiments, the Drug unit is not TZT-1027. In some embodiments, the Drug unit is not auristatin E, dolastatin 10, or auristatin PE.

Exemplary ligand-drug conjugate compounds have the following structures wherein "mAb-s-" represents an anti-CD19 antibody:

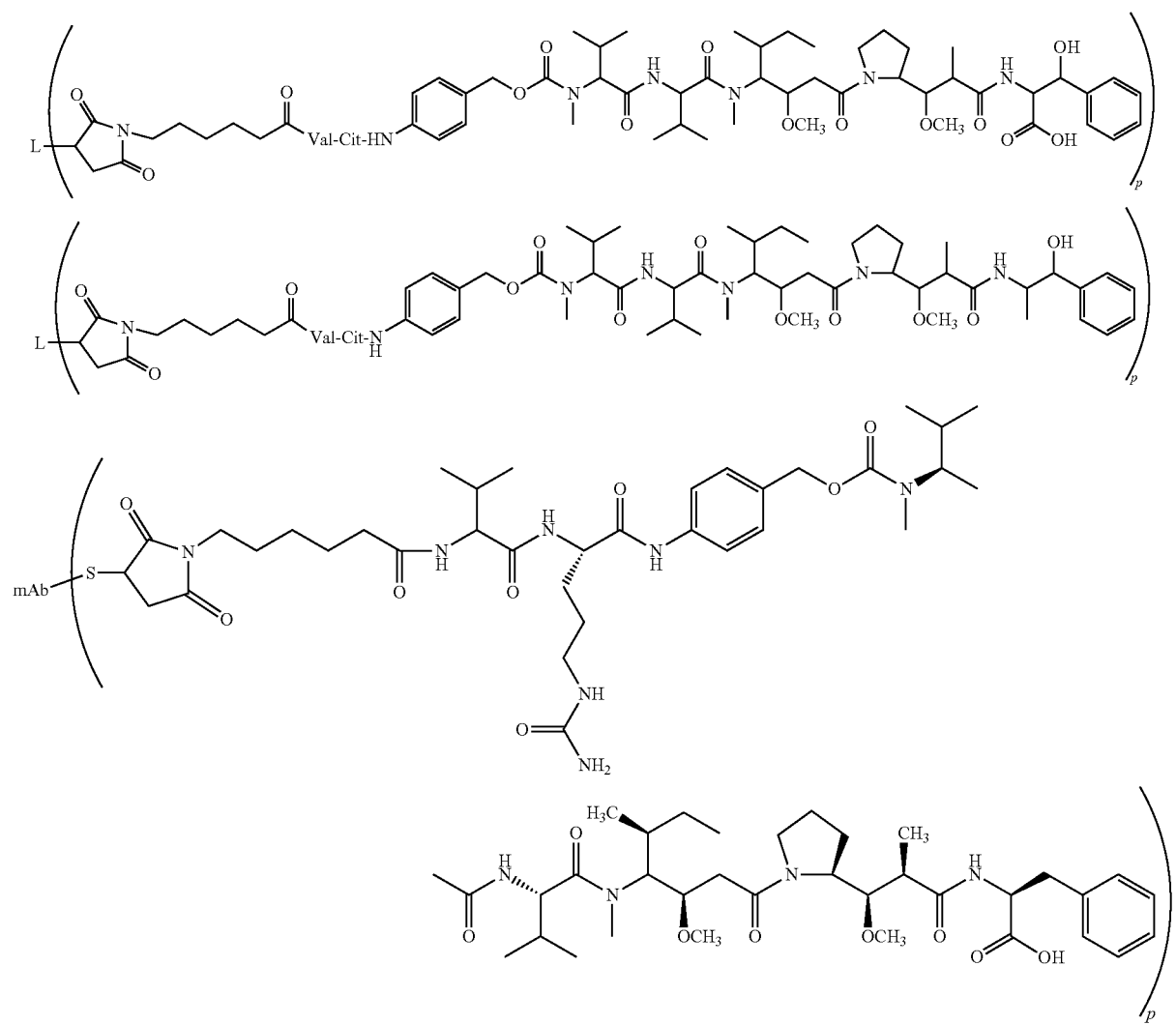

L-MC-vc-PAB-MMAF

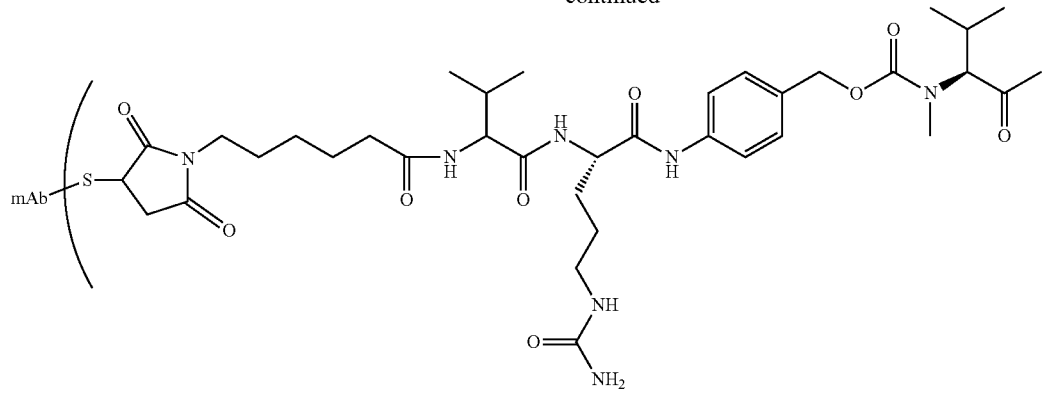

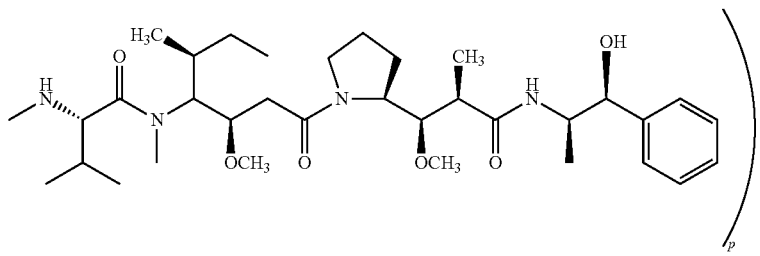

L-MC-vc-PAB-MMAE

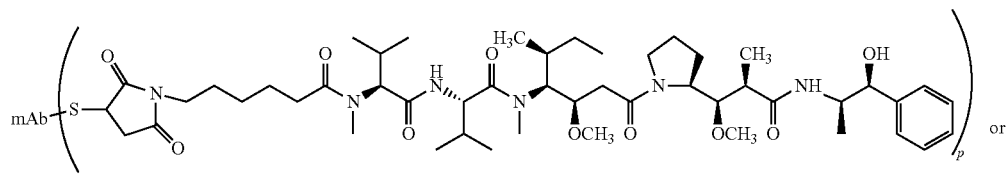

L-MC-MMAE

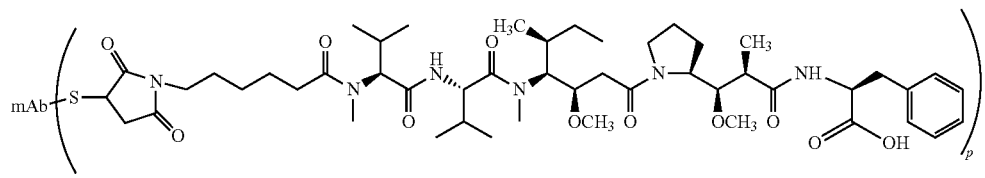

L-MC-MMAF or pharmaceutically acceptable salt or solvate forms thereof, wherein Val is valine, and Cit is citrulline.

In certain embodiments, the Drug is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the Drug is tacrolimus, cyclosporine or rapamycin. In further embodiments, the Drug is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin, goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Rituximab, Sargramostim, streptozocin, tamoxifen, temozolomide, teniposide, testolactone, thioguanine, toremifene, Tositumomab, Trastuzumab, tretinoin, uracil mustard, valrubicin, vinblastine, vincristine, vinorelbine and zoledronate.

In some embodiments, the Drug moiety is an immunomodulatory agent. The immunomodulatory agent can be, for example, gancyclovir, etanercept, tacrolimus, cyclosporine, rapamycin, cyclophosphamide, azathioprine, mycophenolate mofetil or methotrexate. Alternatively, the immunomodulatory agent can be, for example, a glucocorticoid (e.g., cortisol or aldosterone) or a glucocorticoid analogue (e.g., prednisone or dexamethasone).

In some embodiments, the immunomodulatory agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, and leukotriene receptor antagonists.

Suitable cyclooxygenase inhibitors include meclofenamic acid, mefenamic acid, carprofen, diclofenac, diflunisal, fenbufen, fenoprofen, ibuprofen, indomethacin, ketoprofen, nabumetone, naproxen, sulindac, tenoxicam, tolmetin, and acetylsalicylic acid.

Suitable lipoxygenase inhibitors include redox inhibitors (e.g., catechol butane derivatives, nordihydroguaiaretic acid (NDGA), masoprocol, phenidone, Ianopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, Ionapalen, esculin, diethylcarbamazine, phenantroline, baicalein, proxicromil, thioethers, diallyl sulfide and di-(1-propenyl) sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products WAY 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG 14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SK&F-104493, Leo Denmark SR-2566, Tanabe T-757 and Teijin TEI-1338.

In certain embodiments, the cytotoxic or cytostatic agent is a dolastatin. In certain embodiments, the cytotoxic or cytostatic agent is of the auristatin class. Thus, in a specific embodiment, the cytotoxic or cytostatic agent is MMAE (Formula XI). In another specific embodiment, the cytotoxic or cytostatic agent is AFP (Formula XVI).

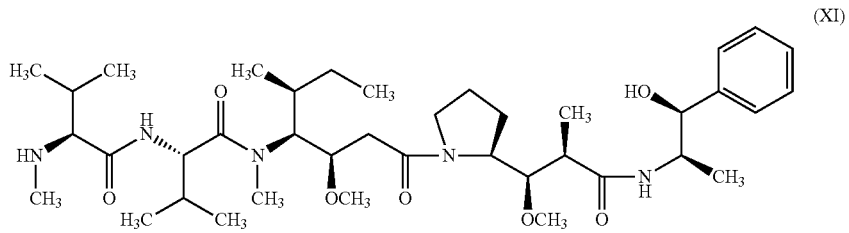 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

(XI)

In certain embodiments, the cytotoxic or cytostatic agent is a compound of formulas XII-XXI or pharmaceutically acceptable salt or solvate form thereof:

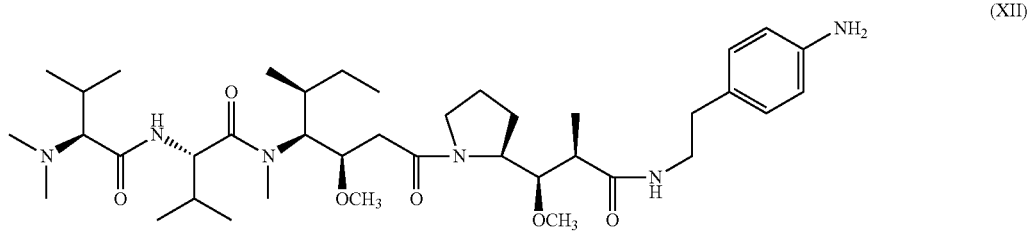

(XII)

-continued
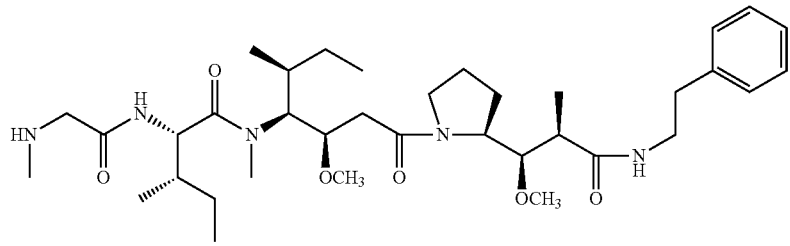
(XIII)
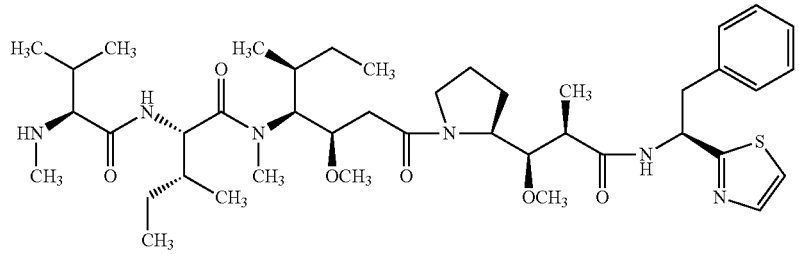
(XIV)
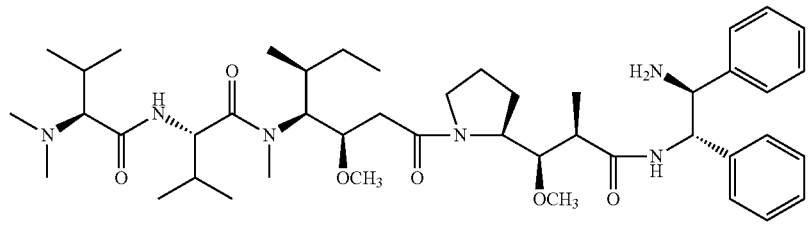
(XV)
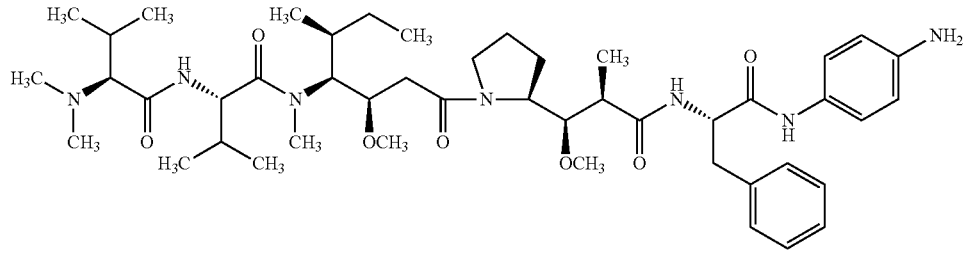
(XVI)
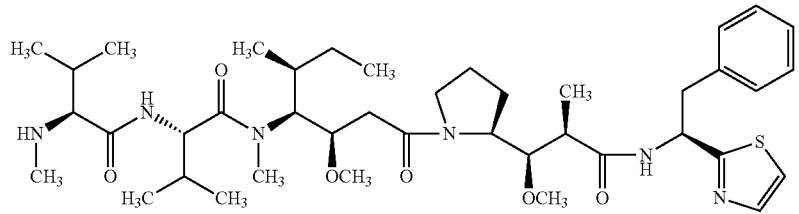
(XVII)
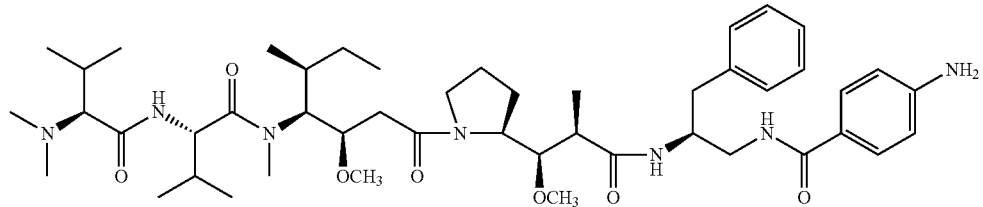
(XVIII)

(XVIV)

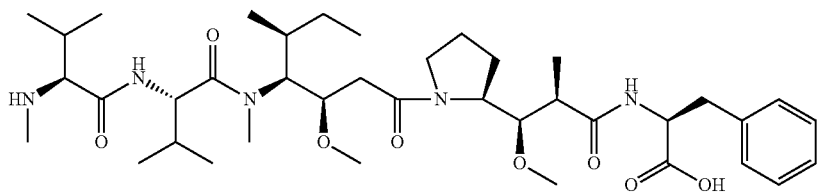

(XX)

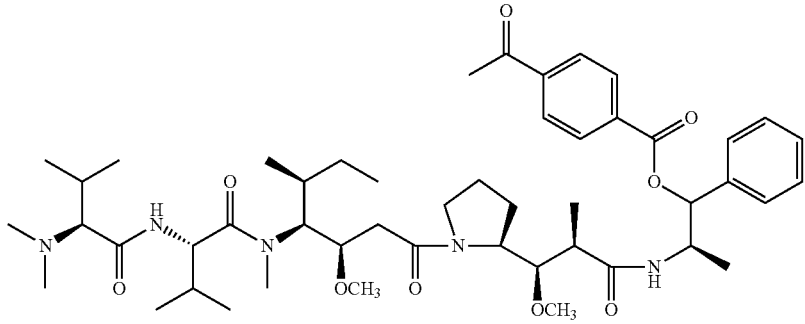

(XXI)

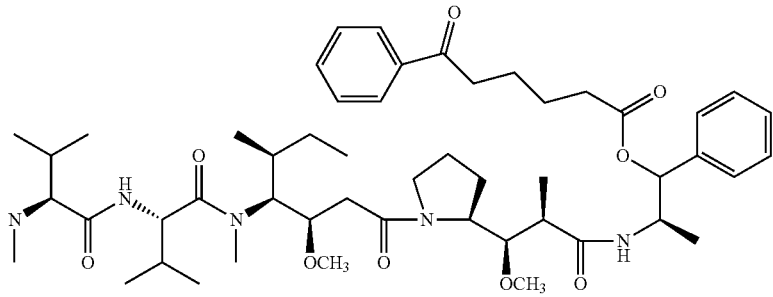

Methods of determining whether a Drug or Ligand-Drug conjugate exerts a cytostatic and/or cytotoxic effect on a cell are known. Generally, the cytotoxic or cytostatic activity of a Ligand Drug conjugate can be measured by: exposing mammalian cells expressing a target protein of the Ligand Drug conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Ligand Drug conjugate.

For determining whether a Ligand Drug conjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of $^3$H-thymidine during the final 8 hours of the 72-hour period. The incorporation of $^3$H-thymidine into cells of the culture is measured in the presence and absence of the Ligand Drug conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that a Ligand Drug conjugate is useful in the treatment of cancers.

Cell viability can be measured by determining in a cell the uptake of a dye such as neutral red, trypan blue, or ALAMAR™ blue (see, e.g., Page et al., 1993, Intl. J. Oncology 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, J. Natl. Cancer Inst. 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, J. Immunol. Methods 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane.

Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, *Cancer Research* 55:3110-16).

The effects of Ligand Drug conjugates can be tested or validated in animal models. A number of established animal models of cancers are known to the skilled artisan, any of which can be used to assay the efficacy of a Ligand Drug conjugate. Non-limiting examples of such models are described infra. Moreover, small animal models to examine the in vivo efficacies of Ligand Drug conjugates can be created by implanting human tumor cell lines into appropriate immunodeficient rodent strains, e.g., athymic nude mice or SCID mice.

Ligand Unit

The Ligand unit (L) has at least one functional group that can form a bond with a functional group of a Linker unit. Useful functional groups that can be present on a Ligand unit, either naturally, via chemical manipulation or via engineering, include, but are not limited to, sulfhydryl (—SH), amino, hydroxyl, carboxy, the anomeric hydroxyl group of a carbohydrate, and carboxyl. In some embodiments, a Ligand unit functional group is a sulfhydryl group. The sulfhydryl group is typically a solvent accessible sulfhydryl group, such as a solvent accessible sulfhydryl group on a cysteine residue. Sulfhydryl groups can be generated by reduction of an intramolecular or intermolecular disulfide bond of a Ligand. Sulfhydryl groups also can be generated by reaction of an amino group of a lysine moiety of a Ligand using 2-iminothiolane (Traut's reagent) or another sulfhydryl generating reagent.

In some embodiments, one or more sulfhydryl groups are engineered into a Ligand unit, such as by amino acid substitution. For example, a sulfhydryl group can be introduced into a Ligand unit. In some embodiments, a sulfhydryl group is introduced by an amino acid substitution of serine or threonine to a cysteine residue, and/or by addition of a cysteine residue into a Ligand unit (an engineered cysteine residue). In some embodiments, the cysteine residue is an internal cysteine residue, i.e., not located at the N-terminus or C-terminus of the Ligand moiety.

In an exemplary embodiment, a cysteine residue can be engineered into an antibody heavy or light variable region (e.g., of an antibody fragment, such as a diabody) by amino acid substitution. The amino acid substitution is typically introduced into the framework region and is located distal to the epitope-binding face of the variable region. For example, the amino acid substitution can be at least 10 angstroms, at least 20 angstroms or at least 25 angstroms from the epitope-binding face or the CDRs. Suitable positions for substitution of a cysteine residue can be determined based on the known or predicted three dimensional structures of antibody variable regions. (See generally Holliger and Hudson, 2005, *Nature BioTechnology* 23(9):1126-1136.) In exemplary embodiments, a serine to cysteine amino acid substitution is introduced at amino acid position 84 of the $V_H$ region and/or position 14 of the $V_L$ region (according to the numbering system of Kabat et al., Sequences of Proteins of Immunological Interest, 5th edition, (Bethesda, Md., NIH) 1991).

To control the number of Drug or Linker unit-Drug units attached to a Ligand unit, one or more cysteine residues can be eliminated by amino acid substitution. For example, the number of solvent accessible cysteine residues in an immunoglobulin hinge region can be reduced by amino acid substitution of cysteine to serine residues.

In some embodiments, a Ligand unit contains 1, 2, 3, 4, 5, 6 7 or 8 solvent-accessible cysteine residues. In some embodiments, a Ligand unit contains 2 or 4 solvent-accessible cysteine residues.

Compositions and Methods of Administration

The CD19 binding agents and ligand-drug conjugate compounds can be in any form that allows for the compound to be administered to a patient for treatment of a CD19-associated disorder. Various delivery systems are known and can be used to administer the CD19 binding agents and ligand-drug conjugate compounds. Methods of introduction include, but are not limited to, intradermal, intramuscular, intraperitoneal, intravenous, and subcutaneous routes. Administration can be, for example by infusion or bolus injection. In certain preferred embodiments, administration of both the chemotherapeutic agent and the antibody-drug conjugate compound is by infusion. Parenteral administration is the preferred route of administration.

The CD19 binding agents and ligand-drug conjugate compounds can be administered as pharmaceutical compositions comprising one or more pharmaceutically compatible ingredients. For example, the pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients are known in the art. The composition, if desired, can also contain minor amounts of wetting or emulsifying agents, or pH buffering agents. Examples of suitable pharmaceutical carriers are described in "Remington's Pharmaceutical Sciences" by E. W. Martin. The formulations correspond to the mode of administration.

In typical embodiments, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed, for example, with an infusion bottle containing sterile pharmaceutical grade water or saline. Where the pharmaceutical is administered by injection, an ampoule of sterile water for injection or saline can be, for example, provided so that the ingredients can be mixed prior to administration.

The amount of the compound that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a compound such that a suitable dosage will be obtained. Typically, this amount is at least about 0.01% of a compound by weight of the composition.

For intravenous administration, the composition can comprise from about 0.01 to about 100 mg of a compound per kg of the animal's body weight. In one aspect, the composition can include from about 1 to about 100 mg of a compound per kg of the animal's body weight. In another aspect, the amount administered will be in the range from about 0.1 to about 25 mg/kg of body weight of a compound.

Generally, the dosage of a compound administered to a patient is typically about 0.01 mg/kg to about 100 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. In some embodiments, the dosage administered is between about 0.1 to 4 mg/kg, 0.1 to 3.2 mg/kg, or 0.1 to 2.7 mg/kg of the subject's body weight over a treatment cycle. In some embodiments, the dosage administered is between about 0.5 to 4 mg/kg, even more preferably 0.5 to 3.2 mg/kg, or even more preferably 0.5 to 2.7 mg/kg of the subject's body weight over a treatment cycle.

The pharmaceutical compositions are generally formulated as sterile, substantially isotonic and in full compliance with all Good Manufacturing Practice (GMP) regulations of the U.S. Food and Drug Administration.

Autoimmune Disease

The CD19 binding agents described herein, as well as ligand-drug conjugate compounds, can be useful for treating or preventing an immunological disorder. Treatment or prevention of the immunological disorder, according to the methods described herein, can achieved by administering to a subject in need of such treatment or prevention an effective amount of the CD19 binding agent or ligand-drug conjugate compound. In some preferred embodiments, the ligand-drug conjugate will (i) bind to activated immune cells that express CD19 and that are associated with the disease state and (ii) exert a cytotoxic, cytostatic, or immunomodulatory effect on the activated immune cells.

Immunological diseases that are characterized by inappropriate activation of immune cells and that can be treated or prevented by the methods described herein can be classified, for example, by the type(s) of hypersensitivity reaction(s) that underlie the disorder. These reactions can be typically classified into four types: anaphylactic reactions, cytotoxic (cytolytic) reactions, immune complex reactions, or cell-mediated immunity (CMI) reactions (also referred to as delayed-type hypersensitivity (DTH) reactions). (See, e.g., *Fundamental Immunology*, William E. Paul ed., Raven Press, N.Y., 3rd ed. 1993.)

Specific examples of such immunological diseases include, but are not limited to, rheumatoid arthritis, multiple sclerosis, endocrine ophthalmopathy, uveoretinitis, systemic lupus erythematosus, myasthenia gravis, Grave's disease, glomerulonephritis, autoimmune hepatological disorder, autoimmune inflammatory bowel disease, anaphylaxis, allergic reaction, Sjogren's syndrome, juvenile onset (Type I) diabetes mellitus, primary biliary cirrhosis, Wegener's granulomatosis, fibromyalgia, inflammatory bowel disease, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, presenile dementia, demyelinating diseases, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyl), and telangiectasia), adult onset diabetes mellitus (Type II diabetes), male and female autoimmune infertility, ankylosing spondolytis, ulcerative colitis, Crohn's disease, mixed connective tissue disease, polyarteritis nedosa, systemic necrotizing vasculitis, juvenile onset rheumatoid arthritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic encephalomyelitis, toxic epidermal necrolysis, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Eaton-Lambert syndrome, relapsing polychondritis, cryoglobulinemia, Waldenstrom's macroglobulemia, Epstein-Barr virus infection, mumps, Evan's syndrome, and autoimmune gonadal failure.

Accordingly, the methods described herein encompass treatment of disorders of B lymphocytes (e.g., systemic lupus erythematosus, Goodpasture's syndrome, rheumatoid arthritis, and type I diabetes), $Th_1$-lymphocytes (e.g., rheumatoid arthritis, multiple sclerosis, psoriasis, Sjorgren's syndrome, Hashimoto's thyroiditis, Grave's disease, primary biliary cirrhosis, Wegener's granulomatosis, tuberculosis, or graft versus host disease), or $Th_2$-lymphocytes (e.g., atopic dermatitis, systemic lupus erythematosus, atopic asthma, rhinoconjunctivitis, allergic rhinitis, or chronic graft versus host disease). Generally, disorders involving dendritic cells involve disorders of $Th_1$-lymphocytes or $Th_2$-lymphocytes.

The present invention includes treatment of an autoimmune disease, for example an autoimmune disease that is mediated at least in part by B cells. Examples of autoimmune diseases include acute necrotizing hemorrhagic leukoencephalitis; Addison's disease; Agammaglobulinemia; Allergic asthma; Allergic rhinitis; Alopecia greata; Amyloidosis; Ankylosing spondylitis; Anti-GBM/Anti-TBM nephritis; Antiphospholipid syndrome; Autoimmune aplastic anemia; Autoimmune dysautonomia; Autoimmune hepatitis; Autoimmune hyperlipidemia; Autoimmune immunodeficiency; Autoimmune inner ear disease; Autoimmune myocarditis; Autoimmune thrombocytopenic purpura; Axonal & neuronal neuropathies; Balo disease; Behcet's disease; Bullous pemphigoid; Cardiomyopathy; Castleman disease; Celiac sprue (nontropical); Chagas disease; Chronic fatigue syndrome; Chronic inflammatory demyelinating polyneuropathy; Churg-Strauss syndrome; Cicatricial pemphigoid/benign mucosal pemphigoid; Crohn's disease; Cogans syndrome; Cold agglutinin disease; Congenital heart block; Coxsackie myocarditis; CREST disease; Essential mixed cryoglobulinemia; Demyelinating neuropathies; Dermatomyositis; Devic disease; Discoid lupus; Dressler's syndrome; Endometriosis; Eosinophilic fasciitis; Erythema nodosum; Experimental allergic encephalomyelitis; Evans syndrome; Fibromyalgia; Fibrosing alveolitis; Giant cell arteritis (temporal arteritis); Goodpasture's syndrome; Graves' disease; Guillain-Barre syndrome; Hashimoto's disease; Hemolytic anemia; Henoch-Schonlein purpura; Herpes gestationis; Hypogammaglobulinemia; Idiopathic thrombocytopenic purpura; IgA nephropathy; Immunoregulatory lipoproteins; Inclusion body myositis; Insulin-dependent diabetes (type1); Interstitial cystitis; Juvenile arthritis; Juvenile diabetes; Kawasaki syndrome; Lambert-Eaton syndrome; Leukocytoclastic vasculitis; Lichen planus; Lichen sclerosus; Ligneous conjunctivitis; Linear IgA disease (LAD); Lupus (SLE); Lyme disease; Meniere's disease; Microscopic polyangiitis; Mixed connective tissue disease; Mooren's ulcer; Mucha-Habermann disease; Multiple sclerosis; Myasthenia gravis; Myositis; Narcolepsy; Neutropenia; Ocular cicatricial pemphigoid; Osteoarthritis; Palindromic rheumatism; Paraneoplastic cerebellar degeneration; Paroxysmal nocturnal hemoglobinuria; Parsonnage-Turner syndrome; Pars planitis (peripheral uveitis); Pemphigus; Peripheral neuropathy; Perivenous encephalomyelitis; Pernicious anemia; POEMS syndrome; Polyarteritis nodosa; Type I, II, & III autoimmune polyglandular syndromes; Polymyalgia rheumatica; Polymyositis; Post-myocardial infarction syndrome; Postpericardiotomy syndrome; Progesterone dermatitis; Primary biliary cirrhosis; Psoriasis; Psoriatic arthritis; Idiopathic pulmonary fibrosis; Pyoderma gangrenosum; Pure red cell aplasia; Raynauds phenomenon; Reflex sympathetic dystrophy; Reiter's syndrome; Relapsing polychondritis; Restless legs syndrome; Rheumatic fever; Rheumatoid arthritis; Sarcoidosis; Schmidt syndrome; Scleritis; Scleroderma; Sjogren's syndrome; Sperm & testicular autoimmunity; Stiff person syndrome; Subacute bacterial endocarditis; Sympathetic ophthalmia; Takayasu's arteritis; Temporal arteritis/Giant cell arteritis; Thrombocytopenic purpura; Autoimmune thyroid disease; Tolosa-Hunt syndrome; Transverse myelitis & necrotizing myelopathy; Ulcerative colitis; Undifferentiated connective tissue disease; Uveitis; Vasculitis; Vesiculobullous dermatosis; Vitiligo; and Wegener's granulomatosis. The more common autoimmune diseases that are of especial interest include (a) connective tissue diseases such as systemic lupus erythematosus, rheumatoid arthritis, systemic sclerosos (scleroderma), Sjogren's syndrome, (b) neuromuscular diseases such as multiple sclerosos, myasthenis gravis, Guillain-Barre syndrome, (c) endocrine diseases such as Hashimoto's thryoiditis, Grave's disease, insulin-dependent (type 1) diabetes, and (d) gastrointestinal diseases such as inflammatory bowel disease (including Crohn's disease and ulcerative colitis), and (e) other diseases such as vasculitis syndromes, hematologic autoimmune diseases, and autoimmune skin diseases.

The autoimmune disease for example includes the presence of autoantibodies. The autoantibody can bind specifically to host targets or antigens, for example rheumatoid factor (e.g., in rheumatoid arthritis); topoisomerase (e.g., in scleroderma); myelin basic protein (e.g., in multiple sclerosis); basement membrane collagen type iv protein (e.g., in Goodpasture's syndrome); ganglioside (e.g., in Guillain-Barré syndrome); platelets (e.g., chronic idiopathic thrombocytopenia); smooth muscle actin (e.g., in autoimmune hepatitis); bullous pemphigoid antigen 1 and 2; also called hemidesmosome antigens (e.g., in bullous pemphigoid); transglutaminase (e.g., in coeliac disease); desmogein 3 (e.g., in pemphigus vulgaris); p62 or sp100 or mitochondrial (m2) antigens (e.g., in primary biliary cirrhosis); neutrophil cytoplasmic c-ANCA (e.g., in Wegener's granulomatosis); neutrophil perinuclear p-ANCA (e.g., Polyarteritis nodosa, Microscopic polyangiitis, Churg-Strauss syndrome, Systemic vasculitides (non-specific)); double-stranded-DNA (e.g., in systemic lupus erythematosus); exosome complex (e.g., in Scleromyositis); Ro or La antigen (e.g., in systemic lupus erythematosus and neonatal heart block, or primary Sjogren's syndrome); Smith antigen (e.g., in systemic lupus erythematosus); phospholipid antigen (e.g., in antiphospholipid syndrome); SSA or SSB antigen (e.g., in Sjogren's syndrome); centromere (e.g., in CREST syndrome; mitochondria (e.g., in primary biliary cirrhosis); nicotinic acetylcholine receptor (e.g., in myasthenia gravis); voltage-gated calcium channel (e.g., in Lambert-Eaton syndrome); thyroid peroxidase (e.g., in Hashimoto's thyroiditis); TSH receptor (e.g., in Graves' disease); Hu antigen (e.g., in paraneoplastic cerebellar syndrome); voltage-gated potassium channel (e.g., in limbic encephalitis and N-methyl-D-aspartate receptor (e.g., in encephalitis). More than one type of autoantibody can be associated with an immunological disorder or visa versa, and this list in not exhaustive. For example, autoantigens that have been identified in rheumatoid arthritis include joint-associated proteins such as collagen type II, human chondrocyte glycoprotein 39, and proteoglycans; as well as heat shock proteins, citrullinated filaggrin, immunoglobulin, glucose-6-phosphate isomerase, p205, and BiP.

The CD19-binding agent can be administered in an amount effective to mitigate at least one symptom of the autoimmune disorder. In some embodiments, an anti-CD19 full length antibody or antigen-binding fragment thereof or derivative thereof that is not conjugated to a cytotoxic, cytostatic and/or therapeutic agent will be administered. In some other embodiments, a ligand-drug conjugate (i.e., a CD19 binding agent (e.g., a full length antibody or antigen-binding fragment thereof or derivative thereof) conjugated to a cytotoxic, cytostatic and/or therapeutic agent) will be administered. The invention provides treatment of an autoimmune disease, including autoimmune diseases that are refractory to conventional therapy with at least one CD19-binding agent of ligand-drug conjugate compounds of the present invention. The CD19 binding agent or ligand-drug conjugate compound is optionally administered in combination with another therapy, e.g., surgery, anti-inflammatory drug therapy, hormone/enzyme replacement therapy, plasmapheresis and immunosuppressant therapy. Anti-inflammatory drug therapies include steroids, e.g., corticosteroids such as prednisone; as well as NSAIDs such as salicylates and other COX inhibitors. Hormone replacement therapy includes thyroid hormone replacement (e.g., in Hashimoto's Thryoiditis) Immunosuppressant drugs include glucocorticoids, alkylating agents (e.g., cyclophosphamide, often effective in SLE), and antimetabolites (e.g., methotrexate, azathioprine and mercaptopurine). Other therapies include antithyroid drug therapy or removal of the thyroid gland surgically or by radioiodine (e.g., in Grave's disease).

In some embodiments, the CD19-binding agents of the present invention will deplete B cells.

Cancer

Exemplary CD19 binding agents are useful for treating or preventing a CD19-expressing cancer. Treatment or prevention of a CD19-expressing cancer, according to the methods described herein, can be achieved by administering to a subject in need of such treatment or prevention an effective amount of the CD19 binding agent. In some embodiments, an anti-CD19 full length antibody or antigen-binding fragment thereof or derivative thereof that is not conjugated to a cytotoxic, cytostatic and/or therapeutic agent will be administered. In some other embodiments, a ligand-drug conjugate (i.e., a CD19 binding agent (e.g., a full length antibody or antigen-binding fragment thereof or derivative thereof) conjugated to a cytotoxic, cytostatic and/or therapeutic agent) will be administered. In some exemplary embodiments, a ligand-drug conjugate of the present invention will (i) bind to CD19-expressing cancer cells and (ii) exert a cytotoxic or cytostatic effect to, for example, inhibit the proliferation of the CD19-expressing cancer cells, or kill CD19-expressing cancer cells.

Cancers that can be treated or prevented by the methods described herein include, for example, B cell malignancies, including, for example, leukemias and lymphomas, including, but not limited to, B cell subtype non-Hodgkin's lymphoma (NHL) including low grade/follicular NHL, small lymphocytic (SL) NHL, intermediate grade/follicular NHL, intermediate grade diffuse NHL, diffuse large B-cell lymphoma, follicular lymphoma, high grade immunoblastic NHL, high grade lymphoblastic NHL, high grade small noncleaved cell NHL, mantle cell lymphoma, and bulky disease NHL; Burkitt's lymphoma; multiple myeloma; pre-B acute lymphoblastic leukemia and other malignancies that derive from early B cell precursors; common acute lymphoblastic leukemia; chronic lymphocytic leukemia; hairy cell leukemia; Null-acute lymphoblastic leukemia; Waldenstrom's Macroglobulinemia; and pro-lymphocytic leukemia; diffuse large B cell lymphoma, pro-lymphocytic leukemia, light chain disease; plasmacytoma; osteosclerotic myeloma; plasma cell leukemia; monoclonal gammopathy of undetermined significance (MGUS); smoldering multiple myeloma (SMM); indolent multiple myeloma (IMM); or Hodgkin's lymphoma, provided that the cancers express the CD19 antigen.

In therapeutic applications, at least one CD19 binding agent (e.g., an antibody or a ligand-drug conjugate) can be administered to a patient suspected of, or already known to be suffering from, a CD19-associated disorder, e.g., a cancer. The agent for example is administered in an amount sufficient to abolish, or at least lessen, at least one symptom of the disorder.

In prophylactic applications of treatment, at least one agent can be administered to a patient at risk of developing or suffering a relapse of a CD19-associated disorder. The patient is for example a patient in apparent remission of a CD19-associated disorder, for whom there is a possibility of a relapse, or a patient who is at enhanced risk of an increase in at least one symptom of a CD19-associated disorder relative to the general population. Patients known to be at high risk of a CD19-associated disorder or its relapse include, e.g., patients diagnosed with an aggressive form of the disorder, or with genetic or histological abnormalities associated with the disorder or its staging (e.g., malignancy), or with an associated risk factor (e.g., familial history or another CD19 associated disorder or EBV infection), or patients that have undergone a stem cell transplant. In some embodiments, a CD19 binding agents or ligand-drug conjugate compound of the present invention will be administered as a maintenance therapy to a patient who has undergone a stem cell transplant for the treatment of a CD19 expressing cancer.

The agent can be administered before a suspected onset or increase or exacerbation or relapse of the disorder, in an amount sufficient to eliminate, or reduce the risk of, or delay the onset or relapse of the disorder.

The CD19 binding agents and ligand-drug conjugate compounds are useful for treating cancer and other diseases in which CD19 is expressed or overexpressed, relative to normal (e.g., non-cancerous tissue). The CD19 binding agents can also be used to treat CD19-associated disorders in which CD19 is not overexpressed relative to normal. For example, the disorder can include an increased count of CD19-positive B cells. In some embodiments, the CD19 binding agents and ligand-drug conjugate compounds are administered as a monotherapy. In other embodiments, the CD19 binding agents and the ligand-drug conjugate compounds are co-administered with another therapeutic agent, or administered sequentially with another therapeutic agent. In some embodiments, the CD19 binding agents and ligand-drug conjugate compounds are co-administered with chemotherapeutics, including standard of care chemotherapeutics, or administered sequentially.

The response of the patient can be monitored by determining the effect of the agent on a CD19-associated disorder.

Multi-Drug Therapy for Cancer

Methods for treating cancer including administering to a patient in need thereof an effective amount of a CD19 binding agent and another therapeutic agent. In some embodiments, the additional therapeutic agent will be an anti-cancer agent. In some embodiments, the CD19 binding agent will be an anti-CD19 full length antibody or antigen-binding fragment thereof or derivative thereof that is not conjugated to a cytotoxic, cytostatic and/or therapeutic agent. In some other embodiments, the CD19 binding agent will be a ligand-drug conjugate (i.e., a CD19 binding agent (e.g., a full length antibody or antigen-binding fragment thereof or derivative thereof) conjugated to a cytotoxic, cytostatic and/or therapeutic agent).

In some embodiments, the other therapeutic agent will be an agent that is standard of care for the specific disease to be treated or is part of a salvage regimen for the specific disease to be treated. Anti-cancer agents and chemotherapeutic regimens include, for example, anti-cancer antibodies, including, for example, anti-CD52 antibodies (e.g., Alemtuzumab), anti-CD20 antibodies (e.g., Rituximab), and anti-CD40 antibodies (e.g., SGN40); chemotherapeutic regimens including, for example, CHOP (cyclophosphamide, doxorubicin, vincristine, and prednisone); CVP (cyclophosphamide, vincristine, and prednisone); RCVP (Rituximab+CVP); RCHOP (Rituximab+CHOP); RICE (Rituximab+ifosamide, carboplatin, etoposide); RDHAP, (Rituximab+dexamethasone, cytarabine, cisplatin); RESHAP (Rituximab+etoposide, methylprednisolone, cytarabine, cisplatin); gemcitabine; combination treatment with vincristine, prednisone, and anthracycline, with or without asparaginase; combination treatment with daunorubicin, vincristine, prednisone, and asparaginase; combination treatment with teniposide and Ara-C (cytarabine); combination treatment with methotrexate and leucovorin; combination treatment with bleomycin, doxorubicin, etoposide, mechlorethamine, prednisone, vinblastine, and vincristine; small molecule inhibitors; and proteosome inhibitors including, for example, bortezomib.

The present invention encompasses methods of treating lymphomas using the described CD19 binding agents (either conjugated (e.g., ligand-drug conjugate) or unconjugated) as a monotherapy or in combination therapy with, for example, anti-lymphoma antibodies, including, for example, anti-CD20 antibodies, i.e., Rituximab, and/or anti-CD40 antibodies, i.e., SGN-40.

The present invention encompasses methods of treating lymphomas using the described CD19 binding agents (either conjugated (e.g., ligand-drug conjugate) or unconjugated) as a monotherapy or in combination therapy with, for example, chemotherapeutic regimens for the treatment of lymphomas including, for example, CHOP (cyclophosphamide, doxorubicin, vincristine, and prednisone), CVP (cyclophosphamide, vincristine, and prednisone) and/or other anthracycline B chemotherapy regimens.

The present invention encompasses methods of treating indolent lymphomas using the described CD19 binding agents (either conjugated (e.g., ligand-drug conjugate) or unconjugated) as a monotherapy or in combination therapy with, for example, RCVP (Rituximab+CVP) and/or RCHOP (Rituximab+CHOP).

The present invention encompasses methods of treating subjects suffering from relapsed or refractory lymphoma using the described CD19 binding agents (either conjugated (e.g., ligand-drug conjugate) or unconjugated) as a monotherapy or in combination therapy with, for example, RICE (Rituximab+ifosamide, carboplatin, etoposide), RDHAP, (Rituximab+dexamethasone, cytarabine, cisplatin), RESHAP (Rituximab+etoposide, methylprednisolone, cytarabine, cisplatin), gemcitabine and/or an immune modulatory drugs, i.e., lenalidomide.

The present invention encompasses methods of treating a subject that has relapsed disease or that is refractory to treatment with Rituximab or other therapy for the treatment of cancer, e.g., CHOP, CVP, CHOP, RICE, RDHAP, RCHOP, RCVP, RESHAP. In one aspect, the methods include, for example, administering a ligand-drug conjugate of the present invention to the subject. In certain embodiments, the ligand-drug conjugate comprises a CD19 binding agent conjugated to an auristatin compound. In one aspect, the CD19 binding agent is a humanized BU12 antibody.

The present invention encompasses methods of treating a subject that has a cancer characterized by the level of CD21 expression. The cancer can have no, low levels, or high levels of CD21 expression. In one aspect, the methods include, for example, administering a ligand-drug conjugate of the present invention to the subject. In certain embodiments, the ligand-drug conjugate comprises a CD19 binding agent conjugated to an auristatin compound. In one aspect, the CD19 binding agent is a humanized BU12 antibody.

The present invention encompasses methods of treating ALL using the described CD19 binding agents (either conjugated (e.g., ligand-drug conjugate) or unconjugated) as a monotherapy or in combination therapy with, for example, a chemotherapeutic regimen that includes the combination of vincristine, prednisone, and anthracycline, with or without asparaginase. Alternative chemotherapeutic regimens include, for example, combinations of daunorubicin, vincristine, prednisone, and asparaginase; combinations of teniposide and ara-C (cytarabine); combinations of methotrexate and leucovorin; combinations of bleomycin, doxorubicin, etoposide, mechlorethamine, prednisone, vinblastine and vincristine ("Stanford 5 Regimen").

In some embodiments, methods for treating cancer including administering to a patient in need thereof an effective amount of an CD19 binding agent or ligand-drug conjugate compound in combination with radiation treatment, and optionally another therapeutic agent In some embodiments, the CD19 binding agent or CD19 ligand-drug conjugate compound is administered concurrently or sequentially with an anti-cancer agent (e.g., a chemotherapeutic agent) and/or with radiation therapy. In some embodiments, the chemotherapeutic agent or radiation therapy is administered at least an hour, five hours, 12 hours, a day, a week, a month, several months (e.g., up to three months), prior or subsequent to administration of a compound of the present invention.

Where a compound of the present invention and chemotherapeutic drug(s) are administered separately, the number of dosages of each compound given per day, may not necessarily be the same, e.g. where one compound may have a greater duration of activity, and will therefore, be administered less frequently. The compound of the present invention and the additional anti-cancer agent, can be administered via the same or different routes of administration. They can be administered according to simultaneous or alternating regimens, at the same or different times during the course of the therapy, concurrently in divided or single forms. Administration of either or both agents can be on a continuos basis, e.g., by infusion or via an implanted reservoir.

In some embodiments, the chemotherapeutic agent to be administered in combination with the compounds of the present invention, is one with which treatment of the cancer has not been found to be refractory. In another embodiment, the chemotherapeutic agent is one with which the treatment of cancer has been found to be refractory.

In some embodiments, methods of treatment of cancer with a compound of the present invention are provided as an alternative to chemotherapy or radiation therapy where the chemotherapy or the radiation therapy has proven or can prove too toxic, e.g., results in unacceptable or unbearable side effects, for the subject being treated.

Compounds of the present invention can also be used in an in vitro or ex vivo fashion, such as for the treatment of certain cancers.

Also within the scope of the invention are kits comprising an isolated CD19 binding agent that specifically binds to human CD19 or a ligand-drug conjugate comprising a CD19 binding agent, and instructions for use. The kit can further contain a least one additional reagent. Kits typically include a label indicating the intended use of the contents of the kit. The term label includes any writing, or recorded material supplied on or with the kit, or which otherwise accompanies the kit.

The invention also includes diagnostic use of a humanized CD19 antibody. For example, the humanized CD19 antibody can be used as a diagnostic imaging agent alone and/or in combination with other diagnostic imaging agents and/or in conjunction with therapeutic applications. The diagnostic agent can be used in vivo in human patients known to have or have had a CD19-associated disorder. Optionally, the disorder includes CD19-positive cells that are discrete localized, e.g., in a solid tumor.

In one such method, the CD19 binding agent can be directly or indirectly labeled with a detectable label, such as a fluorophore, and optionally contacted with a target cell or a patient sample in vitro or in vivo. The presence and/or density of CD19 in a sample or individual can be determined In vivo methods of determination can include imaging techniques such as PET (positron emission tomography) or SPECT (single photon emission computed tomography).

The patient or sample (an optionally a control as well) is for example contacted with a CD19 binding agent under conditions that allow for formation of a complex between the agent and CD19 antigen if present. Complex formation is then detected in the test patient and compared to binding in a control (e g, using an FACS analysis or Western blotting). Any statistically significant difference in the formation of complexes between the control and the test sample/patient is indicative of the presence of a CD19-associated disorder. The control can be e.g., a similar reading taken from the same patient at a different location or timepoint or a reading taken from non-diseased subjects, or a predetermined statistical value based on multiple readings taken from individuals selected at random or not known to be suffering from the disorder. The diagnostic tests can be used to identify patients with a CD19-associated disorder, or to determine the extent of such a disorder in a particular patient, or to monitor the course of a disorder over time, or the effect of a chosen treatment on a disorder.

All publications and patent documents cited above are hereby incorporated by reference in their entirety for all purposes to the same extent as if each were so individually denoted.

The invention will be further described with reference to the following examples; however, it is to be understood that the invention is not limited to such examples.

The following examples of specific aspects for carrying out the present invention are offered for illustrative purposes only, and are not intended to limit the scope of the present invention in any way.

EXAMPLES

Example 1

Design of Humanized BU12 Heavy Chain Variable Region:

BU12 $V_H$ was aligned to functional human germline $V_H$ exons. Selection of the $V_H$ exon was made based on framework homology and canonical structure. Human germline $V_H$ exons $V_H$2-70 and $V_H$4-31 were selected to provide frameworks for humanization. Human germline $J_H$4 exon was selected to provide humanized FR4 sequence based on its identity (85%) with FR4 of BU12 $V_H$.

BU12 $V_H$ was aligned against the mouse $V_H$ exon germline sequences to identify regions of somatic mutation which may have structural implications. BU12 $V_H$ was found to have high homology to the functional CB17H-10$V_H$ exon with potential framework regions of somatic mutation at H75, H82A and H89.

BU12 $V_H$ was aligned against the selected human germline $V_H$ exon ($V_H$2-70 or $V_H$4-31) and differences between BU12 $V_H$ and the human framework at residues described in the literature to effect CDR structure or $V_H$/$V_L$ interactions were identified. For the $V_H$4-31 such residues changes were found at positions H24, H27, H29 and H71. Additionally non-homologous framework regions were identified and the crystal structure of a homologous $V_H$ domain (1ETZ) was used to determine the positions of non-homologous residues and assess their likely impact on CDR structure.

Humanizing Mutations in Heavy Chain Variants

| $V_H$ Variant | $V_H$ Exon Acceptor Sequence | Donor Framework Residues |
|---|---|---|
| $V_H$A | VH2-70 | None |
| $V_H$B | VH2-70 | H75 |
| $V_H$C | VH2-70 | H79 |
| $V_H$D | VH2-70 | H81, H82, H82A, H82B, H82C |
| $V_H$E | VH2-70 | H89 |
| $V_H$F | VH4-31 | None |
| $V_H$G | VH4-31 | H71 |
| $V_H$H | VH4-31 | H24, H27, H29 |
| $V_H$I | VH4-31 | H24, H27, H29, H71 |
| $V_H$J | VH4-31 | H75 |
| $V_H$K | VH4-31 | H78, H79 |
| $V_H$L | VH4-31 | H89 |

Non-homologous FR Residues BU12 $V_H$ vs. $V_H$2-70

| Position | Change | Comments |
|---|---|---|
| H41 | S → P | Loop region - exclude |
| H75 | S → K | Possible somatic mutation/charge change |
| H79 | F → P | Aromatic in core |
| H81 | K → T | Core (continuous region) |
| H82 | I → M | Core (continuous region) |
| H82A | A → T | Core (continuous region) |
| H82B | S → N | Core (continuous region) |
| H82C | V → M | Core (continuous region) |
| H84 | T → P | Loop region - exclude |
| H89 | A → T | Possible somatic mutation |

Specific Mutations in BU12 Heavy Chain Variants

| Variant | H75 | H79 | H81 | H82 | H82A | H82B | H82C | H89 |
|---|---|---|---|---|---|---|---|---|
| cBU12 VH | S* | F* | K* | I* | A* | S* | V* | A* |
| VH2-70 | K | V | T | M | T | N | M | T |
| HA | K | V | T | M | T | N | M | T |
| HB | S* | V | T | M | T | N | M | T |
| HC | K | F* | T | M | T | N | M | T |
| HD | K | V | K* | I* | A* | S* | V* | T |
| HE | K | V | T | M | T | N | M | A* |

*Mouse residues

Non-Homologous FR Residues BU12 V11 vs. VH4-31

| Position | Change | Comments |
|---|---|---|
| H3 | T → Q | Surface accessible distant from CDRs - exclude |
| H24 | F → V | Impacts CDR1 structure |
| H27 | F → G | Impacts CDR1 structure |
| H29 | L → I | Impacts CDR1 structure |
| H41 | S → P | Loop region - exclude |
| H71 | K → V | Impacts CDR2 structure |
| H75 | S → K | Possible somatic mutation/charge change |
| H78 | V → F | Aromatic in core |
| H79 | F → P | Aromatic in core |
| H83 | D → T | Loop region - exclude |
| H89 | A → V | Possible somatic mutation |

Specific Mutations in BU12 Heavy Chain Variants

| Variant | H24 | H27 | H29 | H71 | H75 | H78 | H79 | H89 |
|---|---|---|---|---|---|---|---|---|
| cBU12 VH* | F* | F* | L* | K* | S* | V* | F* | A* |
| VH4-31 | V | G | I | V | K | F | S | V |
| HF | V | G | I | V | K | F | S | V |
| HG | V | G | I | K* | K | F | S | V |
| HH | F* | F* | L* | V | K | F | S | V |
| HI | F* | F* | L* | K* | K | F | S | V |
| HJ | V | G | I | V | S* | F | S | V |
| HK | V | G | I | V | K | V* | F* | V |
| HL | V | G | I | V | K | F | S | A* |

*Mouse residues

Example 2

Design of Humanized BU12 Light Chain Variable Region:

BU12 $V_L$ was aligned to functional human germline $V_H$ exons. Usage of L6 is high (~11%) so this was chosen as the best framework for BU12 $V_L$ humanization. A10, with the best homology to BU12 $V_L$ was also chosen. Human germline $J_\kappa 2$ exon was selected to provide humanized FR4 sequence based on its identity (77%) to FR4 of BU12 $V_L$.

BU12 $V_L$ was aligned against the mouse $V_L$ exon germline sequences to identify regions of somatic mutation which may have structural implications. The closest matches were ac4, kn4 and kk4. Potential sites of somatic mutation were identified at positions L40, L41, L42, L69, L71, L72 and L83.

BU12 $V_L$ was aligned against the selected human germline and $V_L$ exon (L6 or A10) and differences between BU12 $V_L$ and the human framework at residues described in the literature to effect CDR structure or $V_H/V_L$ interactions were identified. Such residue differences occur at positions L2 and L71. Additionally non-homologous framework regions were identified and the crystal structure of a homologous $V_L$ domain (1QOK) was used to determine the positions of non-homologous residues and assess their likely impact on CDR structure.

Humanizing Mutations in Light Chain Variants

| $V_L$ Variant | $V_H$ Exon Acceptor Sequence | Donor Framework Residues |
|---|---|---|
| $V_L A$ | VL-L6 | None |
| $V_L B$ | VL-L6 | L2 |
| $V_L C$ | VL-L6 | L71 |
| $V_L D$ | VL-L6 | L2, L71 |
| $V_L E$ | VL-L6 | L40, L41, L42 |
| $V_L F$ | VL-L6 | L69, L70, L71, L72 |
| $V_L G$ | VL-L6 | L83 |
| $V_L H$ | VL A10 | None |
| $V_L I$ | VL A10 | L2, L71 |

Non-Homologous FR Residues BU12 VL vs. L6 and A10

| Position | Change | Comments |
|---|---|---|
| L2 | N → I | L2 known to impact CDR1 structure |
| L40 | S → P | Possible somatic mutation |
| L41 | S → G | Possible somatic mutation |
| L42 | T → Q | Possible somatic mutation |
| L69 | N → T | Possible somatic mutation |
| L70 | S → D | Charge in strand packing against CDR1 |
| L71 | H → F | Somatic mutation/L71 known to impact CDR1 structure |
| L72 | F → T | Possible somatic mutation |
| L83 | V → F | Possible somatic mutation |

Specific Mutations in BU12 Light Chain Variants

| Variant | L2 | L40 | L41 | L42 | L69 | L70 | L71 | L72 | L83 |
|---|---|---|---|---|---|---|---|---|---|
| cBU12 VL* | N* | S* | S* | T* | N* | S* | H* | F* | V* |
| L6 | I | P | G | Q | T | D | F | T | F |
| LA | I | P | G | Q | T | D | F | T | F |
| LB | N* | P | G | Q | T | D | F | T | F |
| LC | I | P | G | Q | T | D | H* | T | F |
| LD | N* | P | G | Q | T | D | H* | T | F |
| LE | I | S* | S* | T* | T | D | F | T | F |
| LF | I | P | G | Q | N* | S* | H* | F* | F |
| LG | I | P | G | Q | T | D | F | T | V* |

*Mouse residues

Specific Mutations in BU12 Light Chain Variants

| Variant | L2 | L71 |
|---|---|---|
| cBU12* | N* | H* |
| A10 | I | F |
| LH | I | F |
| LI | N* | H* |

*Mouse residues

Example 3

Figure 13:
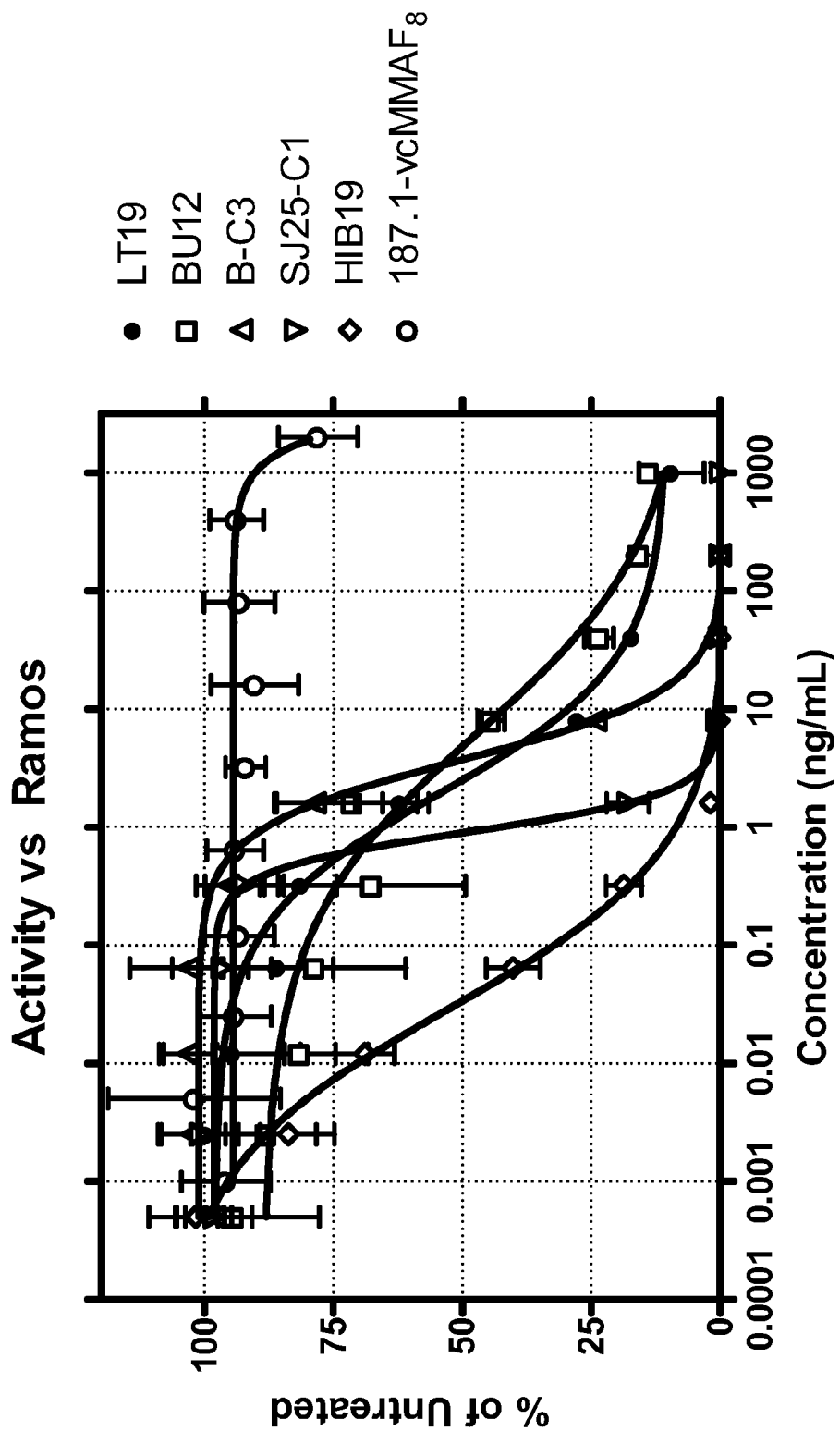
FIG. 13: Ramos cells were cultured with anti-CD19 antibodies cross-linked with a 2-fold excess of goat-anti-mouse ligand drug conjugate (vcMMAF8). Cultures were incubated for 96 hours and labeled with 50 µM resazurin. Values are the mean±SD of four replicates within a single experiment.

A panel of anti-CD19 antibodies was screened on a panel of CD19+ NHL cell lines (FIG. 13). All of the antibodies evaluated were able to deliver drug although there were differences between the cell lines.

| Cell Line | Disease Type | CD19 Molecules/Cell | $IC_{50}$ (ng/mL) of various anti-CD19 Antibodies linked with 2°-ADC | | | | |
|---|---|---|---|---|---|---|---|
| | | | LT19 | HIB19 | cBU12 | SJ25-C1 | B-C3 |
| CA46 | Burkitt's Lymphoma, EBV− | 60527 | 4 | 1 | 7 | 4 | 17 |
| HS Sultan | Burkitt's Lymphoma, EBV+ | 59669 | 112 | 97 | 100 | 150 | 234 |

| Cell Line | Disease Type | CD19 Molecules/Cell | IC₅₀ (ng/mL) of various anti-CD19 Antibodies linked with 2°-ADC | | | | |
|---|---|---|---|---|---|---|---|
| | | | LT19 | HIB19 | cBU12 | SJ25-C1 | B-C3 |
| HT | Diffuse Mixed Lymphoma | 35813 | 111 | ~1000 | 238 | ND | ND |
| MC 116 | Undifferentiated Lymphoma | 29210 | 192 | 188 | 186 | ~200 | 195 |
| Ramos | Burkitt's Lymphoma, EBV- | 34377 | 1 | 1 | 5 | 3 | 13 |
| Toledo | Diffuse Large Cell Lymphoma | 28657 | 584 | ~1000 | ~1000 | 512 | 359 |

Anti-CD19 antibodies deliver 2°-goat-anti-mouse-vcM-MAF to CD19⁺ cell lines. Cell lines were cultured with different anti-CD19 antibodies cross-linked with a 2-fold excess of goat-anti-mouse ADC (187.1-vcMMAF8). Cultures were incubated for 96 hours and labeled with 50 μM resazurin. There was no effect of 187.1-vcMMAF on the growth of any of the cell lines tested. Values are the mean±SD of four replicates within a single experiment.

Example 4

Antitumor activity of anti-CD19 antibody-drug conjugate compounds on Ramos tumor model in SCID mice was determined. The results generally show that murine and chimeric BU12 antibody drug conjugates had poor activity as compared to other chimeric anti-CD19 antibody drug conjugates and as compared to humanized BU12 antibody drug conjugates. See FIGS. 3, 4, 5, 7 and 8.

Example 5

Variants of humanized BU12 antibody, in which amino acid residues in the Fc domain of IgG1 known to be important for binding to FcγR can be mutated to impair binding to one or more FcγR, can be generated using standard molecular biology techniques.

For example, IgG1v1 contains the following mutations: E233P:L234V:L235A, according to the Kabat numbering scheme. The amino acid sequence of IgG1V1 is shown in SEQ ID NO:35.

Further Fc domain variants of humanized anti-CD19 antibodies can be similarly generated, including, for example, Fc domain variants with one or more non-conservative amino acid substitutions, introduction of one or more cysteine residues, or introduction of one or more sites for N-linked glycosylation, in or in proximity to the Fc domain involved in the binding interaction to one or more Fcγ receptors.

Example 6

Preparation of a hBU12 Antibody Drug Conjugate

One hundred thirty milligrams of the hBU12 mAb (Lot #'s PR208 (69 mg) and 1033154 (100 mg)) were combined and concentrated to provide 141 mg at a concentration of 10.8 mg/mL, based on a molecular weight of 150 kD and an extinction coefficient of 1.47 AU·mL·mg⁻¹·cm⁻¹.

The auristatins MMAE and MMAF were conjugated to the purified antibody as follows. The antibody (130 mg, 867 nmol) was incubated 45 mM at 37° C. with 2.17 nmol of TCEP (representing a 25% excess of reductant for the desired reduction level of 4 free thiols per antibody) with 1 mM DTPA as a cation scavenger. The reduction level was determined by performing a microscale test conjugation with the following test compound:

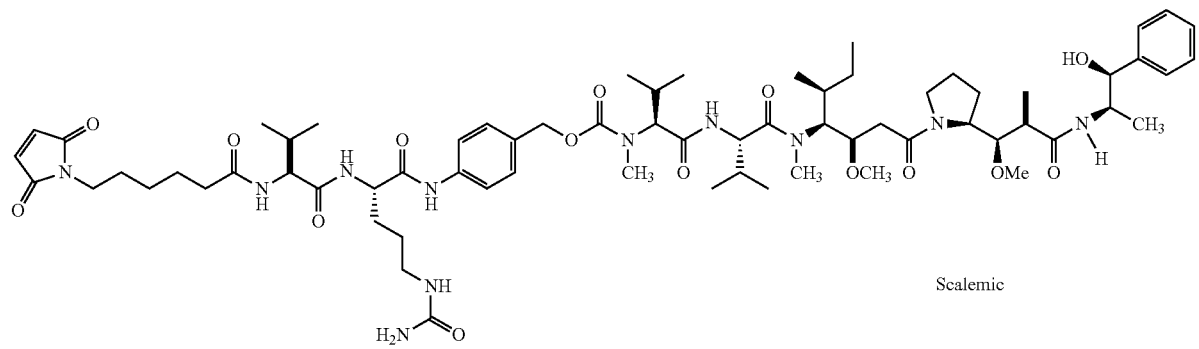 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

Scalemic

The drug loading distribution was characterized by HIC chromatography. This mAb exhibited a reduction pattern occasionally seen with murine antibodies, wherein the distribution is weighted at 0 and 10 drugs per antibody, with 4- and 6-loaded antibody being represented at lower levels. The mean drug loading was higher than desired: 4.9 drugs/Ab. Incremental quantities of DTNB (217 nmol, then 303.8 nmol) were added to re-oxidize antibody disulfides, thereby reducing the drug loading level to an assayed level of 4.1 drugs/Ab.

The partially reduced mAb (97 mg, 647 nmol) was conjugated with MMAF by addition of 795 μL of DMSO to the approximately 9.0 mL of mAb solution, followed by 203.1 μL of a 19.1 mM DMSO solution of the following compound, maleimidocaproyl-Val-Cit-MMAF (3.88 μmol).

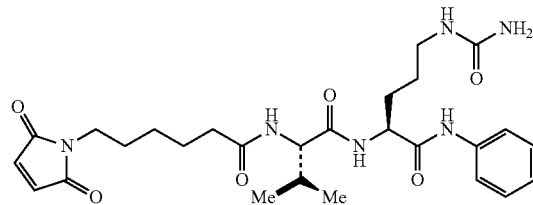
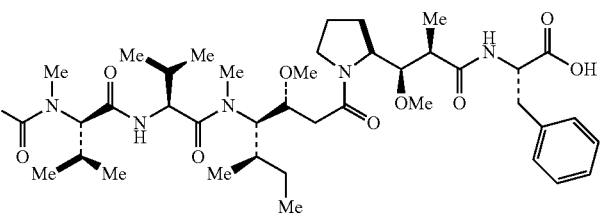

Scalemic

The conjugation reaction was allowed to proceed for 100 minutes at 0° C. Residual maleimidocaproyl-Val-Cit-MMAF was quenched by addition of 194 μL of 100 mM N-acetyl cysteine. The reaction mixture was then dialyzed against 4 L of PBS three times using a 25000 MWCO membrane at 4° C. to remove DMSO, unreacted or quenched drug, and other small-molecule contaminants resulting from the conjugation process, and concentrated. The product contained 4.1 drugs/Ab.

Example 7

Activity of the Anti-CD19 Auristatin Antibody Drug Conjugate hBU12-vcMMAE (also Referred to as hBU12-MC-vc-PAB-MMAE) Against Rituximab Sensitive and Resistant Lymphomas and in CD21 High and Low Lymphomas:

Materials and Methods

Flow cytometric analysis to determine CD19 and CD21 expression levels on tumor cell lines: To evaluate CD19 and CD21 copy numbers on tumor cell lines, cells were incubated for 30 minutes on ice with PE-conjugated murine anti-CD19 and anti-CD21 antibodies (BD Pharmingen, San Diego, Calif.), washed with cold staining medium and evaluated with a Becton Dickison FACScan flow cytometer. Quantitative determination of CD19 and CD21 on the cell surface was determined using a DAKO QiFiKit flow cytometric indirect immunofluorescence assay and murine antibodies as described by the manufacturer (DAKO A/S, Glostrup, Denmark).

Saturation binding studies to determine binding affinity: Cells were incubated with 10 μg/ml hBU12 or hBU12-vcM-MAE for 0.5 h at 4C, and washed. One set of cells was transferred to 37° C. and harvested at selected timepoints. For detection, a secondary PE-conjugated antibody was used and the amount of remaining surface-bound antibody determined by flow cytometry. Alternatively, cells were incubated on ice with AlexaFluor488-labeled hBU12 antibody or drug conjugates for 1 h, washed with cold PBS, and binding assessed with a Becton Dickison FACScan flow cytometer. The apparent Kd values were determined using the One Site Binding algorithm from Prism (GraphPad Software, San Diego, Calif.).

CD19 internalization kinetic studies: To generate radiolabeled antibody-drug conjugates, custom synthesized [3H]-vcMMAE (24.7 Ci/mmol, Moravek Biochemicals, Brea, Calif.) was used to prepare the radiolabeled hBU12-vcM-MAE conjugate. Calculations of radioactivity were made. The amount of free drug found inside of the cells from 1 mL of culture was added to the amount of free drug detected in 1 mL of culture medium and this value was used to determine the concentration of total drug released in the cell culture.

Triplicate results were averaged and the standard deviation for those values was calculated using the STDEVPA function in Microsoft Excel.

Lysosomal co-localization studies of hBU12 and hBU12-ADCs: Ramos cells were incubated with 1 ug/ml hBU12 or hBU12-ADCs on ice or for 20 minutes or 4 hours at 37° C. After the incubation, the cells were washed with cold PBS to remove unbound antibody or ADC and then fixed and permeabilized with BD Cytofix/Cytoperm (BD Biosciences, San Jose, Calif.). The antibody and ADCs were detected with AlexaFluor-488 labeled goat anti-human IgG (Molecular Probes, Eugene, Oreg.). Lysosomal compartments were visualized by staining with AlexaFluor647-labeled LAMP-1 antibody (mouse CD107, BD Biosciences). Nuclear compartments were stained with DAPI (4',6-diamidino-2-phenylindole, Roche, Base1, Switzerland). Fluorescence images were acquired with a Carl Zeiss Axiovert 200M microscope.

Cytotoxicity and Growth Arrest Assays: Tumor cells were incubated with hBU12 and the drug conjugates for 96 h. Cell viability was measured by Alamar Blue (Biosource International, Camarillo, Calif.) dye reduction as previously reported (Doronina, 2003 #1834). Cells were incubated for 4 h with the dye and dye reduction measured on a Fusion HT fluorescent plate reader (Perkin Elmer, Waltham, Mass.). Results are reported as IC50, the concentration of compound needed to yield a 50% reduction in viability compared to vehicle-treated cells (control=100%). For growth arrest and apoptosis studies, cells were first treated with the antibody and ADCs and then processed using the Annexin V-FITC Apoptosis Detection kit (BD Pharmingen), according to the manufacturer's directions. For analysis of cell cycle position following exposure to ADCs, the cells were labeled for 20 minutes with bromodeoxyuridine (BrdUrd, Sigma, St. Louis, Mo.). Nascent DNA synthesis was detected using an anti-BrdUrd antibody (BD Biosciences) and total DNA content was detected with propidium iodide (PI). Cells were then analyzed by flow cytometry.

In vivo model of subcutaneous lymphomas and disseminated human leukemias: Localized, subcutaneous and disseminated models of B cell lymphomas were established in SCID mice. For the subcutaneous model, $5 \times 10^6$ lymphoma cells were implanted into the right flank of female mice. hBU12 and -ADCs or a control compound were administered when tumor volumes reached 100 mm$^3$. Tumor size was monitored at least twice weekly. To establish disseminated disease, $1 \times 10^5$ Nalm6 cells or RS4;11 cells in 0.2 ml PBS were injected into the lateral tail vein of C.B.-17 SCID mice (Harlan, Indianapolis, Ind.). Mice were treated with test compounds 7 days after cells injection and monitored at least twice per week. Mice were terminated when they exhibited signs of disease including weight loss of 15-20%, hunched posture and lack of grooming, cranial swelling and hind limb paralysis. Treatment schedules are as indicated in the figure legends.

Statistical analysis: Tumor quadrupling or triplication times (as indicated) were chosen as time to endpoint (TTE), which were determined by using a non-linear regression analysis for exponential growth of each individual tumor growth data set from each experimental animal. The tumor quadrupling time was calculated based on the tumor volume at the beginning of treatment Animals that did not reach the endpoint were assigned a TTE value equal to the last day of the study. % TGD (tumor growth delay) reflects the delay in reaching TTE relative to control treated tumors, which was determined by using the formula: % TGD=[(T−C)/C]×100, where T and C are the median times in days for treated and control groups, to reach TTE, using the start of treatment as day 1. Statistical analysis and graphic presentations were conducted using Graphpad Prism Software version 4.01 (Graphpad, San Diego, Calif.). Median tumor growth curves show group median tumor volumes as a function of time. The Log rank test was used to analyze the significance of the differences between TTE of treated and control tumor groups, with differences deemed significant (*) at $0.01 < P < 0.05$, and highly significant (**) at $P < 0.01$. In a CR response, the tumor volume is less than 13.5 mm$^3$ for three consecutive measurements during the course of the study. A durable response (DR) is defined as complete absence of palpable tumor during the entire experiment. Standard Pearson correlation analysis (two tailed) was employed, using a 95% confidence interval, to determine significant correlations between CD19 and CD21 expression levels and in vitro cytotoxicity.

Development of Rituxan resistant Ramos and Raji tumors: Parental cells were implanted into 40 SCID mice at a concentration of $5 \times 10^6$ cells per mouse. 2 days following cell implant, mice were treated with rituximab at 8 mg/kg every other day for a total of 9 doses. Out of the 40 mice, roughly 6 developed tumors, when the tumors were approximately 300-400 mm3, the mice were euthanized and the tumors were collected aseptically. Tumors were made into a single cell suspension through disassociation through a nylon filter. While in culture the cells were continuously exposed to various levels of rituximab up to 100 ug/ml. Cell viability was verified several times per week. After one week in culture the cells were implanted into 30 SCID mice. Two days after implant the mice were treated with rituximab at 12 mg/kg in the schedule as before. The in vitro and in vivo selection was repeated once more in 10 SCID mice. The resulting tumors were processed into single cell suspension and frozen in liquid nitrogen. The Raji R2 and Raji H4 cell lines were generated as described in Czuczamn et al., *Clin Cancer Res.* 2008; 14:1561-1570.

Pharmacokinetic characteristics of hBU12-vcMMAE(4) conjugates: Single doses of hBU12-vcMMAE were administered intra-peritoneally to naïve SCID mice. The serum samples were collected at scheduled intervals over a period of 11 weeks to obtain composite pharmacokinetic profiles. The samples were analyzed for antibody drug conjugate concentrations by a qualified multiplex bead-capture assay using an anti-MMAE antibody. The pharmacokinetic analysis was done using non-compartmental and compartmental methods.

Results

Lack of correlation between CD19 and CD21 expression and potency of hBU12-vcMMAE against ALL, CLL and NHL tumor cell lines grown in culture: In order to determine the potency of hBU12-vcMMAE, CD19 positive lymphoma and leukemia cells representing Burkitt's lymphoma, diffuse large B-cell lymphoma (DLBCL), follicular lymphomas (FL), and acute lymphocytic leukemia (ALL) were exposed to increasing concentrations of hBU12-vcMMAE. In addition, the cell surface copy numbers of CD19 and CD21 were determined in order to study a potential correlation between expression of these genes with anti-tumor activity. Potent cytotoxic activity of the hBU12-vcMMAE conjugate was noticed in 15 out of 17 CD19 positive tumor cell lines tested. The T-cell lymphoma cell line Jurkat was used as CD19 negative control cell line. The absence of activity of hBU12-vcMMAE on these control cells suggested that the anti-tumor activity was target dependent. A lack of significant correlations between ADC potency and the levels of CD19 ($p=0.45$, $R2=0.038$) and CD21 ($p=0.55$, $R2=0.028$) expression was noticed (data not shown). In addition, similar potent cytotoxic effects of hBU12-vcMMAE against ALL cell lines were found. In sum, the data demonstrates that CD19 and CD21 expression levels and the tumor subtypes are insufficient to predict the sensitivities of lymphoma and leukemia cell lines towards auristatin based ADCs.

Figure 15:
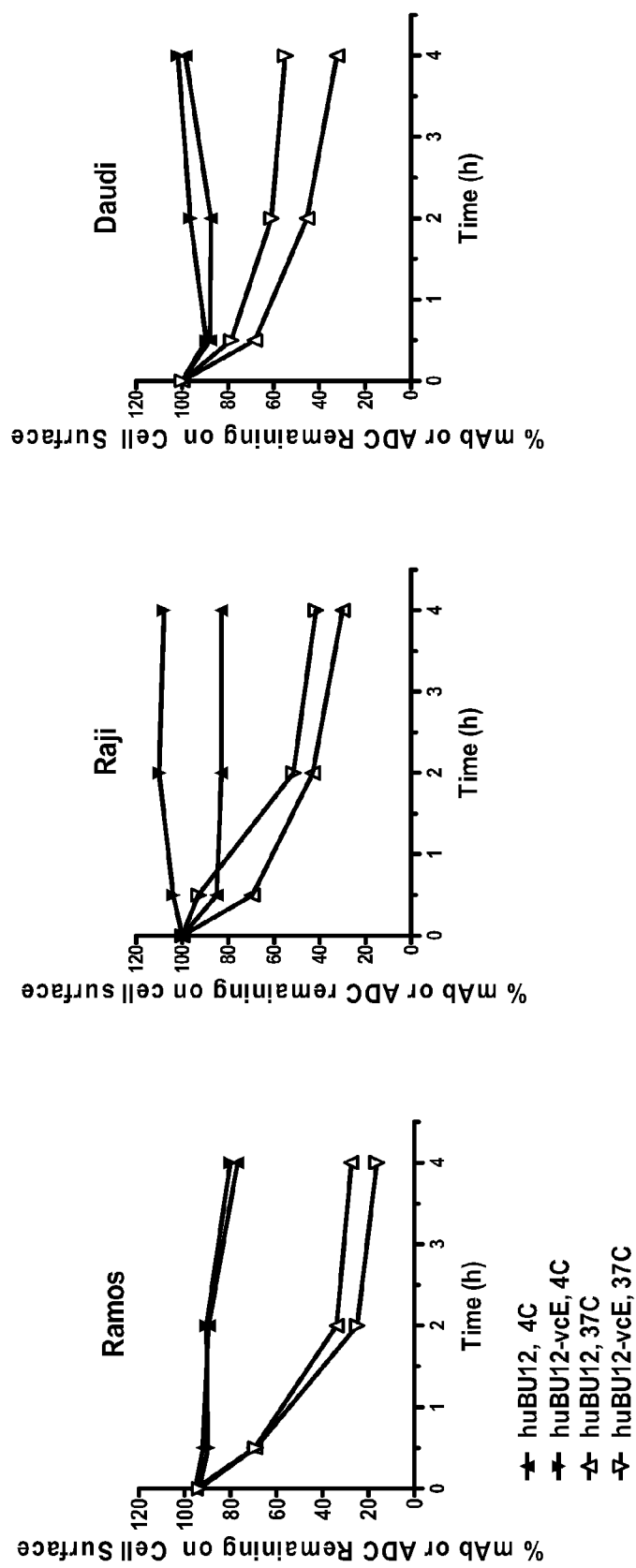
FIG. 15: Internalization kinetics and intracellular trafficking of hBU12-vcMMAE4 on NHL and ALL tumor cell lines.

Internalization kinetics and intracellular trafficking of hBU12-vcMMAE in NHL cell lines: A critical parameter previously shown to determine the anti-tumor effects of certain auristatin based ADCs is the ability of the target antigen to internalize and to translocate to the lysosomal compartment following ligation by the antibody. To study these processes, CD21 low (Ramos and SUDHL-4) and CD21 high tumor cell lines (Raji, Daudi) were incubated with hBU12-vcMMAE and the internalization kinetics by fluorescence activated cell sorting (FACS) was determined. As shown in FIG. 15, hBU12 and hBU12-vcMMAE conjugates internalized rapidly in CD21 low Ramos cells, and >50% of the compounds internalized within 60 minutes post incubation. Somewhat slower internalization kinetics of hBU12-vcMMAE were found in CD2 thigh Raji and Daudi cells. However, the small differences in internalization kinetics did not significantly affect potency, and comparable IC50 values between CD21 low Ramos cells and CD21 high lymphomas were found. Combined, the findings demonstrate that the internalization kinetics of hBU12-vcMMAE on different tumor cell lines does not correlate with cytotoxicity in vitro. Intracellular trafficking of hBU12 and hBU12-vcMMAE conjugates in NHL cell lines was investigated. For this purpose, CD21 low Ramos and SUDHL4 cells were incubated with either naked antibody or hBU12-vcMMAE. Co-immunofluorescence studies revealed that the majority of internalized hBU12 localized to lysosomes, starting as early as 15 minutes post incubation. Comparable subcellular translocation of hBU12 and conjugates to the lysosomal compartment was observed between CD21 low Ramos or HT and CD21 high Daudi and Raji cells (data not shown). Combined, the findings demonstrate that internalization kinetics alone are insufficient to explain the differences in hBU12-vcMMAE potencies against different NHL cell lines.

Free drug release by hBU12-vcE in rituximab sensitive and resistant, CD21 high and low lymphoma cell lines: MMAE interferes with microtubule stability in the cytoplasmic compartment and thus, the amounts of active, free MMAE drug released in tumor cells is critical for anti-lymphoma effects. To investigate theses aspects, CD21 high Daudi and CD21 high, rituximab resistant Raji R2 and Raji 4H cells were incubated with hBU12-vcMMAE and the levels of free drug released with CD21 low Ramos cells were compared. The cellular release of free, active drug was quantified by combining the radioactivity that was retained within cells and that had escaped into the supernatant over time. There was no difference in free drug release between CD21 low cells (Ramos) and CD21 high cells (Daudi). Therefore, it is unlikely that variations in free drug release account for the >50 fold differences in the IC50 values between these different lymphoma cell lines. In conclusion, high CD21 levels may only minimally interfere with the intracellular release of free drug from internalized hBU12-vcMMAE.

Figure 16A:
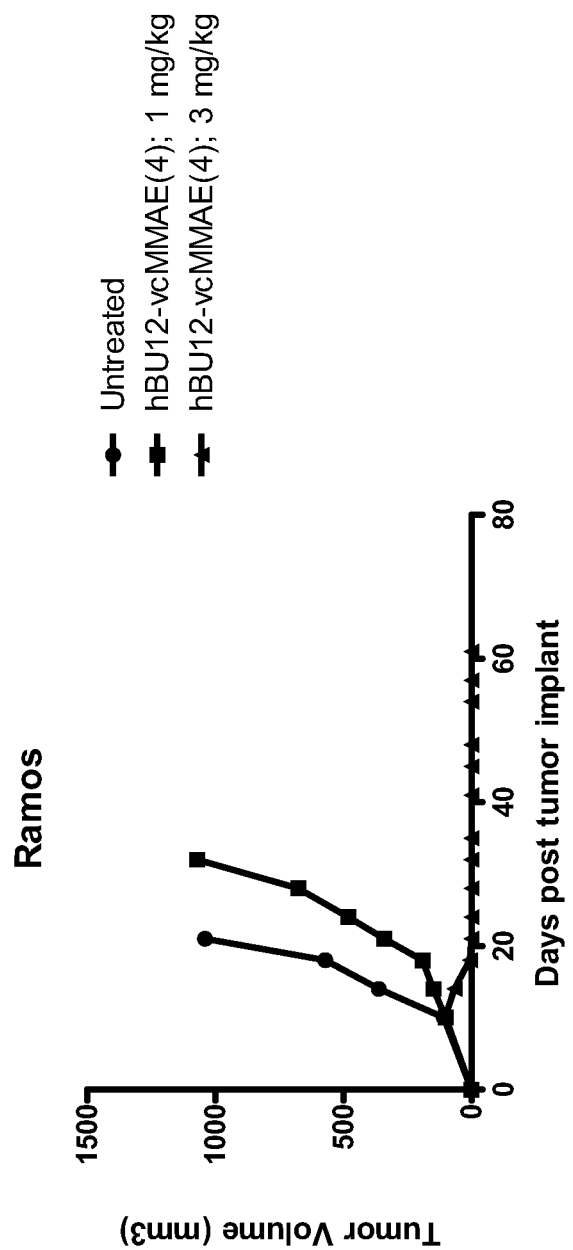
FIGS. 16A-16E: Xenograft experiments testing hBU12-vcMMAE4 in models of NHL. SCID mice were implanted subcutaneously with 5×10$^6$ cells of tumor cells in the right flank and treatment was initiated when the average tumor volume reached 100 mm$^3$. Treatment was intraperitoneally with 1 or 3 mg/kg, q4dx4 of hBU12-vcMMAE4. There were 7-10 mice per each treatment group. 16A.) Growth curve of the NHL cell line (Burkitt's lymphoma); 16B.) Growth curve of the follicular lymphoma cell lines DOHH2. 16C.) Growth curve of the diffuse large B cell lymphoma (DLBCL) cell line DLCL2. 16D.) Survival curve of mice implanted with the ALL cell line RS4;11 via tail vein. Treatment of mice was initiated on day 7 post tumor implantation at a q4dx4, schedule, intraperitoneally. 16E.) Survival curve of mice implanted with the ALL cell line Nalm-6 via tail vein. Treatment was initiated on day 7 post tumor implantation, with a single dose of hBU12-vcMMAE4 at the indicated dose, via intraperitoneal injections.
Figure 16B:
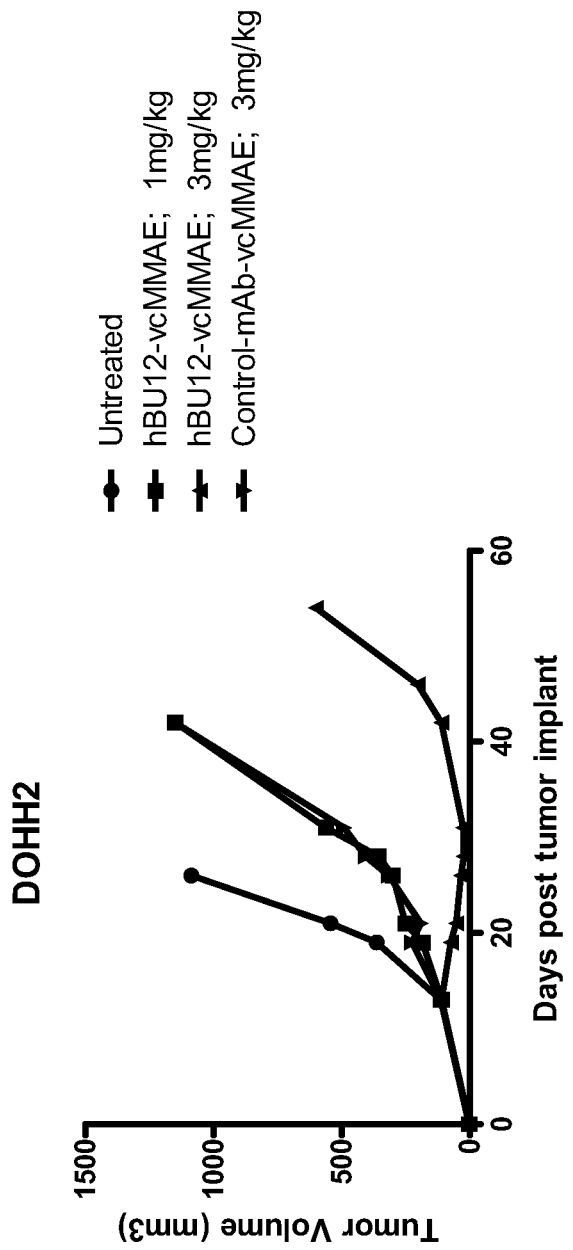
Figure 16C:
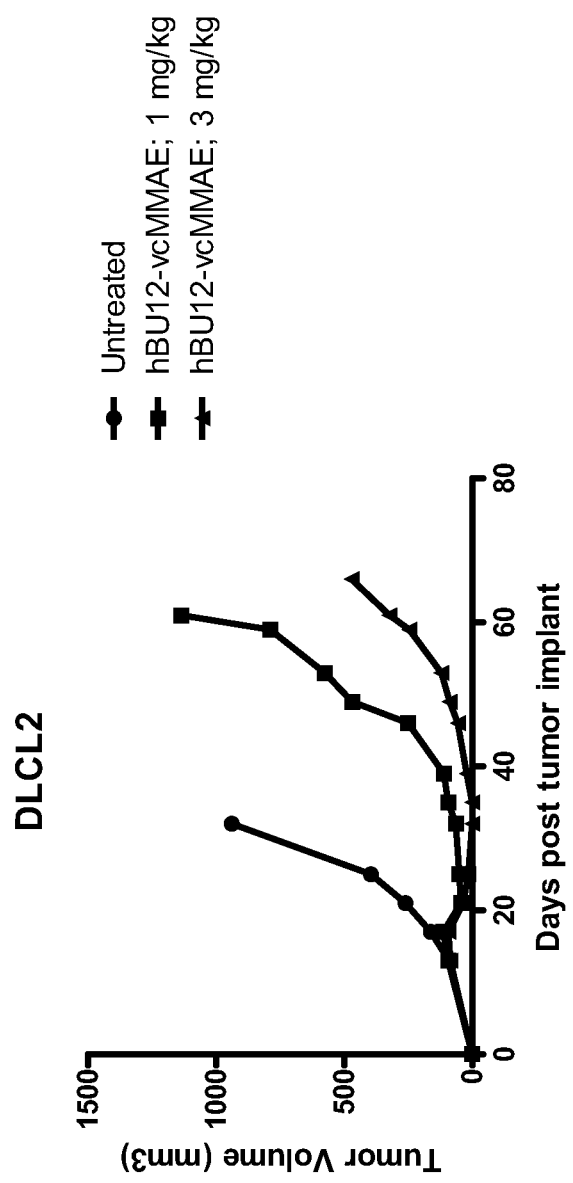
Figure 16D:
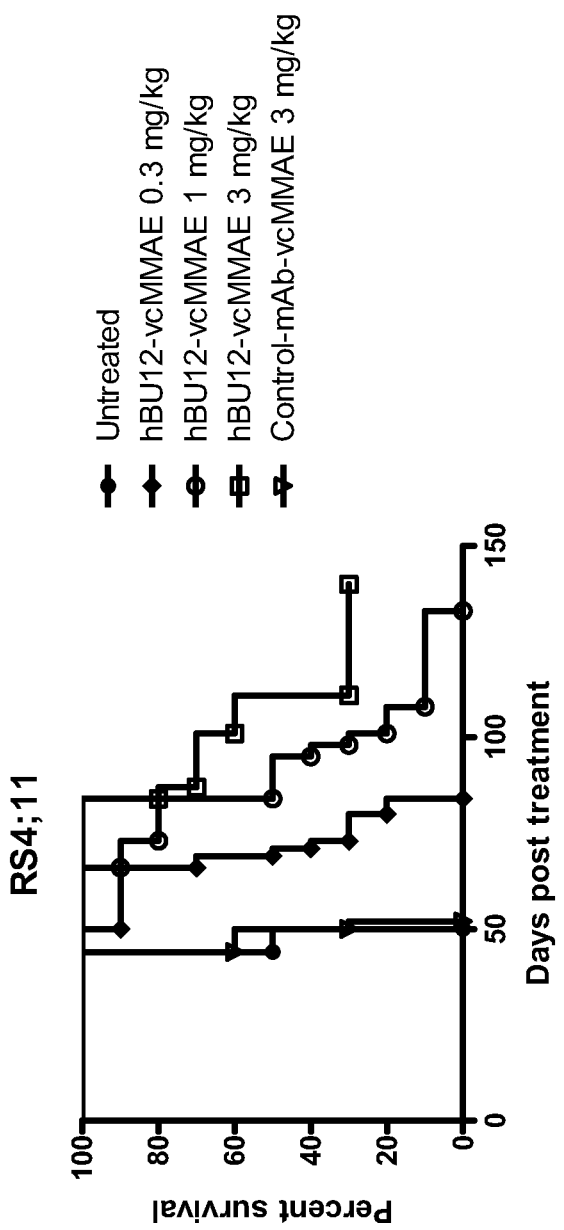
Figure 16E:
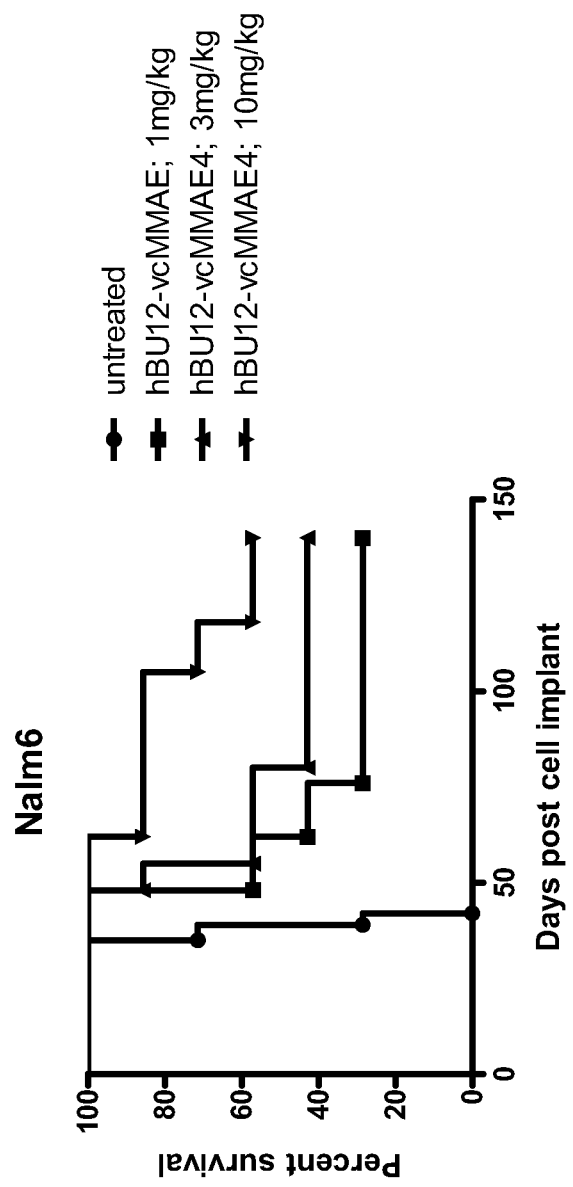

Efficacy of hBU12 conjugates in models of NHL and ALL hBU12-vcMMAE was tested in single dose and multi dose experiments using different NHL cell lines xenografted into SCID mice (FIG. 16A-E and data not shown). When tested against Burkitt's lymphoma, 7/8 durable responses were observed at the 3 mg/kg hBU12-vcMMAE dose, administered q4dx4 (FIG. 16A)). When tested against DOHH2 tumor (Follicular lymphoma), significant inhibition of tumor growth rates as illustrated by 2/10 DRs at the 3 mg/kg dose level (FIG. 16B) were observed. When tested against SUDHL4 lymphomas (DLBCL), there was also a significant inhibition of tumor growth rates (FIG. 16C). In the disseminated RS4;11 model representing ALL, a significant increase in survival of mice treated with hBU12-vcMMAE was observed, resulting in a delay of disease onset from ~45 days in control or untreated animals to >90 days in mice treated with 3 mg/kg of vcE conjugates (FIG. 16D). Similar observations were made when testing hBU12-vcMMAE in a second model of disseminated ALL (Nalm6), where single dose administration resulted in 30-60% durable responses FIG. 16E). Combined, these data demonstrate potent anti-tumor effects of hBU12-vcMMAE in different models of NHL and ALL, irrespective of their CD21 expression status.

Figure 17A:
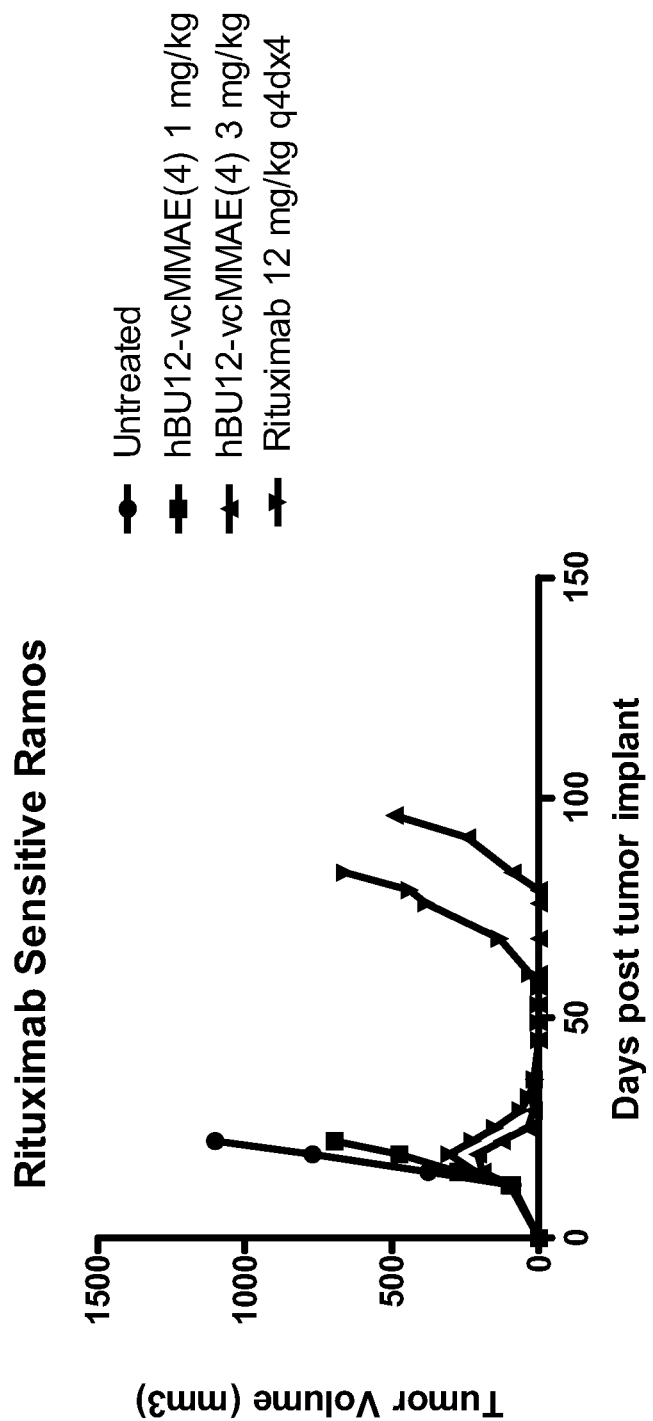
Figure 17B:
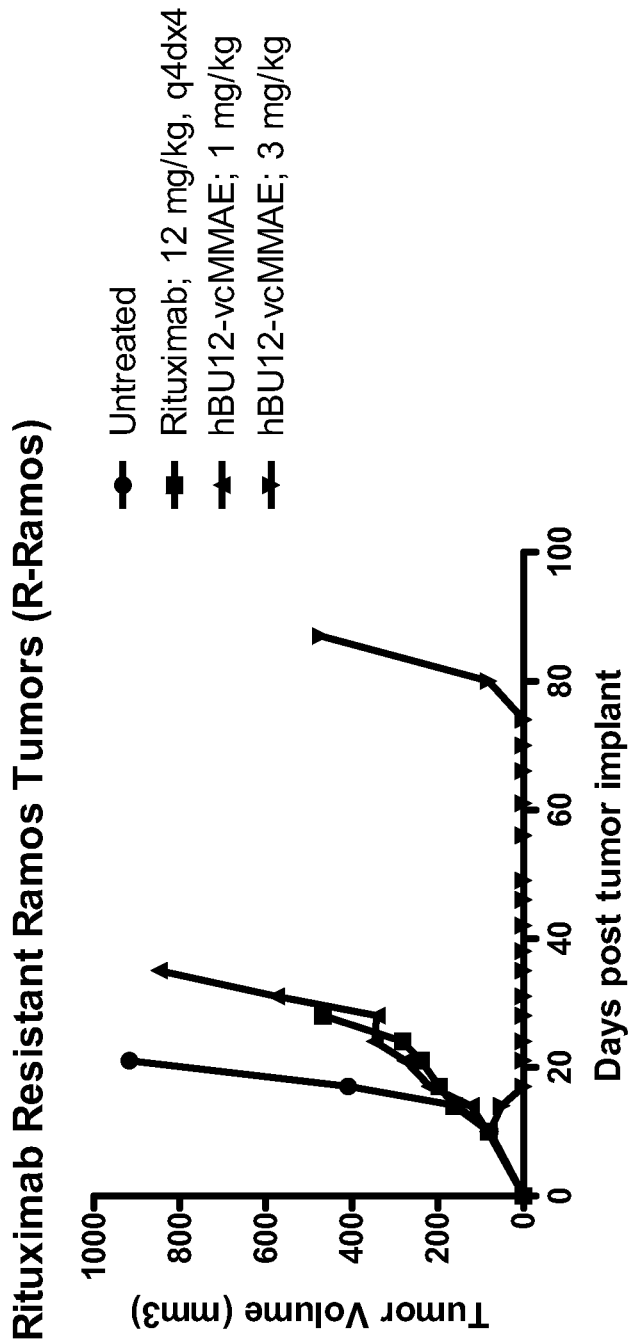
Figure 17D:
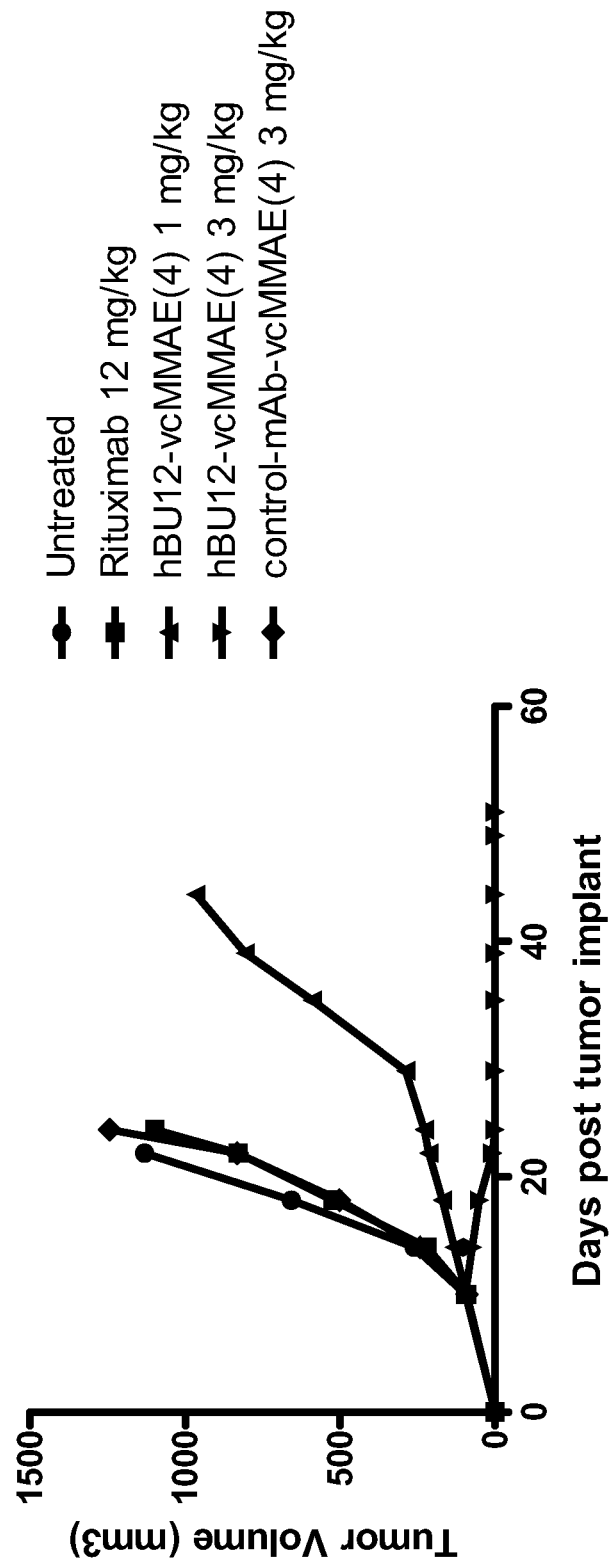

Antitumor activity hBU12-vcE against rituximab resistant lymphomas: In order to develop a preclinical models that mimic the refractoriness of NHL tumors to rituximab treatment, Ramos tumor cells were generated that were rendered refractory by repeated in vitro and in vivo passaging of tumor cells in mice, concurrent with rituximab treatment as described in materials and methods. To determine the expression levels of CD20 and CD19, cells from R-Ramos tumors were isolated and comparable levels of CD20 and CD19 expression in rituximab resistant Ramos tumors were found (FIG. 17C). Compared with high doses of rituximab (12 mg/kg, q4dx4), hBU12-vcMMAE treatment resulted in a significant difference in % tumor growth delay (TGD) between the parental and rituximab resistant tumors Importantly, similar antitumor activities by hBU12-vcMMAE in rituximab sensitive and resistant cell lines were found, suggesting that the mechanism rendering NHL cells resistant to rituximab does interfere with hBU12-vcMMAE potency. To further validate these findings, hBU12-vcMMAE was tested in conjunction with two additional, rituximab resistant NHL cell lines described previously (Raji 2R and 4RH 27; FIG. 17D and data not shown), and both cell lines were shown to express similar levels of CD19 and CD20 compared to the parental clone. In support of the previous findings testing rituximab resistant Ramos tumors, hBU12-vcMMAE treatment induced similar durable response compared to the rituximab sensitive parental Raji clone. In conclusion, potent anti-tumor activities for CD19-ADCs on rituximab resistant cell lines were observed.

Example 8

Figure 18:
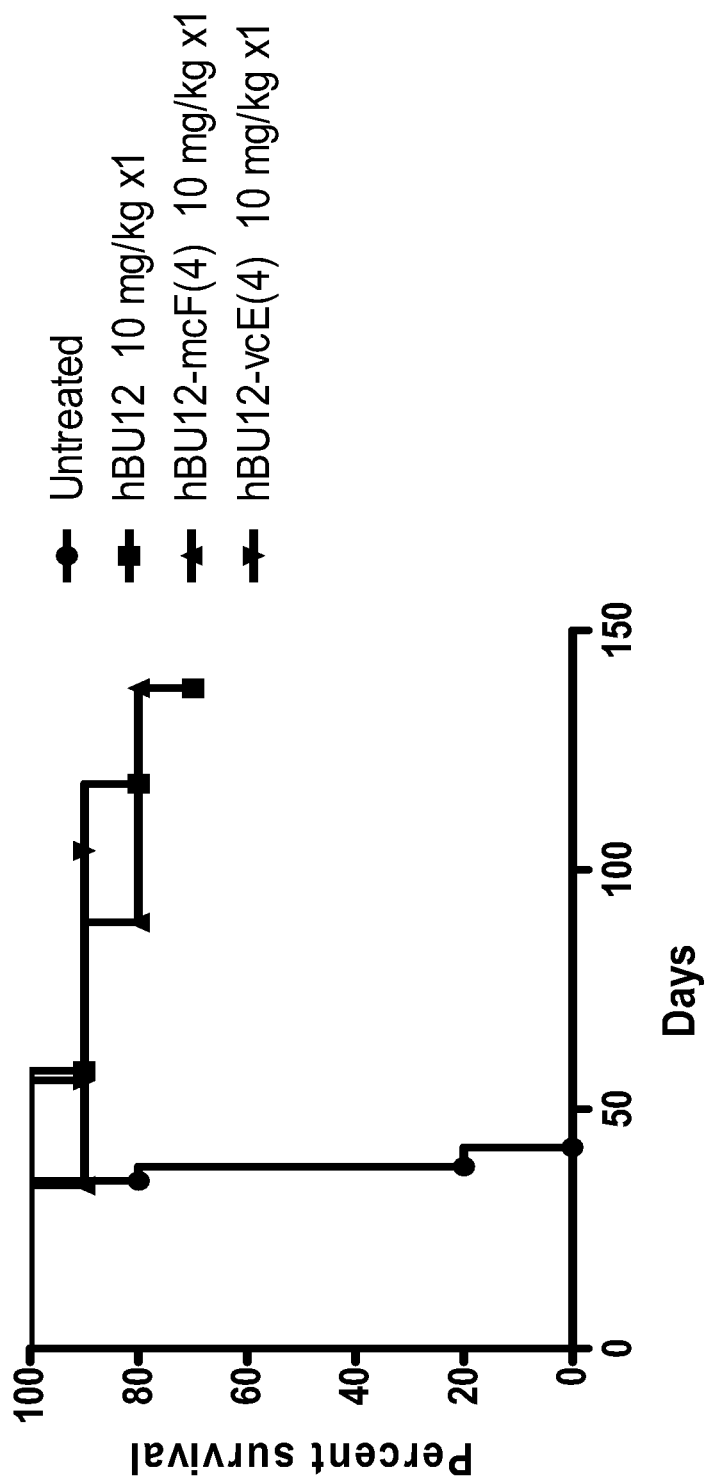
FIG. 18: Activity of hBU12 in disseminated model of ALL. The mice received a single dose of 10 mg/kg hBU12, hBU12-vcE(4) or hBU12-mcF(4), IP, on day 1 post tumor implanatation. There were 10 mice per group.

Role of Effector Cells in Mediating Therapeutic Effects of the Humanized Anti-CD19 Antibody hBU12 in Preclinical Models of NHL and ALL:

The ability of the humanized anti-CD19 antibody hBU12 to induce CDC, ADCC and ADCP against human lymphoma and leukemia cell lines was investigated. Potent ADCC and ADCP was found and ADCC was slightly reduced when hBU12 was conjugated to the vcMMAE drug linker. When tested on activated, human primary B-cell isolates, direct anti-proliferative effects of the hBU12 and conjugates was observed. A lack of CDC anti-tumor effects was noticed for all hBU12 compounds. To determine the relevance of effector cell mediates activities for therapeutic activity of hBU12, human lymphoma and leukemia cells were implanted either subcutaneously into SCID mice or via tail vein injections (disseminated model). The most potent anti-tumor effects were observed in disseminated models, consistent with the notion that the access of effector cells to the tumor cells is less limiting in the disseminated model (FIGS. 18 and 19). In order to identify the nature of the cells mediating anti-tumor effects, effector cell ablation experiments were conducted in a disseminated model of NHL (Ramos). NK cells, neutrophils or macrophages were selectively depleted and the effects on tumor growth inhibition of hBU12 in tumor bearing mice were measured. Ablation of macrophage and neutrophils almost completely abolished the anti-tumor effects of hBU12, while depletion of NK cells was associated with a moderate decrease in activity. In conclusion, the findings demonstrate that hBU12 induced anti-tumor effects via effector cell mediated ADCP and ADCC activities.

Material and Methods

For in vivo depletion studies, rabbit anti-asialo-GM-1 antibody was obtained from Wako Pure Chemical Industries, Ltd. (Richmond, Va.), rat anti-mouse-Gr-1 antibody was obtained from BD Biosciences (San Diego, Calif.). Liposome-encapsulated clodronate (CEL) was prepared as previously described(Van Rooijen and Sanders 1994). Clodronate was a gift of Roche Diagnostics GmbH (Mannheim, Germany). Tumor-bearing mice were depleted of effector cells using specific antibody or CEL as described previously (Van Rooijen and Sanders 1994; van Rooijen and Sanders 1997; McEarchern, Oflazoglu et al. 2007). Natural killer (NK) cells were depleted by i.p. injection of anti-asialo-GM 1 (1.25 mg/kg). Mice were given a total of 3 doses once every 5 days, beginning the day of tumor cell implantation. Macrophages were depleted by i.p. injection of CEL (100 µl/10 gr) on the day of tumor injection and every 3 days thereafter for a total of 5 doses. Cell depletion was confirmed by flow cytometric analysis of splenocytes, lymph nodes and blood (data not shown).

What is claimed:

1. A method for treating a CD19-associated disorder in a mammalian subject comprising administering an antibody or antigen-binding fragment that specifically binds to human CD19 in an amount effective to treat the disorder in the mammalian subject; the antibody or antigen-binding fragment comprising a heavy chain variable region amino acid sequence as set forth in SEQ ID NO:29 with 0, 1 or 2 substitutions at the alternative positions specified in SEQ ID NO:29 relative to SEQ ID NO:9 and a light chain variable region amino acid sequence as set forth in SEQ ID NO:30 with 1 or 2 substitutions at the alternative positions specified in SEQ ID NO:30 relative to SEQ ID NO:17, one of which is position L83 by Kabat numbering is occupied by V; wherein the antibody or antigen-binding fragment binds to CD19 with a dissociation constant of $1\times10^{-7}$ M; wherein the CD19-associated disorder is a CD19-expressing cancer or an immunological disorder characterized by activated immune cells expressing CD19.

2. The method of claim 1, wherein the CD19-associated disorder is a CD19 expressing cancer.

3. The method of claim 1, wherein the heavy chain variable region has the amino acid sequence of SEQ ID NO:9.

4. The method of claim 1, wherein the light chain variable region has the amino acid sequence of SEQ ID NO:24.

5. The method of claim 1, wherein the antibody comprises a human IgG constant region and is administered.

6. The method of claim 5, wherein the isotype of the IgG constant region is IgG1, IgG2, or IgG1V1.

7. The method of claim 1, wherein the antibody or antigen-binding fragment is conjugated to an anti-tubulin agent.

8. The method of claim 7, wherein the anti-tubulin agent is an auristatin.

9. The method of claim 1, wherein the antibody or antigen-binding fragment is a ligand-drug conjugate compound, wherein the ligand drug conjugate compound is of the following formula:

$$L\text{-}(LU\text{-}D)_p \qquad (I)$$

or a pharmaceutically acceptable salt or solvate thereof; wherein:
L is a ligand unit wherein the ligand unit is the antibody or antigen-binding fragment; and
(LU-D) is a Linker unit-Drug unit moiety, wherein:
LU- is a Linker unit, and
-D is a Drug unit having cytostatic or cytotoxic activity against the target cells; and
p is an integer from 1 to about 20.

10. The method of claim 9, wherein the drug unit has the formula $D_E$, $D_F$ or $D_Z$:

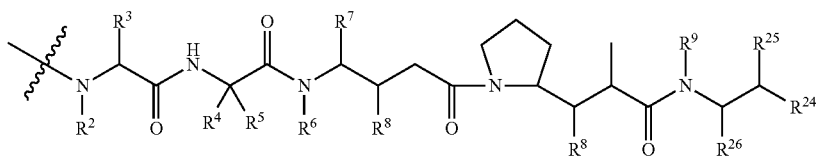

$D_E$

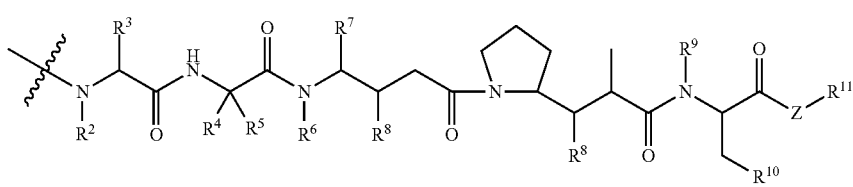

$D_F$

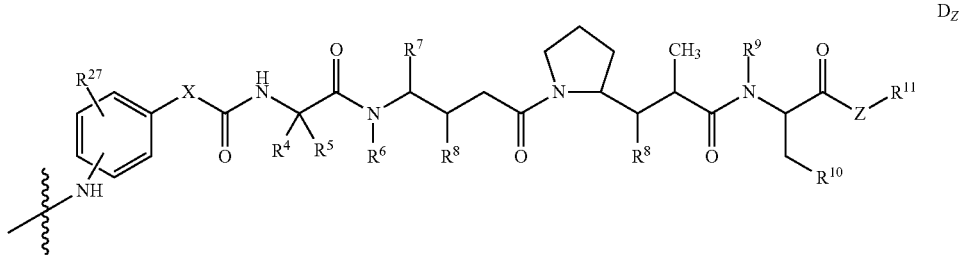

$D_Z$ or a pharmaceutically acceptable salt or solvate form thereof;

wherein, independently at each location:

$R^2$ is $C_1$-$C_{20}$ alkyl, $C_2$-$C_{20}$ alkenyl, or $C_2$-$C_{20}$ alkynyl;

$R^3$ is H, $C_1$-$C_{20}$ alkyl, $C_2$-$C_{20}$ alkenyl, $C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), aryl, —$C_1$-$C_{20}$ alkylene(aryl), —$C_2$-$C_{20}$ alkenylene(aryl), —$C_2$-$C_{20}$ alkynylene(aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle);

$R^4$ is H, $C_1$-$C_{20}$ alkyl, $C_2$-$C_{20}$ alkenyl, $C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), aryl, —$C_1$-$C_{20}$ alkylene(aryl), —$C_2$-$C_{20}$ alkenylene(aryl), —$C_2$-$C_{20}$ alkynylene(aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle);

$R^5$ is H or $C_1$-$C_8$ alkyl;

or $R^4$ and $R^5$ jointly form a carbocyclic ring and have the formula —$(CR^aR^b)_s$— wherein $R^a$ and $R^b$ are independently H, $C_1$-$C_{20}$ alkyl, $C_2$-$C_{20}$ alkenyl, $C_2$-$C_{20}$ alkynyl, or carbocycle and s is 2, 3, 4, 5 or 6, $R^6$ is H, $C_1$-$C_{20}$ alkyl, $C_2$-$C_{20}$ alkenyl, or $C_2$-$C_{20}$ alkynyl;

$R^7$ is H, $C_1$-$C_{20}$ alkyl, $C_2$-$C_{20}$ alkenyl, $C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), aryl, —$C_1$-$C_{20}$ alkylene(aryl), —$C_2$-$C_{20}$ alkenylene(aryl), —$C_2$-$C_{20}$ alkynylene(aryl), heterocycle, —$C_1$-$C_{20}$ alkylene(heterocycle), —$C_2$-$C_{20}$ alkenylene(heterocycle), or —$C_2$-$C_{20}$ alkynylene(heterocycle);

each $R^8$ is independently H, OH, $C_1$-$C_{20}$ alkyl, $C_2$-$C_{20}$ alkenyl, $C_2$-$C_{20}$ alkynyl, —O—($C_1$-$C_{20}$ alkyl), —O—($C_2$-$C_{20}$ alkenyl), —O—($C_1$-$C_{20}$ alkynyl), or carbocycle;

$R^9$ is H, $C_1$-$C_{20}$ alkyl, $C_2$-$C_{20}$ alkenyl, or $C_2$-$C_{20}$ alkynyl;

$R^{24}$ is aryl, heterocycle, or carbocycle;

$R^{25}$ is H, $C_1$-$C_{20}$ alkyl, $C_2$-$C_{20}$ alkenyl, $C_2$-$C_{20}$ alkynyl, carbocycle, —O—($C_1$-$C_{20}$ alkyl),—O—($C_2$-$C_{20}$ alkenyl), —O—($C_2$-$C_{20}$ alkynyl), or $OR^{18}$ wherein $R^{18}$ is H, a hydroxyl protecting group, or a direct bond where $OR^{18}$ represents =O;

$R^{26}$ is H, $C_1$-$C_{20}$ alkyl, $C_2$-$C_{20}$ alkenyl, or $C_2$-$C_{20}$ alkynyl, aryl, heterocycle, or carbocycle;

$R^{10}$ is aryl or heterocycle;

Z is O, S, NH, or $NR^{12}$, wherein $R^{12}$ is $C_1$-$C_{20}$ alkyl, $C_2$-$C_{20}$ alkenyl, or $C_2$-$C_{20}$ alkynyl;

$R^{11}$ is H, $C_1$-$C_{20}$ alkyl, $C_2$-$C_{20}$ alkenyl, $C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene(carbocycle), aryl, —$C_1$-$C_{20}$ alkylene(aryl), —$C_2$-$C_{20}$ alkenylene(aryl), —$C_2$-$C_{20}$ alkynylene(aryl), heterocycle, —$C_1$-$C_{20}$ alkylene(heterocycle), —$C_2$-$C_{20}$ alkenylene(heterocycle), —$C_2$-$C_{20}$ alkynylene(heterocycle) —$(R^{13}O)_m$—$R^{14}$, or —$(R^{13}O)_m$—$CH(R^{15})_2$;

m is an integer ranging from 1-1000;

$R^{13}$ is $C_2$-$C_{20}$ alkylene, $C_2$-$C_{20}$ alkenylene, or $C_2$-$C_{20}$ alkynylene;

$R^{14}$ is H, $C_1$-$C_{20}$ alkyl, $C_2$-$C_{20}$ alkenyl, or $C_2$-$C_{20}$ alkynyl;

each occurrence of $R^{15}$ is independently H, COOH, —$(CH_2)_n$—$N(R^{16})_2$, —$(CH_2)$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl;

each occurrence of $R^{16}$ is independently H, $C_1$-$C_{20}$ alkyl, $C_2$-$C_{20}$ alkenyl, $C_2$-$C_{20}$ alkynyl or —$(CH_2)_n$—COOH;

n is an integer ranging from 0 to 6;

$R^{27}$ is H, $C_1$-$C_{20}$ alkyl, $C_2$-$C_{20}$ alkenyl, $C_2$-$C_{20}$ alkynyl, O—($C_1$-$C_{20}$ alkyl), —O—($C_2$-$C_{20}$ alkenyl), —O—($C_2$-$C_{20}$ alkynyl), halogen, —$NO_2$, —COOH, or —C(O)$OR^{28}$ wherein $R^{28}$ is H, $C_1$-$C_{20}$ alkyl, $C_2$-$C_{20}$ alkenyl, $C_2$-$C_{20}$ alkynyl, aryl, heterocycle, —$(CH_2CH_2O)_r$—H, —$(CH_2CH_2O)_r$—$CH_3$, or —$(CH_2CH_2O)_r$—$CH_2CH_2C(O)OH$; wherein r is an integer ranging from 1-10; and X is —$(CR^{29}_2)_l$— wherein $R^{29}$ is H, $C_1$-$C_{20}$ alkyl, $C_2$-$C_{20}$ alkenyl, $C_2$-$C_{20}$ alkynyl and l is an integer ranging from 0 to 10; wherein said alkyl, alkenyl, alkynyl, alkylene, alkenylene, alkynyklene, aryl, carbocyle, and heterocycle radicals, whether alone or as part of another group, are optionally substituted.

11. The method of claim 10, wherein the ligand-drug conjugate compound has the formula,

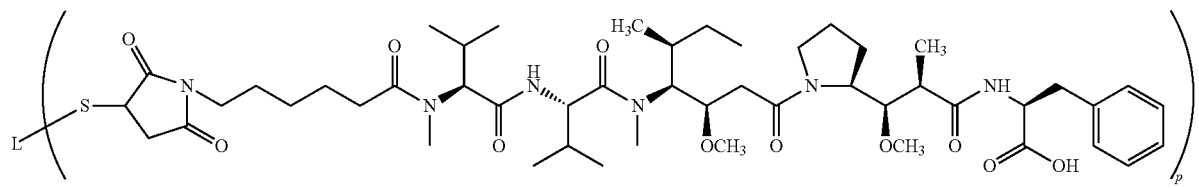

or a pharmaceutically acceptable salt or solvate form thereof, wherein L is the antibody or antigen-binding fragment thereof and p is from 1 to 8.

12. The method of claim 2, wherein the CD19 expressing cancer is chronic leukemia, lymphoma, or multiple myeloma.

13. A method for treating a subject that has a CD19-expressing cancer that is refractory to treatment with rituximab comprising administering to the subject an antibody or antigen binding fragment that specifically binds to human CD19 in an amount effective to treat the disorder in the mammalian subject; the antibody or binding fragment comprising a heavy chain variable region amino acid sequence as set forth in SEQ ID NO:29 with 0, 1 or 2 substitutions at the alternative positions specified in SEQ ID NO: 29 relative to SEQ ID NO:9 and a light chain variable region amino acid sequence as set forth in SEQ ID NO:30 with 1 or 2 substitutions at the alternative positions specified in SEQ ID NO:30 relative to SEQ ID NO:17, one of which is position L83 by Kabat numbering is occupied by V; wherein the antibody or antigen-binding fragment binds to CD19 with a dissociation constant of $1 \times 10^{-7}$ M.

14. A method for treating a subject that has a hematological malignancy comprising administering to the subject administering an antibody or antigen binding fragment that specifically binds to human CD19 in an amount effective to treat the disorder in the mammalian subject; the antibody or binding fragment comprising a heavy chain variable region amino acid sequence as set forth in SEQ ID NO:29 with 0, 1 or 2 substitutions at the alternative positions specified in SEQ ID NO:29 relative to SEQ ID NO:9 and a light chain variable region amino acid sequence as set forth in SEQ ID NO:30 with 1 or 2 substitutions at the alternative positions specified in SEQ ID NO:30 relative to SEQ ID NO:17, one of which is position L83 by Kabat numbering is occupied by V; wherein the antibody or antigen-binding fragment binds to CD19 with a dissociation constant of $1 \times 10^{-7}$ M.

15. The method of claim 14, wherein the hematological malignancy is non-Hodgkin's lymphoma or acute lymphoblastic leukemia.

* * * * *